US012697596B2

(12) United States Patent
Ricoult et al.

(10) Patent No.: US 12,697,596 B2
(45) Date of Patent: Aug. 4, 2026

(54) COMPOSITIONS, SYSTEMS, AND METHODS OF MAKING AND USING ENCAPSULATED LYOPHILISED MICROSPHERES

(71) Applicants: ILLUMINA CAMBRIDGE LIMITED, Cambridge (GB); ILLUMINA, INC., San Diego, CA (US); ILLUMINA SINGAPORE PTE LTD, Singapore (SG)

(72) Inventors: Sébastien Ricoult, Sawston (GB); Pascale Mathonet, Bishop's Stortford (GB); Elliot Lawrence, Brandon (GB); Niall Gormley, Cambridge (GB); Justin Davidson, San Diego, CA (US); Kim Schneider, Cambridge (GB); Antoine Francais, Cambridge (GB); Jessica Walsh, Cambridge (GB); Johan Sebastian Basuki, Singapore (SG); Shima Gholizadeh, San Diego, CA (US)

(73) Assignees: Illumina Cambridge Limited, Cambridge (GB); Illumina, Inc., California (CA); Illumina Singaore PTE LTD, Singapore (SG)

( * ) Notice: Subject to any disclaimer, the term of this patent is extended or adjusted under 35 U.S.C. 154(b) by 1138 days.

(21) Appl. No.: 17/659,037

(22) Filed: Apr. 13, 2022

(65) Prior Publication Data

US 2022/0331770 A1     Oct. 20, 2022

Related U.S. Application Data

(60) Provisional application No. 63/174,325, filed on Apr. 13, 2021.

(51) Int. Cl.
| | |
|---|---|
| *C12Q 1/68* | (2018.01) |
| *B01J 13/04* | (2006.01) |
| *C12Q 1/6876* | (2018.01) |
| *C12Q 1/6869* | (2018.01) |

(52) U.S. Cl.
CPC .......... B01J 13/043 (2013.01); C12Q 1/6876 (2013.01); *C12Q 1/6869* (2013.01)

(58) Field of Classification Search
CPC ...... B01J 13/043; B01J 13/00; B01J 13/0034; C12Q 1/6876; C12Q 1/6869
See application file for complete search history.

(56) References Cited

U.S. PATENT DOCUMENTS

| | | | |
|---|---|---|---|
| 5,843,347 | A | 12/1998 | Nguyen et al. |
| 6,288,902 | B1 | 9/2001 | Kim et al. |
| 6,355,431 | B1 | 3/2002 | Chee et al. |
| 6,482,518 | B1 | 11/2002 | Short et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,414,116 | B2 | 8/2008 | Milton et al. |
| 7,427,673 | B2 | 9/2008 | Balasubramanian et al. |
| 8,053,192 | B2 | 11/2011 | Bignell et al. |
| 8,895,249 | B2 | 11/2014 | Shen et al. |
| 9,309,502 | B2 | 4/2016 | Piepenburg et al. |
| 9,877,922 | B2 | 1/2018 | Lee et al. |
| 2002/0034514 | A1 | 3/2002 | Rivera |
| 2002/0102578 | A1 | 8/2002 | Dickinson et al. |
| 2005/0100900 | A1 | 5/2005 | Kawashima et al. |
| 2006/0188901 | A1 | 8/2006 | Barnes et al. |

(Continued)

FOREIGN PATENT DOCUMENTS

| | | | |
|---|---|---|---|
| WO | 9106678 | A1 | 5/1991 |
| WO | 9844151 | A1 | 10/1998 |

(Continued)

OTHER PUBLICATIONS

Lumay et al., "Influence of Mesoporous Silica on Powder Flow and Electrostatic Properties on Short and Long Term," Journal of Drug Delivery Science and Technology 53:101192 2019.

Fang et al., "Universal Nature-Inspired Coatings for Preparing Noncharging Surfaces," ACS Applied Material and Interfaces 9:32220-32226 2017.

Guo et al., "Highly Flexible, Thermally Stable, and Static Dissipative Nanocomposite with Reduced Functionalized Graphene Oxide Processed Through 3D Printing," Composites Part B: Engineering 208:108598 2021.

Baytekin et al., "Control of Surface Charges by Radicals as a Principle of Antistatic Polymers Protecting Electronic Circuitry," Science 341:1368-1371 2013.

(Continued)

*Primary Examiner* — Jezia Riley
(74) *Attorney, Agent, or Firm* — Heslin Rothenberg Farley & Mesiti P.C.

(57) ABSTRACT

The present disclosure relates to a composition comprising a shell surrounding a core, wherein the core comprises one or more lyophilised microspheres. Also described herein is a method comprising providing one or more lyophilised microspheres; and coating the one or more lyophilised microspheres with a shell under conditions effective to encapsulate the one or more lyophilised microspheres. The present disclosure further relates to a system comprising one or more composition as described herein, and one or more lyophilised cake, wherein the one or more composition and the one or more lyophilised cake are combined under conditions effective to form a rehydration system. Also described herein is a method of controlling release of one or more encapsulated microspheres comprising providing a composition as described herein and mixing the composition with a rehydration solution under a first condition effective to control release of one or more lyophilised microspheres from the composition.

20 Claims, 88 Drawing Sheets

(56) References Cited

U.S. PATENT DOCUMENTS

| | | | |
|---|---|---|---|
| 2006/0240439 | A1 | 10/2006 | Smith et al. |
| 2006/0281109 | A1 | 12/2006 | Barr Ost et al. |
| 2007/0166705 | A1 | 7/2007 | Milton et al. |
| 2008/0108082 | A1 | 5/2008 | Rank et al. |
| 2012/0270305 | A1 | 10/2012 | Reed et al. |
| 2013/0079232 | A1 | 3/2013 | Kain et al. |
| 2013/0260372 | A1 | 10/2013 | Buermann et al. |
| 2021/0040555 | A1* | 2/2021 | Glezer ............... G01N 33/5308 |

FOREIGN PATENT DOCUMENTS

| | | | |
|---|---|---|---|
| WO | 0018957 | A1 | 4/2000 |
| WO | 0063437 | A2 | 10/2000 |
| WO | 2005065814 | A1 | 7/2005 |
| WO | 2006064199 | A1 | 6/2006 |
| WO | 2007010251 | A2 | 1/2007 |
| WO | 2007123744 | A2 | 11/2007 |
| WO | 2008042067 | A2 | 4/2008 |
| WO | 2013117595 | A2 | 8/2013 |
| WO | 2013131962 | A1 | 9/2013 |
| WO | 2016130704 | A2 | 8/2016 |

OTHER PUBLICATIONS

Maroni et al., "Film Coating for Oral Pulsatile Release," International Journal of Pharmaceutics 457:362 2013.

Joshi et al., "Film Coatings for Taste Masking and Moisture Protection," International Journal of Pharmaceutics 457:395 2013.

Zema et al., "Different HPMC Viscosity Grades as Coating Agents for an Oral Time and/or Site-Controlled Delivery System: An Investigation into the Mechanisms Governing Drug Release," International Journal of Pharmaceutical Sciences 96:1527 2007.

Yang et al., "An Update of Moisture Barrier Coating for Drug Delivery" Pharmaceutics, vol. 11, No. 436, pp. 1-16. Sep. 1, 2019.

Bentley et al., "Accurate Whole Human Genome Sequencing Using Reversible Terminator Chemistry," Nature 456:53-59, p. 42, lines 11-12. 2008.

Uhlmann et al., "Antisense Oligonucleotides: A New Therapeutic Principle," Chemical Reviews 90:543-584. 1990.

* cited by examiner

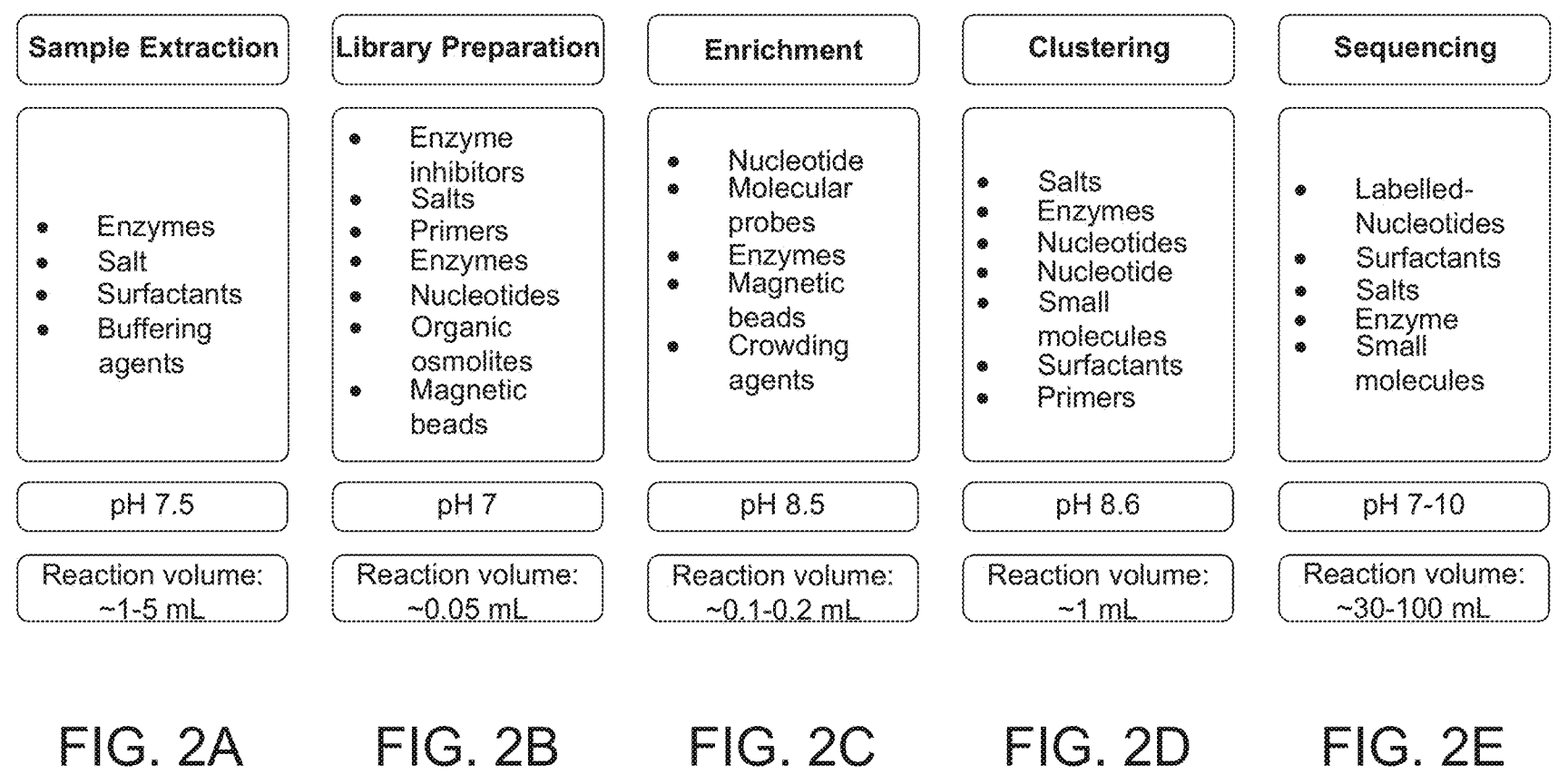

Sample Extraction

- Enzymes
- Salt
- Surfactants
- Buffering agents pH 7.5

Reaction volume: ~1-5 mL

FIG. 2A

Library Preparation

- Enzyme inhibitors
- Salts
- Primers
- Enzymes
- Nucleotides
- Organic osmolites
- Magnetic beads pH 7

Reaction volume: ~0.05 mL

FIG. 2B

Enrichment

- Nucleotide
- Molecular probes
- Enzymes
- Magnetic beads
- Crowding agents pH 8.5

Reaction volume: ~0.1-0.2 mL

FIG. 2C

Clustering

- Salts
- Enzymes
- Nucleotides
- Nucleotide
- Small molecules
- Surfactants
- Primers pH 8.6

Reaction volume: ~1 mL

FIG. 2D

Sequencing

- Labelled-Nucleotides
- Surfactants
- Salts
- Enzyme
- Small molecules pH 7-10

Reaction volume: ~30-100 mL

FIG. 2E

Blue 102: OTS Gelatin capsule filled with microspheres

Yellow 104: OTS Gelatin capsule filled with microspheres quick dipped in hot paraffin wax

102

104

Gelatine Dissolves @37°C

Paraffine-coated Gelatine capsule Dissolves @58°C

106

108

| | % excipient | Rehydration time (min) |
|---|---|---|
| Trehalose | 5-40 | <1 |
| Carrageenan | 0.125-1 | <1 |
| Gelatin | 1.25-10 | >60 |
| Phenilalanine/Tre | 1/4-2/8 | 5.5- >60 |
| Leucine/Tre | 1/4-2/8 | 1- >30 |
| Isoleucine/Tre | 1/4-2/8 | 1-15 |

1% Leucine/4% Trehalose: 12 min rehydration

Dry
202

1 min
204

2 min
206

5 min
208

10 min
210

12 min
212

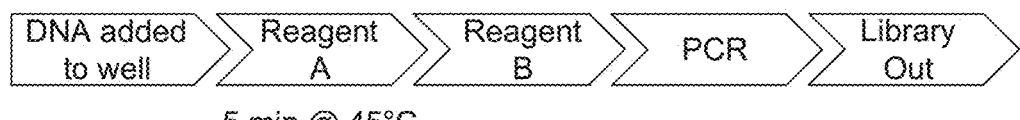

5 min @ 45°C

FIG. 8A

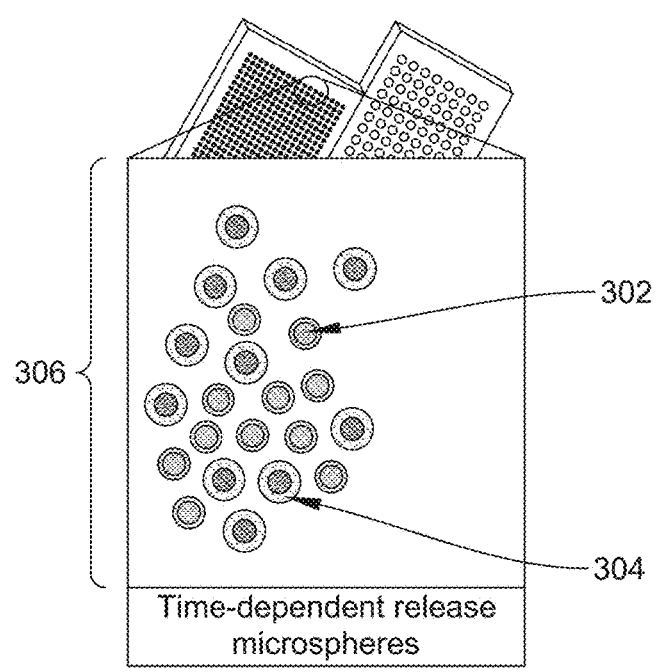

306

302

304

Time-dependent release microspheres

FIG. 8B

| Reagent | Active reagent volume (µL) | Number of $\phi600\mu m$ µSpheres | Active reagent composition | Encapsulation shell composition | Encapsulation shell release trigger |
|---|---|---|---|---|---|
| A | 40 | 354 | • BLT<br>• Tris pH7<br>• MgCl$_2$<br>• Indexed primers<br>• Q5 polymerase<br>• Bst3.0 | N/A | - |
| B | 10 | 89 | • Tris pH9<br>• dNTPs<br>• NaCl<br>• betaine | Gelatin or carrageenan | Time |
| B' | 10 | 89 | • Tris pH9<br>• dNTPs<br>• NaCl<br>• betaine | Pectin or Carrageenan or Waxes | Temperature |

FIG. 8C

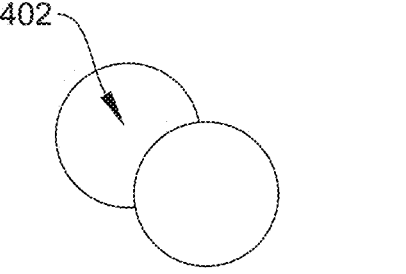
FIG. 9A
FIG. 9B
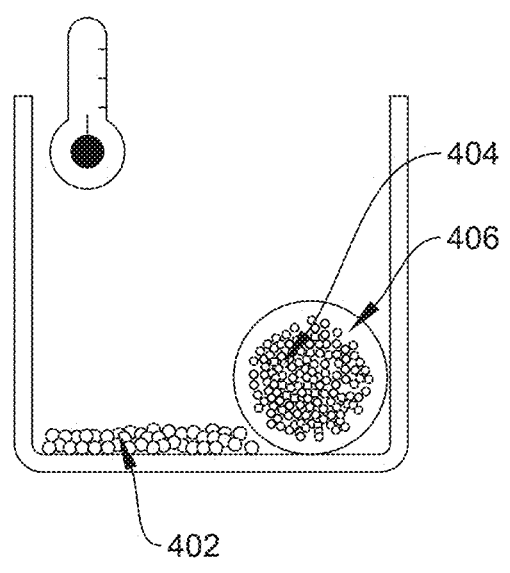
FIG. 9C
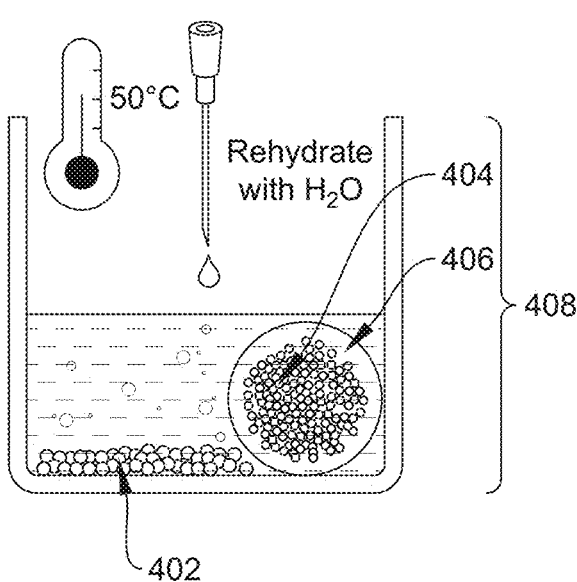
FIG. 9D

Same unit dose repeated
across different reagents
to achieve overall x3 dose

Peak area of ffN

3'OH of ffN

Diphosphate of ffN

☒ Day 1   ☒ Day 2

Peak area of ffN

☒ Day 1   ☒ Day 2

100mM
MOPS
pH 8
18%
Trehalose
0.05%
CHAPS

3'OH of ffN

Diphosphate of ffN

Kollicoat Protect is a mixture of Kollicoat IR and Gohsenol EG

Clustering performance of ExAmp spiked with
Coating materials by cBOT 1st base assay

| 1 | Methocel HPMC E5 |
|---|---|
| 2 | Kollidon V64 |
| 3 | Kollicoat IR |
| 4 | Gohsenol EG 05 |

| 1 | Efka 6783 |
|---|---|
| 2 | Luviquat FC550 |
| 3 | Efka 6786 |
| 4 | Control (TCX1 only) |

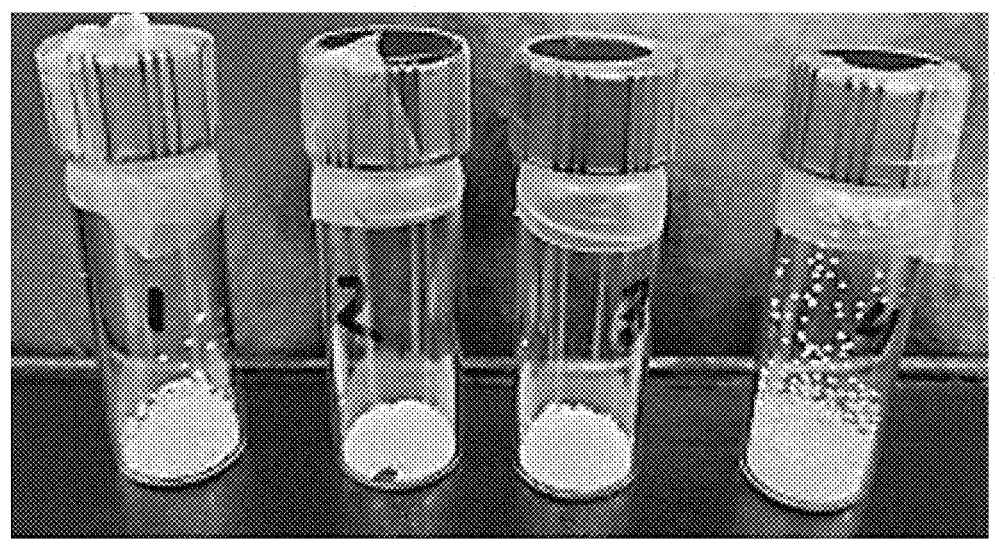
Atto 20%      +1% Efka      +1.5%      +1% Tween
Ctrl          6783          Tris.HCl    20
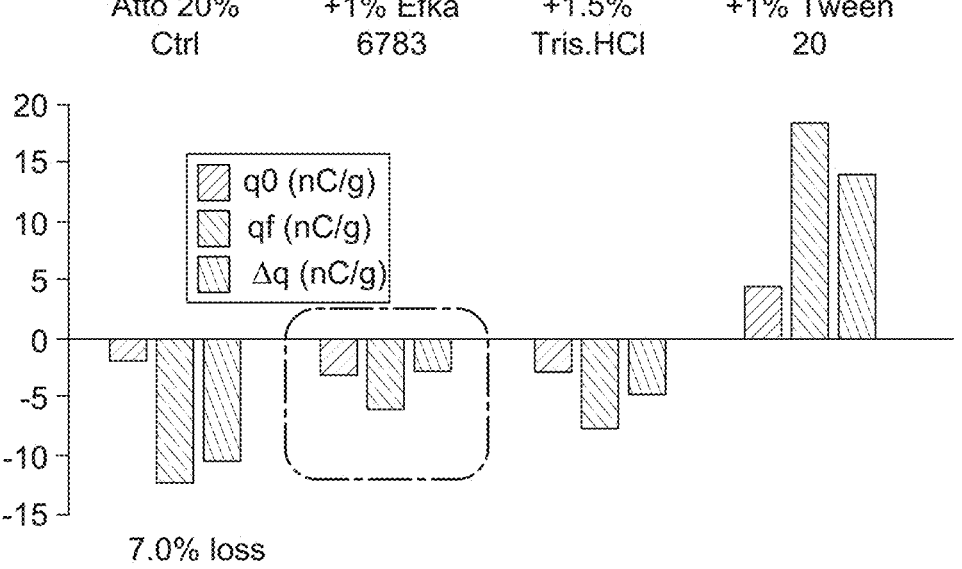
7.0% loss
FIG. 25A

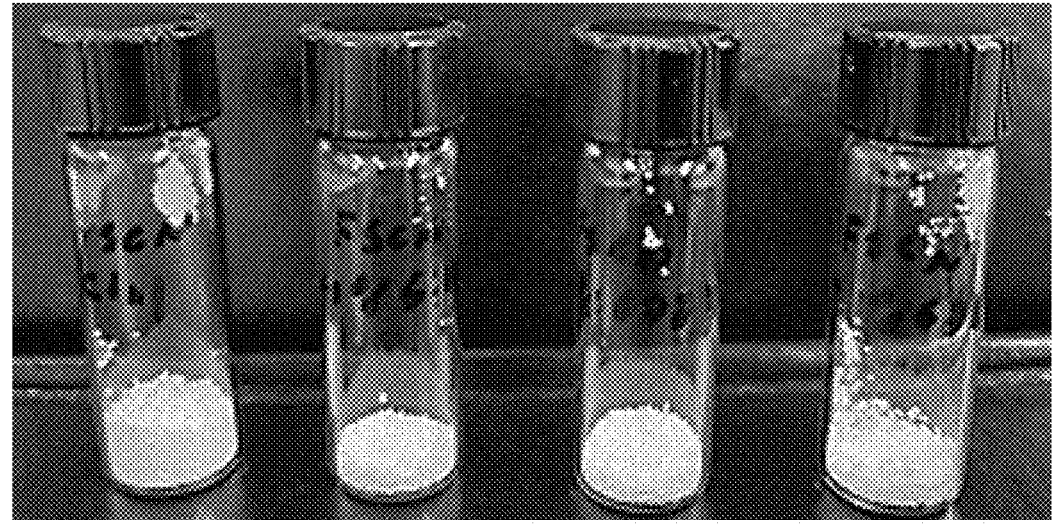
FSCN 20%          +1% Efka          +2% Efka          +1% Efka
Ctrl               6783              6783              6786
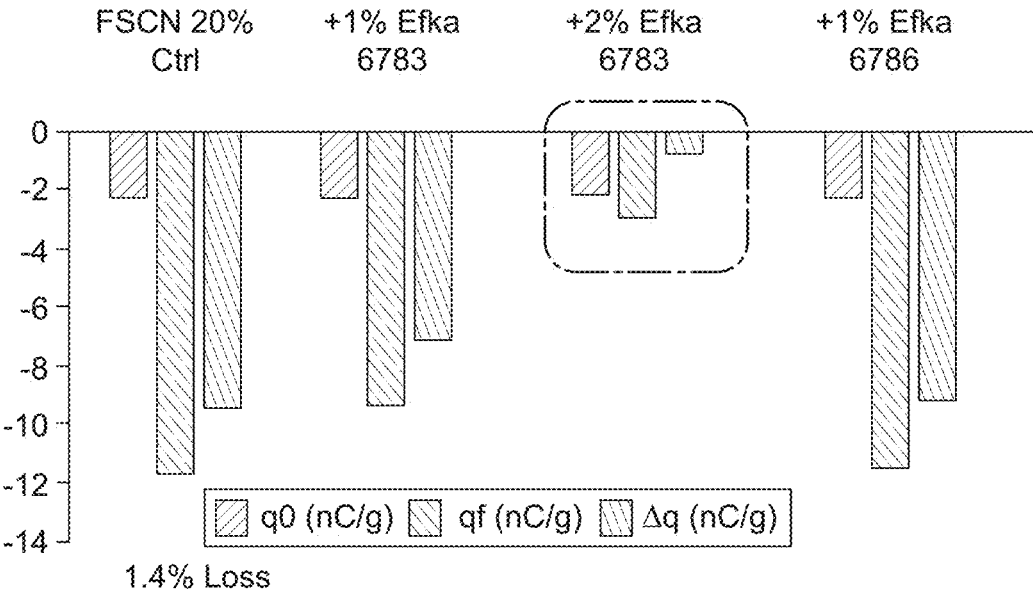
1.4% Loss
FIG. 25B Atto and FSCN (both 20% trehalose) are dry-compounded with the help of Anti-static agent Efka IO 6783 in Matrix format
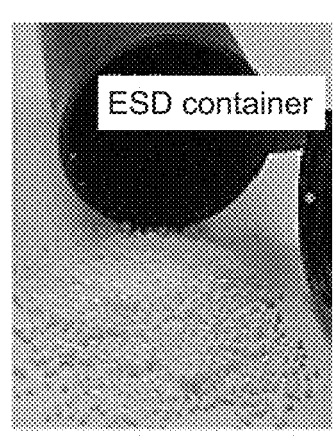
$$\left( N_d - \underset{\underset{N_d}{|}}{\overset{\overset{R_1}{|}}{N}} - cCH_1CH_2CH_2H \right) X$$
No anti-static         W/ 1% Efka IO
FIG. 25C

SHELL
Eudragit L-100-55 + Magnesium stearate

CORE
35% Sucrose + fluorescein or 35% trehalose + methyl blue

Weight gain from coating is 5-7%

800um FSCN Wurster-Spray 20% Coated
w/ Kollidon VA64 + Efka 6783 + PEG (#6)

Cryo Ion-Mill SEM of DNA Rec. 15% Coated
w/ Kollidon VA64 + Efka 6783 + PEG (#8)

Cryo Ion-Mill SEM of ffN 10% Coated w/
Kollidon VA64 + Efka 6783 + PEG (#11)

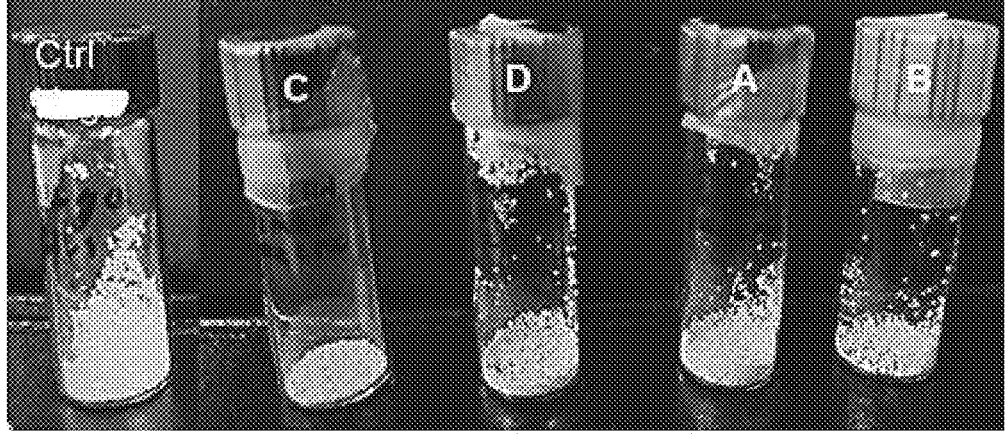
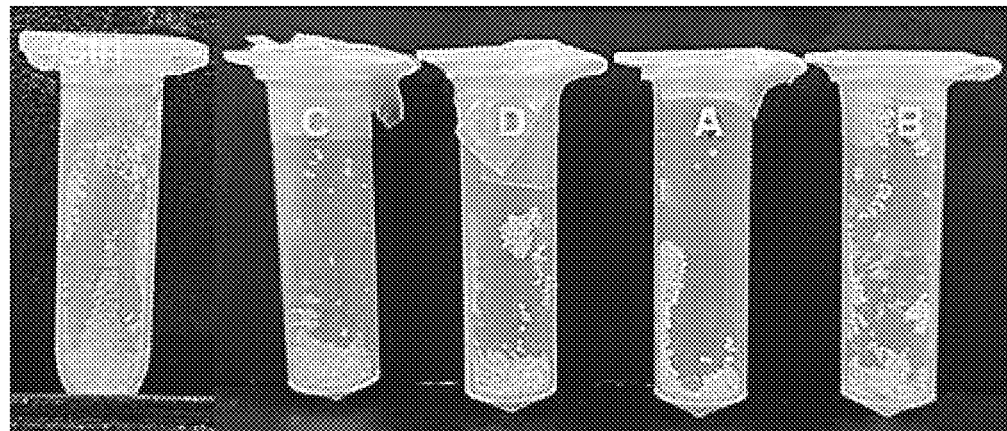
A: Coated w/ 10% Kollidon VA64 & Efka 6783
B: Coated w/ 10% Kollidon VA64
C: Coated w/ 15% Kollicoat Protect & Efka 6783
D: Coated w/ 10% Kollicoat Protect
FIG. 29A

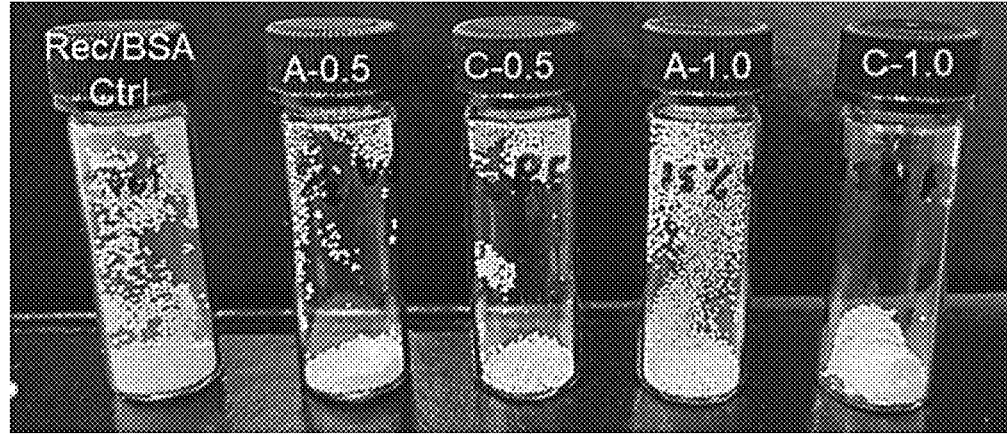
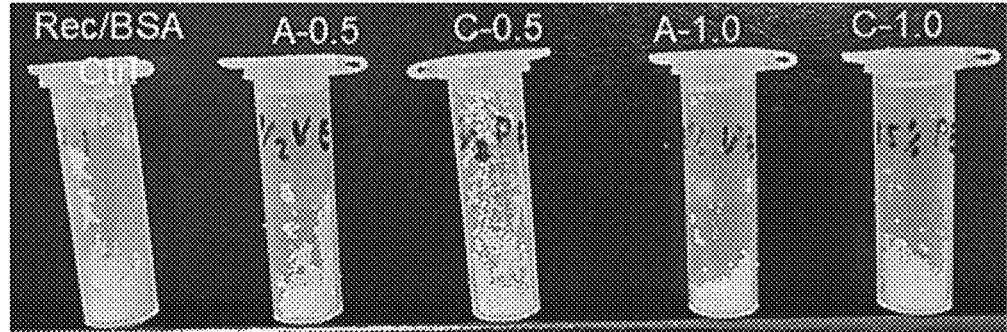
A-0.5: Coated w/ 7.5% Kollidon VA64 & Efka 6783
A-1.0: Coated w/ 15% Kollidon VA64 & Efka 6783
C-0.5: Coated w/ 7.5% Kollicoat Protect & Efka 6783
C-1.0: Coated w/ 15% Kollicoat Protect & Efka 6783
FIG. 30A

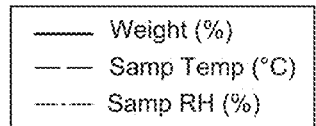
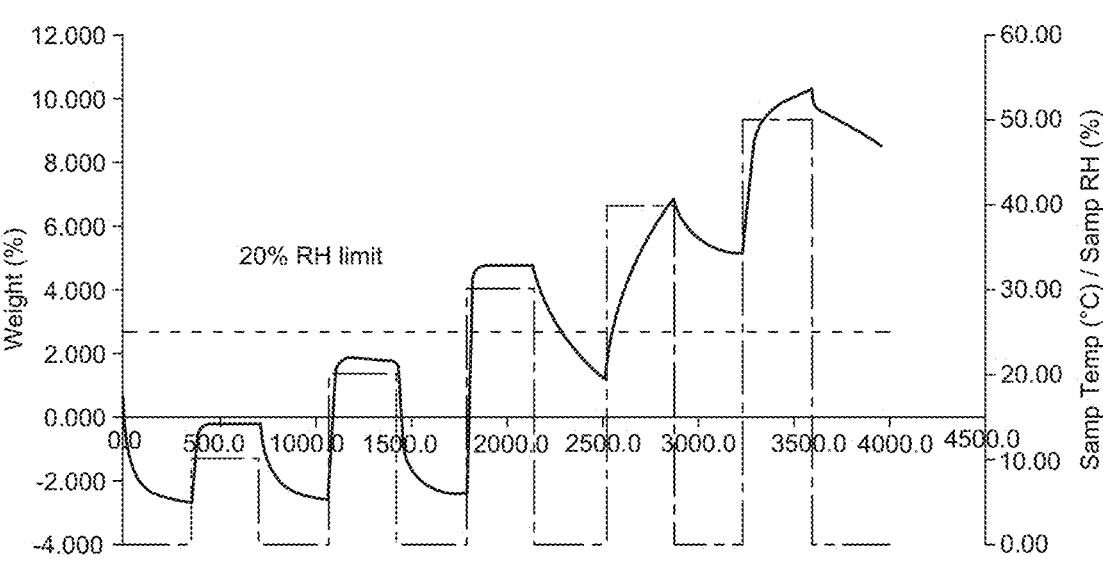
Rec/BSA(AP1) Uncoated Ctrl
FIG. 33A

Rec/BSA coated w/ 15% Protect+Efka 6783

Rec/BSA coated w/ 15% VA64+Efka 6783

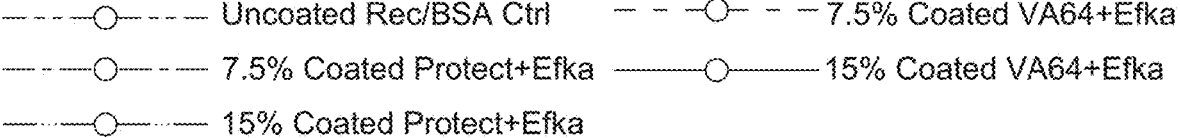
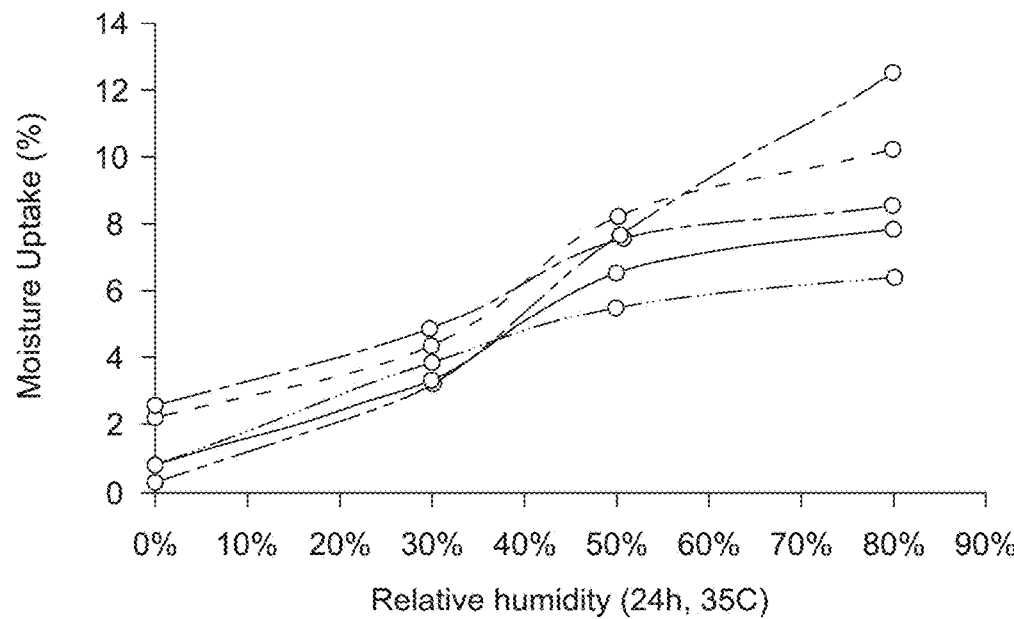
FIG. 34B

Kollidon VA64, Efka, Eudragit are soluble in spray-coating
solution (15% water/solvent) and buffer
**Aqueous Solution
(pH 7.5 buffer)**
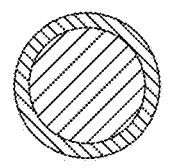
Spray solvent (IPA-based)
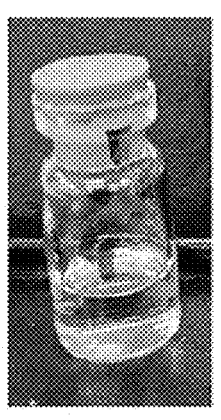 
Coating Solution
in solvent
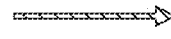
 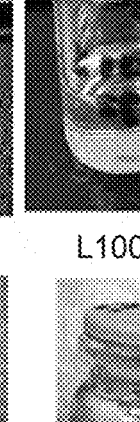
VA64      L100-55
**Rehydration in
IMX (SBS)
or ExAmp**
VA64      L100-55
 
Spray-coating
solution
15% water,
34% acetone,
51% IPA
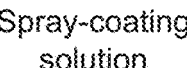
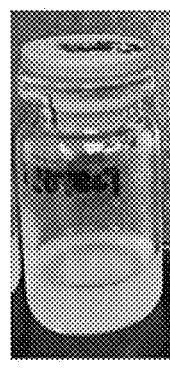 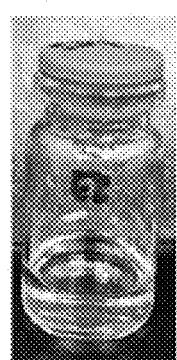
Protect      HPMC E3
Protect      HPMC E3
FIG. 36

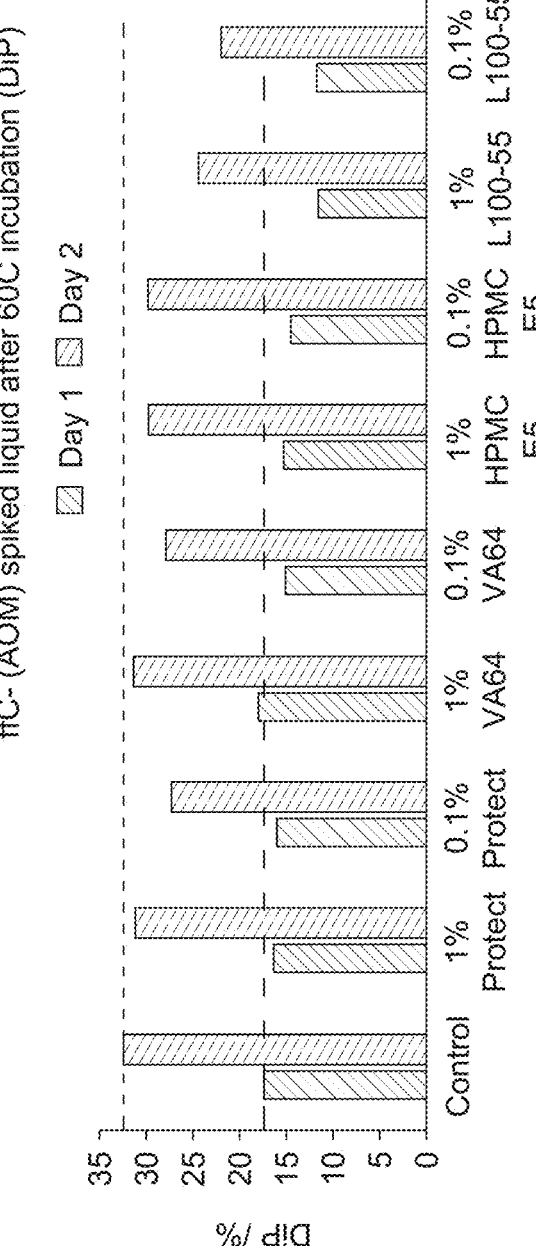
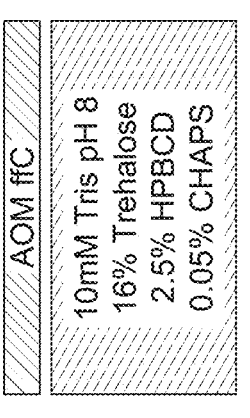
FIG. 37C

| Coating | ffN | | | | DNA Recombinase / BSA | |
| --- | --- | --- | --- | --- | --- | --- |
| | Formulation A | Formulation B | Formulation C | Formulation D | Formulation A | Formulation C |
| Yield (%) | 95 | 80 | 100 | 100 | 94 | 88 |
| Loss on drying | 3.77 | 3.91 | 5.99 | 5.12 | 2.76 | 3.03 |
| Res. Moisture (%RH) | 0.90 | 0.42 | 0.51 | 0.35 | 0.72 | 0.34 |
| Rehydration | Dissipates by 1 mins | Dissipates by 3.5 mins | Dissipates by 1.5 mins | Dissipates by 3 mins | Instant | Instant |
| Foam | No | No | No | No | Dissipates by 0.5 min | No foam |
| Precipitates | No | No | No | No | No | dissolves <30s |
| Size distribution (0.5, μm) | 414.6 | 392.5 | 268.2 | 367.9 | 378.6 | 362.5 |
| Trib. Affinity (nC/g) | 3.35 | 3.76 | -0.912 | 1.24 | -0.0117 | -0.71 |

FIG. 44

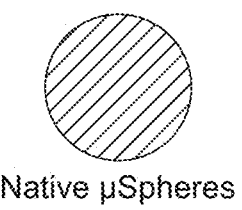
Native µSpheres
Core: ffN (20%w/v)
Shell: None
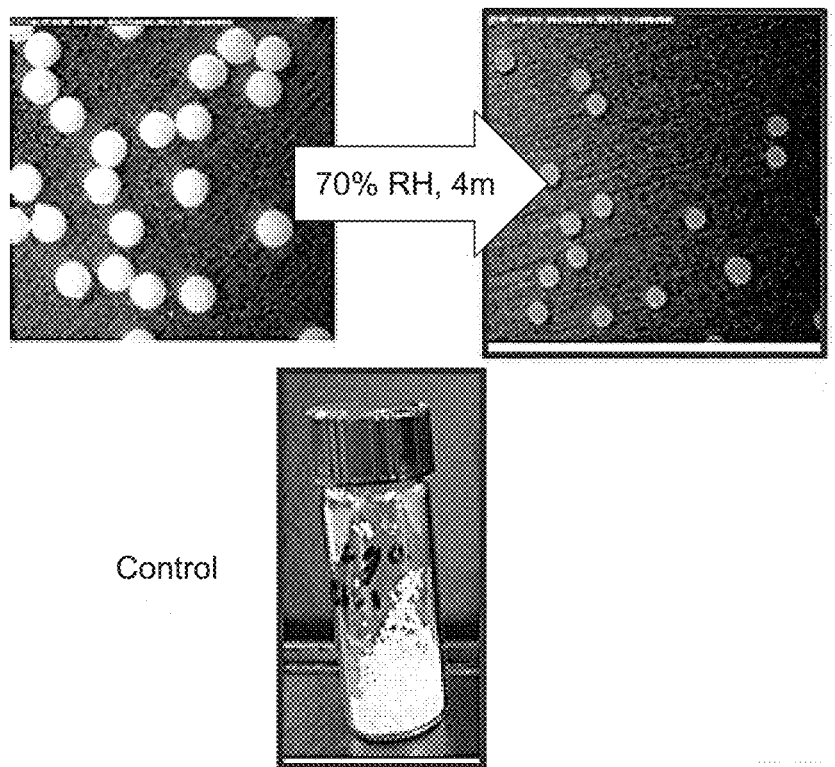
70% RH, 4m
Control
FIG. 46A

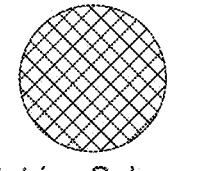
Matrix µSpheres
Core: ffN/Kollidon Protect (20%)
Shell: None
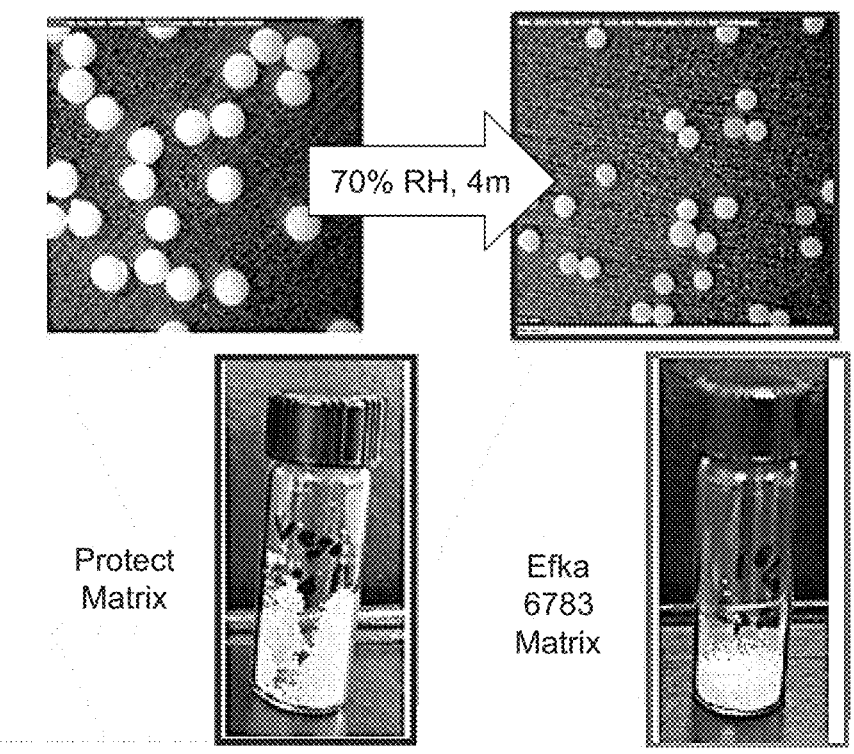
FIG. 46B

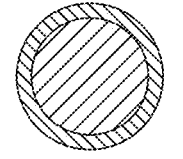
Core-Shell µSpheres
Core: ffN (20%)
Shell: Kollidon Protect & Efka IO 6783
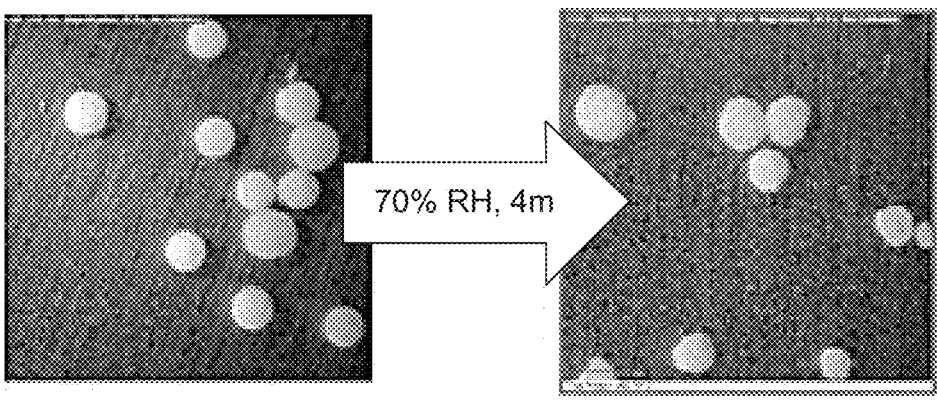
70% RH, 4m
Coated w/
Protect &
Efka
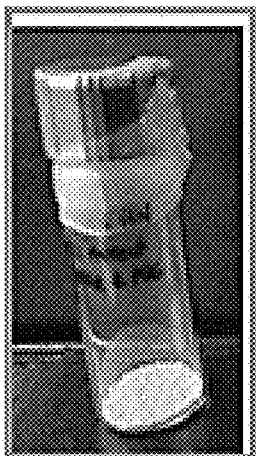
FIG. 46C A method comprising providing one or more lyophilised microspheres, and

602

Coating the one or more lyophilised microspheres with a shell under conditions effective to encapsulate said one or more lyophilised microspheres

604

COMPOSITIONS, SYSTEMS, AND METHODS OF MAKING AND USING ENCAPSULATED LYOPHILISED MICROSPHERES

This application claims benefit of U.S. Provisional Patent Application Ser. No. 63/174,325, filed Apr. 13, 2021, which is hereby incorporated by reference in its entirety.

FIELD

The present disclosure relates generally to compositions, systems, and methods of making and using encapsulated lyophilised microspheres.

BACKGROUND

Many current sequencing platforms use "sequencing by synthesis" ("SBS") technology and fluorescence based methods for detection. Alternative sequencing methods and improved sample preparation processes that allow for more cost effective, rapid, and convenient sequencing and nucleic acid detection are desirable as complements to SBS.

Current protocols for SBS technology routinely employ a sample preparation process that converts DNA or RNA into a library of fragmented, sequenceable templates. Sample preparation methods often involve multiple steps, material transfers, and expensive instruments to effect fragmentation, and, therefore, are often difficult, tedious, expensive, and inefficient.

Libraries including polynucleotides are generally prepared in any suitable manner to attach oligonucleotide adapters to target polynucleotides. Sequencing may result in determination of the sequence of the whole, or a part of the target polynucleotides. The number of steps involved to transform nucleic acids into adapter-modified templates in solution ready for cluster formation and sequencing can be reduced, or in some instances even minimized, by the use of transposase mediated fragmentation and tagging. This process, referred to as "tagmentation," involves the modification of nucleic acids by a transposome complex comprising transposase enzyme complexed with adapters comprising transposon end sequence, as described in, for example, WO 2016/130704. Methods for immobilizing and amplifying prior to sequencing are described in, for instance, U.S. Pat. No. 8,053,192, WO 2016/130704, U.S. Pat. Nos. 8,895,249, and 9,309,502. A library of templates may be used to prepare clustered arrays of nucleic acid colonies, as described in U.S. Pat. Publ. No. 2005/0100900, U.S. Pat. No. 7,115,400, WO 00/18957, and WO 98/44151, by solid-phase amplification and more particularly solid phase isothermal amplification.

Sequencing can be carried out using any suitable sequencing technique, and methods for determining the sequence of immobilized and amplified adapter-target-adapter molecules, including strand re-synthesis, are known in the art and are described in, for instance, U.S. Pat. No. 8,053,192, WO2016/130704, U.S. Pat. Nos. 8,895,249, and 9,309,502. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. Exemplary SBS systems and methods are described in U.S. Pat. Publ. No. 2007/0166705, 2006/0188901, 2006/0240439, 2006/0281109, 2012/0270305, and 2013/0260372, U.S. Pat. No. 7,057,026, WO 05/065814, U.S. Pat. Publ. No. 2005/0100900, WO 06/064199, and WO 07/010,251, U.S. Pat. Publ. No. 2013/0079232.

The stability of the reagents involved with sample preparation including, for example, PCR, varies depending on a variety of factors. Historically, reagents have been wet thereby often involving freezing for ship and storage. Moving to dry reagents may allow for ambient transport and storage, but dry reagents may be more sensitive than wet reagents to environmental conditions. If reagents are exposed to undesirable environmental conditions on manufacture, transport, storage, or during library preparation, quality and efficiency of the resulting library may be affected. Likewise, pH of reagents like SBS buffers varies during sequencing and there is a need for improved stabilization of these buffers to increase SBS performance. Reagents involved with sample preparation may be highly sensitive to changes in humidity, light, and moisture and, as a result, are notoriously difficult to keep stable.

Moreover, lyophilised microspheres which may be used in sample preparation often degrade upon exposure to mechanical stress during transport and storage and may unfavorably shed their outer covering. The resulting powder may be problematic in clogging membranes used in sample preparation and might result in variations in the desired end concentration after rehydration has been achieved. Static charge is also a risk for dispensing and dry compounding microspheres.

Tribocharging is realized by (frictional) contact through particle—particle and/or particle—wall interaction. During contact, charge transfer occurs, and after parting two oppositely charged objects are obtained. Static is realized by the ability of the material (particle or wall) to dissipate electrostatic charge, which is associated with the conductivity of the material.

Lyophilized microspheres are typically manufactured from non-conductive materials (e.g., trehalose). The necessity to handle and store lyophilized microspheres in dry environment is attributed to limited tolerance of the microspheres against ambient humidity. Therefore, in dry environments, static behavior and tribocharging are expected in lyophilized microspheres, which are exhibited through adhesion of the microspheres onto the wall of the container. The risk associated with static is the difficulty to handle microspheres for dry filling into cartridges. Upon dry storage, microspheres tend to adhere onto the wall of cartridges, which lead to cross-contamination between cartridge wells and inaccuracy during rehydration.

Therefore, there is a need for improved sample preparation compositions and processes. In particular, there is a need for sequencing reagents with improved stability and associated methods that demonstrate improved efficiency of workflow and tagmented library production and, in turn, increased read enrichment for the resulting libraries. There is also a need for compositions and methods that will improve the read enrichment for the resulting libraries as well as simplify workflows.

The present disclosure is directed to overcoming these and other deficiencies in the art.

SUMMARY

A first aspect relates to a composition comprising a shell surrounding a core, wherein the core comprises one or more lyophilised microspheres.

In one implementation, the shell comprises one or more of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

In one implementation, the shell comprises a shell additive. In one implementation, the shell additive comprises a static mitigation material, a moisture barrier material, or a combination thereof. In one implementation, the shell additive is a static mitigation material present in an amount no more than 40% w/w concentration of the shell. In one implementation, the shell additive is a moisture barrier material present in an amount no more than 90% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or the oleate derivative is selected from magnesium stearate, triglycerol stearate, Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris (hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof.

In one implementation, the core comprises one or more reagent selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In one implementation, the reagent is a polymerase. In one implementation, a volume of the reagent in the core is between about 0.1 μL and about 50 μL.

In one implementation, the shell comprises a reagent.

In one implementation, the core further comprises one or more additional agent, wherein the additional agent is selected from one or more sugar, one or more amino acid, one or more polymer, one or more mesoporous silica, one or more quaternary amine, and any combination thereof. In one implementation, when the additional agent comprises one or more sugar, the sugar is selected from trehalose, mannitol, cyclodextrin, dextran, sucrose, or any combination thereof. In another implementation, when the additional agent comprises one or more amino acid with a hydrophobic side chain. In yet another implementation, when the additional agent comprises one or more polymer, the polymer is selected from polyvinylpyrrolidone, polyvinyl alcohol, or a combination thereof.

In one implementation, the core comprises a core additive. In one implementation, the core additive comprises a static mitigation material. In one implementation, the core additive is a static mitigation material present in an amount no more than 25% w/w concentration of the core. In one implementation, the core additive is present in an amount of at least 0.5% w/w concentration of the core. In one implementation, the core additive is in an amount between about 2% w/w and about 10% w/w of the core. In one implementation, the core additive is a water-insoluble additive, a water-soluble additive, an entero-soluble additive, or any combination thereof. In one implementation, the core additive comprises one or more of a polymer, a copolymer, a block copolymer, a second polyvinyl alcohol (PVA), a conductivity promoter, an ammonium salt, an imidazolium salt, a polyether compound, or any combination thereof. In one implementation, the polyether compound is selected from polyethylene glycol, polypropylene glycol, a block copolymer derived from ethylene oxide (EO) and propylene oxide (PO), or any combination thereof. In one implementation, the polymer is neutral, cationic, or anionic. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the composition is used for performing multiple co-assay reactions. In one implementation, the shell comprises more than one lyophilised microsphere, and wherein the reagents in the more than one lyophilised microsphere are different.

A second aspect relates to a method. The method comprises providing one or more lyophilised microspheres; and coating the one or more lyophilised microspheres with a shell under conditions effective to encapsulate the one or more lyophilised microspheres.

In one implementation, the method further comprises covering the shell with an outer layer, under conditions effective to surround the encapsulated microsphere with the outer layer. In one implementation, the covering is carried out for a period of time sufficient to provide the outer layer with a defined thickness.

In one implementation, the shell, the outer layer, or both the shell and the outer layer comprise one or more of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

In one implementation, the shell comprises a shell additive. In one implementation, the shell additive comprises a static mitigation material, a moisture barrier material, or a combination thereof. In one implementation, the shell additive is a static mitigation material present in an amount no more than 40% w/w concentration of the shell. In one implementation, the shell additive is a moisture barrier material present in an amount no more than 90% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or oleate derivative is selected from magnesium stearate, triglycerol stearate, Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof.

In one implementation, the shell surrounds a core, the core comprising one or more reagent selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In one implementation, the reagent is a polymerase. In one implementation, a volume of the reagent in the core is between about 0.1 μL and about 50 μL.

In one implementation, the shell comprises a reagent.

In one implementation, the encapsulated microsphere has a diameter between about 100 μm and 1000 μm.

In one implementation, the core further comprises one or more additional agent, wherein the additional agent comprises one or more sugar, one or more amino acid, one or more polymer, one or more mesoporous silica, one or more quaternary amine, or any combination thereof. In one implementation, when the additional agent comprises one or more sugar, the sugar is selected from trehalose, mannitol, cyclodextrin, dextran, sucrose, or any combination thereof. In another implementation, when the additional agent comprises one or more amino acid with a hydrophobic side chain. In yet another implementation, when the additional agent comprises a polymer, the polymer is selected from polyvinylpyrrolidone, polyvinyl alcohol, or a combination thereof.

In one implementation, the core comprises a core additive. In one implementation, the core additive comprises a static mitigation material. In one implementation, the core additive is a static mitigation material present in an amount no more than 25% w/w concentration of the core. In one implementation, the core additive is present in an amount of at least 0.5% w/w concentration of the core. In one implementation, the core additive is in an amount between about 2% w/w and about 10% w/w of the core. In one implementation, the core additive is a water-insoluble additive, a water-soluble additive, an entero-soluble additive, or any combination thereof. In one implementation, the core additive comprises one or more of a polymer, a copolymer, a block copolymer, a second polyvinyl alcohol (PVA), a conductivity promoter, an ammonium salt, an imidazolium salt, a polyether compound, or any combination thereof. In one implementation, the polyether compound is selected from polyethylene glycol, polypropylene glycol, a block copolymer derived from ethylene oxide (EO) and propylene oxide (PO), or any combination thereof. In one implementation, the polymer is neutral, cationic, or anionic. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof.

In one implementation, the method further comprises contacting the reagents with a sample to perform multiple co-assay reactions. In one implementation, the shell comprises more than one lyophilised microsphere, and the reagents in the more than one lyophilised microsphere are different.

A third aspect relates to a system. The system includes one or more composition as described herein, and one or more lyophilised cake, wherein the one or more composition and the one or more lyophilised cake are combined under conditions effective to form a rehydration system.

In one implementation, the system further comprises one or more shell layers positioned between the one or more encapsulated microspheres and the one or more lyophilised cakes. In another implementation, the shell layers comprise a material selected from carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

In one implementation, the shell comprises a shell additive. In one implementation, the shell additive comprises a static mitigation material, a moisture barrier material, or a combination thereof. In one implementation, the shell additive is a static mitigation material present in an amount no more than 40% w/w concentration of the shell. In one implementation, the shell additive is a moisture barrier material present in an amount no more than 90% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or oleate derivative is selected from magnesium stearate, triglycerol stearate, Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof.

A fourth aspect relates to a method of controlling release of one or more encapsulated microspheres. The method includes providing a composition as described herein and mixing the composition with a rehydration solution under a first condition effective to control release of one or more lyophilised microspheres from the composition.

In one implementation, the method further comprises modifying the first condition to a second condition. In one implementation, modifying the first condition comprises one or more of a modifying of temperature, a modifying of exposure time, a modifying of rehydration solution pH, or a modifying of position of encapsulated microspheres in the rehydration solution. In another implementation, a temperature in the first condition and/or the second condition is between about 10° C. and about 90° C. In yet another implementation, pH in the rehydration solution is between about 6.0 and about 10.0.

In one implementation, the first condition is effective to release a first lyophilised microsphere. In another implementation, the second condition is effective to release a second lyophilised microsphere, wherein contents of the second lyophilised microsphere is different from contents of the first lyophilised microsphere. In another implementation, modifying the first condition allows for a sequential release of one or more lyophilised microspheres.

In one implementation, the shell comprises carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

In one implementation, the shell comprises a shell additive. In one implementation, the shell additive comprises a static mitigation material. In one implementation, the shell additive is a static mitigation material present in an amount no more than 40% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or oleate derivate is selected from magnesium stearate, triglycerol stearate, Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof.

In one implementation, the core comprises one or more reagent selected from one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In one implementation, the reagent is a polymerase.

In one implementation, modifying the first condition is effective to release two or more lyophilised microspheres, wherein the two or more lyophilised microspheres comprise different reagents. In one implementation, a volume of the reagent in the core is between about 0.1 µL and about 50 µL.

In one implementation, the shell further comprises a reagent.

In one implementation, the core and/or the rehydration solution further comprise one or more additional agent, wherein the additional agent is selected from one or more sugar, one or more amino acid, one or more polymer, one or more mesoporous silica, one or more quaternary amine, or any combination thereof. In one implementation, when the additional agent comprises a sugar, the sugar is selected from trehalose, mannitol, cyclodextrin, dextran, sucrose, or any combination thereof. In another implementation, when the additional agent comprises one or more amino acid with a hydrophobic side chain. In yet another implementation, when the additional agent comprises a polymer, the polymer is selected from polyvinylpyrrolidone, polyvinyl alcohol, or a combination thereof.

In one implementation, the core comprises a core additive. In one implementation, the core additive comprises a static mitigation material. In one implementation, the core additive is a static mitigation material present in an amount no more than 25% w/w concentration of the core. In one implementation, the core additive is present in an amount of at least 0.5% w/w concentration of the core. In one implementation, the core additive is in an amount between about 2% w/w and about 10% w/w of the core. In one implementation, the core additive is a water-insoluble additive, a water-soluble additive, an entero-soluble additive, or any combination thereof. In one implementation, the core additive comprises one or more of a polymer, a copolymer, a block copolymer, a second polyvinyl alcohol (PVA), a conductivity promoter, an ammonium salt, an imidazolium salt, a polyether compound, or any combination thereof. In one implementation, the polyether compound is selected from polyethylene glycol, polypropylene glycol, a block copolymer derived from ethylene oxide (EO) and propylene oxide (PO), or any combination thereof. In one implementation, the polymer is neutral, cationic, or anionic. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof.

In one implementation, the method further comprises providing an additional composition described herein, and mixing the additional composition under a third condition effective to control release of one or more lyophilised microspheres from the additional composition.

In one implementation, the method further comprises contacting the reagents with a sample to perform multiple co-assay reactions. In one implementation, the shell comprises more than one lyophilised microsphere, and wherein the reagents in the more than one lyophilised microsphere are different. In one implementation, the method further comprises providing one or more lyophilised cakes, and rehydrating the one or more lyophilised cakes.

In accordance with the present disclosure, the compositions, systems, and methods described herein have many benefits including, for example, increasing stability of microspheres, macroencapsulation to enable multi-run cartridges, and microencapsulation to enable simplified workflows and reduced number of reagent wells.

To increase the stability of sequencing reagents and to simplify workflows, there is great interest and an unmet need to encapsulate lyophilised microspheres. The present disclosure describes compositions, systems, and methods relating to encapsulated lyophilised reagents that enable sequential release of lyophilised reagents. One way to enable sequential release of lyophilised reagents is through temperature triggered release, for example, by dipping gelatin capsules filled with microspheres in paraffin wax. Such an approach enables release of microspheres at different temperatures, for example, at between about 30° C. and about 50° C. for a native gelatin capsule and between about 50° C. and about 90° C. for a coated capsule. Similarly, such an approach enables a time-triggered release by addition of additives to a rehydration solution, for example, amino acids, which may delay the rehydration rate of cakes.

There are numerous benefits to the compositions, systems, and methods described herein. For example, the encapsulated lyophilised microspheres provide anti-static protection, by neutralizing charge and decreasing tribocharging affinity, thereby decreasing metering and manufacturing handling complexity (e.g. mesoporous silica, ionic liquids, quaternary amines). Static charge has been identified as the highest risk for dispensing and dry compounding microspheres, as it has a significant impact on metering and mixing of dry microsphere powders during manufacturing. Encapsulating microspheres as described in the compositions, systems, and methods described herein neutralizes the charge of microspheres by, for example, coating the particles with a neutral material with low tribocharging affinity, which greatly improves stability for sequencing.

Likewise, the compositions, systems, and methods described herein provide oxygen protection through a low oxygen permeability polymer coating (e.g., polyvinyl alcohol and/or oxygen scavenger in coating). Similarly, the compositions, systems, and methods described herein provide moisture protection through application of an amphiphilic coating (e.g., amino acids and/or PVP co-polymers). The compositions, systems, and methods described herein further provide protection from mechanical stress, for example, by preventing or reducing fragmentation in manufacturing (e.g., by providing a 40% solute content shell). Such a protective coating increases the mechanical robustness of microspheres and their contents during manufacturing and shipping and eliminates shedding of powders from microspheres that may otherwise result in a powder that clogs membranes.

The compositions, systems, and methods described herein may further provide protection from light exposure, as the reagents are protected from light exposure thereby decreasing manufacturing light constraints. Encapsulation of lyophilised microspheres can improve sequencing quality, enable one-pot library prep, and simplify manufacturing. For example, a microsphere with a coating or shell may comprise a dye or other additive that is opaque or otherwise prevents or reduces the amount of light that is incident upon the core of the microsphere.

The pH of SBS buffers is known to change over the sequencing run. The compositions, systems, and methods described herein may use encapsulation of particles that would otherwise be responsive to pH changes to stabilize these particles (e.g., buffers) to increase SBS performance. The compositions, systems, and methods described herein may further improve control the pH of solutions (e.g., Incorporation Mix ("ICM")) that might change over time while sitting on an instrument. Various solutions may be used throughout the length of an SBS cycle which may take hours and, thus, reagents present in solutions are prone to degradation upon environmental exposure. This is achieved by developing pH sensitive microspheres that release when the buffer dips below a specified pH to release ions and return the buffer to the desired pH. Similarly, the compositions, systems, and methods described herein may improve control of the external charge of microspheres to facilitate dispensing and prevent or reduce stratification in mixed bulks and further permit segregation of reagent components SBS Cleave Mix to prevent or reduce and/or control undesired interactions in a single pot or well. For example, the cleave mix might benefit from segregation of reagents to reduce the thermosensitivity of the mixed reagent which is achieved in the compositions, systems, and methods described herein. Likewise, the compositions, systems, and methods described herein protect polymerase during fully functionalized nucleotide ("ffN") polishing if polishing is involved and protect light-sensitive ffNs from light degradation, especially where environmental conditions involved for polishing degrade the enzyme.

The problem of rectifying deblocked lyophilised ffNs within one well (incorporation mix reagent well) using two incompatible, competing polymerases (polishing polymerase and sequencing polymerase) can be addressed by spatially and temporally segregating the polymerases using the compositions, systems, and methods described herein. In particular, the problem can be solved by encapsulating one polymerase (the sequencing polymerase, as this polymerase is used after the polishing polymerase) in a water-soluble, slowly dissolving film (e.g., polyvinyl alcohol). The issue of timing the release of the sequencing polymerase from its capsule to coincide with the completion of the polishing process can be addressed by tuning the ingredients and their relative amounts in the water-soluble film. Additives could also be used which are temperature- or light-responsive to achieve even finer levels of control.

Lyophilising ffNs achieves increased stability compared to their liquid form but creates elevated 3'OH levels increasing pre-phasing and resulting in decreased run quality. In-lab use of the polishing workflow may be complex. The polishing mix (ffNs, polishing polymerase, polishing oligo, Mg) is prepared and combined separately, incubated for up to an hour at an elevated temperature of 50° C. (to facilitate the polishing reaction), then added to the rest of the incorporation mix where the sequencing polymerase is found. This level of complexity for the user and the sequencer means in its current form this workflow is undesirable, and at scale would be even less so. A solution with minimal and/or no user touch points, as described in the compositions, systems, and methods of the present disclosure, which is as complex or less complex than current sequencer workflows is a viable improvement over existing workflows.

In the sole incorporation reagent well, loose "polishing microspheres" (which may include ffNs, polishing polymerase, polishing oligo, and magnesium enzyme co-factor) are dispensed. Also in this well are the sequencing polymerase microspheres; however, these are encapsulated in a water-soluble, timed-dissolve film. This set-up allows multiple benefits, including, for example, reduced well number. If the current separate preparation of the polishing mix followed by mixing with the grand ICM mix is followed, an individual well may be needed for the polishing reagent. Utilizing the encapsulated compositions, systems, and methods described herein facilitates multiple sequential reactions to occur in the one well thereby minimizing the number of wells. This also influences cartridge footprint, with knock-on gains in terms of environmental impact, including, for example, plastic use and incinerator-waste. The compositions, systems, and methods described herein may be easily scaled, while also providing for reduced fluidics and valving, thereby decreasing sequencer complexity and associated costs. When a rehydration buffer, such as water, is dispensed into the well, the loose polishing microspheres dissolve quickly and the polishing reaction begins to rectify any unblocked ffNs. This rehydration buffer also starts to dissolve the water-soluble film encapsulating the sequencing polymerase.

The compositions, systems, and methods described herein enable benefits in addition to those described above. For example, using lyophilised materials, and segregated lyophilised materials, means additional co-factors for the enzyme such as magnesium can be added to the microspheres themselves rather than having a separate additional rehydration buffer. This may enable reagents of different concentrations and/or types of enzymes, all requiring or benefiting from different amounts of co-factors, salts, pHs, and more, to be rehydrated just with water alone, or even atmospheric water capture. This promotes knock-on reductions in the amount of plastic used in sequencing processes as well as carbon footprint given the reduced weight of reagents when in concentrated and/or lyophilised form.

The encapsulation methodology described herein can be applied to enable an easy way to tune reagent concentrations. For example, a smaller capsule may contain a smaller quantity of lyophilised reagent as compared to a larger capsule, and multiples of this capsule can be placed in the well in line with the needs of the user. This promotes improved user flexibility in terms of throughput, without the potential errors made with dilution/concentration calculations. A unit-based approach, where X number of capsules=Y number of runs allows this flexibility in a more controlled fashion. Such an approach may also grant flexibility to the user in terms of depth of sequencing. An application that involves deep sequencing, for example, cancer screening, may use many capsules, whereas a superficial screening, for example, MRSA, may use fewer capsules.

The compositions, systems, and methods described herein achieve an improved level of control over reagent release (e.g., rehydration of a first reagent, followed by delayed rehydration of one or more subsequent reagents after a period of time) as well as mechanical protection, buffer stabilization, charge control, combination of two or more different reagents in a single microsphere, single well, or single pot, and light protection. In particular, a controlled temporal release of reagents by use of the encapsulated lyophilised microspheres described herein allow for a one-pot for library preparation. Inhibition of tagmentation by reagents involved with the PCR is solved by encapsulating the PCR reagents and releasing them at pre-determined time.

In order to tackle the problem of static and tribocharging, additives are proposed to be incorporated either directly into the microspheres (as lyophilized matrix) or as a coating encapsulating the microspheres. The rationales of the additive are, first, to prevent or reduce charge buildup (increased conductivity) and, second, to decrease surface charge by diffusion and/or dissipation.

Preventing or reducing charge build up may be achieved by higher ion concentration, crystallinity or salinity that will go under competitively shielding via water molecules and as a consequence low propensity to accept charge or higher charge dissipation. The water shielding will also induce reduction in angle of internal friction and consequently reduction in electrostatic charging.

Such additives are exemplified as sodium salt (i.e., sodium chloride, sodium bisulfite, sodium citrate), Trizma (Tris.HCl), MOPS, HEPES, ammonium salt (tetraalkyl ammonium chloride, Efka® IO 6783 or tris(hydroxyethyl) alkylammonium chloride), imidazolium salt (i.e., Efka® IO 6786 or 1-ethyl-3-methylimidazolium salt, polyquaternium or copolymer of vinyl pyrrolidone and vinyl imidazolium, exemplified as Luviquat® FC550, FC370), polyaniline, amino acid (isoleucine, leucine, phenylalanine). Meanwhile, decreasing surface charge may also be achieved through lubrication effect on the surface of microspheres via lowering contact angle with container wall (i.e., stainless steel) or reducing inter particle friction.

Further such additives are exemplified as stearate derivative (i.e., magnesium stearate, triglycerol stearate, Span® 60, Tween® 60), oleate derivative (i.e., glycerol trioleate, Tween® 80), laurate derivative (i.e., lauric acid diethanol-amide, Tween® 20, sodium laureth sulfate), an amino acid, tocopherol acetate, piperidyl sebacate, and Makon® 17R4 (polyethylene glycol/polypropylene glycol block copolymer).

BRIEF DESCRIPTION OF THE DRAWINGS

FIGS. 2A-2E show a formulation overview of core reagents used in implementations of the compositions, systems, and methods described herein. FIG. 2A demonstrates an overview of sample extraction, FIG. 2B demonstrates an overview of library preparation, FIG. 2C demonstrates an overview of enrichment, FIG. 2D demonstrates an overview of clustering, and FIG. 2E demonstrates an overview of sequencing.

FIG. 4A shows an OTS gelatin capsule filled with microspheres (102) and an OTS gelatin capsule filled with microspheres and quick dipped in hot wax (104). FIG. 4B shows an OTS gelatin capsule filled with microspheres (106), which dissolves at 37° C. and an OTS gelatin capsule filled with microspheres and quick dipped in hot wax (108), which dissolves at 58° C.

FIG. 7A demonstrates percent of excipients and their respective rehydration time. FIG. 7B shows rehydration of an example composition described herein.

FIGS. 8A-8C show that the encapsulated lyophilised microspheres described in the compositions, systems, and methods of the present disclosure enable one-pot ligation protocol. FIG. 8A demonstrates the steps of a one-pot ligation protocol. FIG. 8B demonstrates time-dependent release of microspheres. FIG. 8C shows data for Reagent A, Reagent B, and an additional reagent. Reagent B'.

FIGS. 9A-9D show one implementation of the encapsulated lyophilised microspheres as described in the compositions, systems, and methods of the present disclosure, where all-in-one polishing microspheres may contain ffNs, polishing polymerase, and polishing oligo, while sequencing polymerase microspheres may contain sequencing polymerase. FIG. 9A shows all-in-one polishing microspheres (402) which contain ffNs, polishing polymerase, and polishing oligo. FIG. 9B shows sequencing polymerase microspheres (404) which contain sequencing polymerase. FIG. 9C shows encapsulated polymerase microspheres (406) and all-in-one polishing microspheres (402) in a single well (408). FIG. 9D shows encapsulated polymerase microspheres (406) and all-in-one polishing microspheres (402) in a single well (408) with an elevated temperature and rehydrated with water.

FIG. 10A shows all-in-one polishing microspheres (402) which contain ffNs, polishing polymerase, and polishing oligo. FIG. 10B shows sequencing polymerase microspheres (404) which contain sequencing polymerase. FIG. 10C shows encapsulated polymerase microspheres (406) (×3 units) and all-in-one polishing microspheres (402) (×3 units) in a single well (408). FIG. 10D shows the same unit dose repeated across different reagents to achieve overall ×3 (triple or three times) dose.

FIG. 11A shows all-in-one polishing microspheres (402) that may contain ffNs, polishing polymerase, and polishing oligo. FIG. 11B shows sequencing polymerase microspheres (404) that may contain sequencing polymerase and may be encapsulated (406) and inside a single well alongside all-in-one polishing microspheres (402). FIG. 11C shows that the encapsulated lyophilised microspheres (406) may be rehydrated with water at 50° C. FIG. 11D shows that after one hour the all-in-one microspheres (402) begin to dissolve, and polishing begins. FIG. 11E shows that the all-in-one microspheres (402) dissolve, polishing is completed, and encapsulated polymerase microspheres (406) dissolve after a delay. In FIG. 11F, all the microspheres become fully dissolved, and ICM is then ready to use.

FIG. 14A describes manufacturing and point of use for encapsulated lyophilised microspheres. FIG. 14B shows an implementation of a first cake, a wax, and a second cake in a tube.

FIG. 15A shows AOM SBS cleave mix with Pd (550) in the core and THP (552) in the shell. FIG. 15B shows ffN/Pol beads with Pol (554) in the core and ffNs (556) in the shell. FIG. 15C shows light protection of ffNs with ffNs (560) in the core and a light blocking shell (558).

FIG. 16A shows phasing and prephasing metrics for various additives. FIG. 16B shows error rate and Q30 for various additives. FIG. 16C shows intensity of all lanes and all channels for additives in FIGS. 16A and 16B. FIG. 16D shows phasing and prephasing metrics for various additives. FIG. 16E shows error rate and Q30 for various additives. FIG. 16F shows intensity of all lanes and all channels for additives in FIGS. 16D and 16E. FIG. 16G shows titration of Efka® IO 6783 sequencing, in particular, phasing and prephasing metrics. FIG. 16H shows error rate and Q30 for Efka® IO 6783. FIG. 16I shows intensity of all lanes and all channels for FIGS. 16G and 16H.

FIG. 17A shows peak area of ffN. FIG. 17B shows 3'OH of ffN. FIG. 17C shows diphosphate of ffN. FIG. 17D shows peak area of a second ffN. FIG. 17E shows 3'OH of a second ffN. FIG. 17F shows diphosphate of a second ffN.

FIGS. 25A-25C show Atto and FSCN (fluorescein) microspheres containing additives as matrix format. The anti-static property of the additive is assessed by adhesion of microspheres to container and their charge density is measured by GranuCharge. Low Δq value indicates low tribocharging. The matrix format of 1% Efka® IO 6783 minimizes tribocharging. FIG. 25A shows results of a first set of additives tested (Atto 20%, +1% Efka® IO 6783, +1.5% Tris.Hcl, and +1% Tween 20) both in terms of visual results (top) and percent loss (bottom). FIG. 25B shows results of a second set of additives tested (FSCN 20% Ctrl, +1% Efka® IO 6783, +2% Efka® IO 6783, and +1% Efka® IO 6786) both in terms of visual results (top) and percent loss (bottom). FIG. 25C shows Atto and FSCN (both 20% trehalose) are dry-compounded with the help of anti-static agent Efka® IO 6783 in matrix format.

FIG. 26A shows visual results of a first set of additives (ffN+25% T Ctrl, +1% Efka® IO 6783, +1% Efka® IO 6786, +1.5% Tris.HCl, +2% isoleucine). FIG. 26B shows visual results of a second set of additives (a second ffN+20% T Ctrl, +0.5% LDA, +1% Makon® 17R4, +1.5% Kollidon® VA64, +2% Kollicoat® Protect). FIG. 26C demonstrates charge density of various additives tested in FIGS. 26A and 26B.

FIG. 27A shows an example shell and core in accordance with the present disclosure. FIG. 27B shows weight gain from coating is 5-7%. FIG. 27C shows a reduction in static in coated versus uncoated compositions. FIG. 27D demonstrates an increased moisture barrier in coated versus uncoated compositions. FIG. 27E shows triggered release in coated compositions.

FIGS. 28A and 28B show images of a plurality (FIG. 28A) and a single (FIG. 28B) microspheres of 800 μm FSCN Wurster-Spray 20% coated with Kollidon VA64 and Efka® IO 6783 and PEG (#6). FIGS. 28C and 28D show images of a plurality (FIG. 28C) and a single (FIG. 28D) microspheres of cryo ion-mill SEM of Rec/BSA 15% coated with Kollidon VA64 and Efka® IO 6783 and PEG (#8). FIGS. 28E and 28F show images of a plurality (FIG. 28E) and a single (FIG. 28F) microspheres of cryo ion-mill SEM of an ffN 10% coated with Kollidon VA64 and Efka® IO 6783 and PEG (#11).

FIGS. 29A-29B depict ffN microspheres containing additives as coating format. The anti-static property of the additive is assessed by adhesion to container and measured by GranuCharge. FIG. 29A shows a visual representation of various ffN microspheres containing additives as coating format. FIG. 29B shows charge density of the various ffN microspheres in FIG. 29A.

FIGS. 30A-30B show DNA recombinase/BSA microspheres containing additives as coating format. The anti-static property of the additive is assessed by adhesion to container and measured by GranuCharge. FIG. 30A shows a visual representation of various DNA recombinase/BSA microspheres containing additives as coating format. FIG. 30B shows charge density of the various DNA recombinase/BSA microspheres in FIG. 30A.

FIG. 31A shows ffN microspheres. FIG. 31B shows 5% Kollidon® VA64 in dry matrix. FIG. 31C shows 5% Makon® 17R4 in dry matrix. FIG. 31D shows 5% Efka® 6783 in dry matrix. FIG. 31E shows 10% Kollicoat® Protect in dry matrix. FIG. 31F shows 7.5% isoleucine in dry matrix (bottom right) under varying moisture and time conditions.

FIG. 32A demonstrates results of a ffN Ctrl (18% T, 2% HCD). FIG. 32B demonstrates results of 2% Kollicoat® Protect matrix (10% dry). FIG. 32C shows results of +1% Efka® IO 6783 Matrix (5% dry). FIG. 32D shows results of 1% Kollidon® VA64 matrix (5% dry). FIG. 32E shows results of +1.5% Trizma matrix (7.5% dry). FIG. 32F shows results of +1.5% isoleucine matrix (7.5% dry).

FIGS. 33A-33D depict results of Kollicoat® Protect and VA64 coating, which provided improved moisture protection of Rec/BSA MS. FIG. 33A shows results of Rec/BSA (AP1) uncoated control at 20% RH limit. FIG. 33B shows Rec/BSA coated with 15% protect and Efka® IO 6783 at 30% RH limit. FIG. 33C shows Rec/BSA coated with 15% Kollidon® VA64 and Efka® IO 6783 at 20-30% RH limit. FIG. 33D shows images of coated compositions in FIGS. 33A-33C after exposure to humidity.

FIGS. 34A-34B show that coating minimizes moisture uptake of Rec/BSA microspheres. FIG. 34A shows images of various microspheres under differing humidity conditions. FIG. 34B shows the effect of % RH on uncoated versus coated Rec-BSA microspheres at 35° C. for 24 hours at 30%, 55%, and 80% RH, in a 30 mg sample staged on aluminum pans. In particular, Kollicoat® Protect coating performed better than Kollidon® VA64 in terms of moisture barrier.

FIG. 36 shows results of Kollidon® VA64, Efka®, Eudragit® which are soluble in spray-coating solution (15% water/solvent) and buffer.

FIGS. 37A-37C show diphosphate level of particular ffCs in the presence of polymers (FIG. 37A), 3'OH and diphosphate level of particular ffCs in the presence of polymers (FIG. 37B), diphosphate level of particular ffCs in the presence of polymers (FIG. 37C).

FIG. 40A shows phase and prephasing metrics for various coating materials tested. FIG. 40B shows error rate and Q30 for various coatings tested.

FIG. 40C shows intensity for all lanes and all channels for the coating materials described in FIGS. 40A and 40B.

FIG. 41A shows DNA recombinase activity of polymer-spiked ExAmp (TCS1 v1.0) solution. FIG. 41B shows DNA recombinase activity after incubation at 40° C. for 24 hours.

FIG. 42A shows DNA binding protein3 activity of polymer-spiked ExAmp (TCX1 v1.0) solution. FIG. 42B shows DNA binding protein activity after incubation at 40° C. for 24 hours.

FIG. 43A shows improvements in solubility. FIG. 43B shows improvements in enzyme compatibility. FIG. 34C shows improvements in ffN compatibility. FIG. 34D shows improvements in sequencing.

FIG. 44 depicts physical characterizations of encapsulated microspheres.

FIGS. 46A-46C shows that shell encapsulation improves moisture barrier and mitigates static. FIG. 46A shows native microspheres after exposure to moisture conditions. FIG. 46B shows matrix microspheres after exposure to moisture conditions. FIG. 46C shows core-shell microspheres coated with compositions described herein after exposure to moisture conditions.

FIG. 49A shows results of Run 1, Run 2, and Run 3 of a composition having coated microspheres with three shells—shell 1: Eudragit S100 (fluorescein), shell 2: Eudragit L100 (weak blue), and shell 3: Eudragit L100-55 (rhodamine). FIG. 49B shows transfer of coated microspheres from FIG. 49A from pH 5, to pH 6, to pH 7, to pH 8. FIG. 49C shows release of various coating compositions under different pH conditions.

Figure 1:
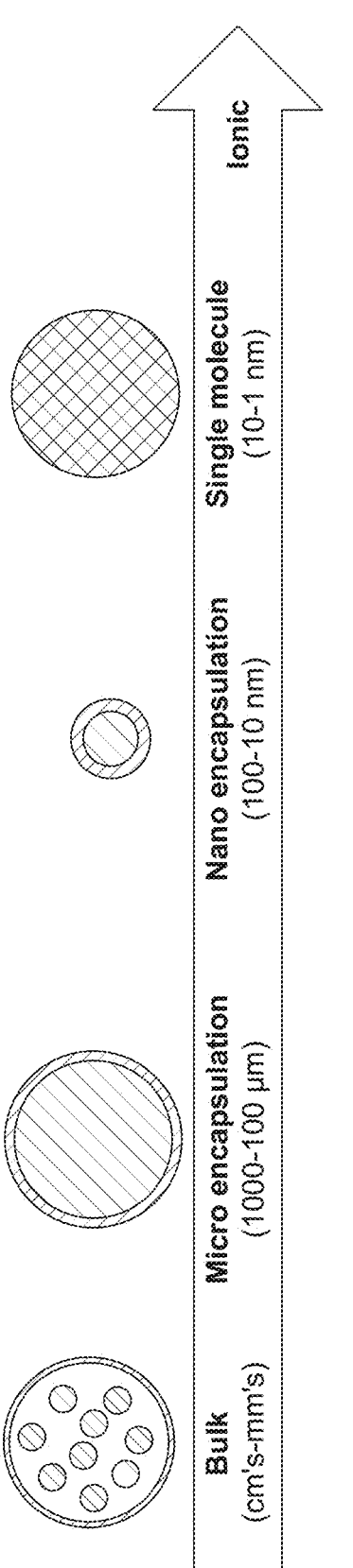
FIG. 1 illustrates types of encapsulation.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

DETAILED DESCRIPTION

A first aspect relates to a composition comprising a shell surrounding a core, wherein the core comprises one or more lyophilised microspheres.

It is to be appreciated that certain aspects, modes, implementations, variations, and features of the present disclosure are described below in various levels of detail in order to provide a substantial understanding of the present technology. Unless otherwise noted, all technical and scientific terms used herein generally have the same meaning as commonly understood by one of ordinary skill in the art. The use of the term "including" as well as other forms is not limiting. The use of the term "having" as well as other forms is not limiting. As used in this disclosure, whether in a transitional phrase or in the body of the claim, the terms "comprise(s)" and "comprising" are to be interpreted as having an open-ended meaning. That is, the terms are to be interpreted synonymously with the phrases "having at least" or "including at least."

The terms "substantially". "approximately", "about", "relatively", or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, fluctuations can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It is further appreciated that certain features described herein, which are, for clarity, described in the context of separate implementations, can also be provided in combination in a single implementation. Conversely, various features which are, for brevity, described in the context of a single implementation, can also be provided separately or in any suitable sub-combination.

The terms "connect", "contact", and/or "coupled" include a variety of arrangements and assemblies. These arrangements and techniques include, but are not limited to, (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (optionally with the presence of one or more additional components therebetween). Components that are in direct physical contact with one another may or may not be in electrical contact and/or fluid contact with one another. Moreover, two components that are electrically connected, electrically coupled, optically connected, optically coupled, fluidly connected, or fluidly coupled may or may not be in direct physical contact, and one or more other components may be positioned between those two connected components.

As described herein, the term "array" may include a population of conductive channels or molecules that may attach to one or more solid-phase substrates such that the conductive channels or molecules can be differentiated from one another based on their location. An array as described herein may include different molecules that are each located at a different identifiable location (e.g., at different conductive channels) on a solid-phase substrate. Alternatively, an array may include separate solid-phase substrates each bearing a different molecule, where the different probe molecules can be identified according to the locations of the solid-phase substrates on a surface to which the solid-phase substrates attach or based on the locations of the solid-phase substrates in a liquid such as a fluid stream. Examples of arrays where separate substrates are located on a surface include wells having beads as described in U.S. Pat. No. 6,355,431, U.S. Pat. Publ. No. 2002/0102578, and WO 00/63437, all of which are hereby incorporated by reference in their entirety. Molecules of the array can be nucleic acid primers, nucleic acid probes, nucleic acid templates, or nucleic acid enzymes such as polymerases and exonucleases.

As described herein, the term "attached" may include when two things are joined, fastened, adhered, connected, or bound to one another. A reaction component, like a polymerase, can be attached to a solid phase component, like a conductive channel, by a covalent or a non-covalent bond. As described herein, the phrase "covalently attached" or "covalently bonded" refers to forming one or more chemical bonds that are characterized by the sharing of pairs of electrons between atoms. A non-covalent bond is one that does not involve the sharing of pairs of electrons and may include, for example, hydrogen bonds, ionic bonds, van der Waals forces, hydrophilic interactions, and hydrophobic interactions.

As described herein, the terms "polynucleotide" or "nucleic acids" refer to deoxyribonucleic acid (DNA), ribonucleic acid (RNA), or analogs of either DNA or RNA made from nucleotide analogs. The terms as used herein also encompasses cDNA, that is complementary, or copy DNA produced from an RNA template, for example by the action of reverse transcriptase. In one implementation, the nucleic acid to be analyzed, for example by sequencing through use of the described systems, is immobilized on a substrate (e.g., a substrate within a flow cell or one or more beads upon a substrate such as a flow cell, etc.). The term immobilized as used herein is intended to encompass direct or indirect, covalent, or non-covalent attachment, unless indicated otherwise, either explicitly or by context. The analytes (e.g., nucleic acids) may remain immobilized or attached to the support under conditions in which it is intended to use the support, such as in nucleic acid sequencing applications. In one implementation, the template polynucleotide is one of a plurality of template polynucleotides attached to a substrate. In one implementation, the plurality of template polynucleotides attached to the substrate include a cluster of copies of a library polynucleotide as described herein.

Nucleic acids include naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose may be bonded to N-1 of a pyrimidine or N-9 of a purine.

A nucleic acid can contain any of a variety of analogs of these sugar moieties that are known in the art. A nucleic acid can include native or non-native bases. A native deoxyribonucleic acid can have one or more bases selected from the group consisting of adenine, thymine, cytosine, or guanine and a ribonucleic acid can have one or more bases selected from the group consisting of uracil, adenine, cytosine or guanine. Useful non-native bases that can be included in a nucleic acid are known in the art.

The term nucleotide as described herein may include natural nucleotides, analogs thereof, ribonucleotides, deoxyribonucleotides, dideoxyribonucleotides and other molecules known as nucleotides. As described herein, a nucleotide may include a nitrogen containing heterocyclic base, a sugar, and one or more phosphate groups. Nucleotides may be monomeric units of a nucleic acid sequence, for example to identify a subunit present in a DNA or RNA strand. A nucleotide may also include a molecule that is not necessarily present in a polymer, for example, a molecule that is capable of being incorporated into a polynucleotide in a template dependent manner by a polymerase. A nucleotide may include a nucleoside unit having, for example, 0, 1, 2, 3 or more phosphates on the 5' carbon. Tetraphosphate nucleotides, pentaphosphate nucleotides, and hexaphosphate nucleotides may be useful, as may be nucleotides with more than 6 phosphates, such as 7, 8, 9, 10, or more phosphates, on the 5' carbon. Examples of naturally occurring nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include nucleotide analogs, such as those that are not present in a natural biological system or not substantially incorporated into polynucleotides by a polymerase in its natural milieu, for example, in a non-recombinant cell that expresses the polymerase. Non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different, or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties are described, for example, in U.S. Pat. Nos. 7,427,673, 7,414,116, and 7,057,026, as well as WO 91/06678 and WO 07/123744, each of which is hereby incorporated by reference in its entirety. It will be understood that in some examples a nucleotide analog having a 3' terminator moiety or lacking a 3' hydroxyl (such as a dideoxynucleotide analog) can be used under conditions where the polynucleotide that has incorporated the nucleotide analog is not further extended. In some examples, nucleotide(s) may not include a reversible terminator moiety, or the nucleotides(s) will not include a non-reversible terminator moiety or the nucleotide(s) will not include any terminator moiety at all.

This disclosure encompasses nucleotides including a fluorescent label (or any other detection tag) that may be used in any method disclosed herein, on its own or incorporated into or associated with a larger molecular structure or conjugate.

The fluorescent label can include compounds selected from any known fluorescent species, for example rhodamines or cyanines. A fluorescent label as disclosed herein may be attached to any position on a nucleotide base, and may optionally include a linker. The function of the linker is generally to aid chemical attachment of the fluorescent label to the nucleotide. In particular implementations Watson-Crick base pairing can still be carried out for the resulting analogue. A linker group may be used to covalently attach a dye to the nucleoside or nucleotide. A linker moiety may be of sufficient length to connect a nucleotide to a compound such that the compound does not significantly interfere with the overall binding and recognition of the nucleotide by a nucleic acid replication enzyme. Thus, the linker can also include a spacer unit. The spacer distances, for example, the nucleotide base from a cleavage site or label.

As used herein, a "nucleoside" is structurally similar to a nucleotide, but is missing the phosphate moieties. An example of a nucleoside analogue is one in which the label is linked to the base and there is no phosphate group attached to the sugar molecule. The term "nucleoside" is used herein in its ordinary sense as understood by those skilled in the art. Examples include, but are not limited to, a ribonucleoside including a ribose moiety and a deoxyribonucleoside including a deoxyribose moiety. A modified pentose moiety is a pentose moiety in which an oxygen atom has been replaced with a carbon and/or a carbon has been replaced with a sulfur or an oxygen atom. A "nucleoside" is a monomer that may have a substituted base and/or sugar moiety.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

The term substrate (or solid support), as described herein, may include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. For example, a substrate may be a glass surface (e.g., a planar surface of a flow cell channel). In one implementation, a substrate may include an inert substrate or matrix which has been "functionalized," such as by applying a layer or coating of an intermediate material including reactive groups which permit covalent attachment to molecules such as polynucleotides. Supports may include polyacrylamide hydrogel supported on an inert substrate such as glass. Molecules (e.g., polynucleotides) may be directly covalently attached to an intermediate material (e.g., a hydrogel). A support may include a plurality of particles or beads each having a different attached analyte.

As used herein, "derivative" or "analogue" means a synthetic nucleotide or nucleoside derivative having modified base moieties and/or modified sugar moieties. Such derivatives and analogs are discussed in, for example, Bücher, NUCLEOTIDE ANALOGS (John Wiley & Son, 1980) and Uhlmann et al., "Antisense Oligonucleotides: A New Therapeutic Principle," Chemical Reviews 90:543-584 (1990), both of which are hereby incorporated by reference in their entirety. Nucleotide analogs may also include modified phosphodiester linkages, including phosphorothioate, phosphorodithioate, alkyl-phosphonate, phosphoranilidate and phosphoramidate linkages. "Derivative". "analog", and "modified" as used herein, may be used interchangeably, and are encompassed by the terms "nucleotide" and "nucleoside" as described herein.

The compositions, systems, and methods described herein include a shell surrounding a core and the core may include one or more lyophilised microspheres (i.e., the composition may include an encapsulated lyophilised microsphere).

As described herein, "encapsulate", "encapsulated", and "encapsulation" include the enclosing of one or more microspheres as described herein. Microencapsulation as described herein refers to the embedding of at least one ingredient, for example, an active agent, into at least one other material, for example, a shell material. Encapsulation in accordance with the present disclosure includes, but is not limited to, bulk encapsulation, macroencapsulation, microencapsulation, nano encapsulation, single molecule, and ionic encapsulation. In accordance with the present disclosure, the compositions, systems, and methods described herein have many benefits including, for example, increasing stability of microspheres, use of macroencapsulation to enable multi-run cartridges, and use of microencapsulation to enable simplified workflows and reduced number of reagent wells. The compositions, systems, and methods described herein use encapsulation of particles that would otherwise be responsive to pH changes to stabilize these buffers and increase SBS performance. The compositions, systems, and methods described herein also use encapsulation to reduce the risk of static charge that otherwise presents difficulty for dispensing and dry compounding microspheres during manufacturing.

As used herein, "microsphere" includes spherical particles that include a shell and a core and have a diameter of 0.1 μm to 1,000 μm. For example, a microsphere may have a diameter of about 0.1 μm, 0.5 μm, 1 μm, 10 μm, 20 μm, 30 μm, 40 μm, 50 μm, 60 μm, 70 μm, 80 μm, 90 μm, 100 μm, 150 μm, 200 μm, 300 μm, 400 μm, 500 μm, 600 μm, 700 μm, 800 μm, 900 μm, 1000 μm, or any diameter between about 0.1 μm and about 1,000 μm. In one implementation, the encapsulated microsphere has a diameter between about 100 μm and 1000 μm.

Microspheres are generally comprised of a polymer shell, for example, biodegradable polymers. Microspheres in accordance with the present disclosure include those prepared by conventional techniques, which are known to those skilled in the art. For example, microspheres may be prepared by freezing a liquid into frozen pellets, followed by placing frozen microspheres in a dryer, for example, a rotational dryer.

As described herein, "macrosphere" may include a plurality of microspheres. Macrospheres are generally of a bigger diameter than microspheres, for example, between 0.1 mm and 1,000 mm. Macrospheres described herein may, for example, have a diameter of about 0.1 mm, 1 mm, 2 mm, 3 mm, 4 mm, 5 mm, 6 mm, 7 mm, 8 mm, 9 mm, 10 mm, 50 mm, 100 mm, 200 mm, 300 mm, 400 mm 500 mm, 600 mm, 700 mm, 800 mm, 900 mm, 1,000 mm, or any diameter between about 0.1 mm and about 1,000 mm. In one implementation, macrospheres (e.g., macrocapsules) will have a dimension ranging between about 5 mm×5 mm×9 mm to about 7 cm×7 cm×2 cm.

Macrospheres in accordance with the present disclosure include those prepared by conventional techniques, which are known to those skilled in the art. The compositions, systems, and methods described herein may include a single lyophilised microsphere, or may include a plurality of lyophilised microspheres and may thereby form a macrosphere. For example, the composition described herein may include anywhere between 1 and over 1,000,000 lyophilised microspheres. In one implementation, the composition includes 1 lyophilised microsphere, or less than 100 lyophilised microspheres, or less than 500 lyophilised microspheres, or any number of microspheres between about 1 and about 1,000, 000. In one implementation, when the shell surrounds more than one lyophilised microsphere, the reagents in the core of the lyophilised microspheres are different.

As described herein, a "shell" includes a composition that surrounds a core. In one implementation, a shell includes an outer layer of a microsphere and, or in the alternative, an outer layer of a macrosphere. In one implementation, the shell includes, for example, a shell material selected from the group consisting of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof. In one example, the shell may include, but is not limited to starch, cellulose, hydrocolloid, alginate, collagen, and any combination thereof. The amount of shell material includes, for example, any amount suitable to produce a desired shell result. In one implementation, the shell material is present in an amount between about 1 wt % and about 100 wt % of the shell. For example, the shell material may be present in about 1 wt %, 2 wt %, 3 wt %, 4 wt %, 5 wt %, 6 wt %, 7 wt %, 8 wt %, 9 wt %, 10 wt %, 15 wt %, 20 wt %, 25 wt %, 30 wt %, 35 wt %, 40 wt %, 45 wt %, 50 wt %, 60 wt %, 70 wt %, 80 wt %, 90 wt %, 100 wt %, of the shell, or any amount therebetween. In one implementation, the shell material is present in an amount between about 10 wt % and about 90 wt %, or between about 10 wt % and about 80 wt %, or between about 10 wt % and about 70 wt %, or between about 10 wt % and about 60 wt %, or between about 10 wt % and about 50 wt %, of the shell.

The shell, as described herein, may include one layer or a plurality of layers of varying compositions. For example, the shell may include one layer, two layers, three layers, four layers, five layers, six layers, seven layers, eight layers, nine layers, ten layers, or more than ten layers. Each of the layers may include the same or different materials from the other layers that are present in the shell.

The shell as described herein, may, in one implementation, include a shell additive. The shell additive may be present in an amount between about 0.01% w/w of the shell and about 99% w/w of the shell. In one implementation, the shell additive is present in an amount between about 10%/t w/w and about 90% w/w of the shell. In one implementation, the shell additive is present in an amount between about 10% w/w and about 40% w/w. In one implementation, the shell additive is a static mitigation material present in an amount no more than 40% w/w concentration of the shell. In one implementation, the shell additive is a moisture barrier material present in an amount no more than 90% w/w of the shell. In one implementation, the shell additive is present in an amount of at least 10% w/w concentration of the shell. For example, the shell additive may, in one implementation, be present in an amount between 0.1% w/w of the shell and about 15.0% w/w of the shell. For example, the shell additive may be present in an amount of about 0.01% w/w, 0.05% w/w, 0.1% w/w, 0.5% w/w, 1.0% w/w, 1.5% w/w, 2.0% w/w, 2.5% w/w, 3.0% w/w, 3.5% w/w, 4.0% w/w, 4.5% w/w, 5.0% w/w, 5.5% w/w, 6.0% w/w, 6.5% w/w, 7.0% w/w, 7.5% w/w, 8.0% w/w, 8.5% w/w, 9.0% w/w, 9.5% w/w, 10.0% w/w, 10.5% w/w, 11.0% w/w, 11.5% w/w, 12.0% w/w, 12.5% w/w, 13.0% w/w, 13.5% w/w, 14.0% w/w, 14.5% w/w, 15% w/w, or any amount therebetween. The amount of shell additive may be any suitable amount to reduce tribocharging of the compositions described herein and/or provide a suitable moisture barrier. The amount of the shell additive may be adjusted to accommodate a particular reagent or combination of reagents, or to accommodate a particular microsphere composition.

In one implementation, the shell additive comprises a static mitigation material, a moisture barrier material, or a combination thereof. In one implementation, the shell additive is a static mitigation material present in an amount no more than 40% w/w concentration of the shell. In one implementation, the shell additive is a moisture barrier material present in an amount no more than 90% w/w concentration of the shell. In one implementation, the shell additive is present in an amount of at least 10% w/w concentration of the shell. In one implementation, the shell additive is in an amount between about 10% w/w and about 90% w/w of the shell. In one implementation, the shell additive is a water-insoluble additive, a water-soluble additive, an entero-soluble additive, or any combination thereof. In one implementation, the shell additive comprises one or more of a polymer, a copolymer, a block copolymer, a second polyvinyl alcohol (PVA), an ammonium salt, a conductivity promoter, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof. In one implementation, the polyether compound is selected from polyethylene glycol, polypropylene glycol, a block copolymer derived from ethylene oxide (EO) and propylene oxide (PO), or any combination thereof. In one implementation, the stearate derivative or oleate derivative is selected from magnesium stearate, triglycerol stearate. Span® 60, Tween® 60, glycerol trioleate, Tween® 80, or any combination thereof. In one implementation, the amino acid is selected from one or more of leucine, isoleucine, phenylalanine, or any combination thereof. In one implementation, the polymer is neutral, cationic, or anionic. In one implementation, the sodium salt is selected from one or more of sodium chloride, sodium bisulfite, sodium citrate, or any combination thereof. In one implementation, the buffer is Trizma, Tris.HCl, or a combination thereof. In one implementation, the ammonium salt is selected from tetraalkyl ammonium chloride, tris(hydroxy-ethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the shell additive comprises ammonium salt, copolymer, polyvinyl alcohol graft polyethylene glycol copolymer, polyvinyl alcohol (PVA), or any combination thereof. The shell may be comprised of polymers, and the maximum concentration of the polymer in the shell may be about 90% (in dry format). One or more static mitigating additive may be added into the polymer coating, and a range between about 10% and about 40% of the shell additive may be present in the shell in dry format.

In various implementations, the shell additive may include a beneficial combination of compounds for improved and unexpected compatibility with SBS reagents. For example, the shell additive may include a polyether compound and a polymer and/or copolymer, or alternatively, a polyether compound, a PVA, and/or a polymer and/or copolymer. In one implementation, the shell additive includes polyethylene glycol, Kollidon® VA64, and Efka® IO 6783, or their chemical equivalent. In another implementation, the shell additive includes polyethylene glycol and Kollidon® VA64, or their chemical equivalent. In another implementation, the shell additive includes polyethylene glycol, Kollicoat® Protect, and Efka® IO 6783®, or their chemical equivalent. In yet another implementation, the shell additive includes polyethylene glycol and Kollicoat® Protect, or their chemical equivalent. In one implementation, the ammonium salt acts as a conductivity promoter. In one implementation, the imidazolium salt acts as a conductivity promoter.

As described herein, a "core" or "core region" includes any material within the surrounding shell. A core in accordance with the present disclosure comprises one or more lyophilised microspheres.

As used herein, the term "compatible" means able to exist or occur together without conflict, that is for example, without substantially degrading the performance or activity of one or more substances that exist or occur together. Likewise, as used herein, the term "incompatible" means unable to exist or occur together without conflict, that is for example, without substantially degrading the performance or activity of one or more substances that exist or occur together.

Lyophilisation in accordance with the present disclosure includes methods in accordance with conventional techniques, which are known to those skilled in the art. Lyophilisation is also referred to herein as freeze-drying. In the present disclosure, the term "lyophilize" or "lyophilizate" will be used as equivalent terms of "lyophilised", "lyophilisate", or "freeze-dried" e.g., with respect to a compositions, systems, or methods described herein.

Lyophilisable formulations can be reconstituted into solutions, suspensions, emulsions, or any other suitable form for administration or use. Lyophilisable formulations are typically first prepared as liquids, then frozen and lyophilised. The total liquid volume before lyophilisation can be less than, equal to, or more than, the final reconstituted volume of the lyophilised formulation. Preferably, the final reconstituted volume of the lyophilised formulation is less than the total liquid volume before lyophilisation. The lyophilisation process is known to those of ordinary skill in the art, and typically includes sublimation of water from a frozen formulation under controlled conditions.

Lyophilised formulations can be stored at a wide range of temperatures. Lyophilised formulations may be stored below 25° C. for example, refrigerated at 2-8° C. or at room temperature (e.g., approximately 25° C.). Preferably, lyophilised formulations are stored below about 25° C., more preferably, at about 4-20° C.; below about 4° C.; below about −20° C.; about −40° C.; about −70° C., or about −80° C. Stability of the lyophilised formulation may be determined in a number of ways known in the art, for example, by visual appearance of the microsphere and/or cake and/or by moisture content. The compositions of the present disclosure can also withstand temperature excursions that might occur during shipping, for example, up to 70° C., for brief periods of time.

Lyophilised formulations are typically rehydrated (interchangeably referred to herein as "reconstituted") for use by addition of an aqueous solution to dissolve the lyophilised formulation. A wide variety of aqueous solutions can be used to reconstitute a lyophilised formulation including water, saline, or another electrolyte or non-electrolyte diluent. Preferably, the lyophilised microspheres described herein are reconstituted using water. Lyophilised formulations may be rehydrated with a solution comprising water (e.g., USP WFI, or water for injection) or bacteriostatic water (e.g., USP WFI with 0.9% benzyl alcohol). However, solutions comprising additives, buffers, excipients, and/or carriers can also be used and are described herein.

Freeze-dried or lyophilised formulations are typically prepared from liquids, that is, from solutions, suspensions, emulsions, and the like. Thus, the liquid that is to undergo freeze-drying or lyophilisation preferably comprises all components desired in a final reconstituted liquid formulation. As a result, when rehydrated or reconstituted, the freeze-dried or lyophilised formulation will render a desired liquid formulation upon reconstitution. A core additive and/or shell additive, when present, may be integrated into the reagent upon rehydration of the compositions described herein.

In one implementation, the core includes, but is not limited to, one or more reagents, for example, one or more enzyme, salt, surfactant, buffering agent, enzyme inhibitor, primer, nucleotide, organic osmolite, magnetic bead, molecular probe, crowding agent, small molecule, labelled-nucleotide, a fluorophore, or any combination thereof. In a preferred implementation, the core is not an aqueous medium.

As used herein, the term "reagent" describes a single agent or a mixture of two or more agents useful for reacting with, interacting with, diluting, or adding to a sample, and may include agents used in nucleic acid reactions, including, for example buffers, chemicals, enzymes, polymerase, primers including those having a size of less than 50 base pairs, template nucleic acids, nucleotides, labels, dyes, or nucleases. A reagent as described herein may, in certain implementations, include enzymes such as polymerases, ligases, recombinases, or transposases; binding partners such as antibodies, epitopes, streptavidin, avidin, biotin, lectins or carbohydrates; or other biochemically active molecules. Other examples reagents include reagents for a biochemical protocol, such as a nucleic acid amplification protocol, an affinity-based assay protocol, an enzymatic assay protocol, a sequencing protocol, and/or a protocol for analyses of biological fluids. According to some of implementations disclosed herein, a reagent may include one or more beads, in particular magnetic beads, depending on specific workflows and/or downstream applications.

In one implementation, a reagent in accordance with the present disclosure is a polymerase. Polymerase in accordance with the present disclosure may include any polymerase that can tolerate incorporation of a phosphate-labeled nucleotide. Examples of polymerases that may be useful in accordance with the present disclosure include but are not limited to phi29 polymerase, a klenow fragment, DNA polymerase I, DNA polymerase III, GA-1, PZA, phi15, Nf, G1, PZE, PRD1, B103, GA-1, 9oN polymerase, Bst, Bsu, T4, T5, T7, Taq, Vent, RT, pol beta, and pol gamma. Polymerases engineered to have specific properties may be used. In one example, the core region may include, but is not limited to, polishing microspheres, sequencing microspheres, and any combination thereof. Polishing microspheres as described herein may include, but are not limited to, ffNs, polymerase useful for polishing ("polishing polymerase"), oligo useful for polishing ("polishing oligo"), magnesium enzyme co-factor, and any combination thereof. In another example, sequencing microspheres may include, but are not limited to, polymerase useful for sequencing ("sequencing polymerase").

A primer as disclosed herein includes a nucleic acid molecule that can hybridize to a target sequence of interest. In several implementations, a primer may function as a substrate onto which nucleotides can be polymerized by a polymerase. However, in some examples, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some examples, the primer is a single-stranded oligonucleotide or polynucleotide.

Non-limiting examples of nucleic acid molecules that may be encapsulated within the microsphere include those described above, for example, DNA, such as genomic or cDNA; RNA, such as mRNA, sRNA or rRNA; or a hybrid of DNA and RNA. The core may further comprise a labelled-nucleotide.

The term "salt" may include salts prepared from toxic or non-toxic acids or bases including inorganic acids and bases and organic acids and bases. Salts may be prepared from, for example, pharmaceutically acceptable non-toxic acids including inorganic and organic acids.

Any surfactant known to one skilled in the art may be used as a reagent in the core. The surfactant may be non-ionic or ionic (specifically cationic or anionic) or may be zwitterionic. Examples of suitable surfactants include but are not limited to polyacrylate surfactants, silicone surfactants, and/or other commercially available surfactants or detergents. Examples of cationic surfactants are cetyldimethylammonium acetamide, octadecyl-dimethylammonium acetamide, tetradecyl-dimethylammonium acetamide, dodecyl-dimethylammonium acetamide, cetyltrimethylammonium, octadcecyl-trimethylammonium, tetradecyl-trimethylammonium, dodecyl-trimethylammonium, dimethyl-dioctadecylammonium, dioctadecyldimethylammonium, and mixtures thereof. Suitable sources of these cations of the cationic surfactant include, but are not limited to, alkyltrimethylammonium salts: such as cetyl trimethylammonium bromide (CTAB) or cetyl trimethylammonium chloride (CTAC); cetylpyridinium chloride (CPC); dimethyldioctadecylammonium chloride; dioctadecyldimethylammonium bromide (DODAB); cetyldimethylammonium acetamide bromide; or other cationic surfactant alike, including lipids. Alternatively, the surfactant may be benzyl hexadecyl dimethyl ammonium chloride (BHDC). The core may include an anionic surfactant which contains an anionic functional group at one end, such as a sulfate, sulfonate, phosphate, and carboxylate functional group. One example of an anionic surfactant is sodium dodecyl sulfate. The core may comprise a neutral surfactant, for example, a polyethelene glycol lauryl ether.

The core may further, or in the alternative, include an enzyme inhibitor, a molecular probe, a crowding agent, organic osmolite, cyclodextrin, adenosine triphosphate (ATP), ethylenediaminetetraacetic acid (EDTA), creatine kinase, creatine phosphate, palladium, lipoic acid, hexaethylene glycol, trihydroxypropanephosphine, sodium ascorbate, or any combination thereof. An enzyme inhibitor as described herein includes any a molecule that binds to an enzyme and decreases its activity. A molecular probe as described herein includes, for example, digoxigenin, 8-Anilinonaphthalene-1-sulfonic acid ("ANS"), porphyrin, BODIPY, cyanine, or any combination thereof. A crowding agent as described herein includes any crowding agent known to those skilled in the art. Examples include, but are not limited to, polyethylene glycol, ficoll, dextran, and serum albumin.

Those skilled in the art of sequencing technologies will appreciate there are additional reagents that may be useful in the compositions, systems, and methods of the present disclosure that are not explicitly described herein.

The core as described herein may, in one implementation, further include one or more additional agents. The one or more additional agent in the core improves the ability to control the release of one or more lyophilised microspheres. In one implementation, the additional agent is selected from one or more sugars, amino acids, polymers, mesoporous silica, quaternary amines, or any combination thereof. In one implementation, when the additional agent comprises sugar, the sugar is selected from trehalose, mannitol, cyclodextrin, dextran, sucrose, or any combination thereof. In another implementation, when the additional agent comprises an amino acid, the amino acid has a hydrophobic side chain. In another implementation, when the additional agent comprises a polymer, the polymer is selected from poly vinylpyrrolidone, polyvinyl alcohol, or a combination thereof. In some implementations, the additional agent may be, for example, one or more co-polymers, ionic liquids, or any combination thereof. The additional agent may be added in any amount suitable to produce a desired effect, for example, between about 0.1 wt % and about 50 wt % of the core. In one implementation, the concentration of the additional agent in the core is about 0.1 wt %, 0.5 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, 30 wt %, 35 wt %, 40 wt %, 45 wt %, or any amount therebetween.

In one implementation, the core further includes a core additive. The core additive may be present in an amount between about 0.01% w/w of the core and about 100% w/w of the core. For example, the core additive may, in one implementation, be present in an amount between 0.1% w/w of the core and about 20.0% w/w of the core. In one implementation, the core additive may be between about 2% w/w and about 10% w/w of the core. For example, the core additive may be present in an amount of about 0.01% w/w, 0.05% w/w, 0.1% w/w, 0.5% w/w, 1.00% w/w, 1.5% w/w, 2.0% w/w, 2.5% w/w, 3.0% w/w, 3.5% w/w, 4.0% w/w, 4.5% w/w, 5.0% w/w, 5.5% w/w, 6.0% w/w, 6.5% w/w, 7.0% w/w, 7.5% w/w, 8.0% w/w, 8.5% w/w, 9.0% w/w, 9.5% w/w, 10.0% w/w, 10.5% w/w, 11.0% w/w, 11.5% w/w, 12.0% w/w, 12.5% w/w, 13.0% w/w, 13.5% w/w, 14.0% w/w, 14.5% w/w, 15.0% w/w, 15.5% w/w, 16.0% w/w, 16.5% w/w, 17.0% w/w, 17.5% w/w, 18.0% w/w, 18.5% w/w, 19.0% w/w, 19.5% w/w, 20.0% w/w or any amount therebetween. The amount of core additive may be any suitable amount to reduce tribocharging of the compositions described herein. The amount of the core additive may be adjusted to accommodate a particular reagent or combination of reagents, or to accommodate a particular microsphere composition.

In one implementation, the core additive comprises a static mitigation material. In one implementation, the core additive is a static mitigation material present in an amount no more than 25% w/w concentration of the core. In one implementation, the core additive is present in an amount of at least 0.5% w/v concentration of the core. In one implementation, the core additive is in an amount between about 2% w/w and about 10% w/w of the core. In one implementation, the core additive is a water-insoluble additive, a water-soluble additive, an entero-soluble additive, or any combination thereof. In one implementation, the core additive comprises one or more of a polymer, a copolymer, a block copolymer, a second polyvinyl alcohol (PVA), a conductivity promoter, an ammonium salt, an imidazolium salt, a polyether compound, or any combination thereof. In one implementation, the polyether compound is selected from polyethylene glycol, polypropylene glycol, a block copolymer derived from ethylene oxide (EO) and propylene oxide (PO), or any combination thereof. In one implementation, the polymer is neutral, cationic, or anionic. In one implementation, the buffer is Trizma, Tris.HCl, or a combination thereof. In one implementation, the ammonium salt is selected from tetraalkyl ammonium chloride, tris(hydroxyethyl) alkylammonium chloride, or a combination thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In one implementation, the compositions described herein may be manufactured from about 20% lyophilized formulation (i.e., the formulation contains 20% lyophilised excipient, such as trehalose and other additives). Therefore, the additive (static mitigating or moisture protection) may be incorporated and/or spiked into the lyophilised formulation, followed by drying to give an appropriate concentration in dry format. In one implementation, the ammonium salt acts as a conductivity promoter. In one implementation, the imidazolium salt acts as a conductivity promoter.

The core additive described herein may, in one implementation, include a water-insoluble additive, a water-soluble additive, an entero-soluble additive, or any combination thereof. In one implementation, the core additive may include one or more of a sodium salt, a buffer, a chelating agent, an ammonium salt, imidazolium salt, polyaniline, or any combination thereof. In one implementation, one or more water-soluble core additives are added to the core. In one implementation, the sodium salt is selected from one or more of sodium chloride, sodium bisulfite, sodium citrate, or any combination thereof. In another implementation, the buffer is Trizma (Tris.HCl). In one implementation, the ammonium salt is selected from tetraalkyl ammonium chloride, tris(hydroxyethyl) alkylammonium chloride, or any combination of thereof. In one implementation, the imidazolium salt is selected from 1-ethyl-3-methyl-imidazolium salt or polyquaternium or Luviquat® (copolymer of vinyl pyrrolidone and quaternized vinylimidazole) or a combination thereof. In another implementation, one or more water-soluble additive such as Efka® IO 6783, Efka® IO 6786, Tween® 80, Makon® 17R4, lauric acid diethanolamide, or any combination of one or more of these additives may be included in the core additive composition. In another implementation, one or more water-insoluble additive such as trioleate glycerol, polyaniline, piperidyl sebacate, an amino acid, vitamin E (tocopherol acetate), Span® 60, or any combination of one or more of these additives may be included in the core additive composition. In one implementation. Efka® IO 6783 is used as a core additive in an amount suitable to reduce tribocharging behavior of the composition (for example, an amount of about 5% w/w of the core).

The composition (i.e., encapsulated lyophilised microsphere) may be any appropriate size or volume that is appropriate to encapsulate one or more reagents and suitable for use in library preparation for sequencing. In one implementation, the composition has a volume of reagent in the core region of between about 0.1 μL and about 50 μL. For example, the composition (i.e., encapsulated lyophilised microsphere) may have an active reagent volume of about 0.1 μL, 0.5 μL, 1 μL, 2 μL, 3 μL, 4 μL, 5 μL, 6 μL, 7 μL, 8 μL, 9 μL, 10 μL, 15 μL, 20 μL, 25 μL, 30 μL, 35 μL, 40 μL, 45 μL, 50 μL, or any volume between about 0.1 μL and about 50 μL. In one implementation, the active reagent volume is between about 10 μL and about 40 μL. The composition (i.e., encapsulated lyophilised microsphere) may have a diameter of, for example, about 2 μm to about 120 μm, such as, for example, 2, 3, 4, 5, 6, 7, 8, 9, 10, 15, 20, 25, 30, 35, 40, 45, 50, 60, 70, 80, 90, 100, 110, or 120 μm in diameter, or a diameter within a range defined by any two of the aforementioned values.

The composition described herein may include an additional reagent in the shell of the microsphere. In one implementation, the encapsulated microsphere includes a reagent or additive in the microsphere shell. The reagent in the shell may include, for example, any of the foregoing reagents or additives. In one implementation, the shell contains no nucleic acid molecules, for example, the shell contains no DNA. In one implementation, the shell contains more than one reagent and, or in the alternative, more than one additive.

Likewise, the composition (e.g., encapsulated lyophilised microsphere) described herein may include a low oxygen permeability polymer coating, for example, polyvinyl alcohol and/or oxygen scavenger. Similarly, the composition (e.g., encapsulated lyophilised microspheres) described herein may include amphiphilic coating, for example, amino acids and/or PVP co-polymers. The encapsulated lyophilised microspheres described herein may further provide protection from mechanical stress, for example, by preventing or reducing fragmentation in manufacturing, for example, with a 40% solute content shell. The compositions (e.g., encapsulated lyophilised microspheres) described herein may further provide protection from light exposure, as the reagents may be protected from light exposure thereby decreasing manufacturing light constraints.

The compositions described herein may be used for multiple sequential co-assays comprising lysis, DNA analysis, RNA analysis, protein analysis, tagmentation, nucleic acid amplification, nucleic acid sequencing, DNA library preparation, SBS technology, assay for transposase accessible chromatic using sequencing (ATAC-seq), contiguity-preserving transposition (CPT-seq), single cell combinatorial indexed sequencing (SCI-seq) or single cell genome amplification, or any combination thereof performed sequentially. In one implementation, the composition is used for performing multiple co-assay reactions. The compositions, systems, and methods described herein (e.g., encapsulation of lyophilised microspheres) may, in one implementation, improve sequencing quality, enable one-pot library prep, and simplify manufacturing. As used herein, the term "one-pot reaction" may also be referred to as "transfer-free reaction."

The compositions, systems, and methods described herein may be prepared for various stages of sequencing including, but not limited to, sample extraction, library preparation, enrichment, clustering, and sequencing. In sample extraction compositions, the core may include enzymes, salt, surfactants, buffering agents, and any combination thereof. The sample extraction may occur at a pH of about 7.5 with a reaction volume of between about 1 mL and about 5 mL. In library preparation compositions, the core may include enzyme inhibitors, salts, primers, enzymes, nucleotides, organic osmolites, magnetic beads, and any combination thereof. Library preparation may occur at a pH of about 7 with a reaction volume of about 0.05 mL. In enrichment compositions, the core may include nucleotides, molecular probes, enzymes, magnetic beads, crowding agents, and any combination thereof. Enrichment may occur at a pH of about 8.5 with a reaction volume of between about 0.1 mL and about 0.2 mL. In clustering compositions, the core may include salts, enzymes, one or more nucleotides, small molecules, surfactants, primers, and any combination thereof. Clustering may occur at a pH of about 8.6 with a reaction volume of between about 1 mL and about 5 mL. In sequencing compositions, the core may include labelled-nucleotides, a fluorophore, surfactants, salts, enzymes, small molecules, and any combination thereof. Sequencing may occur at a pH of between about 7 and about 10 with a reaction volume of about 30 mL to about 100 mL.

In one implementation, the shell may rehydrate under a pH between 1 and 14. In one implementation, the shell may include one or more shell layers and each layer may rehydrate under the same or different conditions. For example, the shell may include a plurality of layers that rehydrate under different conditions. In one implementation, the shell may include two or more layers (e.g., three or more layers) that release at different pH levels, for example, one layer may release at a pH of 5, one layer may release at a pH of 5.5, one layer may release at a pH of 6, one layer may release at a pH of 6.5, one layer may release at a pH of 7, one layer may release at a pH of 7.5, and/or one layer may release at a pH of 8.

The core may include any number of different reagents from those described herein or any reagent that may be useful in promoting utility of sequencing systems, for example, SBS technology.

In one implementation, a biological sample contacts the composition. A biological sample, may include, for example, whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. A biological sample can include nucleic acids, such as DNA, genomic DNA, RNA, mRNA or analogs thereof, nucleotides such as deoxyribonucleotides, ribonucleotides or analogs thereof such as analogs having terminator moieties such as those described in Bentley et al., "Accurate Whole Human Genome Sequencing Using Reversible Terminator Chemistry," Nature 456:53-59 (2008); WO/2013/131962; U.S. Pat. No. 7,057,026; WO/2008/042067; WO/2013/117595; U.S. Pat. Nos. 7,329,492; 7,211,414; 7,315,019; 7,405,281; and U.S. Patent Pub. No. 20080108082, all of which are hereby incorporated by reference in their entirety.

A second aspect relates to a method. The method comprises providing one or more lyophilised microspheres; and coating the one or more lyophilised microspheres with a shell under conditions effective to encapsulate the one or more lyophilised microspheres.

This aspect is carried out in accordance with the previously described aspect, in particular with regard to the characteristics of the one or more lyophilised microspheres and their coating, shell, core, and encapsulation.

Any suitable method can be used to form microspheres. Standard microsphere manufacturing techniques will be known to those skilled in the art, and include, preparing frozen pellets and placing those pellets in a dryer as described herein. A variety of microspheres are contemplated in accordance with the compositions, systems, and methods of the present disclosure and include, for example, time sustained release, immediate pulse, timed pulsative release, organic acid Diffucaps® Bead, and alkaline buffer Diffucaps® Bead microspheres. There are also a variety of types of encapsulation encompassed by the compositions, systems, and methods described herein, including, but not limited to, bulk-, micro-, nano-, single molecule, and ionic encapsulation.

Modifications to standard microsphere production are used to manufacture the compositions described herein. For example, one or more additional feed buffer tanks and one or more suitable nozzles and/or nozzle plates may be added to standard microsphere production equipment. Other modifications may be made, in particular, to a solidification system, to produce various types of shells and include compounds such as hydrocolloids, alginate, and pectin among others as described herein.

In one implementation, two liquid solutions are prepared: one liquid solution for the core and one liquid solution for the shell. A double nozzle system may be installed (i.e., a single or multi-nozzle system with annular gap nozzles) which allows for production to begin. Additional factors are important and adjustable based on size and type of compositions sought to be prepared. For example, interfacial tension, viscosities of core and shell, nozzle diameter ratio of inner and outer nozzle, and pressure ratio of core and shell may all be considered and adjusted.

In one implementation, an air brush is used to generate encapsulated lyophilised microspheres. In one implementation, a filtration membrane may be added and may reduce quantity of lyophilised microspheres exiting the chamber during air brushing. In another implementation, an aerosolizer is used.

In accordance with the compositions, systems, and methods described herein, liquid is formed, followed by storage at ambient conditions for between one and two days, then microspheres are spray frozen and may be stored at −80° C. Lyophilised microspheres may be placed in a tray or rotary dryer, followed by dry dispensing microspheres into consumables and/or capsules, and, lastly, may be heat sealed with foil on plastic consumables.

The composition (e.g., encapsulated lyophilised microspheres) may be coated with one or more additional compositions to provide enhanced control of microsphere release. In one implementation, the method further includes covering the shell with an outer layer, under conditions effective to surround the encapsulated microsphere with the outer layer.

The composition may be dipped into a wax coating for a specific time so that the composition does not melt and for a specific thickness to eliminate risk of coating being too thick. In one implementation, the covering is carried out for a period of time sufficient to provide the outer layer with a defined thickness. In one implementation, the defined thickness is, for example, about 50 μm. In other implementations, the defined thickness is less than 50 μm, or alternatively, is greater than 50 μm. In one example, a capsule is filled with one or more lyophilised microspheres, and that capsule is dipped in hot wax to provide an outer layer. This process allows for release of microspheres at two different temperatures, the capsule may dissolve at between about 30° C. and about 50° C., while the wax coating may dissolve at between about 50° C. and about 80° C.

In one implementation, the outer layer includes one or more of carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

The present aspect may be applied to enable reagent concentration tuning. For example, a smaller capsule may contain a smaller quantity of lyophilised reagent as compared to a larger capsule, and multiples of this capsule could be placed in a well in line with the needs of the user. In one implementation, a unit-based approach is applied, where X number of capsules=Y number of runs.

A third aspect relates to a system. The system includes one or more composition as described herein, and one or more lyophilised cake, wherein the one or more composition and the one or more lyophilised cake are combined under conditions effective to form a rehydration system.

This aspect is carried out in accordance with the previously described aspect, in particular with regard to the characteristics of the one or more lyophilised microspheres and their coating, shell, core, and encapsulation.

In one implementation, the system further includes one or more shell layers positioned between the one or more encapsulated microspheres and the one or more lyophilised cakes. In one implementation, the shell layers comprise a material selected from carrageenan, shellac, trehalose, paraffin wax, gelatin, hydroxypropyl methylcellulose (HPMC), fullalin, oxygen scavenger, alginate, chitosan, starch film, benzoxaborole-poly(vinyl alcohol) (benzoxaborole-PVA), pectin, polyvinylpyrrolidone (PVP), polyvinyl alcohol, or any combination thereof.

A fourth aspect relates to a method of controlling release of one or more encapsulated microspheres. The method includes providing a composition as described herein and mixing the composition with a rehydration solution under a first condition effective to control release of one or more lyophilised microspheres from the composition.

This aspect is carried out in accordance with the previously described aspects, in particular with regard to the characteristics of the one or more lyophilised microspheres and their coating, shell, core, and encapsulation.

In one implementation, the method further includes modifying the first condition to a second condition. In one implementation, modifying the first condition includes one or more of a modifying of temperature, a modifying of exposure time, a modifying of rehydration solution pH, or a modifying to position of encapsulated microspheres in the rehydration solution.

As described herein, in one implementation, a capsule is filled with one or more lyophilised microspheres, and that capsule is dipped in coating (e.g., hot wax) to provide an outer layer. This process allows for controlled release of microspheres at different temperatures in a transfer-free reaction. The capsule enables release of microspheres at a temperature between about 30° C. and about 50° C., preferably between about 30° C. and about 40° C., while the coating (e.g., hot wax) enables release of microspheres at a temperature between about 50° C. and about 90° C. preferably between about 55° C. and about 85° C. The coating may be of hot wax, preferably paraffin wax. In one implementation, a temperature in the first condition and/or the second condition is between about 10° C. and about 90° C.; preferably between about 30° C. and about 50° C. or between about 50° C. and about 90° C., depending on the composition of the shell and/or outer coating.

Likewise, modifying the first condition may be achieved by addition of one or more additives to the rehydration solution or to the compositions described herein using the additives described herein. In one implementation, the core and, or in the alternative, the rehydration solution further comprises one or more additional agent. The additional agent may be any single additional agent described above or may be any combination of two or more additional agents described above. For example, an amino acid alone or in combination with another amino acid may be used to modify a first condition and promote controlled release of microspheres. Content of the one or more additives will vary and depend on the compositions used and reaction conditions (for example, time, temperature, and pH). In one implementation, the one or more additives are between about 0.1 wt % and 40 wt % of the composition and/or rehydration solution. For example, the concentration of the one or more additives may be 0.1 wt %, 0.5 wt %, 1.0 wt %, 5.0 wt %, 10.0 wt %, 15 wt %, 20 wt %, 25 wt %, 30 wt %, 35 wt %, 40 wt %, or any amount therebetween.

A rehydration (or reconstitution) solution as used herein may include water, deionized water, saline solutions, acidic solutions, basic solutions, detergent solutions and/or buffers, and may be in accordance with rehydration solutions previously described. In a preferred implementation, the rehydration solution is water. In one implementation, reagents described herein having varying concentrations, types of enzymes, and different amounts of co-factors, salts, pHs, and more, can be rehydrated with water alone, or even atmospheric water capture. Additional additives as described herein may be provided in the rehydration solution to further improve control of release of microspheres.

In one implementation, a pH in the rehydration solution is between about 6.0 and about 10.0. A pH of the rehydration solution may be, for example, about 6.0, about 6.5, about 7.0, about 7.5, about 8.0, about 8.5, about 9.0, about 9.5, about 10.0, or any amount therebetween. Rehydration time will vary depending on composition content and reaction conditions (e.g., reagents, temperature, pH). In one implementation, rehydration time may be between 0.1 seconds and 10 hours. For example, rehydration time may be about 0.1 seconds, 1 second, 10 seconds, 30 seconds, 45 seconds, 60 seconds, 5 minutes, 10 minutes, 12 minutes, 15 minutes, 20 minutes, 30 minutes, 40 minutes, 50 minutes, 60 minutes, 70 minutes, 80 minutes, 90 minutes, 2 hours, 5 hours, 8 hours, 10 hours, or any amount of time therebetween.

In one implementation, the first condition is effective to release a first lyophilised microsphere. The first lyophilised microsphere in this implementation is in accordance with the lyophilised microspheres and compositions described herein.

In one implementation, the second condition is effective to release a second lyophilised microsphere, wherein contents of the second lyophilised microsphere are different from content of the first lyophilised microsphere. The second lyophilised microsphere in this implementation is in accordance with the lyophilised microspheres and compositions described herein.

In one implementation, modifying the first condition is effective to release two or more lyophilised microspheres, wherein the two or more lyophilised microspheres comprise different reagents. In one implementation, the contents of a first lyophilised microsphere include a reagent that is different from the reagent of a second lyophilised microsphere, and may thereby reduce thermosensitivity of the mixed reagent.

In one implementation, the method further includes providing an additional composition in accordance with the compositions described herein, and mixing the additional composition under a third condition effective to control release of one or more lyophilised microspheres from the additional composition. The lyophilised microspheres in this implementation are in accordance with the lyophilised microspheres and compositions described herein. In one implementation, reagent components in SBS Cleave Mix are segregated into at least two different lyophilised microspheres, and may thereby prevent or reduce and/or control undesired interactions.

"Modifying" the first, second, or third conditions as described herein includes any change in one or more conditions in the encapsulated microspheres and, or in the alternative, the rehydration solution. Modifying the conditions in one implementation allows for a sequential release of one or more lyophilised microspheres. One way to enable sequential release of lyophilised reagents is through temperature triggered release, for example, by dipping gelatin capsules filled with microspheres in paraffin wax as described herein. Such an approach enables release of microspheres at different temperatures, for example, at between about 30° C. and about 50° C. for a native gelatin capsule and between about 50° C. and about 90° C. for a coated capsule. Similarly, such an approach enables a time-triggered release by addition of additives to a rehydration solution, for example, amino acids. Other reaction characteristics may be modified in addition to or instead of time and, or in the alternative, temperature. For example, pH and humidity may be modified to further control release of one or more encapsulated microspheres and the reagent(s) contained therein.

In another implementation, the compositions, systems, and methods described herein protect a polymerase in a first composition (e.g., an encapsulated lyophilised microsphere). The protection of a polymerase in a first composition during fully functionalized nucleotide ("ffN") polishing may in one implementation protect light-sensitive ffNs from light degradation.

The issue of timing the release of a reagent, for example a sequencing polymerase, from encapsulation to coincide with the completion of a desired reaction, for example, a polishing process, can be addressed by tuning various ingredients in the composition and rehydration solution described herein and the relative amounts of those ingredients. Additives can also be used which are temperature- or light-responsive to achieve even finer levels of control. For example, the problem of rectifying deblocked lyophilised ffNs within one well (incorporation mix reagent well) using two incompatible, competing polymerases (polishing and sequencing) can be addressed by spatially and temporally segregating the polymerases using the compositions, systems, and methods of the present disclosure.

In one example, two capsules may be in a single tube, and those capsules may dissolve with different triggers. In another example, two or more capsules may be stacked along a y-axis or an x-axis in a narrow tube and a second capsule is dissolved upon release of a first capsule when in contact with a liquid, followed by dissolving of a third capsule upon release of the second capsule, when in contact with a liquid, which is repeated for as many capsules as are present in a particular stack. These implementations may likewise be triggered by temperature modifications such as heat. In yet another example, a tube includes a cake formed by lyophilisation, wax may be pipetted into the tube and a capsule dropped in. A user may add liquid which dissolves the capsule first, then when temperature is increased, wax melts and the cake rehydrates. In another example, a tube includes a first cake formed by lyophilisation, and wax is then pipetted into tube. A second liquid is then deposited, lyophilisation is repeated, followed by a deposit of new wax (having, for example, a different melt temperature). A user adds liquid to rehydrate the different cakes once the waxes are melted sequentially.

In one implementation, the method further includes providing one or more lyophilised cakes, and rehydrating the one or more lyophilised cakes.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of inventive subject matter disclosed herein.

In the present disclosure, reference is made to the accompanying drawings that form a part hereof, and in which is shown by way of illustration specific implementations which may be practiced. These implementations are described in detail to enable those skilled in the art to practice the disclosure, and it is to be understood that other implementations may be utilized and that structural, logical and electrical changes may be made without departing from the scope of the present disclosure. The following description of example implementations is, therefore, not to be taken in a limited sense.

The present disclosure may be further illustrated by reference to the following examples.

EXAMPLES

The following examples are intended to illustrate, but by no means are intended to limit, the scope of the present disclosure as set forth in the appended claims.

Example 1—Encapsulated Lyophilised Microsphere Production

Here, encapsulated lyophilised microspheres are produced.

Microspheres may be produced using standard techniques. Frozen pellets are first prepared. Liquid flows into a vessel having a nozzle diameter at a liquid flowrate and a vibration frequency. Deflection power (electrostatic ring) is used at a given tower temperature and height and frozen pellets are produced. Spraying towers may be used to prepare microspheres. Trays go into a tray dryer, and microspheres in their bulk form are placed in a dryer, for example, a rotational dryer. Microsphere production for the encapsulated lyophilised microspheres described herein may build upon and, or in the alternative, change standard microsphere production techniques.

As shown in FIG. 1, there are a variety of types encapsulation encompassed by the compositions, systems, and methods described herein, including, but not limited to, bulk-, micro-, nano-, single molecule, and ionic encapsulation.

One implementation of the method for encapsulation used in accordance with the present disclosure includes wax coating of microspheres. An air brush is used to apply a coating to the microspheres contained in a chamber. The air brush may generate air drafts in the chamber resulting in some microspheres leaving the chamber. Mitigations include the addition of a filtration membrane to prevent microspheres from exiting the chamber or reduce the likelihood of microspheres exiting the chamber. An aerosolizer may be used instead of or in addition to an air brush to reduce air flow generation. An aerosolizer may be more challenging to coat viscous solutions.

Example 2—Encapsulated Lyophilised Microsphere Composition

Here, exemplary formulations in accordance with the present compositions, systems, and methods of the present disclosure are shown. The compositions described herein may be prepared for various stages of sequencing including, but not limited to, sample extraction, library preparation, enrichment, clustering, and sequencing, as shown in FIG. 2.

In sample extraction compositions, the core may include enzymes, salt, surfactants, buffering agents, and any combination thereof. The sample extraction may occur at a pH of about 7.5. The reaction volume may be between about 1 mL and about 5 mL. In library preparation compositions, the core may include enzyme inhibitors, salts, primers, enzymes, nucleotides, organic osmolites, magnetic beads, and any combination thereof. Library preparation may occur at a pH of about 7. The reaction volume may be about 0.05 mL. In enrichment compositions, the core may include one or more nucleotides, molecular probes, enzymes, magnetic beads, crowding agents, and any combination thereof. Enrichment may occur at a pH of about 8.5. The reaction volume may be between about 0.1 mL and about 0.2 mL. In clustering compositions, the core may include salts, enzymes, nucleotides, small molecules, surfactants, primers, and any combination thereof. Clustering may occur at a pH of about 8.6. The reaction volume may be about 1 mL. In sequencing compositions, the core may include labelled-nucleotides, a fluorophore, surfactants, salts, enzymes, small molecules, and any combination thereof. Sequencing may occur at a pH of between about 7 and about 10. The reaction volume may be about 30 mL to about 100 mL.

Various formulations of lyophilisation excipients may be added to the core in implementations of the compositions, systems, and methods described herein including, for example, sugars, amino acids, and polymers. Sugars may include trehalose (10-25%), mannitol (1-10%), cyclodextrin (1-10%), dextran (1-10%), sucrose (1-10%) or any combination thereof. Polymers may include polyvinylpyrrolidone (1-10%), polyvinyl alcohol (1-10%), or a combination thereof. Mesoporous silica and/or quaternary amines may be added to reduce affinity to tribocharging.

Various formulations of shell ingredients may be added to the shell in implementations of the compositions, systems, and methods described herein. Various examples of shell ingredients include carrageenan, shellac, trehalose (20-40%), paraffin wax, gelatin, HPMC, fullalin, oxygen scavenger, alginate, chitosan, gelatin, starch film, benzoxaborole-PVA, pectin, polyvinylpyrrolidone (1-5%), polyvinyl alcohol (1-10%), or any combination thereof. For certain implementations, materials used do not contain any DNA so as to not contaminate any reaction and to avoid using valuable sequencing real estate.

Figure 3:
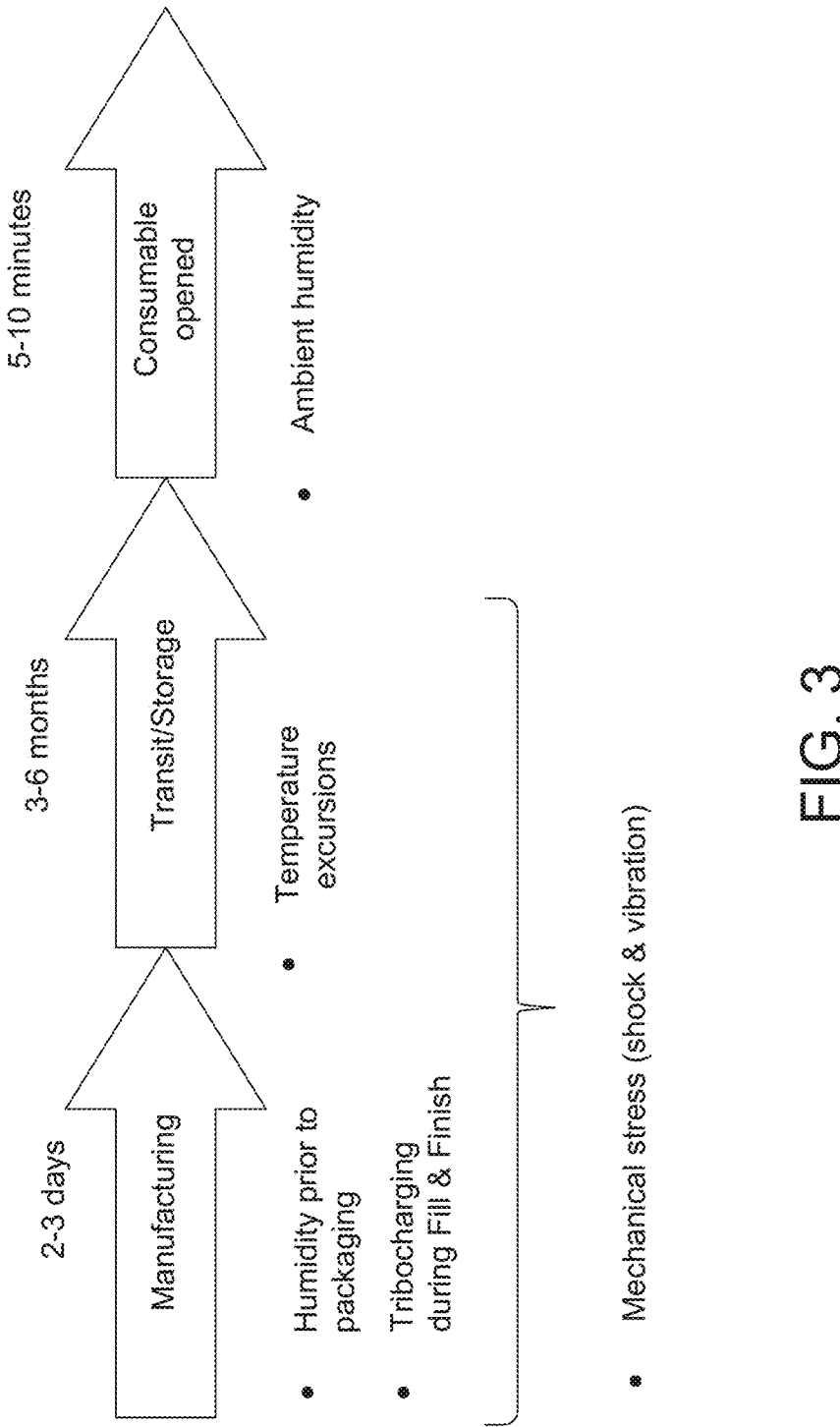
FIG. 3 depicts various stresses subjected on microspheres during manufacturing, transit, storage, and upon opening.

There are a variety of stresses subjected on microspheres as shown in FIG. 3. During manufacturing, for a period of time (e.g., 2-3 days), microspheres are exposed to humidity prior to packaging as well as tribocharging during filling and finishing. During transit and storage, over the course of what may amount to several months (e.g., 3-6 months), microspheres are exposed to temperature excursions. Once a consumable is opened (even if only open for less than 10 minutes), there are a variety of new stresses on microspheres including, for example, ambient humidity that may affect a microsphere within seconds of exposure. In addition, manufacturing, transit, and storage all subject a microsphere to additional mechanical stress such as shock and vibration. The compositions, systems, and methods described herein (e.g., encapsulation of lyophilised microspheres) mitigate the stresses otherwise experienced by microspheres that are not lyophilised and encapsulated.

Moreover, static charge may be a considerable risk for dispensing and dry compounding microspheres. Encapsulating microspheres as described in the compositions, systems, and methods described herein, significantly reduces that risk and greatly improves stability for sequencing.

Likewise, the compositions, systems, and methods described herein provide encapsulated lyophilised microspheres with improved oxygen protection through a low oxygen permeability polymer coating (e.g., polyvinyl alcohol, oxygen scavenger in coating). Similarly, the compositions, systems, and methods described herein provide encapsulated lyophilised microspheres with improved moisture protection by application of an amphiphilic coating (e.g., amino acids and PVP co-polymers). The encapsulated lyophilised microspheres described herein may further provide protection from mechanical stress, for example, by preventing or reducing fragmentation in manufacturing (e.g., 40% solute content shell). Such a protective coating increases the mechanical robustness of microspheres and their contents during manufacturing and shipping and reduces or even eliminates shedding of powders from microspheres.

The encapsulated lyophilised microspheres described herein may further provide protection from light exposure, as the reagents may be protected from light exposure thereby decreasing manufacturing light constraints. Encapsulation can improve sequencing quality, enable one-pot library prep and simplify manufacturing. Benefits and applications of encapsulation of lyophilised microspheres in accordance with the compositions, systems, and methods described herein. SBS applications for the encapsulated lyophilised microspheres described herein are described in FIGS. 15A-15C.

Figure 15C:
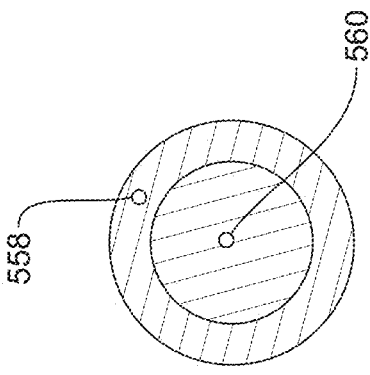
FIGS. 15A-15C describe applications for SBS for the compositions, systems, and methods of the present disclosure.
Figure 15B:
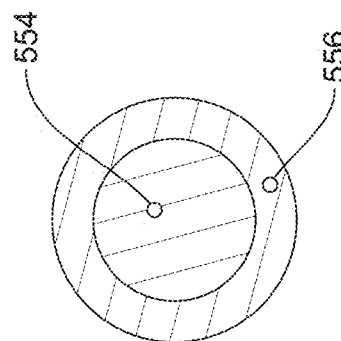
Figure 15A:
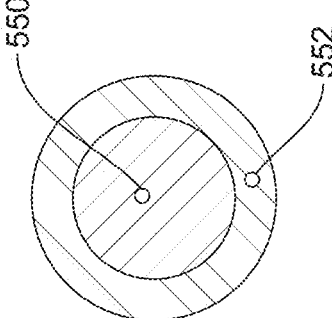
Figure 16A:
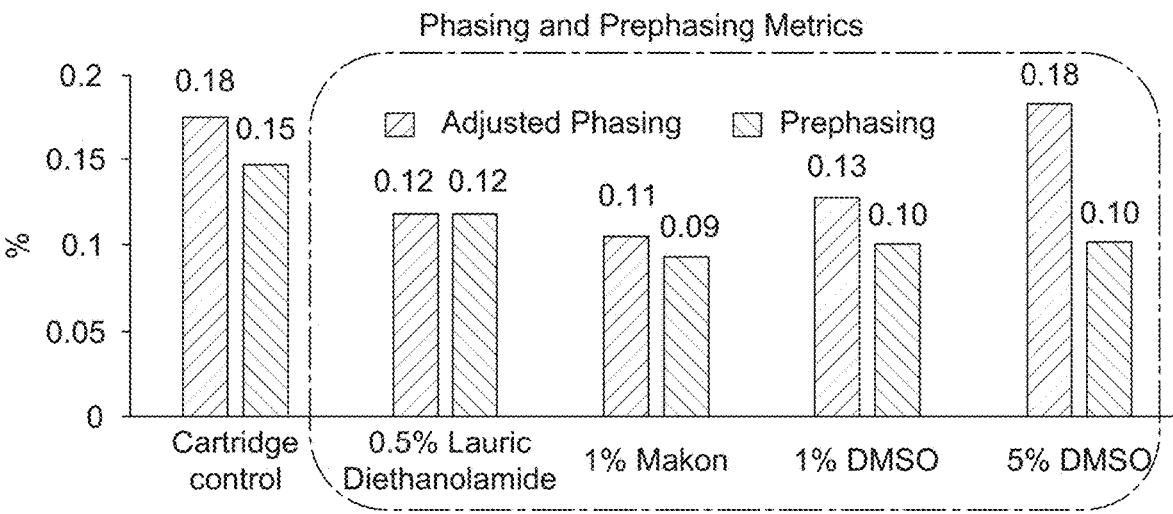
FIGS. 16A-16I show high-throughput sequencing screening of additives. Specific additive, such as Efka® IO 6783, is titrated to find the concentration limit.
Figure 16B:
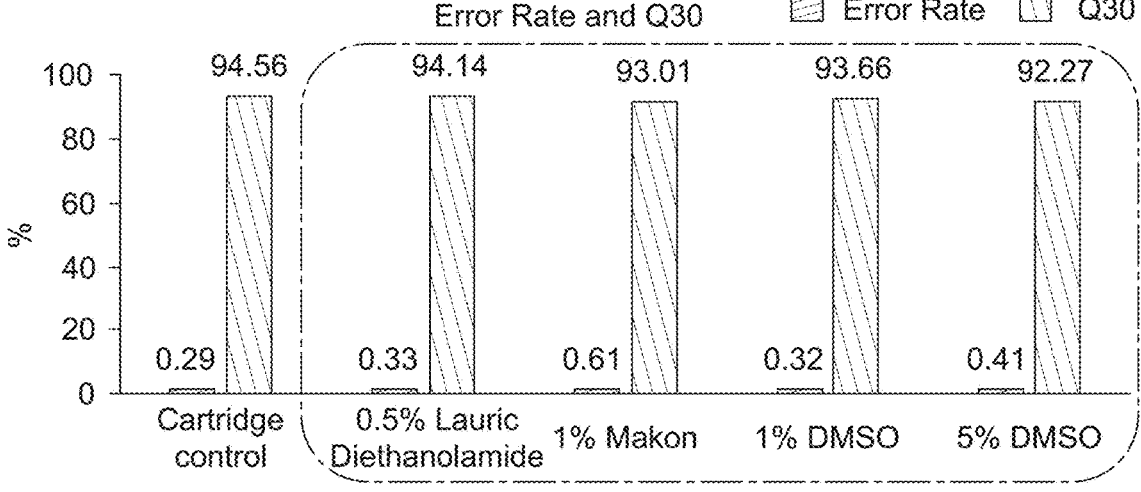
Figure 16C:
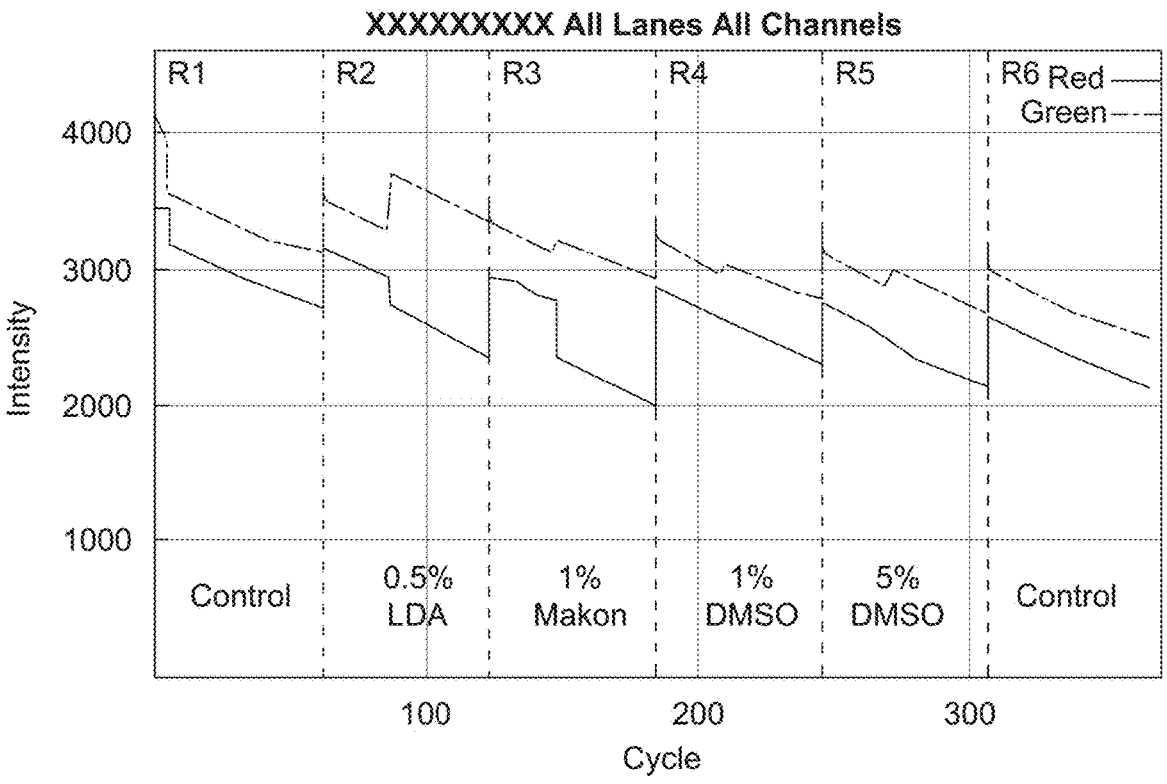
Figure 16D:
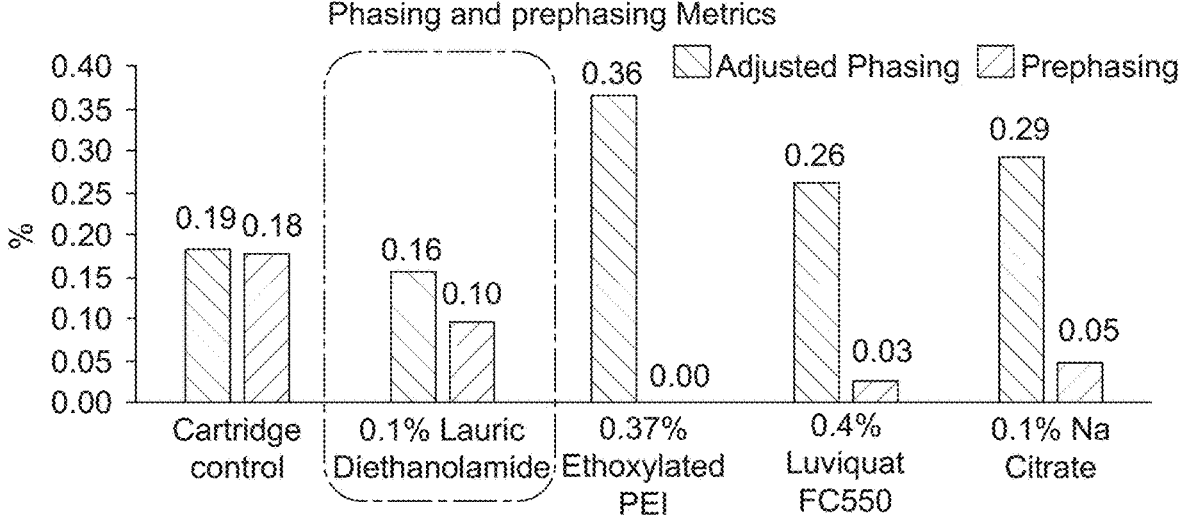
Figure 16E:
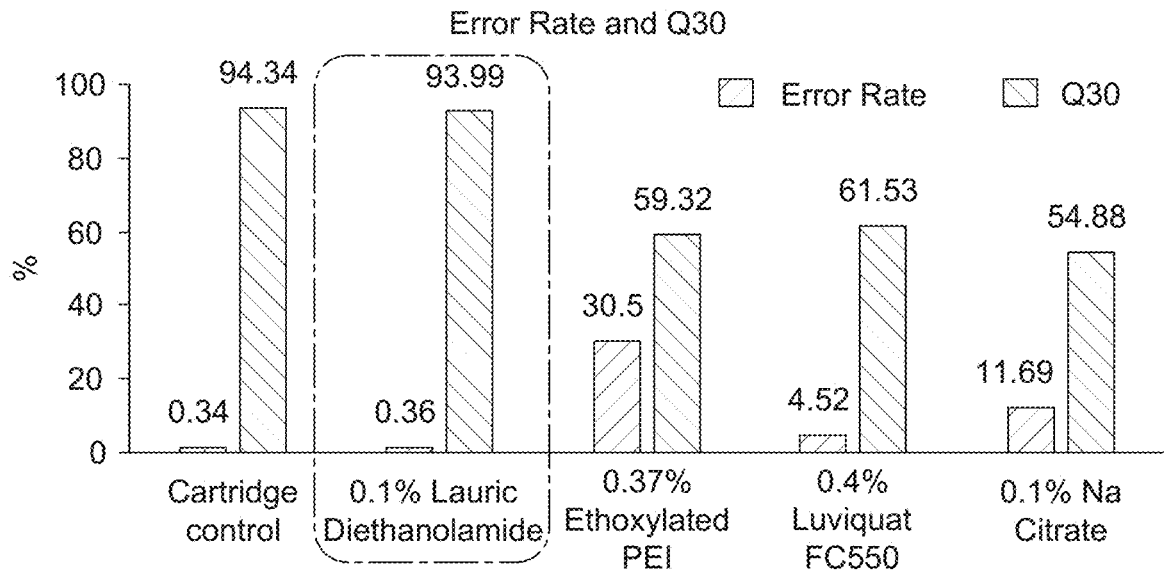
Figure 16F:
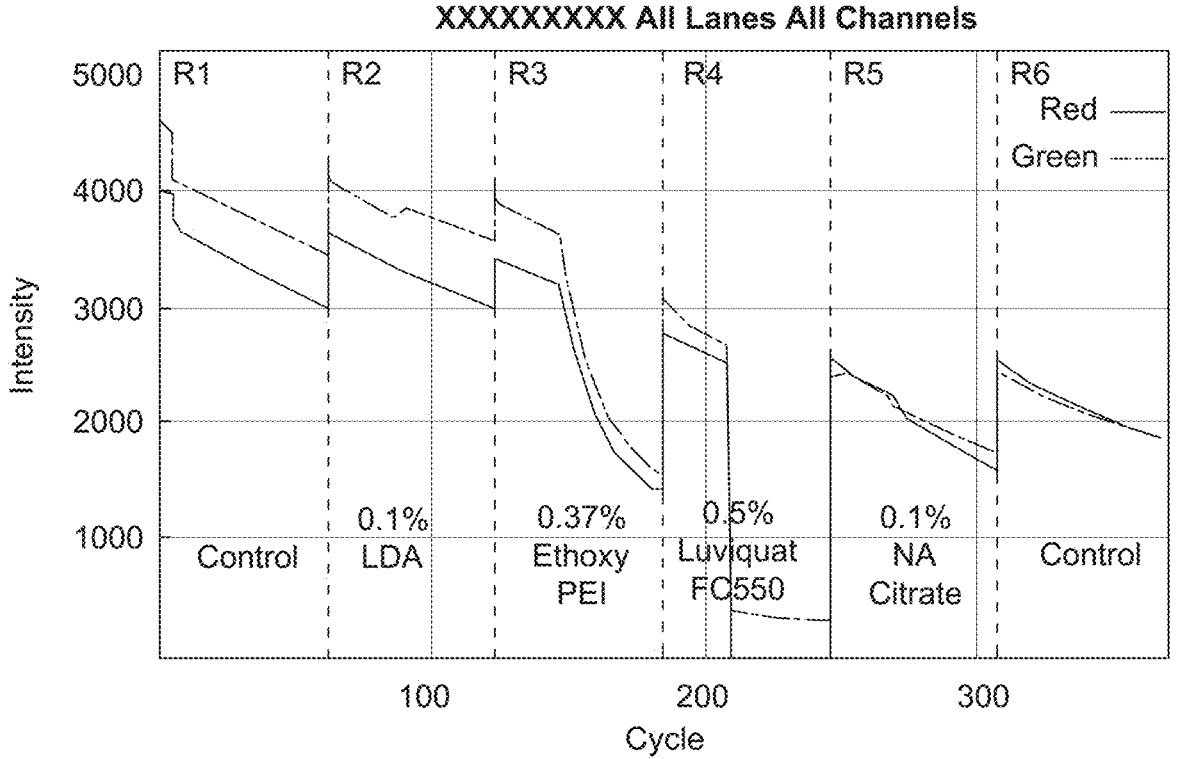
Figure 16G:
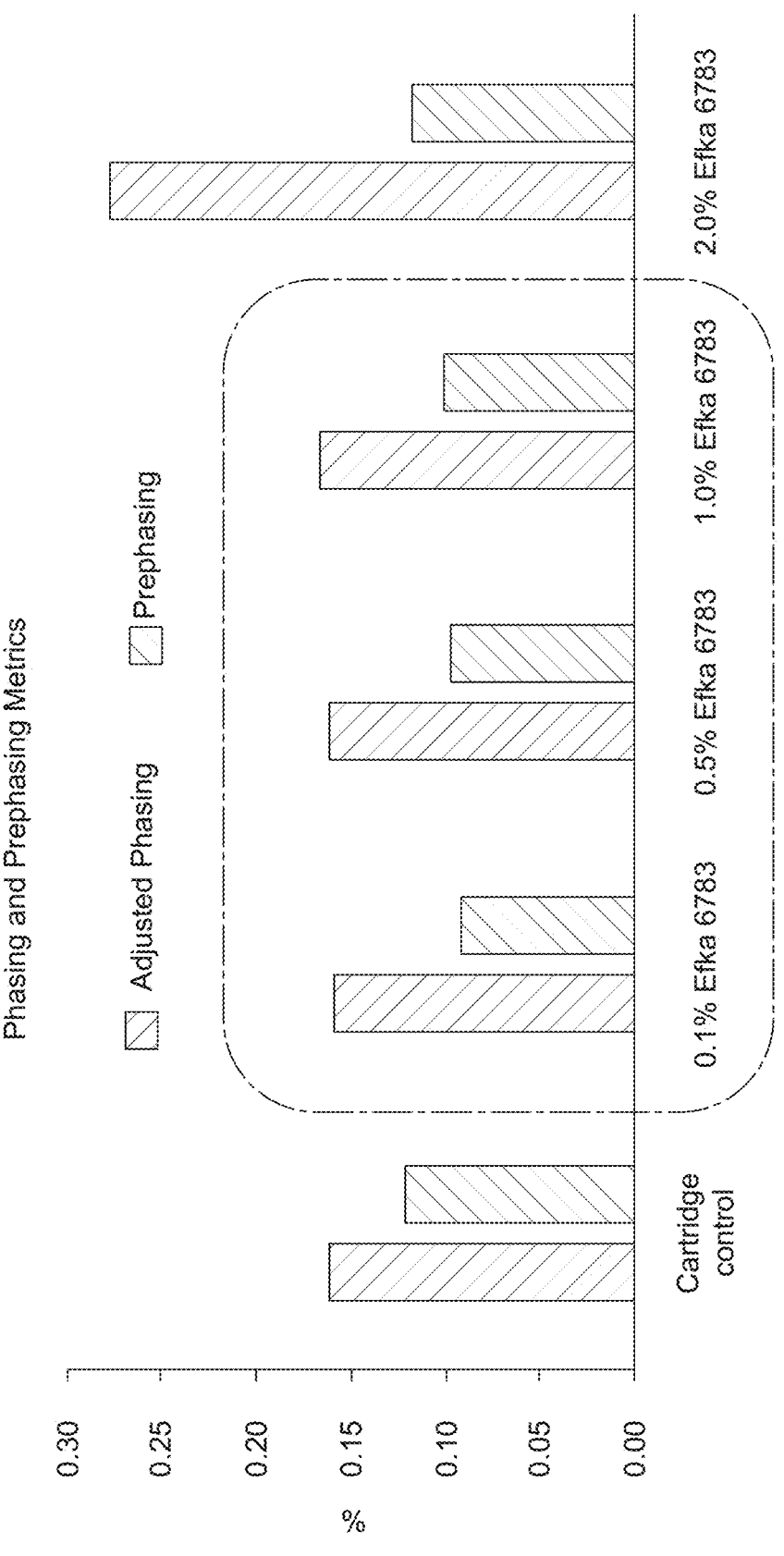
Figure 16H:
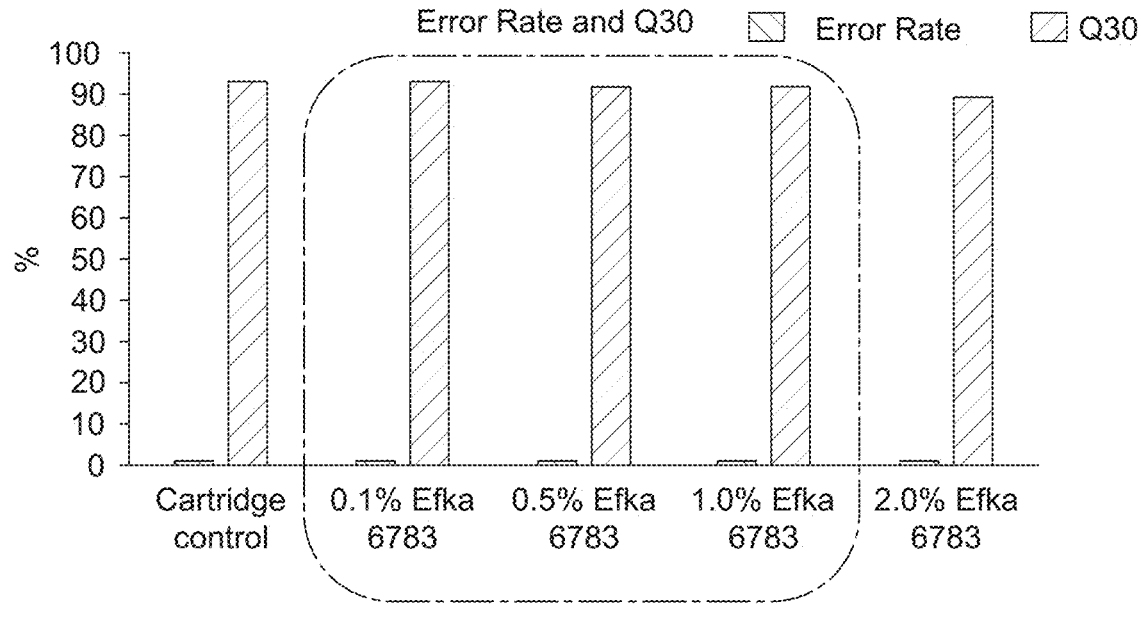
Figure 16I:
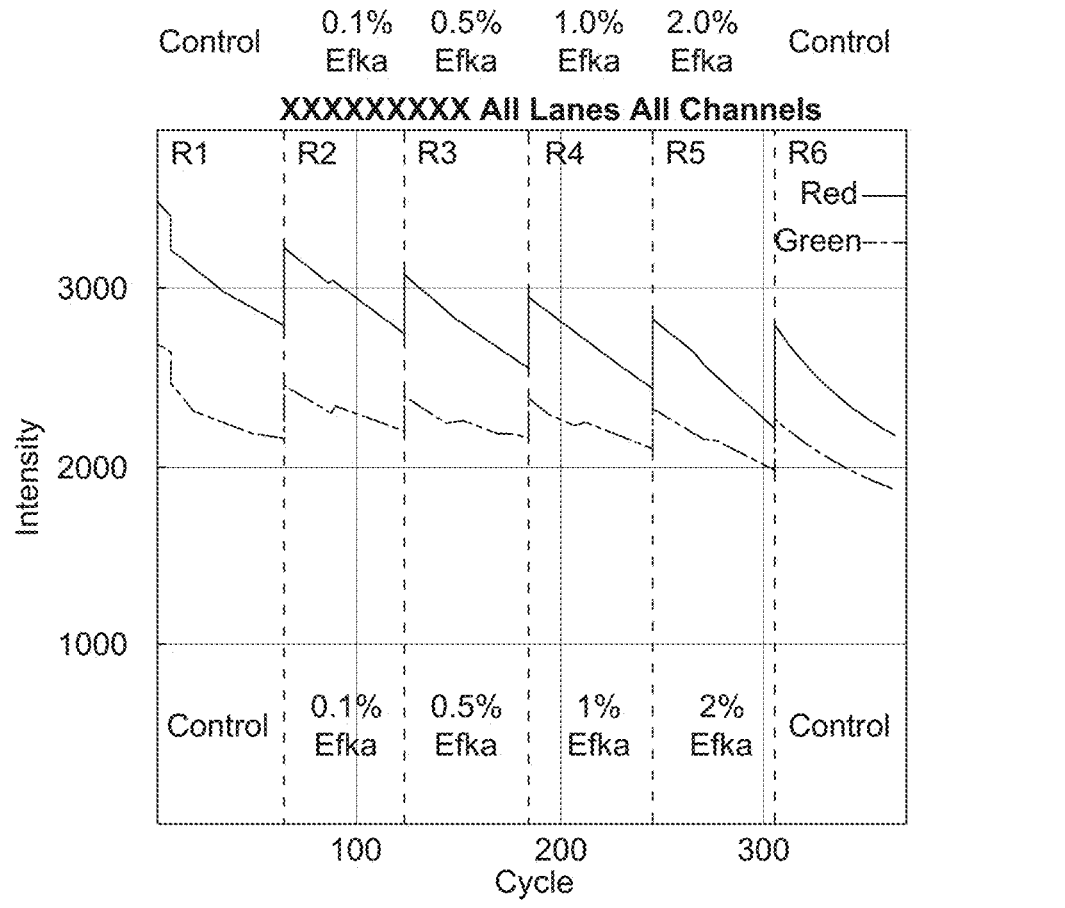
Figure 17A:
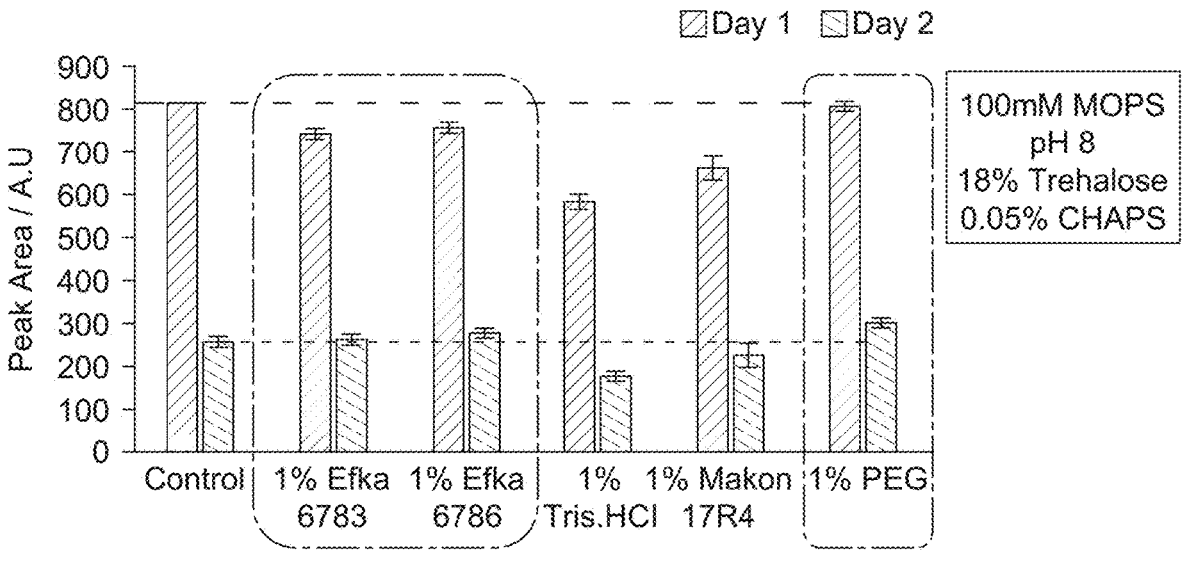
FIGS. 17A-17F show stability of ffCs spiked with 1% additive compared to a control in liquid format post 60° C. incubation for 1-2 days. HPLC analytical results of ffCs incubated with additives described herein and thermally stage at 60° C. for 1 and 2 days are shown. Reduction in ffC peak area and increase in 3'OH as well as DiP indicate degradation of ffN. The effect of additive is compared with control.
Figure 17B:
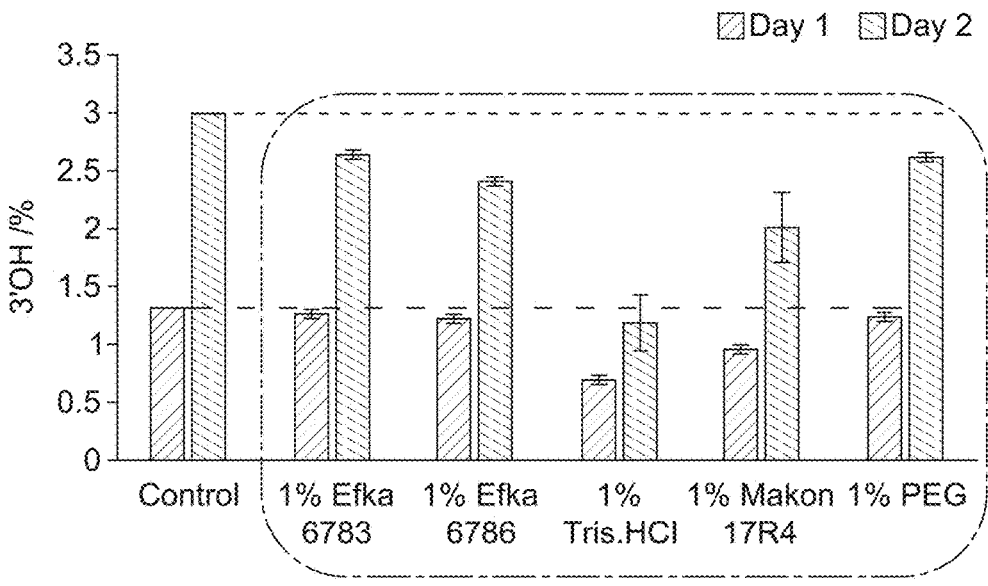
Figure 17C:
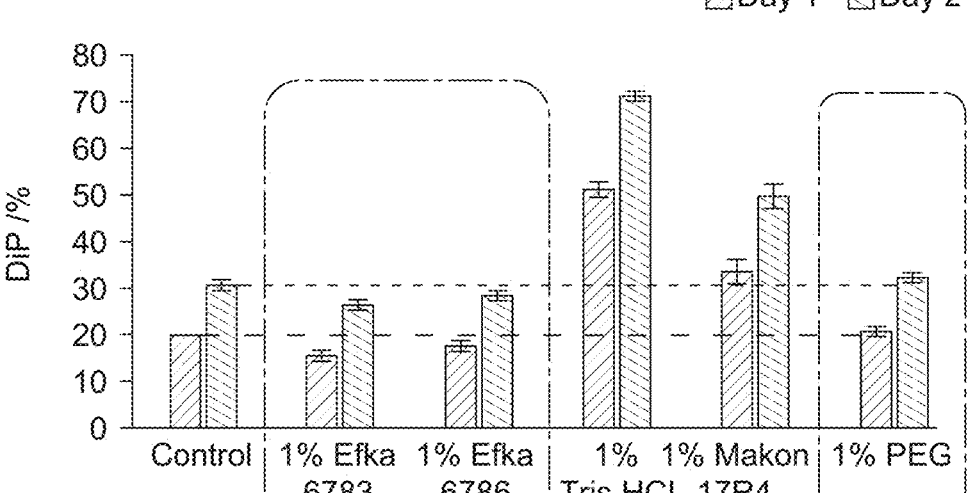
Figure 17D:
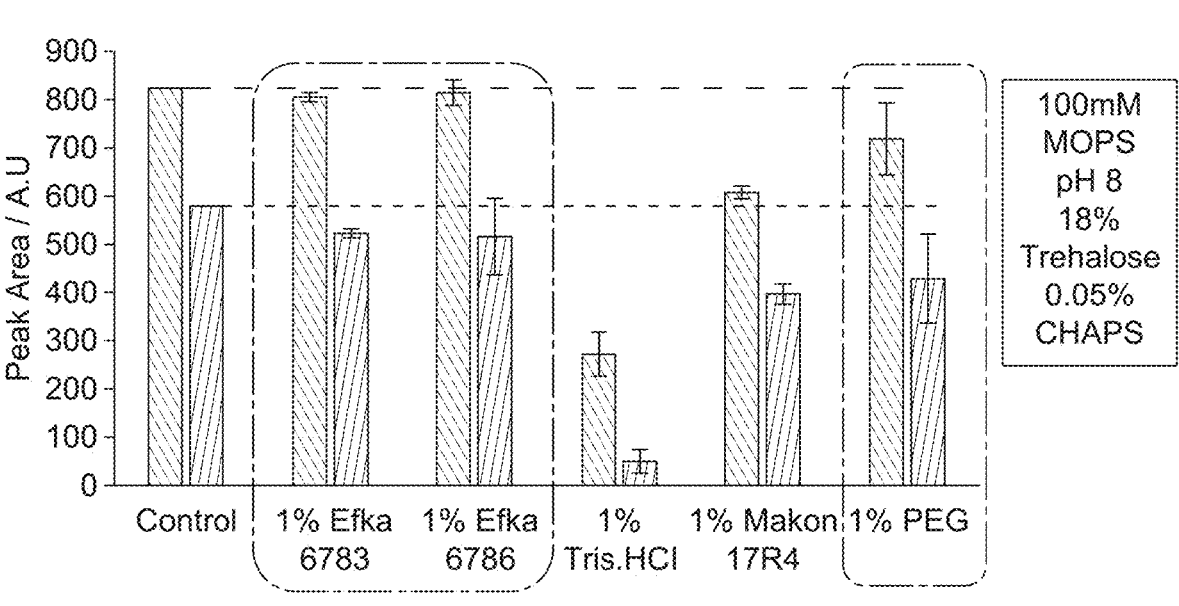
Figure 17E:
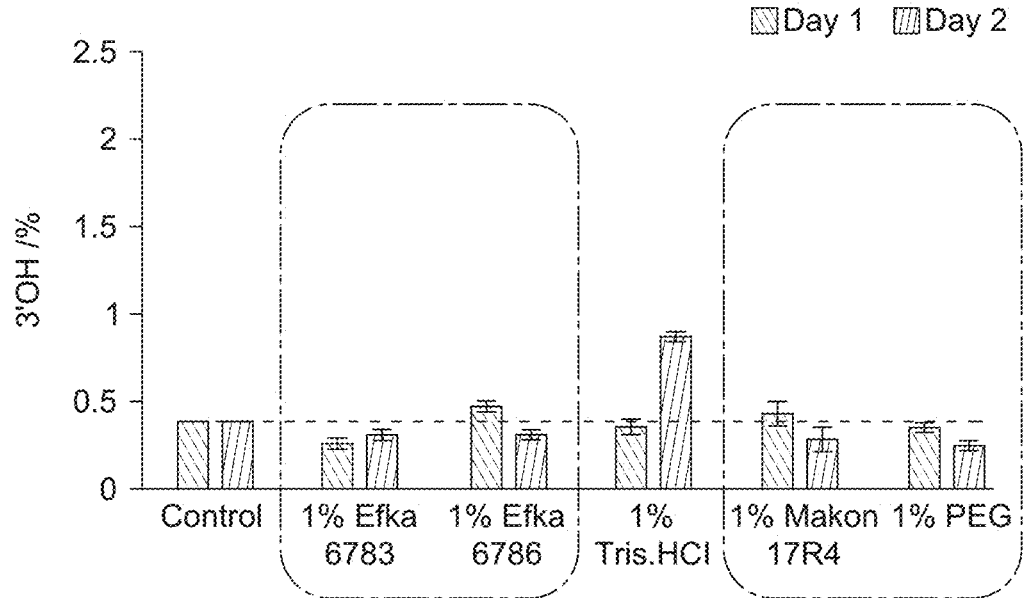
Figure 17F:
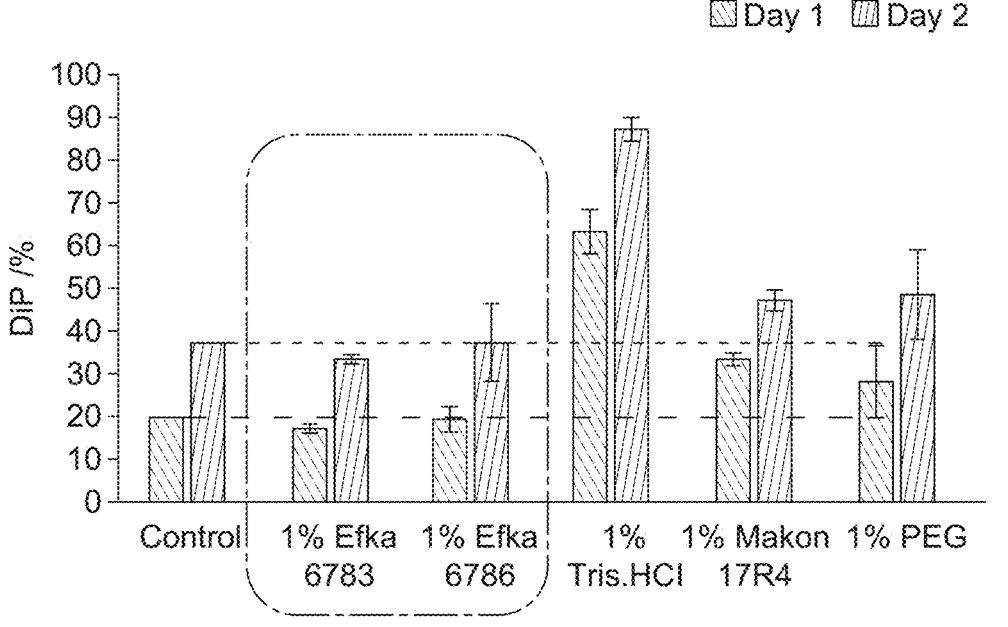

AOM SBS cleave mix with Pd (550) in the core and THP (552) in the shell is shown in FIG. 15A, where the Pd cleave mix might require segregation of Pd and THP to reduce the thermosensitivity of the mixed reagent, ffN/Pol beads with Pol (554) in the core and ffNs (556) in the shell are shown in FIG. 15B; where the polymerase may be protected during ffN polishing if polishing is required. Light protection of ffNs with ffNs (560) in the core and a light blocking shell (558) are shown in FIG. 15C, where light-sensitive ffNs (found in core (560)) are protected from light degradation by a light blocking shell (558).

Example 3—Sequential Release of Lyophilised Reagents

Figure 47:
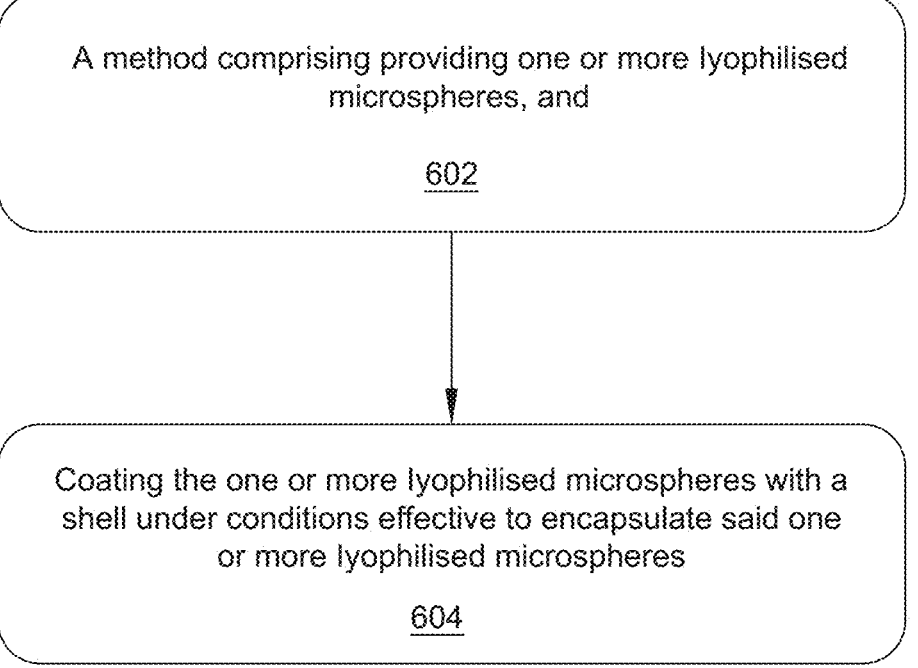
FIG. 47 shows a method as described herein.
Figure 48:
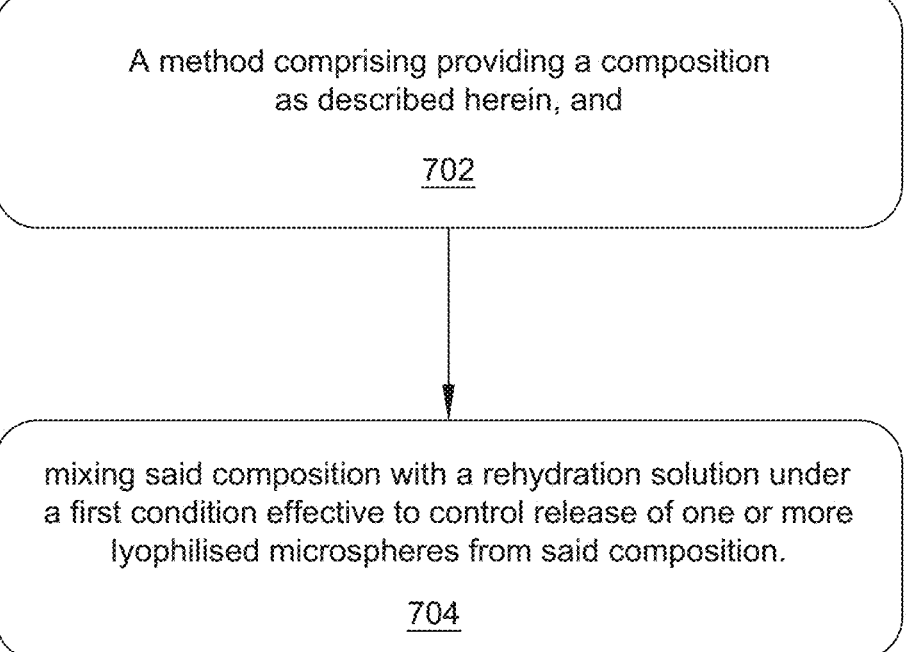
FIG. 48 shows a method as described herein.

To increase the stability of sequencing reagents and to simplify workflows, there is great interest to encapsulate lyophilised microspheres. The present disclosure describes compositions, systems, and methods for encapsulated lyophilised reagents in microspheres that may enable sequential release of lyophilised reagents, as shown for example in FIGS. 47 and 48. In a first method as shown in FIG. 47, one or more lyophilised microspheres are provided (602) and the one or more lyophilised microspheres are coated with a shell under conditions effective to encapsulate the one or more lyophilised microspheres (604). In another method as shown in FIG. 48, a composition described herein is provided (702) and the composition is mixed with a rehydration solution under a first release condition effective to control release of one or more lyophilised microsphere from the composition (704).

One way to enable sequential release of lyophilised reagents is through temperature triggered release, for example, by dipping gelatin capsules filled with microspheres in paraffin wax. Such an approach enables release of microspheres at different temperatures, for example, at between about 30° C. and about 50° C. (e.g., 37° C.) for a native gelatin capsule and between about 50° C. and about 90° C. for a coated capsule (e.g., 58° C.). Similarly, such an approach enables a time-triggered release by addition of additives to a rehydration solution, for example, amino acids, which may delay the rehydration rate of cakes.

Figure 4A:
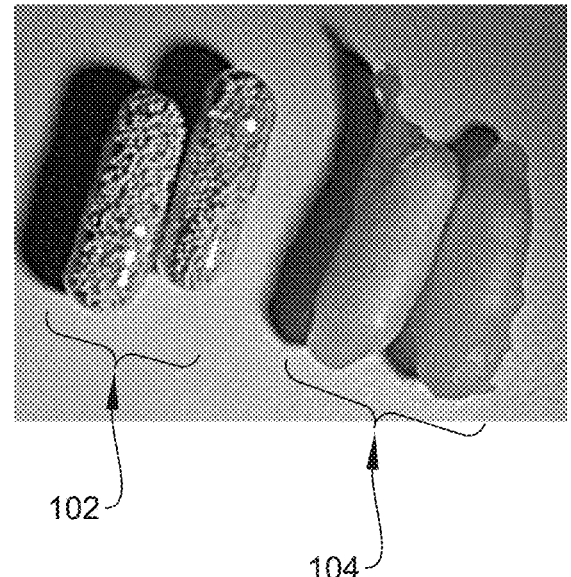
FIGS. 4A-4B depict one implementation of the present disclosure, where a gelatin capsule is filled with microspheres and where the gelatin capsule (which is filled with microspheres) may be coated in an outer covering (e.g., paraffin wax).
Figure 4B:
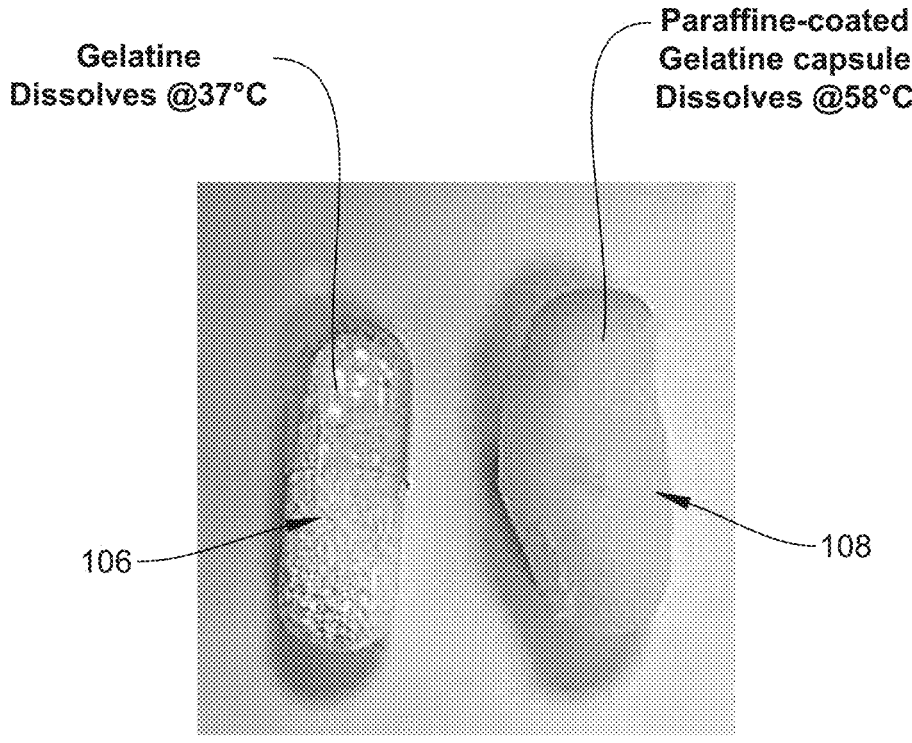
Figure 5:
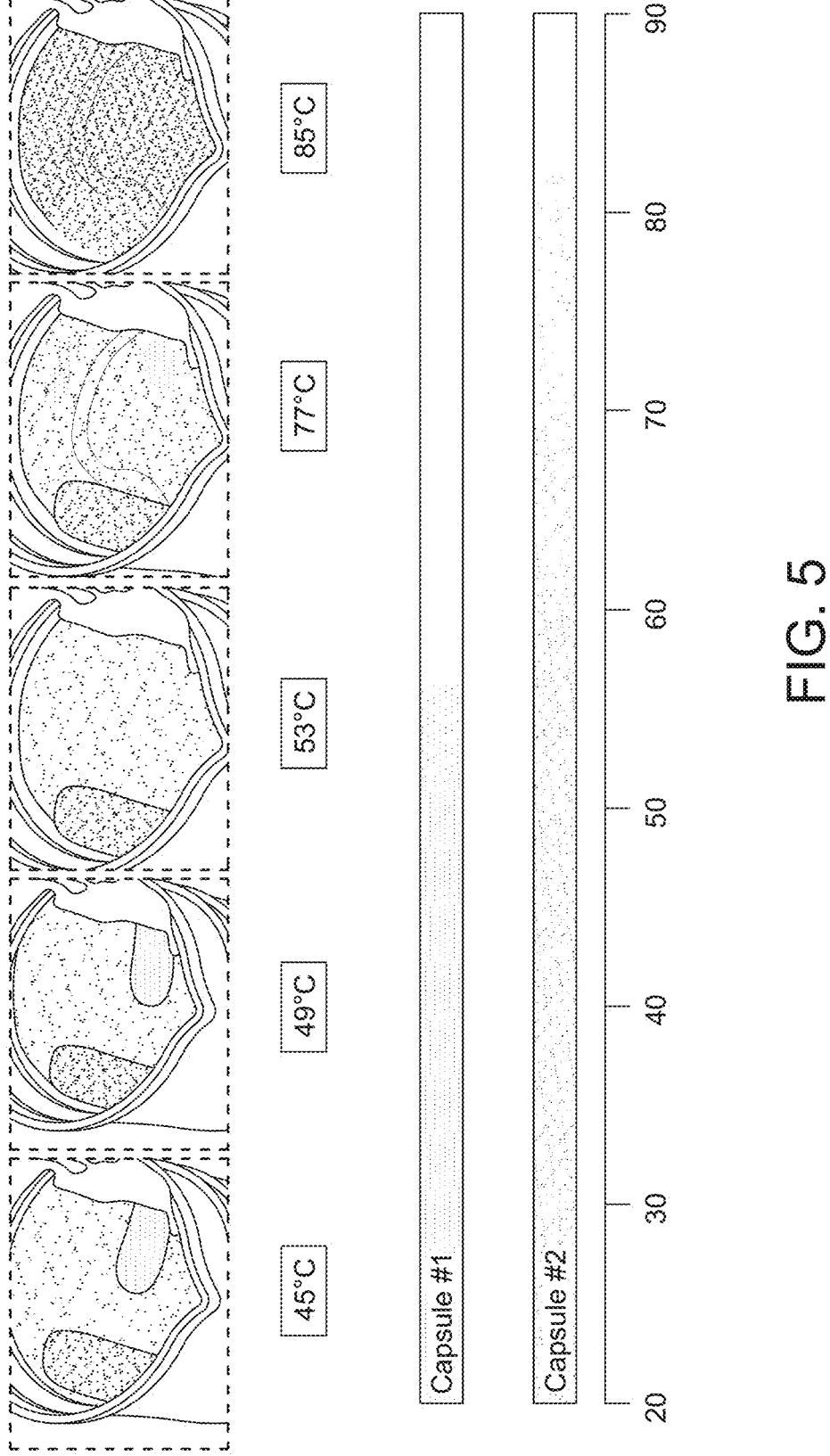
FIG. 5 shows results of a paraffin wax coating of gelatin capsules that enables release of encapsulated lyophilised microspheres at different temperatures.

Here, encapsulated lyophilised microspheres are used to enable sequential release of lyophilised reagents. As shown in FIGS. 4A-4B, in one implementation of the present disclosure, a gelatin capsule may be filled with microspheres and that gelatin capsule which is filled with microspheres may be dipped in hot paraffin wax (or coated in any appropriate outer layer) for a period of time. FIG. 5 depicts a temperature-controlled release for transfer-free reactions. As shown in FIGS. 4A-4B and 5, a paraffin wax coating of gelatin capsules enables the release of microspheres at different temperatures. FIG. 4A shows an OTS gelatin capsule filled with microspheres (102) and an OTS gelatin capsule filled with microspheres and quick dipped in hot wax (104). FIG. 4B shows an OTS gelatin capsule filled with microspheres (106), which dissolved at 37° C. and an OTS gelatin capsule filled with microspheres and quick dipped in hot wax (108), which dissolved at 58° C. The gelatin capsule (102) and/or (106) is capable of releasing microspheres at between about 30° C. and about 50° C. (e.g., 37° C. and/or 50° C.), while the paraffin wax coating (104) and/or (108) is capable of releasing microspheres at between about 50° C. and about 90° C. (e.g., 58° C. and/or 85° C.). In this implementation, a capsule is filled with microspheres and that capsule is quickly dipped in hot wax which should be fast enough so that the capsule does not start melting and to limit the thickness of the wax shell.

Figure 6:
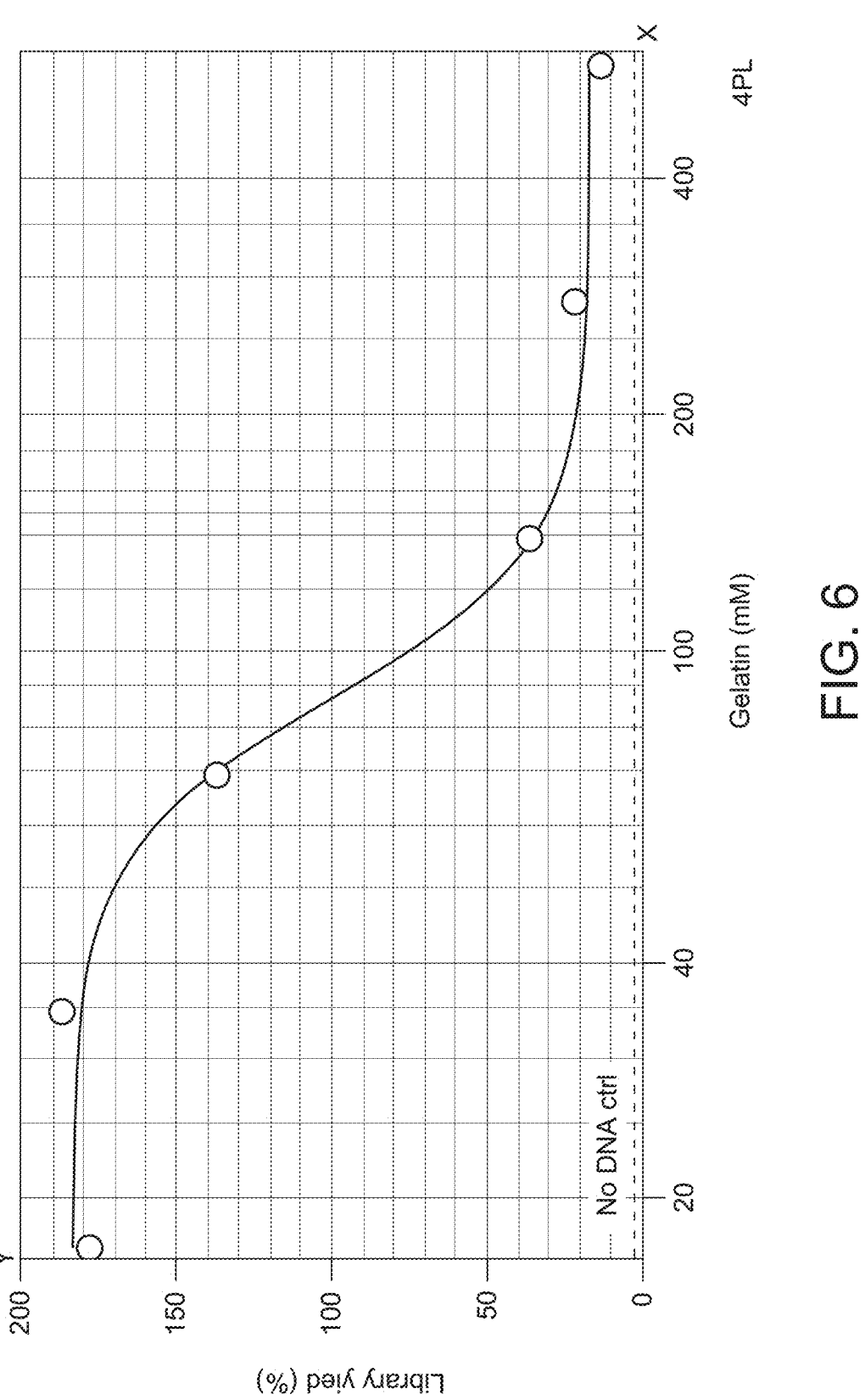
FIG. 6 shows compatibility testing results of Gelatin in Nextera Flex tagmentation.

FIG. 6 shows compatibility testing of Gelatin in Nextera Flex tagmentation. Approximately 80 mM Gelatin can be tolerated in the tagmentation reaction without a drop in library yield. Gelatin (used in OTC capsules) was titrated in Nextera Flex reaction (n=3). Flex was carried out as per standard protocol (100 ng input; 5 cycles amplification). Yields were measured after 2-sided SPRI on Qubit. Yields were normalized to no Gelatin control. Results are compared to no DNA/no gelatin control.

Figures 7A, 7B:
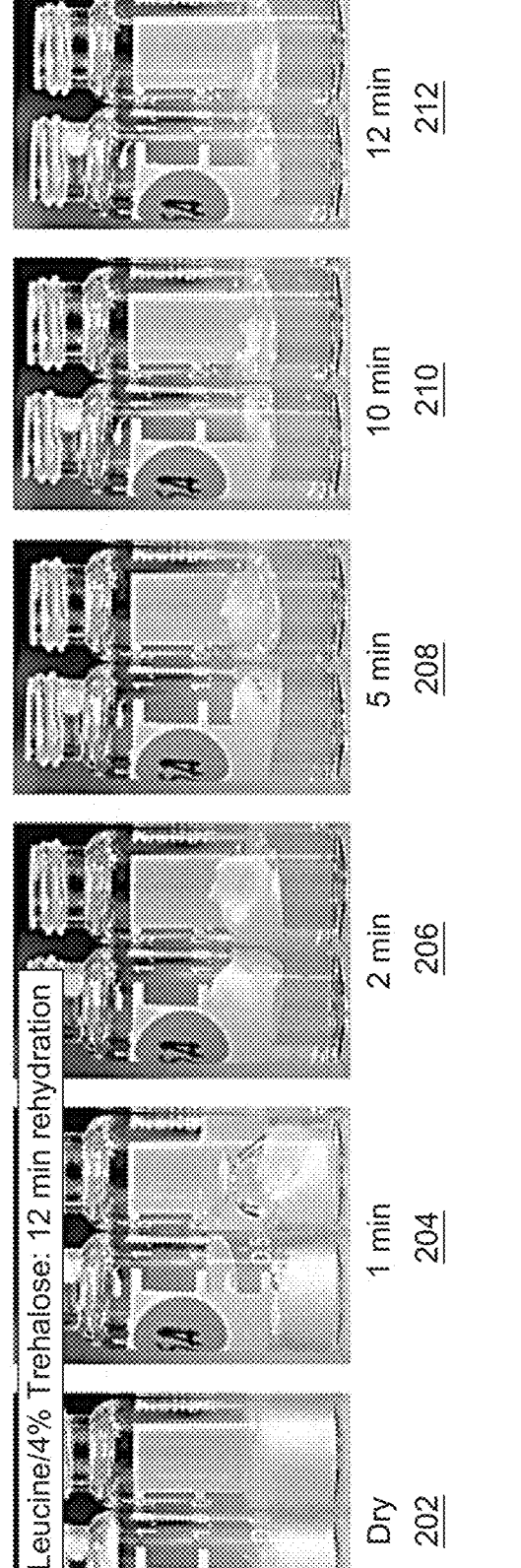
FIGS. 7A-7B show time-controlled release for transfer-free reactions.

FIGS. 7A-7B show time-controlled release for transfer-free reactions. FIG. 7A demonstrates percent of excipients and their respective rehydration time. FIG. 7B shows rehydration of an example composition described herein while dry (202), after 1 minute (204), after 2 minutes (206), after 5 minutes (208), after 10 minutes (210) and after 12 minutes (212). Addition of amino acid excipients enables the delayed release of lyophilised material. Varying quantities of excipients were added with varying rehydration times. In one example, as shown in FIGS. 7A-7B, addition of 1% leucine and 4% trehalose resulted in a rehydration time of 12 minutes (as shown in (202), (204), (206), (208), (210), and (212)). Various other amino acid excipients were tested including trehalose alone, phenylalanine in combination with trehalose, and isoleucine in combination with trehalose at varying concentrations resulting in varying rehydration times. Accordingly, there are various materials that may be added to an encapsulated lyophilised microsphere before rehydration and, or in the alternative, to a rehydration solution during rehydration, that allow for improved control and stability as well as delayed released of the contents of the microsphere including amino acids, PVP co-polymers, mesoporous silica, ionic liquids, quaternary amines, polyvinyl alcohol, oxygen scavengers, phenylalanine, leucine, isoleucine, polyvinyl alcohol, alginate, chitosan, carrageenan, gelatin, HPMC, paraffin wax, starch film, benzoxaborole-PVA, and pectin. Further examples of additives and measures that may be used to control release and trigger mechanisms of encapsulated lyophilised microspheres of the present disclosure include polyvinyl alcohol, alginate, chitosan, gelatin, carrageenan, PODs, hydrogel, starch film, benzoxaborole-PVA, capsule, waxes, pectin, metal organic frameworks, CNT, modified RBCs, polymer matrices, and logic gate photocages. The various additives and measures described herein promote stability of encapsulated lyophilised microspheres, allow macroencapsulation to enable multi-run cartridges, and allow microencapsulation to enable simplified workflows, with for example, a reduced number of reagent wells.

Example 4—Encapsulated Lyophilised
Microspheres for One-Pot Ligation Protocol and
Controlled Release of Encapsulated Lyophilised
Microspheres Here, the encapsulated lyophilised microspheres described enable one-pot ligation protocol as shown in FIGS. 8A-8C. The steps of a one-pot ligation protocol as exemplified in FIG. 8A. FIG. 8B demonstrates time-dependent release of microspheres in a single pot (306) having two different microspheres: (302) which corresponds to Reagent A in FIG. 8A and (304) which corresponds to Reagent B in FIG. 8A. Examples of active reagent volume, number of microspheres, active reagent compositions, encapsulation shell compositions, and encapsulation release triggers for Reagent A. Reagent B, and an additional reagent, Reagent B', are shown in FIG. 8C.

Delayed release of lyophilised microspheres that are encapsulated (e.g., rehydration of a first reagent in a microsphere, followed by rehydration of one or more subsequent reagents after a period of time in the same or in a different microsphere, in the same rehydration solution) along with mechanical protection, buffer stabilization, charge control, reagent combination (e.g., combination of two or more different reagents in a single microsphere, single well, single pot), and light protection are achieved through the compositions, systems, and methods described herein. In particular, a controlled temporal release of reagents by use of the encapsulated lyophilised microspheres described herein allow for a one-pot library preparation. Inhibition of tagmentation by reagents involved with PCR is solved by encapsulating PCR reagents and releasing them at a predetermined time. FIGS. 8A-8C show the presence of encapsulated lyophilised microspheres with different core reagents in a single rehydration solution. Reagent A, for example, is capable of rehydration in less than 1 minute while Reagent B, in this example, rehydrates after 5 minutes, thus avoiding any undesired reactions between Reagent A and Reagent B and allowing for Reagent A and Reagent B to be present in a single pot or well and may allow for a transfer-free reaction. This concept may be used for more than two types of reagents in a single pot or well. For example, Reagent A, Reagent B, and Reagent B' as described in FIGS. 8A-8C, each containing one or more different encapsulated lyophilised microspheres with one or more different reagents may be combined in a single well or pot and rehydrated in a time-dependent manner. Varying quantities of active reagent, number of microspheres, as well as compositions of reagents themselves may be used along with varying compositions of shells for varying periods of time all within a single pot or well. This discovery allows for various steps in PCR for sequencing applications to occur all within the same pot or well and uniquely allows for transfer-free reactions.

The compositions, systems, and methods described herein enable benefits in addition to those described above. For example, using lyophilised materials, and segregated lyophilised materials, means additional co-factors for the enzyme such as magnesium can be added to the microspheres themselves rather than having a separate additional rehydration buffer. This may enable all reagents of different concentrations, types of enzymes, all requiring or benefiting from different amounts of co-factors, salts, pHs, and more, to be rehydrated just with water alone, or even atmospheric water capture. This promotes knock-on reductions in the amount of plastic used in sequencing processes as well as carbon footprint given the reduced weight of reagents when in concentrated and/or lyophilised form.

The encapsulation methodology can be applied to enable an easy way to tune reagent concentrations. For example, a smaller capsule may contain a smaller quantity of lyophilised reagent as compared to a larger capsule, and multiples of this capsule could be placed in the well in line with the needs of the user. This promotes increased user flexibility in terms of throughput, without the potential errors made with dilution/concentration calculations. A unit-based approach, where X number of capsules=Y number of runs allows this flexibility in a more controlled fashion. Another option includes deeper sequencing or longer sequencing (2×500) runs that can use three times the number of capsules ("3X"), whereas a quick superficial screening test may use times fewer capsules ("X").

Example 5—Rectifying Deblocked Lyophilised ffNs in One Well

The problem of rectifying deblocked lyophilised ffNs within one well (for example, an incorporation mix reagent well) using two incompatible, competing polymerases (polishing polymerases and sequencing polymerases) can be addressed by spatially and temporally segregating the polymerases as shown in FIGS. 9A-9D, 10A-10D, and 11A-11F. The problem of spatially and temporally segregating the two polymerases can be solved by encapsulating one polymerase (the sequencing polymerase, as this polymerase is used after the polishing polymerase) in a water-soluble, slowly dissolving film (e.g., polyvinyl alcohol). The issue of timing the release of the sequencing polymerase from its capsule to coincide with the completion of the polishing process can be addressed by tuning the ingredients and their relative amounts in the water-soluble film. Additives could also be used which are temperature- or light-responsive to achieve even finer levels of control.

Lyophilising ffNs achieves increased stability compared to their liquid form but creates elevated 3'OH levels increasing pre-phasing thereby resulting in decreased run quality. In-lab use of the polishing workflow may be complex. The polishing mix (which includes ffNs, polishing polymerase, polishing oligo, and Mg) is prepared and combined separately, incubated for up to an hour at an elevated temperature of 50° C. (to facilitate the polishing reaction), then added to the rest of the incorporation mix where the sequencing polymerase is found. This level of complexity for the user and the sequencer means in its current form this workflow is undesirable, and at scale would be even less so. A solution with minimal and/or no user touch points, which is as complex or less complex than current sequencer workflows, is a viable option.

The compositions, systems, and methods of the present disclosure propose a viable alternative. In the sole incorporation reagent well, loose "polishing microspheres" (which may include ffNs, polishing polymerase, polishing oligo, and magnesium enzyme co-factor) may be dispensed. Also in this well could be the sequencing polymerase microspheres; however, these may be encapsulated in a water-soluble, timed-dissolve film as shown in FIGS. 19A-9D and 10A-10D. This set-up allows multiple benefits, including, for example, reduced well number. If the current separate preparation of the polishing mix followed by mixing with the grand ICM mix is followed, an individual well may be needed for the polishing reagent. Utilizing the encapsulated compositions, systems, and methods described herein facilitates multiple sequential reactions to occur in the one well thereby minimizing the number of wells. This also influences cartridge footprint, with knock-on gains in terms of environmental impact, including, for example, plastic use and incinerator-waste. The compositions, systems, and methods described herein may be easily scaled, while also providing for reduced fluidics and valving, thereby decreasing sequencer complexity and associated costs. When a rehydration buffer, such as water, is dispensed into the well, the loose polishing microspheres dissolve quickly and the polishing reaction begins to rectify any unblocked ffNs. This rehydration buffer also starts to dissolve the water-soluble film encapsulating the sequencing polymerase, see, e.g., FIGS. 10A-10D and 11A-11F.

All-in-one polishing microspheres (402) which contain ffNs, polishing polymerase, and polishing oligo are shown, for example, in FIG. 9A. Sequencing polymerase microspheres (404) which contain sequencing polymerase are shown, for example, in FIG. 9B. Encapsulated polymerase microspheres (406) and all-in-one polishing microspheres (402) in a single well (408) are shown in FIG. 9C. Encapsulated polymerase microspheres (406) and all-in-one polishing microspheres (402) may be placed in a single well (408) with an elevated temperature and rehydrated with water as shown in FIG. 9D.

Figures 10A, 10B:
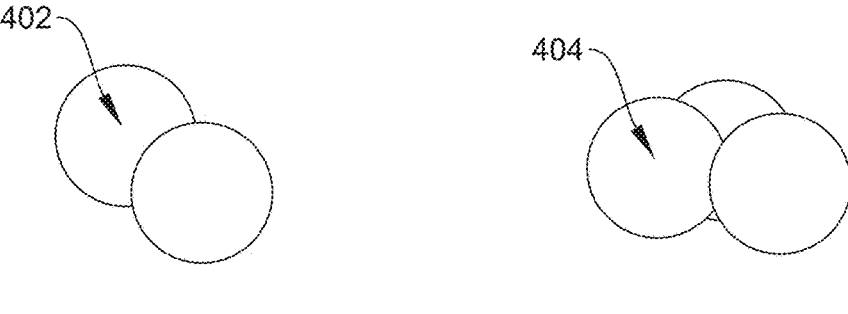
FIGS. 10A-10D show one implementation of the encapsulated lyophilised microspheres as described in the compositions, systems, and methods of the present disclosure, where all-in-one polishing microspheres may contain ffNs, polishing polymerase, and polishing oligo, while sequencing polymerase microspheres may contain sequencing polymerase, where the same unit dose may be repeated across different reagents to achieve a larger dose.
Figures 10C, 10D:
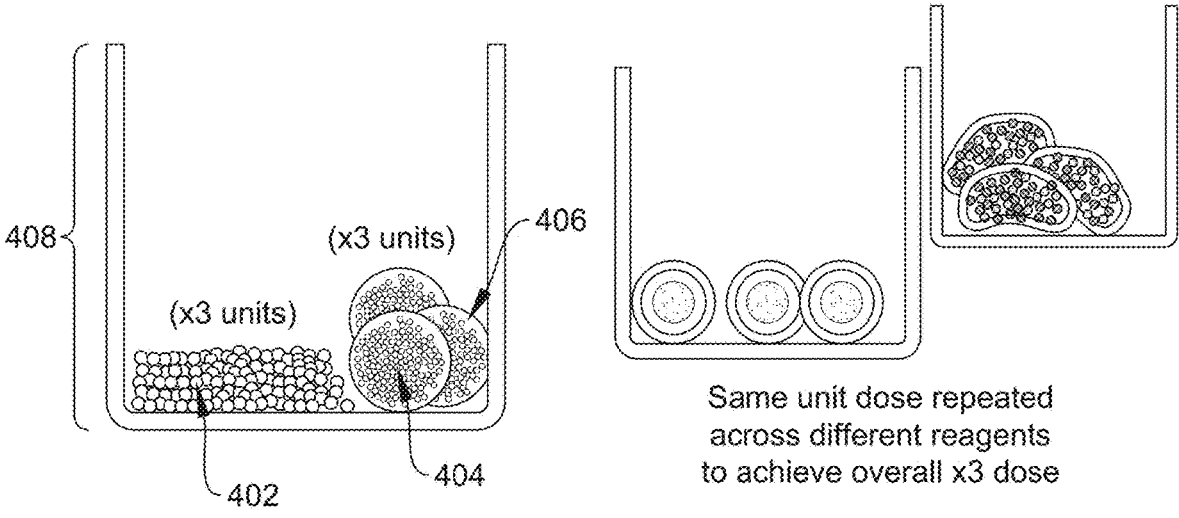

All-in-one polishing microspheres (402) which contain ffNs, polishing polymerase, and polishing oligo are further shown in FIG. 10A. Sequencing polymerase microspheres (404) which contain sequencing polymerase are shown, for example, in FIG. 10B. Encapsulated polymerase microspheres (406) (×3 units) and all-in-one polishing microspheres (402) (×3 units) in a single well (408) are shown in FIG. 10C. The same unit dose may be repeated across different reagents to achieve overall ×3 dose as shown in FIG. 10D.

Figures 11A, 11B, 11C, 11D, 11E, 11F:
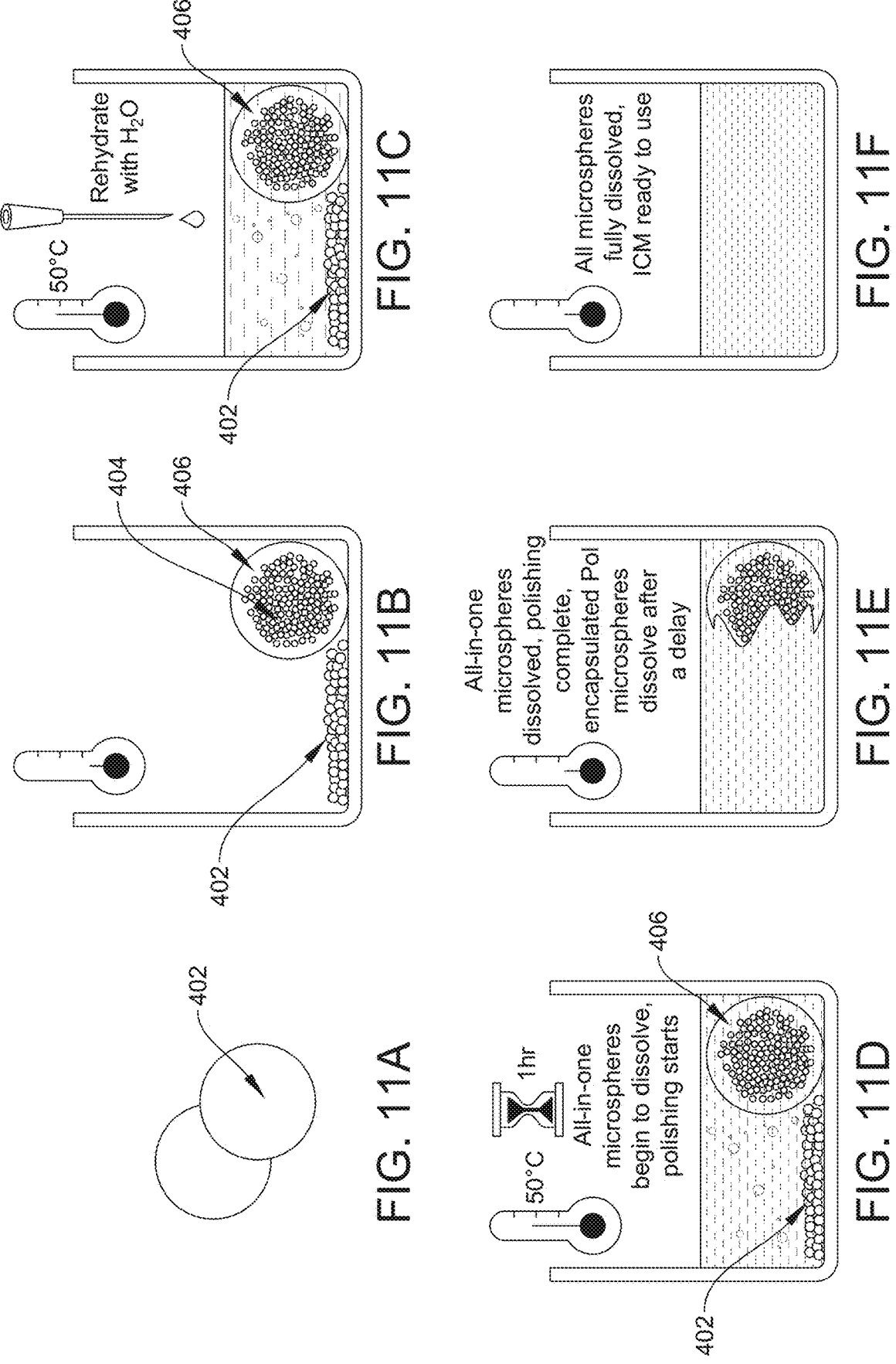
FIGS. 11A-11F show one implementation of the encapsulated lyophilised microspheres as described in the compositions, systems, and methods of the present disclosure.

All-in-one polishing microspheres (402) that may contain ffNs, polishing polymerase, and polishing oligo are further shown, for example, in FIG. 11A. Sequencing polymerase microspheres (404) may be encapsulated (406) and may contain sequencing polymerase, and may be inside a single well alongside all-in-one polishing microspheres (402), as shown in FIG. 11C. Encapsulated lyophilised microspheres (406) may be rehydrated with water at 50° C. are shown in FIG. 11C. After one hour the all-in-one microspheres (402) begin to dissolve, and polishing begins as shown in FIG. 11D. The all-in-one microspheres (402) dissolve, polishing is completed, and encapsulated polymerase microspheres (406) dissolve after a delay as shown in FIG. 11E. The microspheres become fully dissolved, and ICM is then ready to use as shown in FIG. 11F.

Example 6—Discussion and Benefits of Controlling Release of One or More Encapsulated Lyophilised Microspheres The pH of SBS buffers is known to change over the sequencing run. The compositions, systems, and methods described herein use encapsulation of particles that would otherwise be responsive to pH changes to stabilize these buffers and increase SBS performance.

There are numerous benefits to the compositions, systems, and methods described herein. For example, the encapsulated lyophilised microspheres provide anti-static protection, by neutralizing charge and decreasing tribocharging affinity, thereby decreasing metering and manufacturing handling complexity (e.g., with use of mesoporous silica, ionic liquids, quaternary amines). Static charge may be a significant risk for microspheres as it has a significant impact on metering and mixing of dry microsphere powders during manufacturing. Encapsulation may be used to neutralize the charge of the microspheres by coating the particles with a neutral material with low tribocharging affinity.

The compositions, systems, and methods described herein further improve control the pH of solutions that might change over time while sitting on an instrument (e.g. ICM) by developing pH sensitive microspheres that release when the buffer dips below a specified pH to release ions and return the buffer to the desired pH. Similarly, the compositions, systems, and methods described herein improve control of the external charge of microspheres to facilitate dispensing and reduce, if not, prevent, stratification in mixed bulks and further permit segregation of reagent components SBS Cleave Mix to reduce the thermosensitivity of the mixed reagent to reduce or prevent and/or control undesired interactions. Likewise, the compositions, systems, and methods described herein provide encapsulated lyophilised microspheres that protect the polymerase during ffN polishing if polishing is used and protect light-sensitive ffNs from light degradation, especially where environmental conditions involved for polishing degrade the enzyme.

Various applications of the compositions, systems, and methods (e.g., encapsulated lyophilised microspheres) described herein. In one example, two or more capsules may be adjacent to one another in a single tube, and those capsules may dissolve with different triggers. In another example, two or more capsules may be stacked along a y-axis or an x-axis of a narrow tube and a second capsule is dissolved upon release of a first capsule when in contact with a liquid, followed by dissolving of a third capsule upon release of the second capsule when in contact with a liquid, which is repeated for as many capsules as are present in a particular stack. These implementations may likewise by triggered by temperature modifications such as heat. In yet another example, a tube may include a cake formed by lyophilisation, wax may be pipetted into the tube and a capsule dropped in. A user may add liquid which dissolves the capsule first, then when temperature is increased, the wax melts and the cake rehydrates. In another example, a tube may include a first cake formed by lyophilisation, and wax may then be pipetted into the tube. A second liquid is deposited, and lyophilisation is repeated, then new wax is deposited (having, for example, a different melt temperature). A user adds liquid to rehydrate the different cakes once the waxes are melted sequentially.

Figure 12:
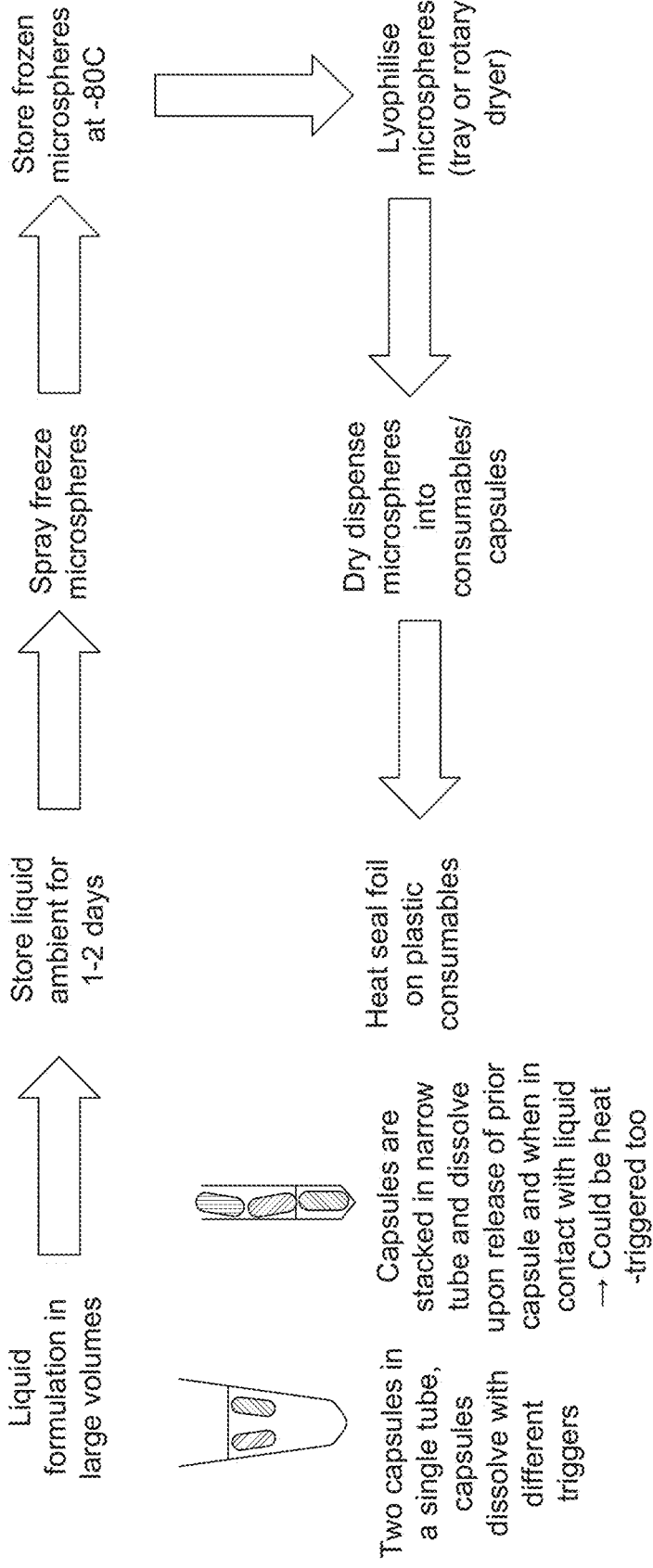
FIG. 12 provides manufacturing process details for encapsulated lyophilised microspheres as described in the compositions, systems, and methods of the present disclosure.

Manufacturing process details for one implementation of the encapsulated lyophilised microspheres described herein are shown in FIG. 12. Liquid formation occurs in large volumes, followed by storage at ambient conditions for a period of time, for example between one to two days, then microspheres are spray frozen and stored at −80° C. Lyophilised microspheres are then placed in a tray or rotary dryer, followed by dry dispensing microspheres into consumables and/or capsules, and lastly heat sealed with foil on plastic consumables. Capsules may be placed in a single tube next to one another and dissolved with different triggers, or, alternatively, may be stacked in a narrow tube and dissolved upon release of a prior capsule and when in contact with a liquid (this implementation may likewise by triggered by heat) as described herein.

Figure 13:
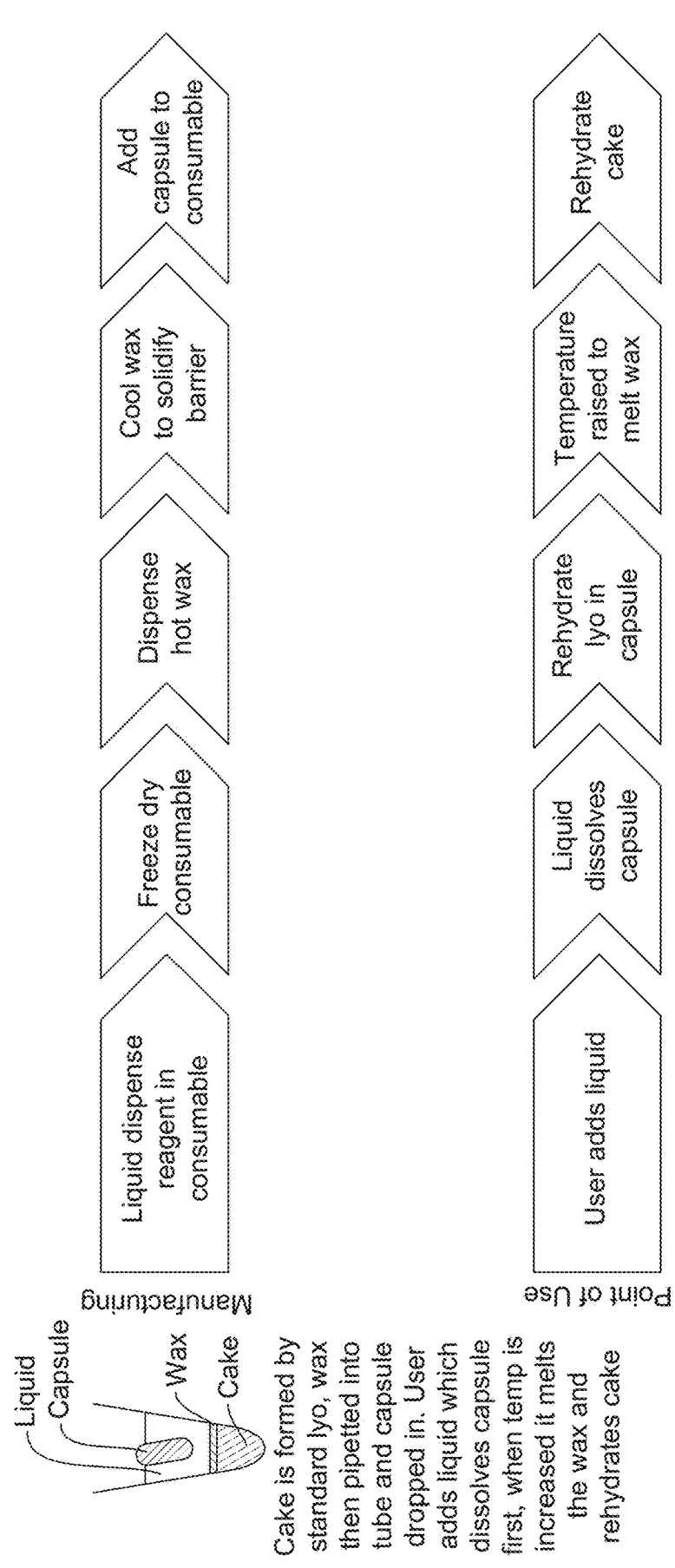
FIG. 13 describes manufacturing and point of use for encapsulated lyophilised microspheres as described in the compositions, systems, and methods of the present disclosure.

Manufacturing and point of use for one implementation of the encapsulated lyophilised microspheres described herein are shown in FIG. 13. In one implementation, during manufacturing, liquid dispenses one or more reagent in a consumable, the consumable is freeze dried, hot wax is dispensed, wax is cooled to solidify a barrier, and a capsule is added to consumable. A lyophilised cake may be formed by hyophilisation, wax may then be pipetted into a tube and a capsule may be dropped in. In one implementation, during point of use, a user adds liquid, the liquid dissolves a capsule, the lyophilised microspheres from the capsule are rehydrated, the temperature is raised to melt wax, and a lyophilised cake is rehydrated.

Figures 14A, 14B:
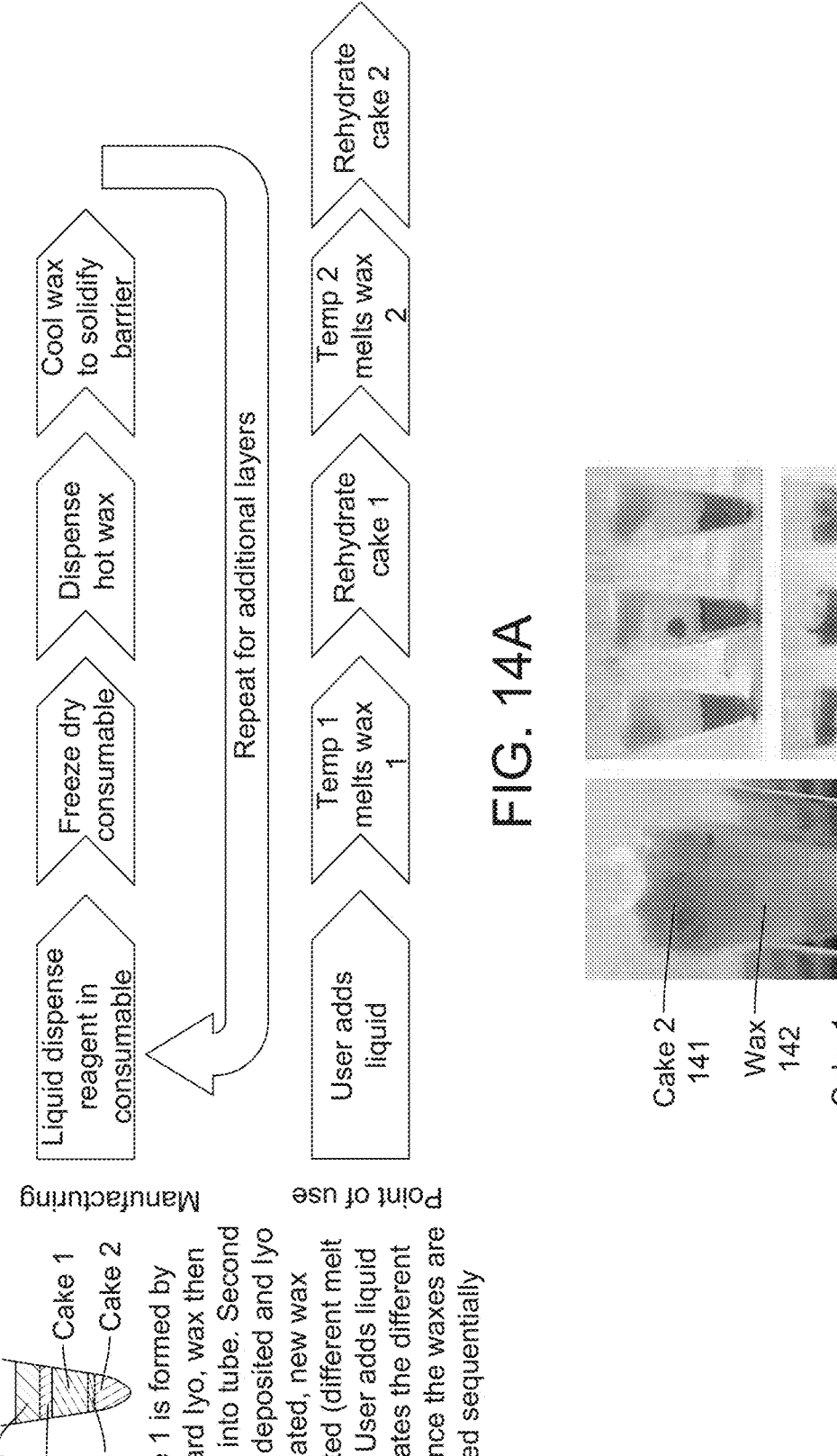
FIGS. 14A-14B depict manufacturing and point of use for encapsulated lyophilised microspheres and cakes as described in the compositions, systems, and methods of the present disclosure.

Manufacturing and point of use for one implementation of the encapsulated lyophilised microspheres and cakes described herein are shown in FIGS. 14A-14B. In one implementation, during manufacturing, liquid dispenses one or more reagent in a consumable, the consumable is freeze dried, hot wax is dispensed, and wax is cooled to solidify a barrier. This process is repeated for additional layers. A lyophilised cake may be formed by lyophilisation, wax may then be pipetted into a tube and a capsule may be dropped in. A second liquid is deposited, lyophilisation repeated, which is followed by a new wax deposit having a different melt temperature. In one implementation, during point of use, a user adds liquid, a first temperature melts a first wax, a first cake is rehydrated, a second temperature melts a second wax, and a second cake is rehydrated. This process is repeated for additional layers.

Example 7—Discussion of Significant Findings of the Compositions Described Herein Significant aspects of the present disclosure include four primary research and development activities: (1) compatibility screening of additive against ffN and sequencing; (2) compatibility screening of additive against ExAmp and clustering; (3) incorporation of the additive into lyophilized matrix to mitigate static; and (4) incorporation of the additive onto coating of microspheres to mitigate static.

While in this and Examples 8-13, there is focus on water-soluble additives as examples, water-insoluble additives may likewise be used. There are metal nanoparticles, graphene fillers, carbon nanotubes, and mesoporous silica, which can be incorporated into the lyophilized or dry reagent described herein. These additives are typically used in solid plastic or polymers for electronic applications.

In the pharmaceutical or biotechnology application, the use of such additives is constrained by their effect on the compatibility with the active ingredients. The dry reagents in the form of lyophilized microspheres contain enzyme, oligonucleotides and ffN (nucleotides). Therefore, it is imperative that the selection of the additive in the reagent microspheres is driven by the compatibility of the additive and function of the additive to mitigate static behavior of the dry microspheres. Particularly, the lyophilized microspheres described herein benefit from being handled in dry environment, which favors the accumulation of electrostatic charge. The incorporation of such additive into the microspheres as matrix or coating format help to mitigate static and tribocharging in dry filling and compounding (blending). Upon rehydration, the additive in the matrix or coating of the lyophilized microspheres is expected to be soluble in aqueous solution as well. Nevertheless, if in situ separation methods of the additive exist, i.e., filtration membrane, the above-mentioned water-insoluble additives can be technically applied as well as coating for the microspheres.

In Table 1, additives were screened based on their solubility in aqueous solution as well as organic solvent (i.e., isopropanol).

Organic solvent solubility may be beneficial when the additives are applied to the lyophilized microspheres as coating. Besides solubility in aqueous solutions (i.e., MOPS and ICM buffers), it is important to find that the additive did not alter the pH of the buffer, which is used to store or stabilize the active ingredients.

In this example, water-soluble additives, such as Efka® IO 6783, 6786, Tween® 80, Makon® 17R4, lauric acid diethanolamide, may be beneficial, since they can be incorporated directly into the matrix of lyophilized microspheres. Water-insoluble additives, such as trioleate glycerol, polyaniline, piperidyl sebacate, vitamin E (tocopherol acetate), Span® 60, can be incorporated into the microspheres with the help of DMSO.

Example 8—Compatibility Screening of Additive Against ffN and Sequencing

In order to screen their compatibility against sequencing performance, additives were spiked to the incorporation mixture (IMX) containing ffNs and polymerase. Their detrimental effects were monitored by increase of phasing, pre-phasing metrics and error rate, as well as reduction in Q30. As shown in FIGS. 16A-16I, Lauric acid diethanolamide, Makon® 17R4 and Efka® IO 6783 may be compatible due to their comparable sequencing results as control (non-spiked IMX).

Promising material, such as Efka® IO 6783, was screened at different concentration spiked in the IMX to gauge the compatibility limit (i.e., 2% w/v).

TABLE 1

Solubility screening of additives that are selected to mitigate static and tribocharging of lyophilized microspheres. Weight % of additive soluble and its effect on pH in solution (promising additives) are summarized.

| Static mitigating additive | Water | IPA | MOPS | pH | 7.5 | ICM pH 9.9 | |
|---|---|---|---|---|---|---|---|
| Efka ® IO 6783 | 2.0% | 7.44 | 2.0% | 2.0% | 7.55 | 2.0% | 7.55 |
| Efka ® IO 6786 | 2.0% | — | 2.0% | 2.0% | — | 2.0% | — |
| Larostat 902A | 2.0% | 6.89 | 2.0% | 2.0% | 7.51 | 2.0% | 7.51 |
| Sodium lauryl sulfate | 0.5% | 8.91 | 0.1% | 0.5% | 7.57 | 0.5% | 7.57 |
| Sodium oleate | x | | x | | x | | x |
| Stearic acid | x | | 0.5% | | x | | x |
| Magnesium stearate | x | | x | | x | | x |
| Sodium citrate tribasic dihydrate | 2.0% | 8.52 | x | 2.0% | 7.5 | 2.0% | 7.5 |
| Sodium L-Ascorbate | 2.0% | 7.59 | x | 7.0% | 7.55 | 2.0% | 9.95 |
| Span ® 60 | x | | x | | x | | x |
| Tween ® 60 | x (at 1% w/1% DMSO) | | 1.0% | | x | | x |
| polyethyleneimine (80% ethoxylated) (37 wt % in water) | 2.0% | 11.19 | 2.0% | 2.0% | 8.04 | 2.0% | 10.1 |
| Lauric acid diethanolamide | 2.0% | 9.82 | 2.0% | | x | 2.0% | 9.99 |
| Luviquat ® FC370 (40 wt % in water) | 10.0% | 7.16 | x | 10.0% | 7.60 | 10.0% | 9.75 |
| Luviquat ® FC550 (40 wt % in water) | 10.0% | 6.75 | x | 10.0% | 7.36 | 10.0% | 9.76 |
| Triglycerol monosterate | x | | x | | x | | x |
| Piperidyl Sebacate | x (at 0.1% w/0.1% DMSO) | | 2.0% | x (at 0.1% w/0.1% DMSO) | | x (at 0.1% w/0.1% DMSO) | |
| Vitamin E/Tocopherol acetate | x (at 0.1% w/0.1% DMSO) | | 2.0% | x (at 1% w/1% DMSO) | | x (at 0.1% w/0.1% DMSO) | |
| Trioleate Glycerol | x | | 2.0% | | x | | x |
| Polyaniline | x (at 0.1%/0.1% DMSO) | | x | (at 1% w/0.1% DMSO) | | x (at 0.1% w/0.1% DMSO) | |
| Coumarin 6 | x | | x | | x | | x |
| Tween 80 | 2.0% | 7.45 | 2.0% | 2.0% | 7.52 | 2.0% | 9.91 |
| Makon ® 17R4 | 2.0% | 7.6 | 2.0% | 2.0% | 7.52 | 2.0% | 9.94 |

Additives, such as ethoxylated PEI and Luviquat® FC550, which are reported to be used as anti-static agent, may not be compatible for sequencing. Sequencing results of the additives are summarized in Table 2 below, which help to down-select anti-static additive for SBS micro-spheres (ffN and polymerase).

These additives were incorporated into ExAmp as lyo-philized cakes as well. In order to gauge the anti-static property of the additives, the cakes were powdered and their charge potential was measured using Keyence (as matrix format). In dry environment (3% relative humidity) the

TABLE 2

| | | % Phasing (≤0.2) | % Prephasing (≤0.2) | Q30 (%≥90) | Error Rate |
|---|---|---|---|---|---|
| Classification of additives | IMX spiked with additives | | | | |
| Buffer/Salt | 2% Tris•HCl | ✓ | ✓ | 92.50 | 0.51 |
| | 0.1% Sodium Chloride | x | ✓ | 57.34 | 43.20 |
| Solvent | 5% DMSO | ✓ | ✓ | 92.27 | 0.41 |
| Static | 1% Efka ® IO 6783 | ✓ | ✓ | 92.78 | 0.41 |
| mitigating | 0.5% Efka ® IO 6786 | ✓ | ✓ | 92.99 | 0.37 |
| Additive | 0.5% Isoleucine | ✓ | ✓ | 92.93 | 0.34 |
| | 0.5% Lauric Acid Diethanolamide | ✓ | ✓ | 94.14 | 0.33 |
| | 1% Makon ® 17R4 | ✓ | ✓ | 93.01 | 0.61 |
| | 0.5% tocopherol acetate w/0.5% DMSO | ✓ | ✓ | 96.97 | 0.17 |
| | 0.5% piperidyl sebacate w/0.5% DMSO | ✓ | ✓ | 96.97 | 0.20 |
| | 0.5% Triethylcitrate | ✓ | ✓ | 95.96 | 0.21 |
| | 0.5% Tween ® 80 | x | ✓ | 98.45 | 34.51 |
| | 0.4% Luviquat ® FC370 | x | x | 48.60 | 43.22 |
| | 0.4% Luviquat ® FC550 | x | ✓ | 61.53 | 4.52 |
| | 0.1% Sodium Citrate | x | ✓ | 54.88 | 11.69 |
| | 0.1% Sodium Lauryl Sulfate | x | ✓ | 85.54 | 2.90 |
| | 0.4% Ethoxylated Polyethylenimine | x | x | 59.32 | 30.50 |

Summary of sequencing performance of IMX (SBS incorporation mixture spiked with Additives In addition to spiking the IMX, the compatibility of the additive with ffN was screened as well (FIGS. 17A-17F). Two blue ffC from different sequencing platforms were selected due to their thermal sensitivity to deblocking (3'OH generation) and triphosphate hydrolysis (DiP generation). Additives were incubated with the ffN aqueous formulation (or rehydrated lyo formulation) at 60° C. for 1 day and 2 days. In comparison with control, significant increase in 3'OH and DiP as well as reduction in peak area were observed. Except Tris.HCl, promising additive such as Efka® IO 6783 may be compatible with ffN.

Example 9—Compatibility Screening of Additive Against ExAmp and Clustering

Figure 18:
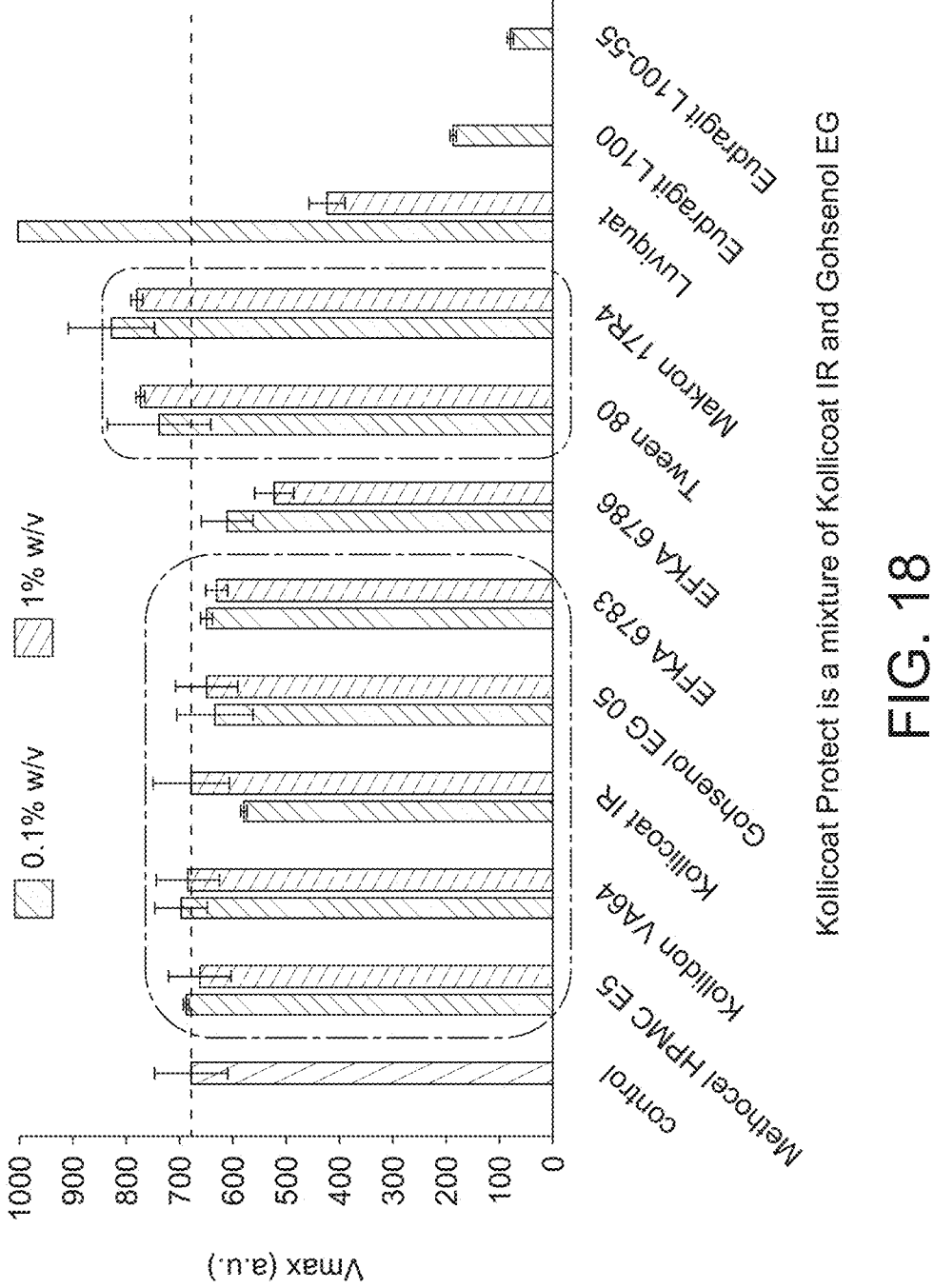
FIG. 18 shows DNA recombinase activity of exclusion amplification (ExAmp) solution incubated with additives described herein.

The same additives were incubated with aqueous ExAmp formulation (TCX V1.0) as well. The activity of DNA recombinase (sensitive enzyme component of ExAmp) was assessed in the presence of the additive at 0.1% and 1% w/v (FIG. 18). Most of the additives resulted in comparable activity as control, except Efka® IO 6786, Luviquat® and Eudragit®.

Figure 19A:
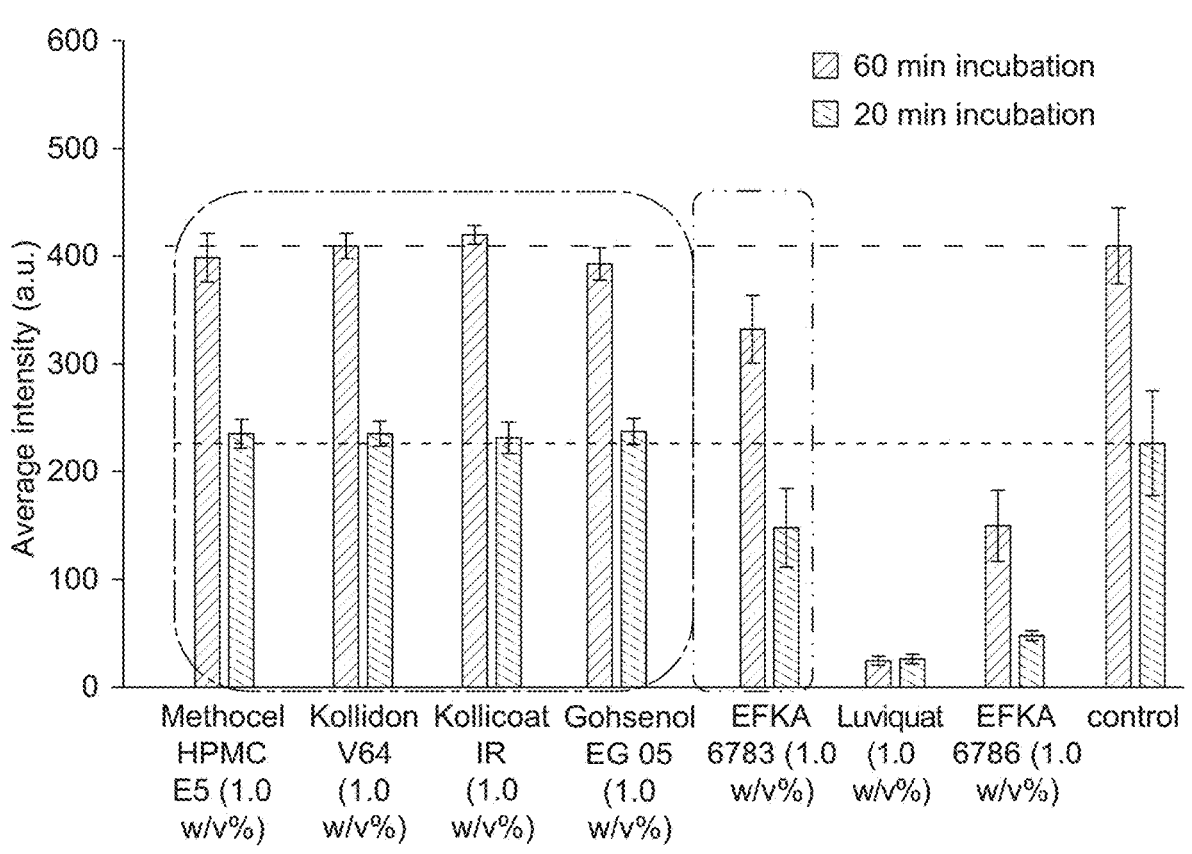
FIGS. 19A-19B show clustering performance of ExAmp spike with coating materials by cBOT first base assay, in particular, ExAmp average intensity (FIG. 19A) and clustering functionality (FIG. 19B) of ExAmp solution incubated with additives described herein via cBOT first base incorporation kinetic.
Figure 19B:
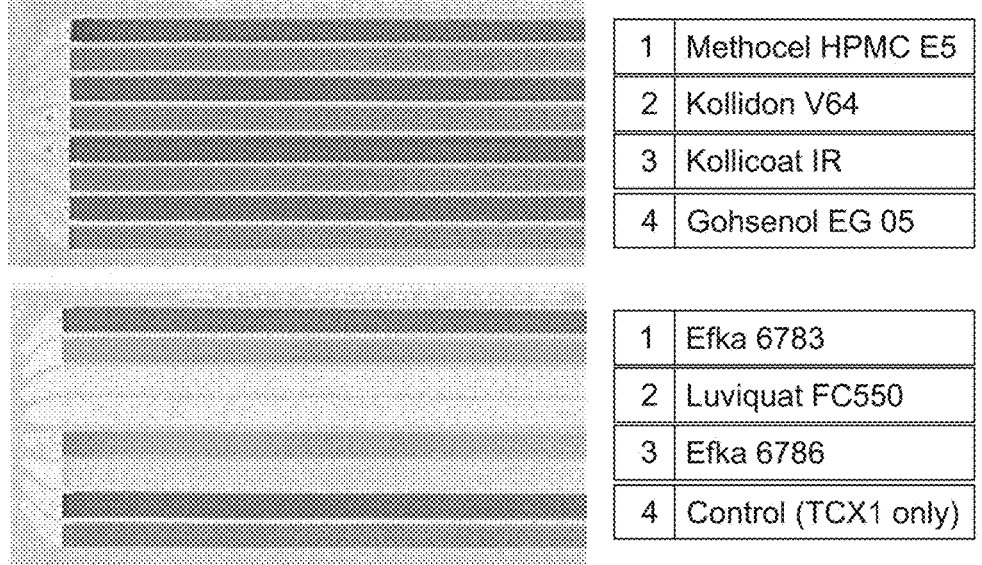
Figure 20:
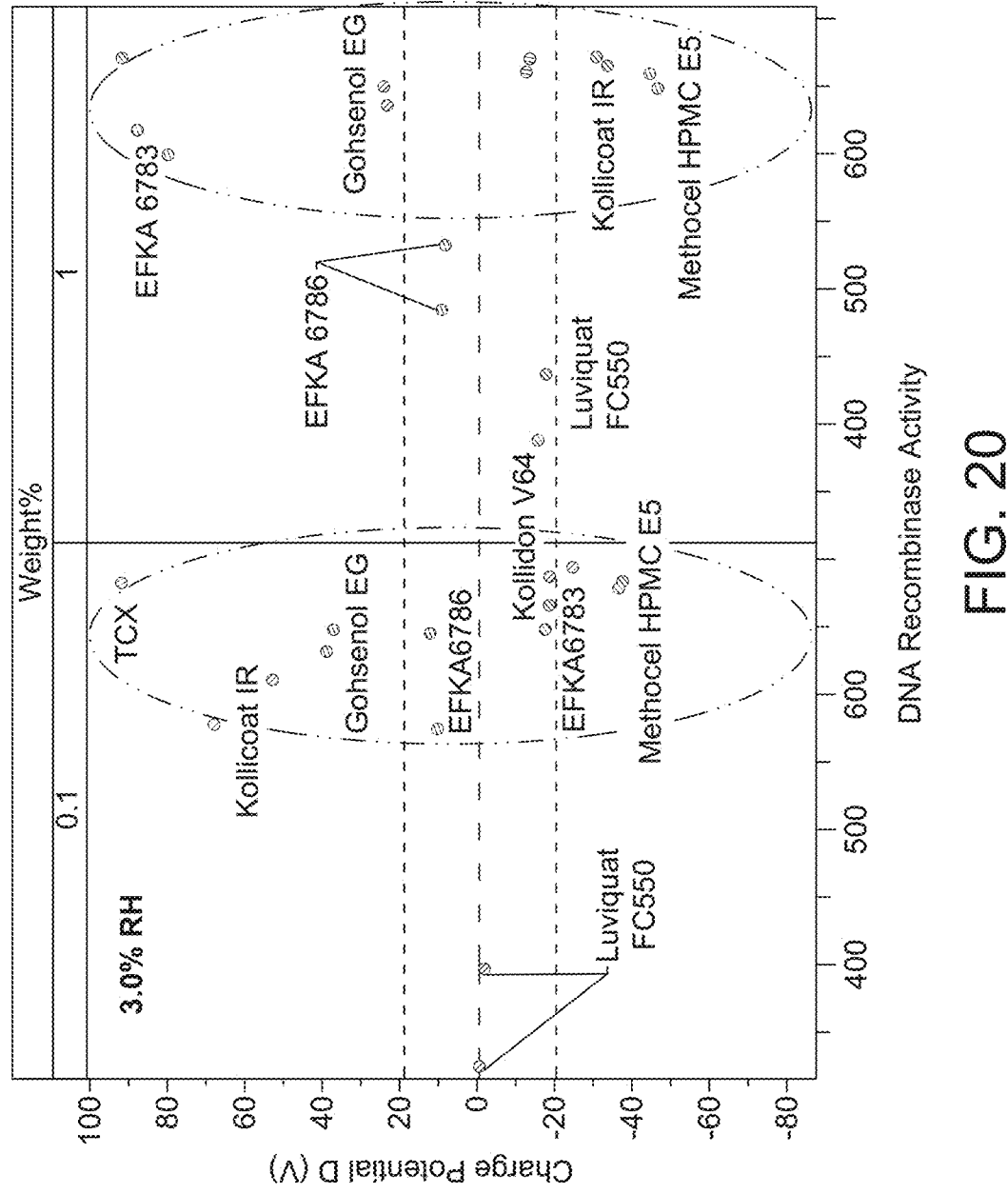
FIG. 20 depicts charge potential (via Keyence) measurement (at 3% RH) of powdered lyophilized cake of ExAmp containing additives at different concentration (matrix).

The clustering functionality of ExAmp was assessed using cBOT first base incorporation kinetic (FIGS. 19A-19B). The result corroborated the DNA recombinase activity assay. Incompatible additives such as Luviquat® and Eudragit® exhibit low clustering intensity. On the other hand, Ekfa IO 6783 was slightly detrimental to DNA recombinase activity and clustering functionality, particularly, when the ExAmp is staged at higher temperature (i.e., 40° C. 1 day). Therefore, the concentration of Efka® IO 6783 may benefit from being maintained in ExAmp solution (or rehydrated microspheres) below about 1% w/v.

static was more pronounced (FIG. 20). It is unexpected that Efka® IO 6783 is effective even at 0.1% w/v in 20% lyophilized formulation.

Moreover, Kollidon® VA64, Efka® IO 6786, and Luviquat® are effective at 0.1% and 1% w/v. However, Luviquat® and Efka® IO 6786 were not sufficiently compatible with ExAmp.

Figure 21:
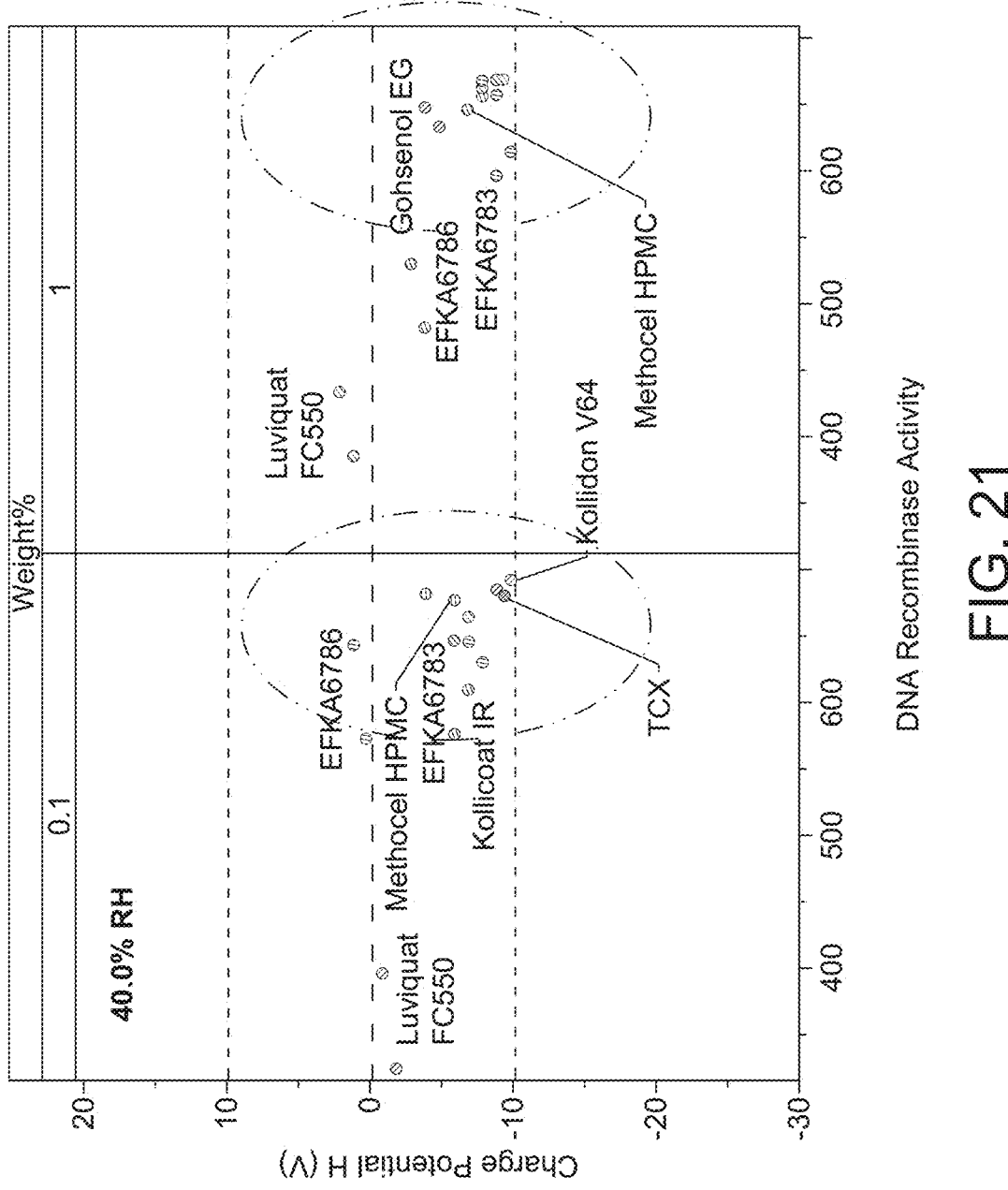
FIG. 21 shows charge potential (via Keyence) measurement (at 40% RH) of powdered lyophilized cake of ExAmp containing additives at different concentration (matrix).

At higher relative humidity (40% RH, FIG. 21), the charge potentials of the powdered lyophilized cakes were decreased, indicative of the small static and tribocharging behaviors.

Since there is interest in larger library of anti-static additives, water-insoluble additives were explored in this ExAmp compatibility assay. DMSO at the same concentration of the additive was added as well to help the aqueous solubility of these hydrophobic additives. Since a lyophilised formulation of TCX V1.0 may contain 7.5% HPBCD, it helps with the aqueous solubility of the additives as well.

Figure 22:
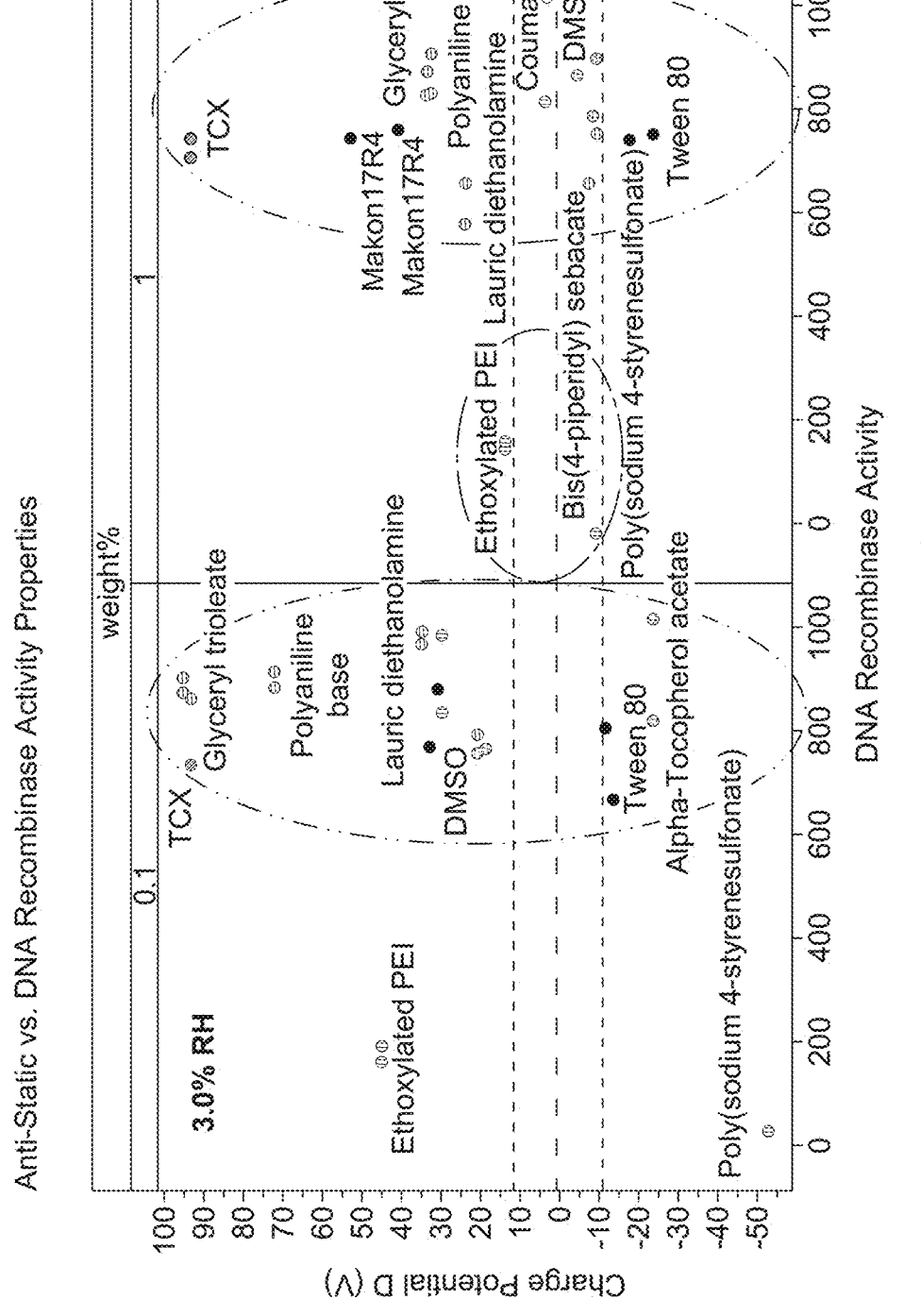
FIG. 22 depicts charge potential (via Keyence) measurement (at 3% RH) of powdered lyophilized cake of ExAmp containing additives at different concentration (matrix).
Figure 23:
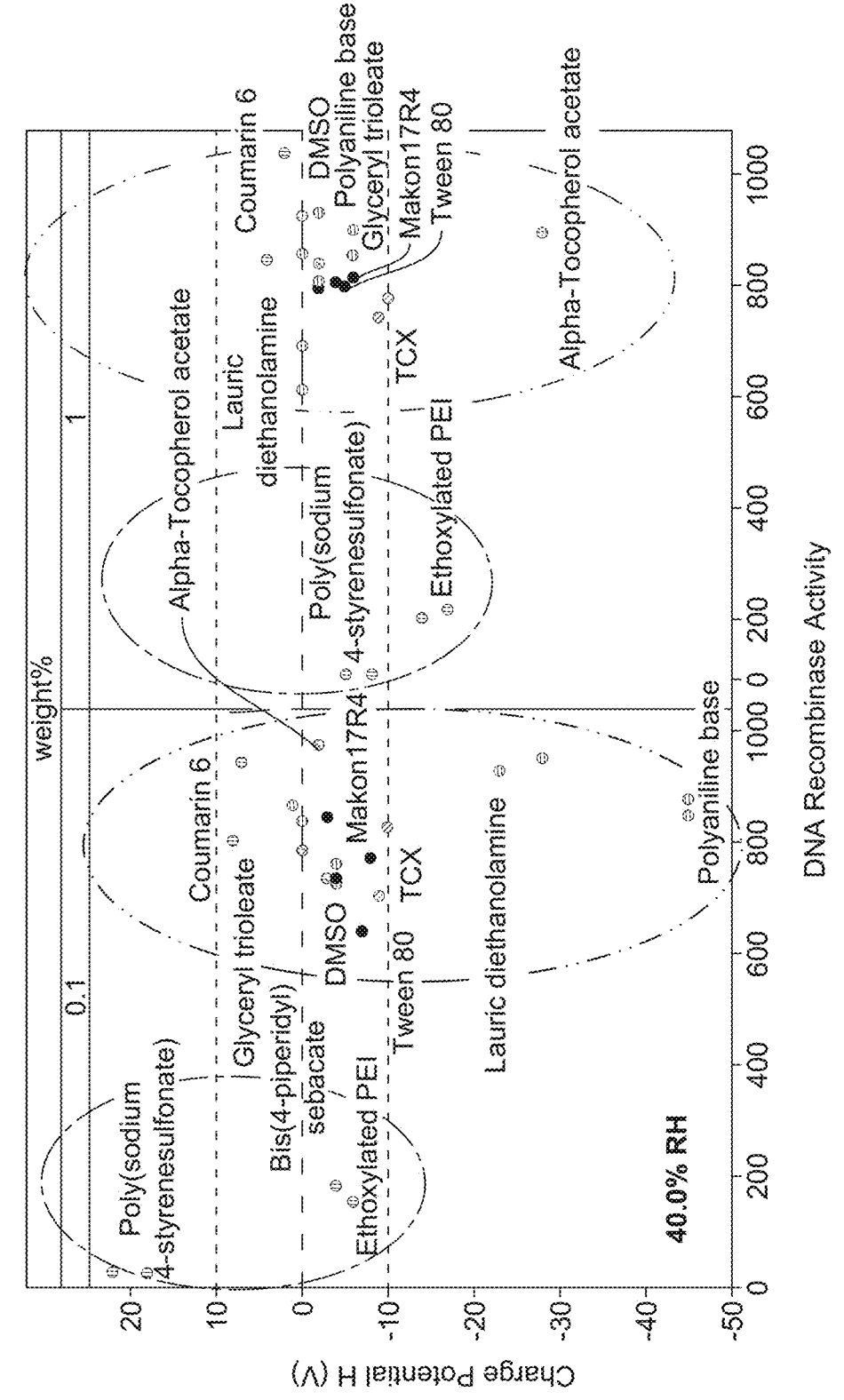
FIG. 23 depicts charge potential (via Keyence) measurement (at 40% RH) of powdered lyophilized cake of ExAmp containing additives at different concentration (matrix).

FIGS. 22 and 23 exhibit the charge potential measurement of powdered lyophilized cake of ExAmp at 3% and 400% relative humidity, respectively. Lauric acid diethanolamide, coumarin 6, tocopherol acetate, bis(4-piperidyl sebacate) and even DMSO were shown to reduce the charge potential of ExAmp powder.

Figure 24:
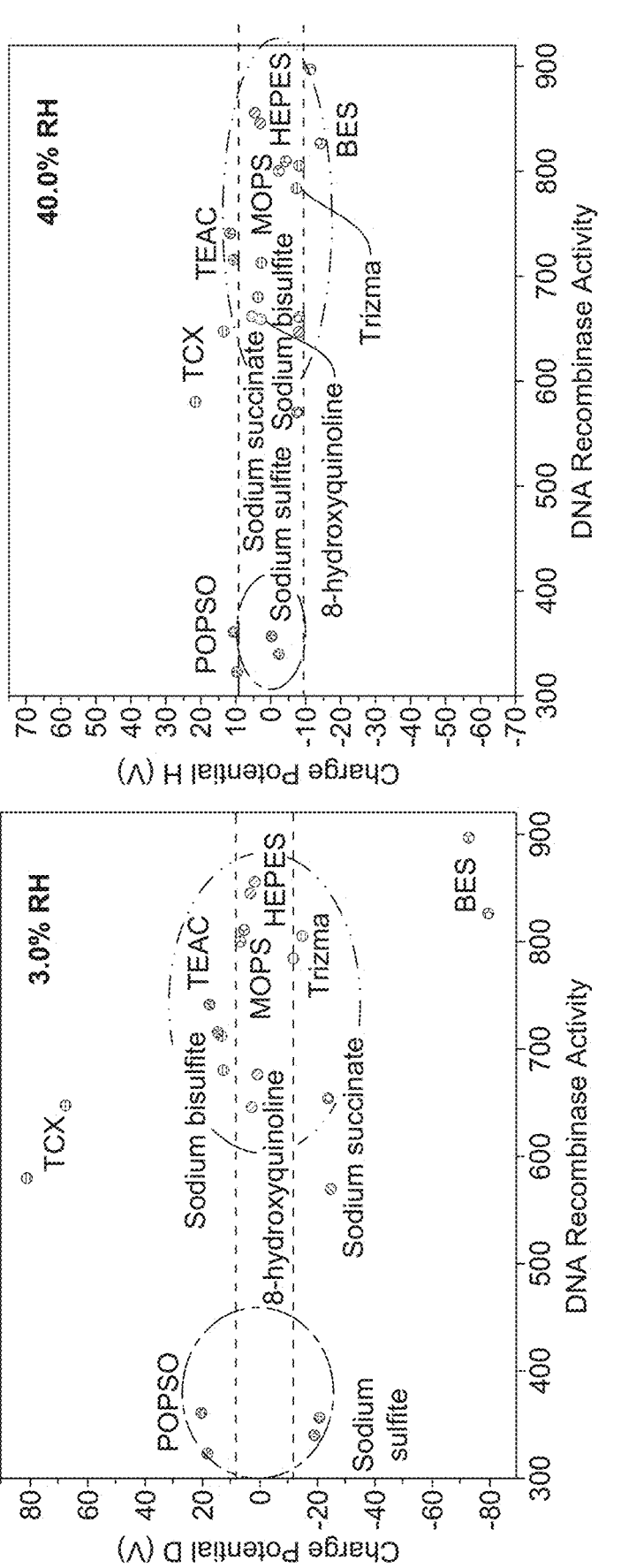
FIG. 24 shows charge potential (via Keyence) measurement (at 3% and 40% RH) of powdered lyophilized cake of ExAmp containing salt/buffer at different concentration (matrix).

The effect of lyo formulation excipients on the charge potential of ExAmp powdered cake was explored (FIG. 24). Many of these excipient are salts and buffers used in the lyophilized formulation anyway. HEPES, MOPS and tetraalkyl ammonium chloride were found to be effective at both concentration (0.1% and 1% w/v spiked into 20% lyophilization formulation) to reduce charge potential of ExAmp powder. This unexpected finding helps with the design of lyophilized formulation, particularly using salt/ buffer, which is also promising to mitigate static and tribo-charging of the lyophilized microspheres format. In particular, they were shown to be compatible with DNA recombinase activity in ExAmp as well.

Example 10—Incorporation of the Additive Into Lyophilized Matrix to Mitigate Static In order to test the anti-static effectiveness of the additives in microspheres, these additives were lyophilized together as matrix format. FIG. 25A-25C shows the incorporation of additives in Atto microspheres as well as fluorescein (FSCN) microspheres as matrix format (both containing 20% trehalose). The anti-static property of the additive is assessed by adhesion of microspheres to container and their charge density is measured by GranuCharge. Low Δq value indicates low tribocharging. The matrix format of 1% Efka® IO 6783 minimized tribocharging. FIG. 25A shows results of a first set of additives tested (Atto 20%, +1% Efka® IO 6783, +1.5% Tris.Hcl, and +1% Tween 20) both in terms of visual results (top) and percent loss (bottom). FIG. 25B shows results of a second set of additives tested (FSCN 20% Ctrl, +1% Efka® IO 6783, +2% Efka® IO 6783, and +1% Efka® IO 6786) both in terms of visual results (top) and percent loss (bottom). FIG. 25C shows Atto and FSCN (both 20% trehalose) are dry-compounded with the help of anti-static agent Efka® IO 6783 in matrix format The adhesion of the microspheres onto glass and plastic (polypropylene) wall of the container indicates their static and tribocharging behaviors. Lyophilised formulation matrix spiked with 1% Efka® IO 6783 appears to demonstrate low static and tribocharging. The charge density measurement using GranuCharge corroborated the anti-static and anti-tribocharging behavior of Efka® IO 6783 (low q0 and Δq values). Moreover, when both Atto and FSCN microspheres are spiked with Efka® IO 6783, they can blend more homogeneously.

Figure 26A:
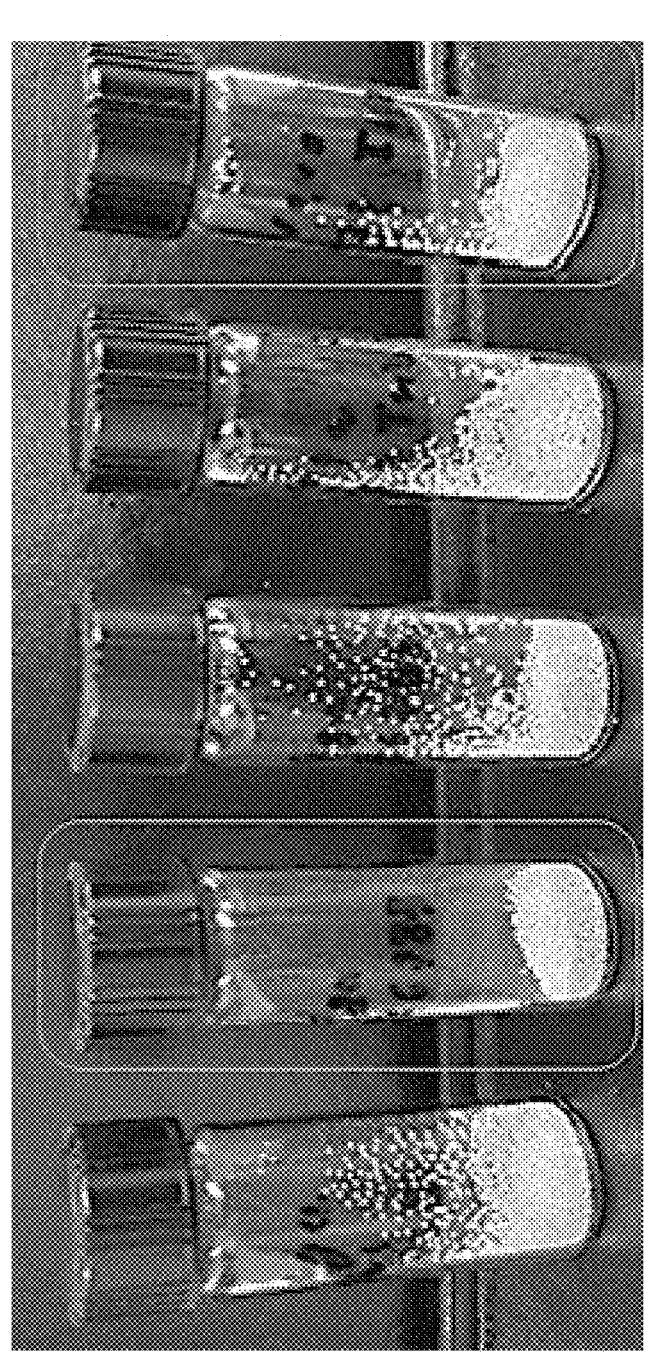
FIGS. 26A-26C show ffN microspheres containing additives as matrix format. The anti-static property of the additive is assessed by adhesion to container and measured by GranuCharge.
Figure 26B:
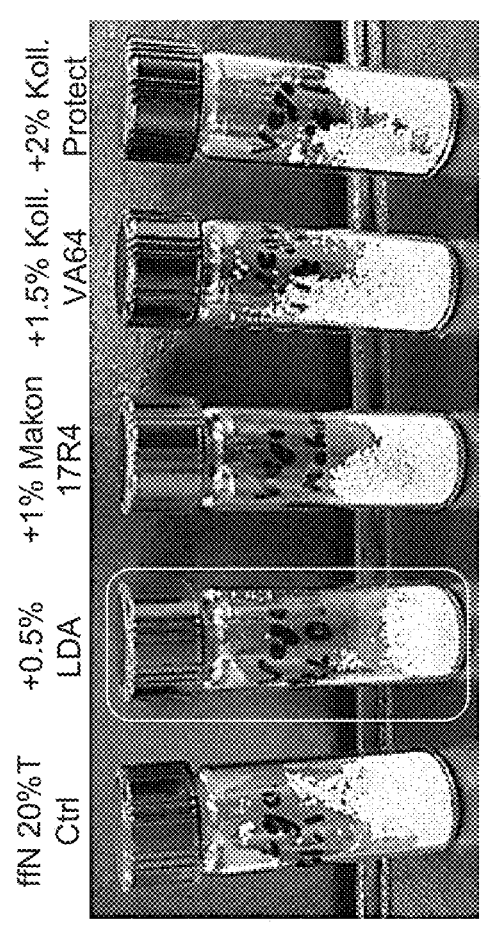
Figure 26C:
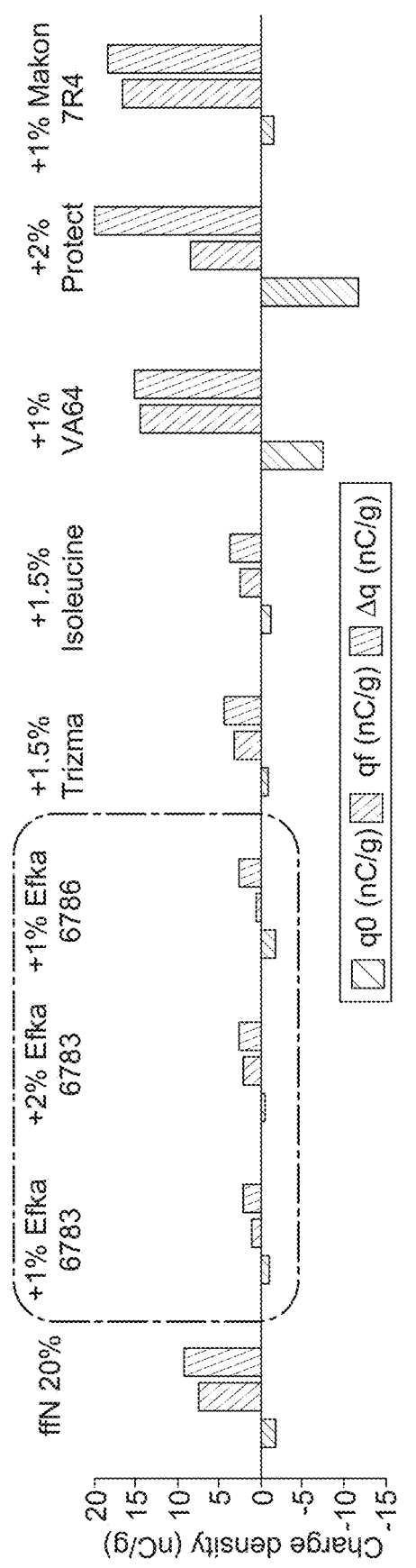
Figure 27A:
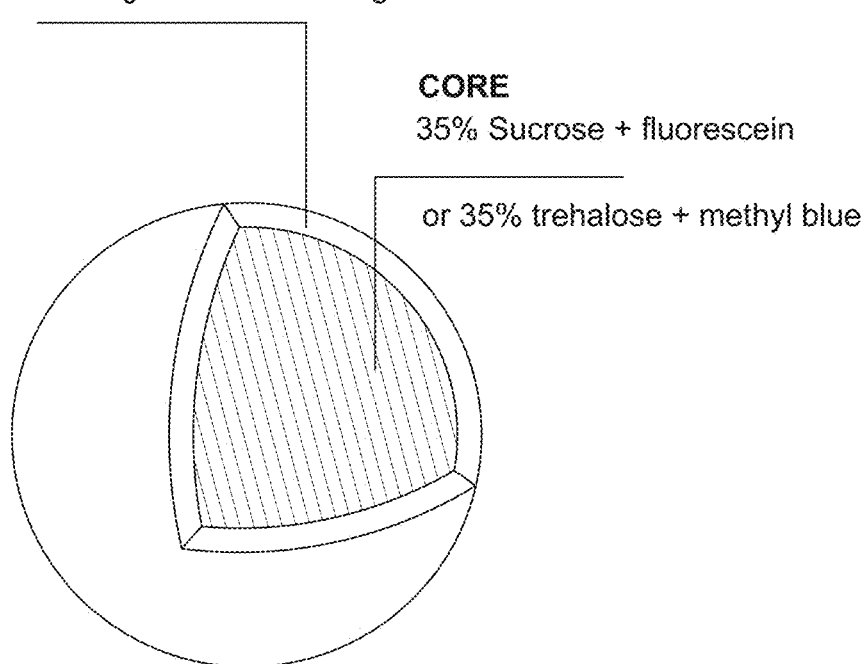
FIGS. 27A-27E show FSCN (fluorescein) and MB (methylene blue) microspheres coated with Eudragit® L100 and magnesium stearate. The static and tribocharging behavior of the microspheres are mitigated through the presence of coating, as shown by GranuCharge measurement and microspheres dry blending experiments.
Figure 27B:
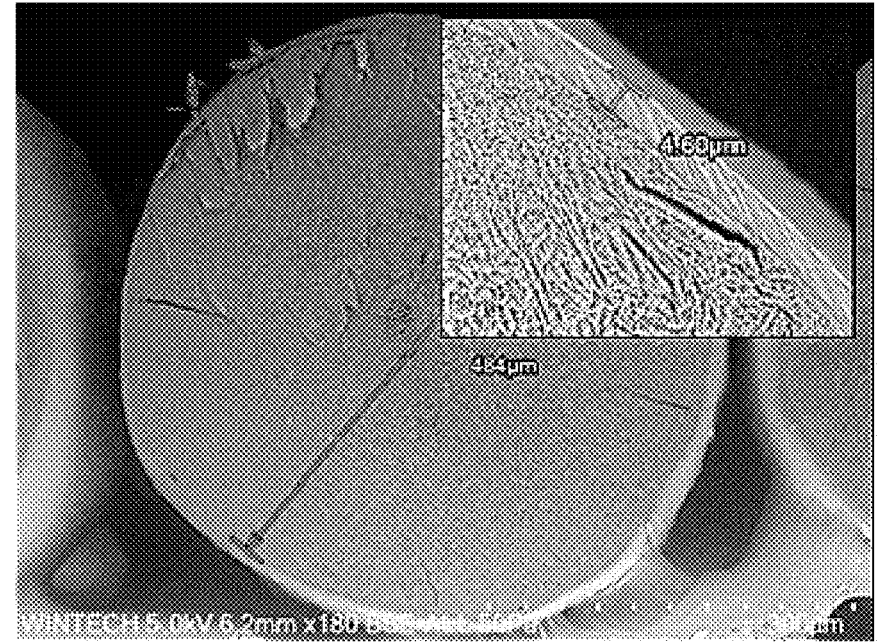
Figure 27C:
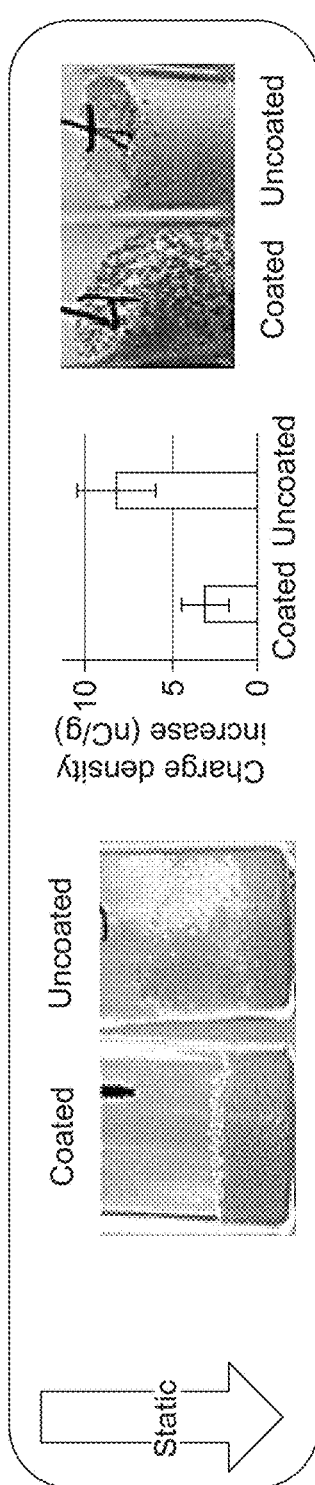
Figure 27D:
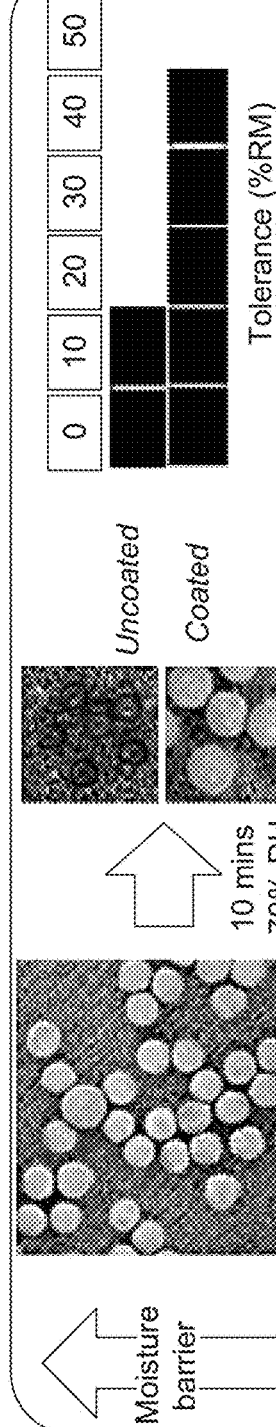
Figure 27E:
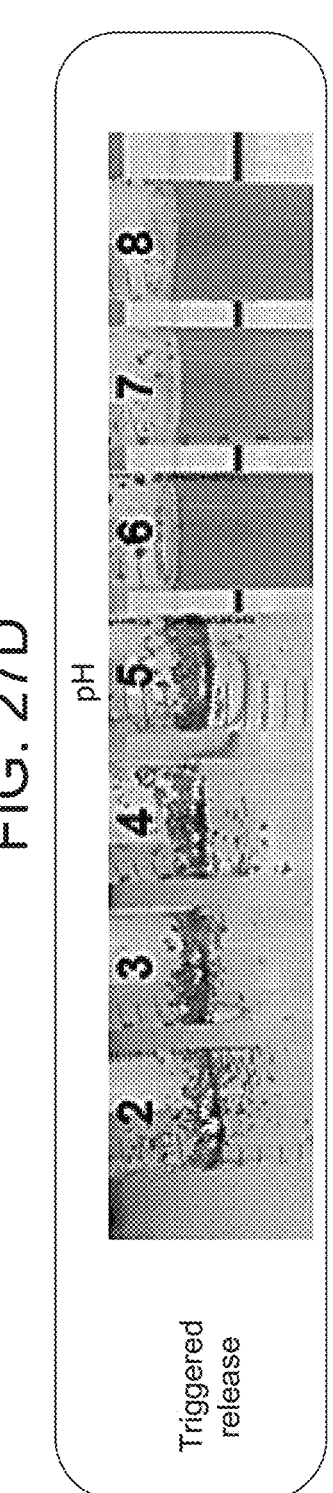

Static and tribocharging behaviors of ffN microspheres were screened in the presence of additives (as matrix format). Efka® IO 6783, lauric acid diethanolamide and isoleucine seemed to be effective in glass container. Nevertheless, Efka® IO 6783, Efka® IO 6786 and Makon® 17R4 seemed to be effective in plastic container. GranuCharge measurement provided the charge density of the microspheres containing additives in matrix format (FIG. 26A-26C). ffN microspheres containing additives as matrix format are shown in FIGS. 26A-26C. The anti-static property of the additive is assessed by adhesion to container and measured by GranuCharge. FIG. 26A shows visual results of a first set of additives (ffN+25% T Ctrl, +1% Efka® IO 6783, +1% Efka® IO 6786, +1.5% Tris.HCl, +2% isoleucine). FIG. 26B shows visual results of a second set of additives (a second ffN+20% T Ctrl, +0.5% LDA, +1% Makon® 17R4, +1.5% Kollidon® VA64, +2% Kollicoat® Protect). FIG. 26C demonstrates charge density of various additives tested in FIGS. 26A and 26B.

Low charge density from Efka® IO 6783 and Isoleucine containing microspheres corroborated with the behavior inside glass container.

Example 11—Incorporation of the Additive Onto Coating of Microspheres to Mitigate Static Water-insoluble additives, like magnesium stearate, can be applied as coating on the surface of microspheres, since typically organic solvent are used in the spray-coating process of microspheres. FIGS. 27A-27E demonstrates that Eudragit® L100 and magnesium stearate coating decreased charge density of the microspheres, measured by GranuCharge. As exhibited by matrix format, the adhesion of coated microspheres onto glass and plastic containers is greatly reduced due to the presence of the additive in the coating. Dry blending of microspheres (core: trehalose and dye) can be achieved with coating. Nevertheless, upon rehydration magnesium stearate can be a challenge due to its hydrophobicity. If such additive can be separated in situ, through centrifugation or filtration membrane, magnesium stearate can be an attractive anti-static additive for the microspheres.

Figure 28A:
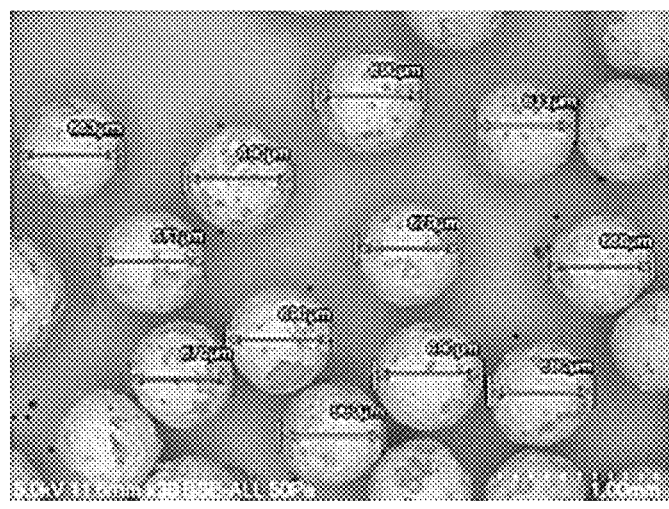
FIGS. 28A-28F show SEM images of fluorescein (FSCN), DNA recombinase/BSA, and ffNs microspheres coated with Kollidon® VA64, Efka® IO 6783, and PEG at different coating level.
Figure 28B:
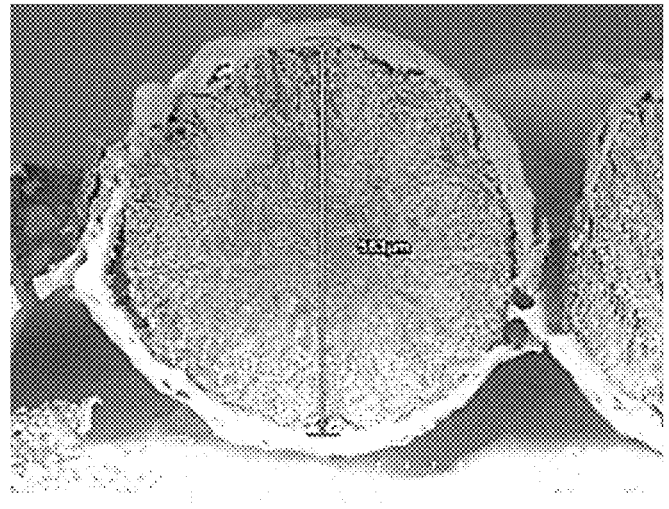
Figure 28C:
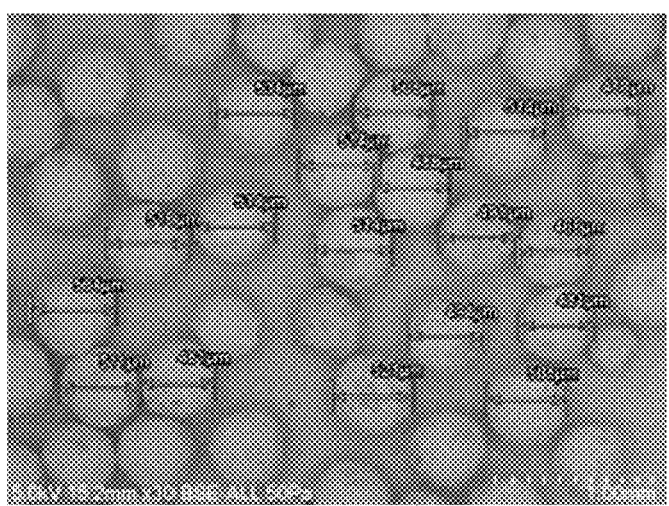
Figure 28D:
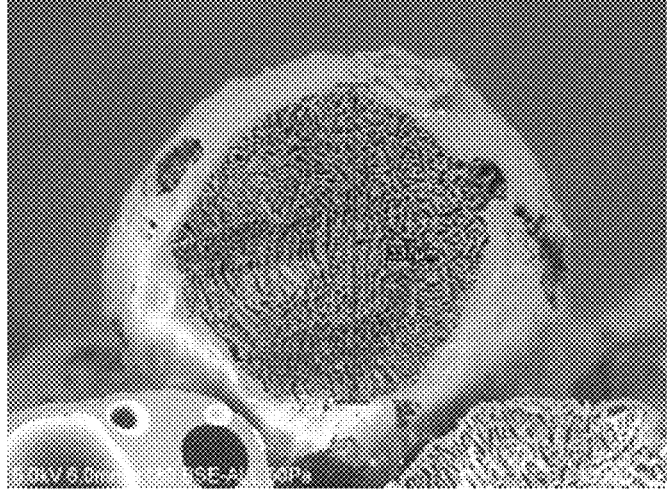
Figure 28E:
Figure 28F:
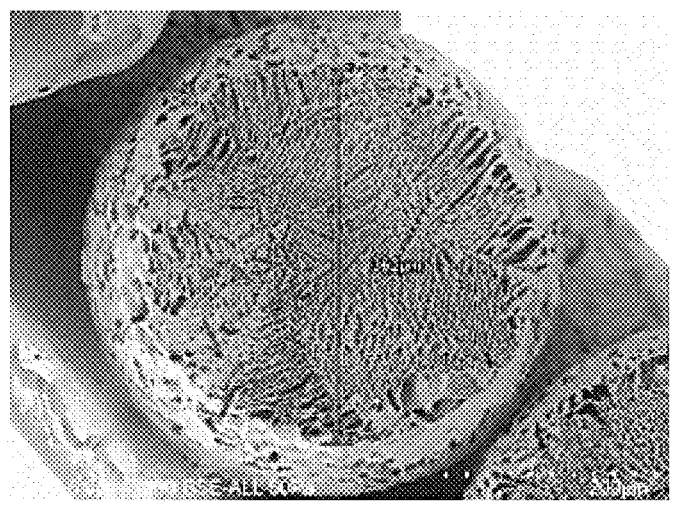

Based on the ffN, sequencing and ExAmp compatibility screening, Efka® IO 6783, Kollidon® VA64, Kollicoat® IR, and PEG were selected as alternative water-soluble coating materials. FIGS. 28A-28F display the SEM images of fluorescein (FSCN). DNA recombinase/BSA and ffNs microspheres coated with Kollidon® VA64, Efka® IO 6783, and PEG at different coating level. The presence of the coating can be observed encapsulating the lyophilized microspheres. Images of a plurality (FIG. 28A) and a single (FIG. 28B) microspheres of 800 μm FSCN Wurster-Spray 20% coated with Kollidon VA64 and Efka® IO 6783 and PEG (#6) are shown in FIGS. 28A and 28B. Images of a plurality (FIG. 28C) and a single (FIG. 28D) microspheres of cryo ion-mill SEM of Rec/BSA 15% coated with Kollidon VA64 and Efka® IO 6783 and PEG (#8) are shown in FIGS. 28C and 28D. Images of a plurality (FIG. 28E) and a single (FIG. 28F) microspheres of cryo ion-mill SEM of an ffN 10% coated with Kollidon VA64 and Efka® IO 6783 and PEG (#11) are shown in FIGS. 28E and 28F.

Figure 29B:
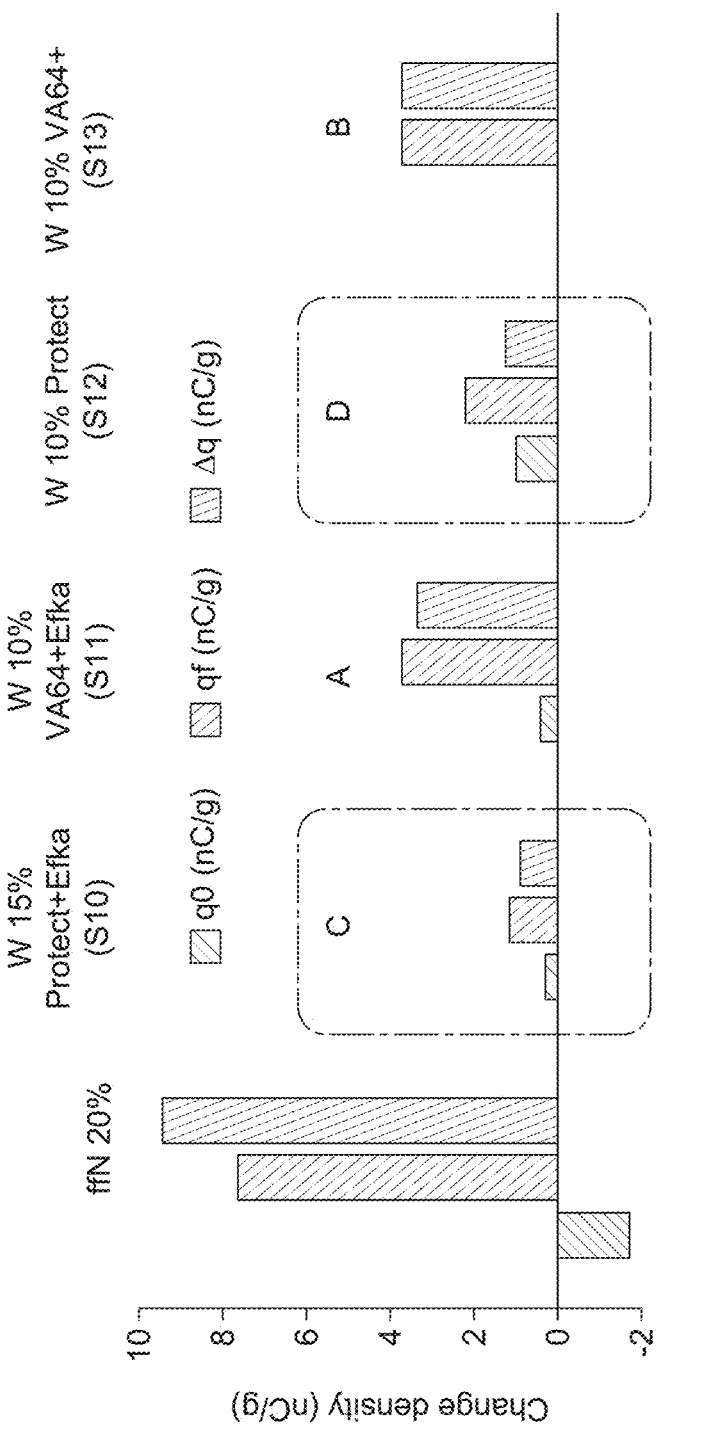

Static and tribocharging behavior of the coated microspheres were assessed in comparison with the uncoated control microspheres (FIGS. 29A-29B). While the uncoated control microspheres exhibit high tribocharging in the container adhesion experiment and GranuCharge measurement, the presence of coating seemed to decrease the charge density of the microspheres. In particular, the presence of Efka® IO 6783 reduced the adhesion of the coated microspheres onto the glass container. Nevertheless, coating containing Kollicoat® Protect appeared to exhibit lower tribo-charging measured by GranuCharge.

Figure 30B:
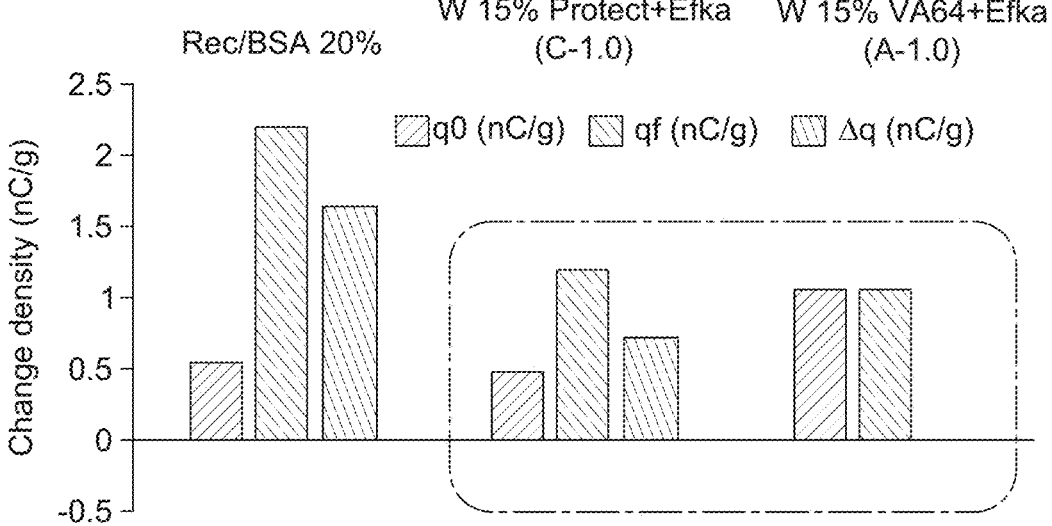
Figure 31A:
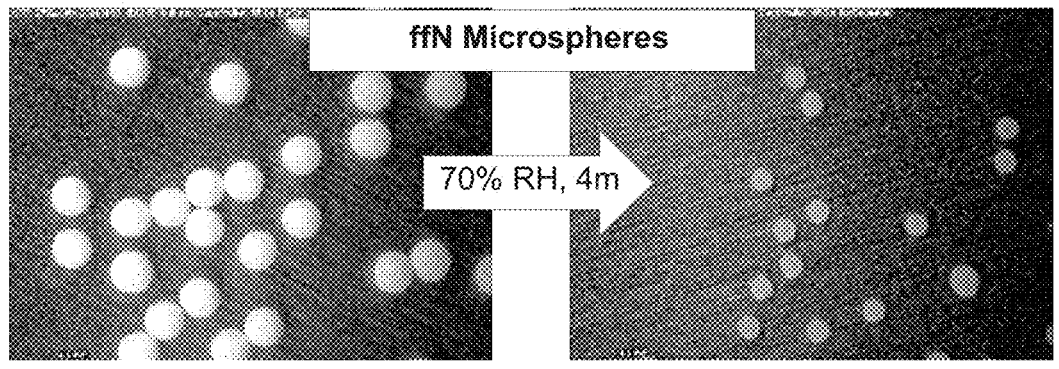
FIGS. 31A-31F depict stability of compositions described herein.
Figure 31B:
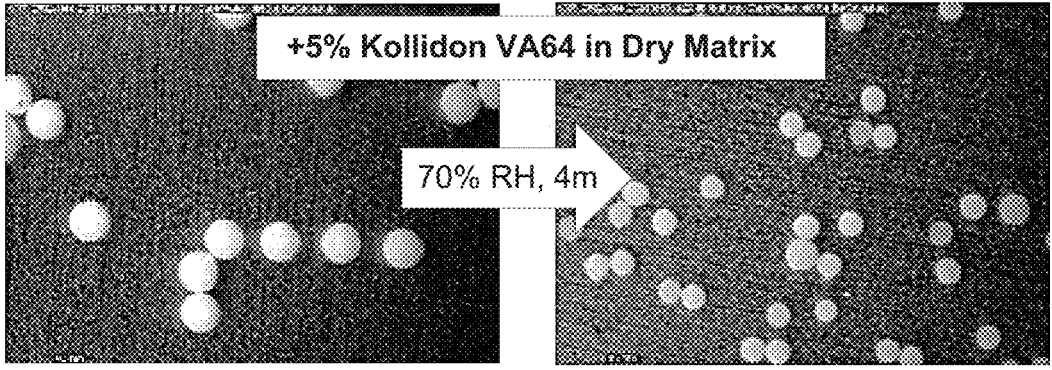
Figure 31C:
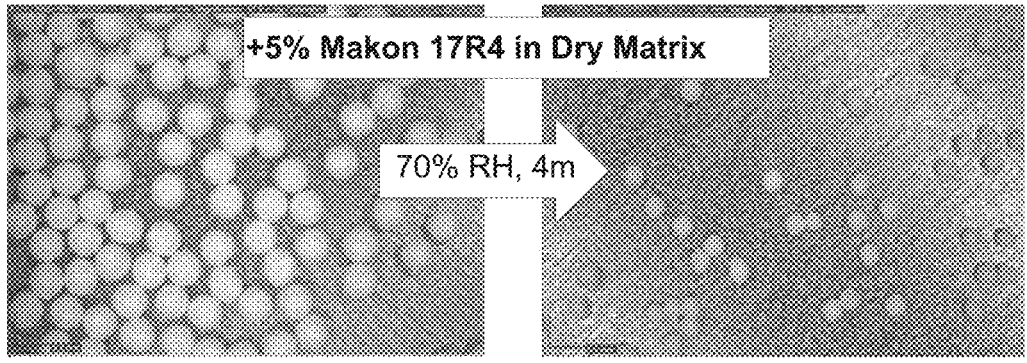
Figure 31D:
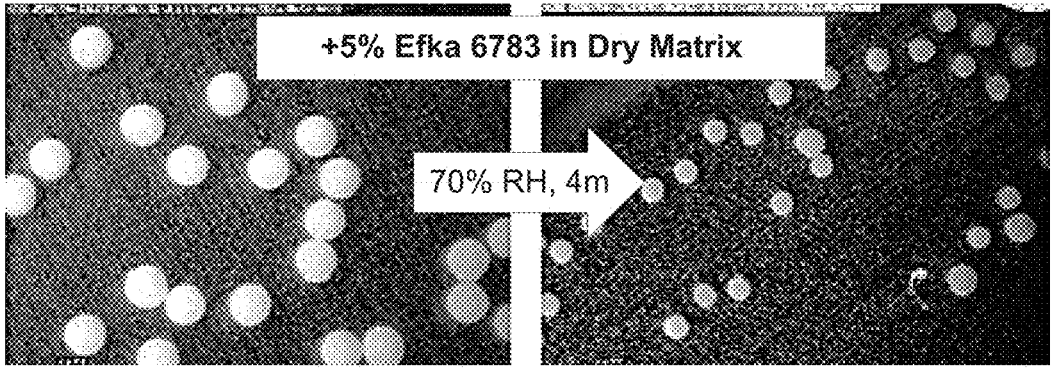
Figure 31E:
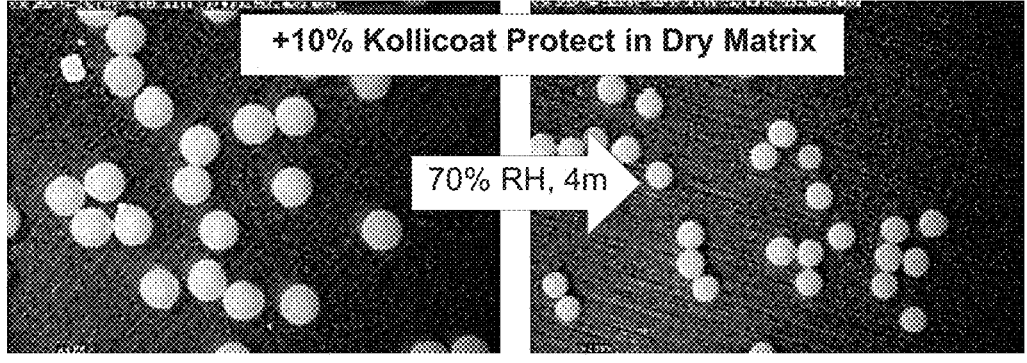
Figure 31F:
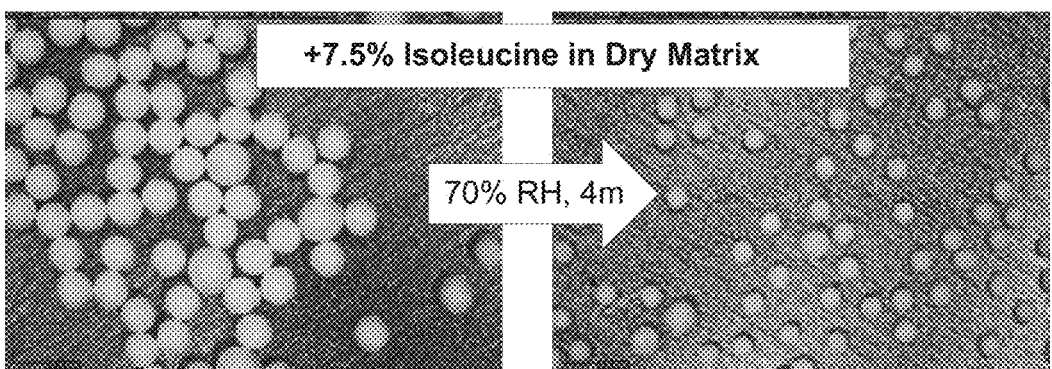

The same coating formulation (A: Kollidon® VA64 vs C: Kollicoat® Protect) were applied onto DNA recombinase/BSA microspheres. Different coating levels were investigated in the coating process of these microspheres (FIGS. 30A-30B). Coating level of 7.5% (weight gain through coating) did not improve the adhesion of the microspheres onto glass and plastic containers significantly. Nevertheless, at higher coating level 15% the adhesion of coated microspheres onto plastic container was greatly reduced. This was evidenced by lower charge density Δq value from GranuCharge measurement, which indicated decreased tribocharging. It is noteworthy that Kollicoat® Protect coating seemed to be more effective on glass container, meanwhile both coating materials (Kollidon® VA64 and Kollicoat® Protect) when they contain Efka® IO 6783 decreased the adhesion of coated microspheres onto plastic containers.

Stability of compositions described herein, including, ffN microspheres, 5% Kollidon® VA64 in dry matrix, 5% Makon® 17R4 in dry matrix, 5% Efka® 6783 in dry matrix, 10% Kollicoat® Protect in dry matrix, and 7.5% isoleucine in dry matrix under varying moisture and time conditions, are shown in FIGS. 31A-31F.

Figure 32A:
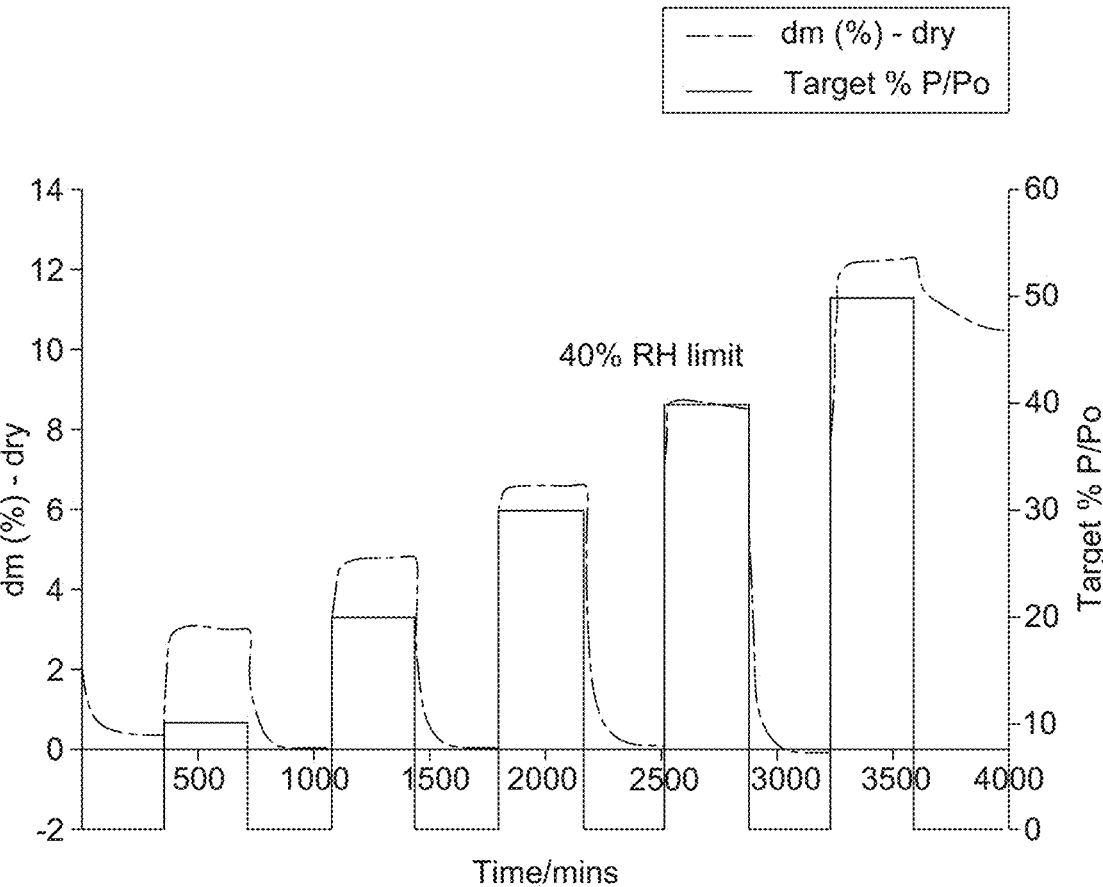
FIGS. 32A-32F show results of measurement of tolerance of microspheres against relative humidity by dynamic vapor sorption. Isoleucine in matrix increases humidity tolerance of ffN microspheres.
Figure 32B:
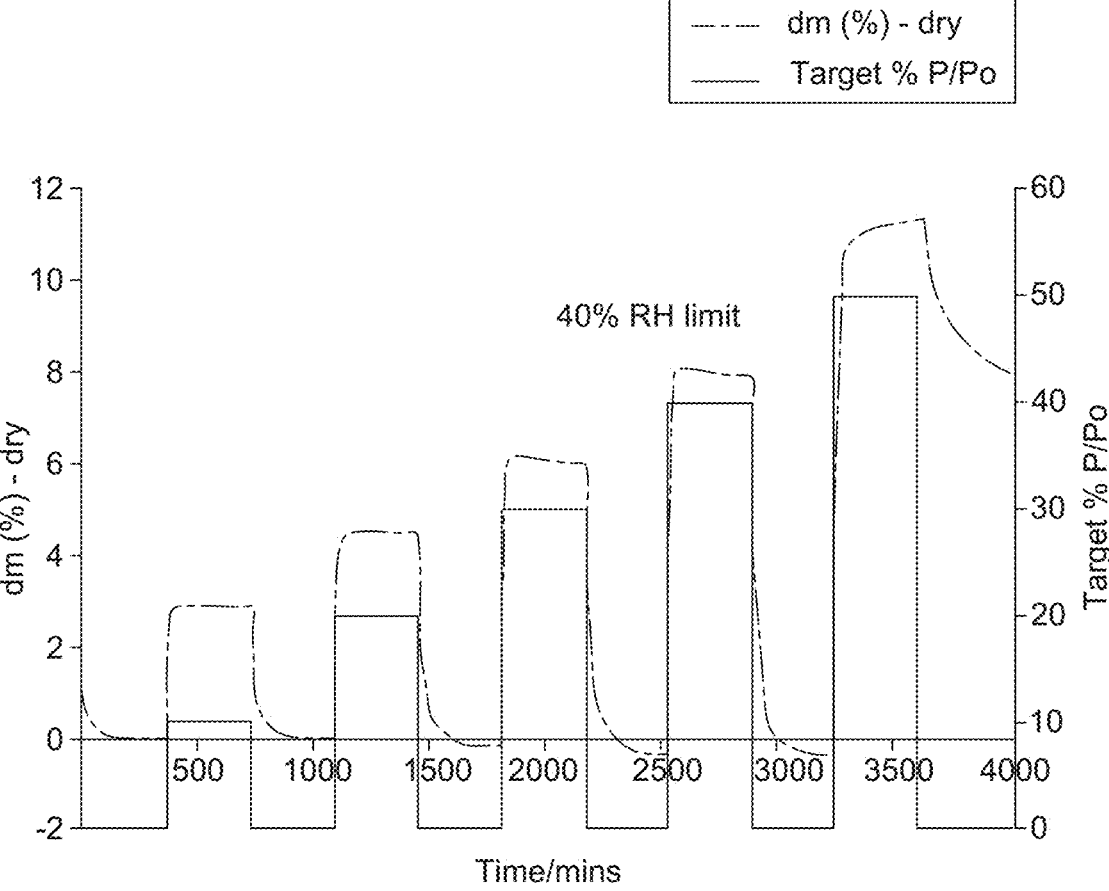
Figure 32C:
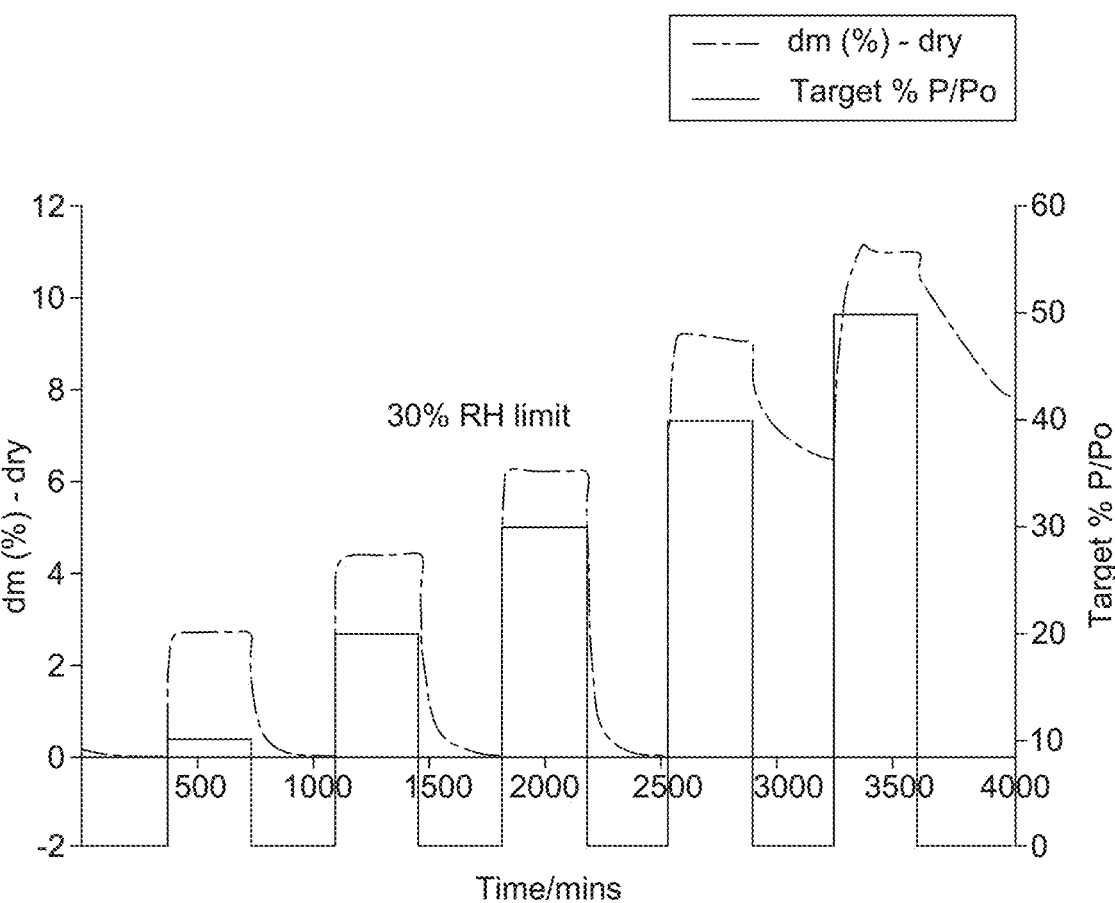
Figure 32D:
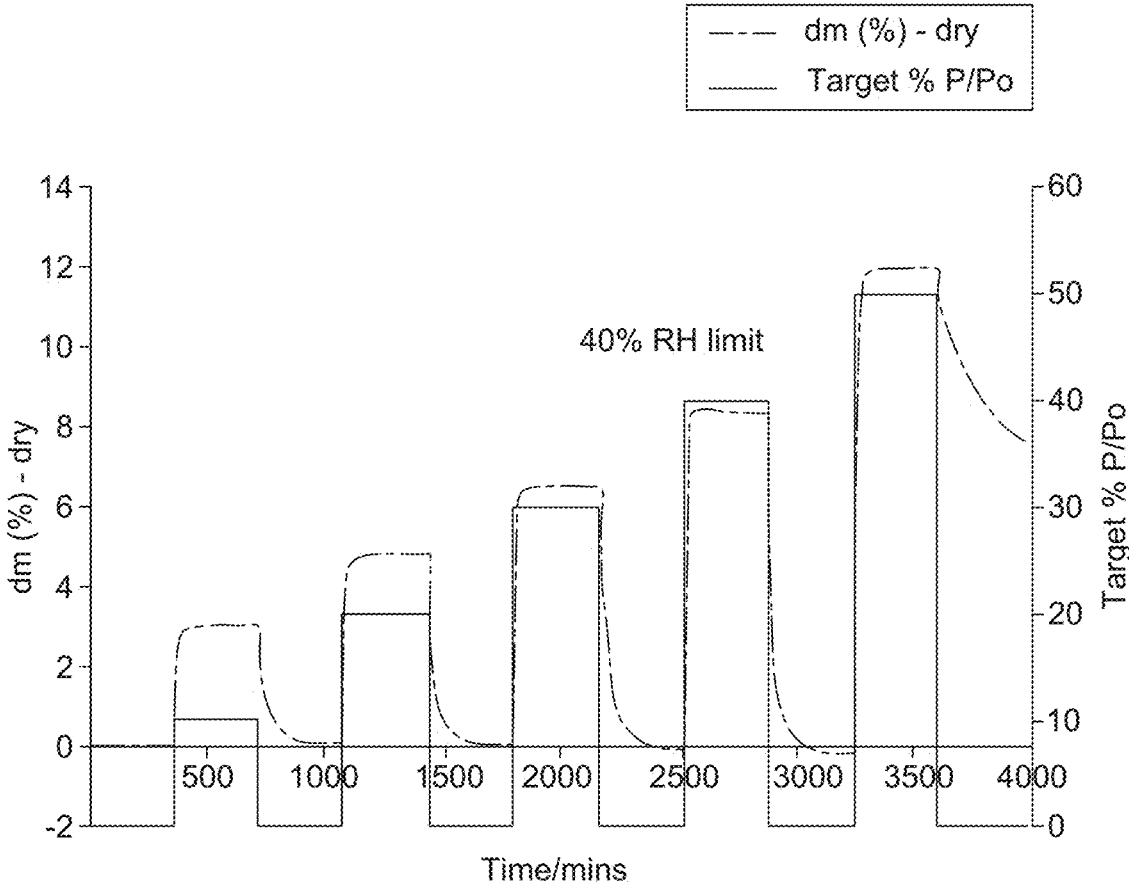
Figure 32E:
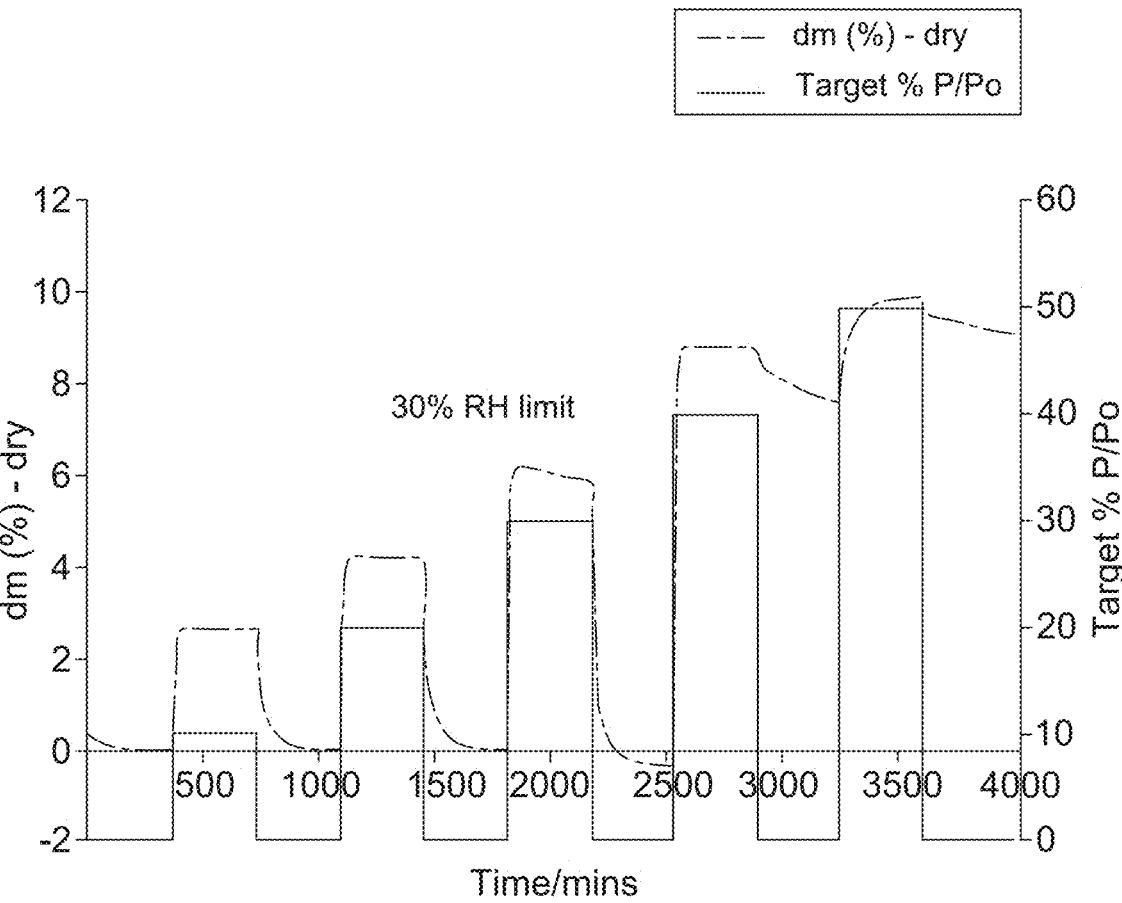
Figure 32F:
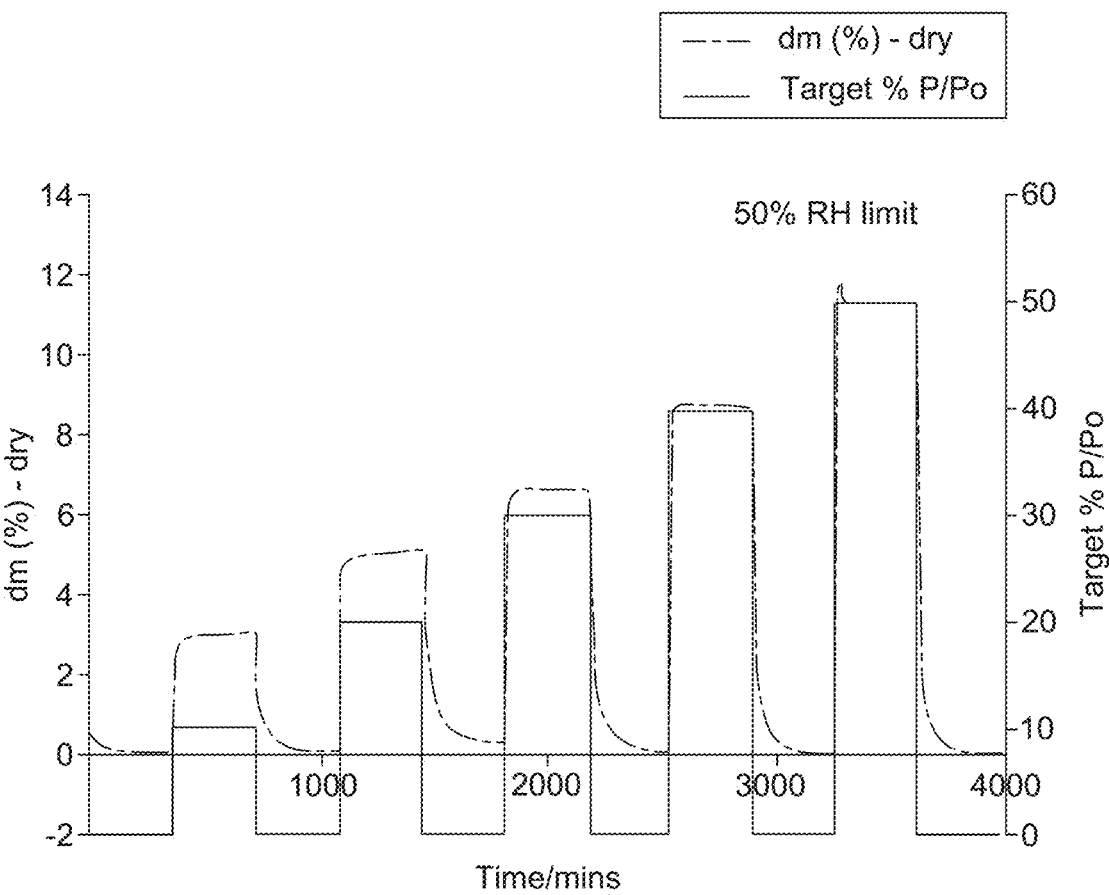
Figure 33B:
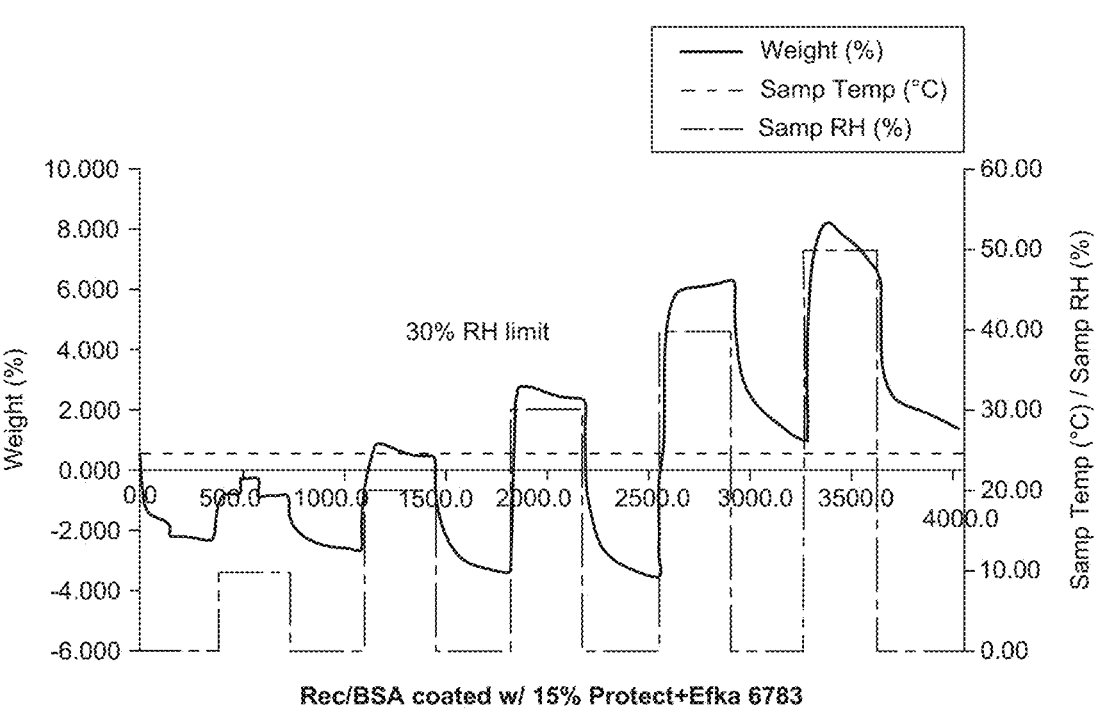
Figure 33C:
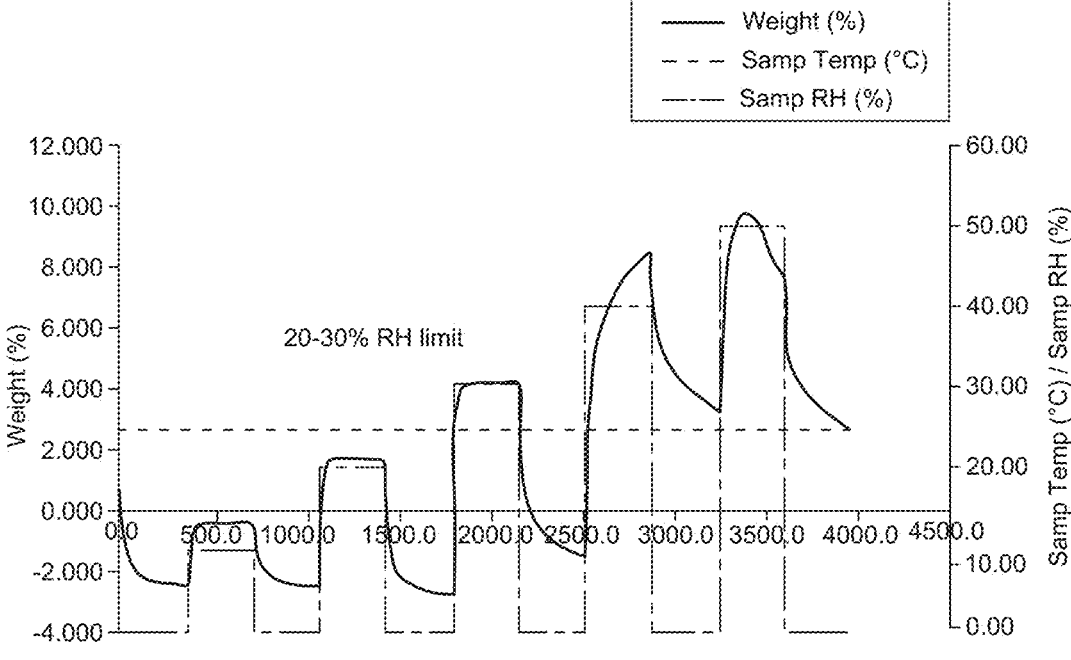
Figure 33D:
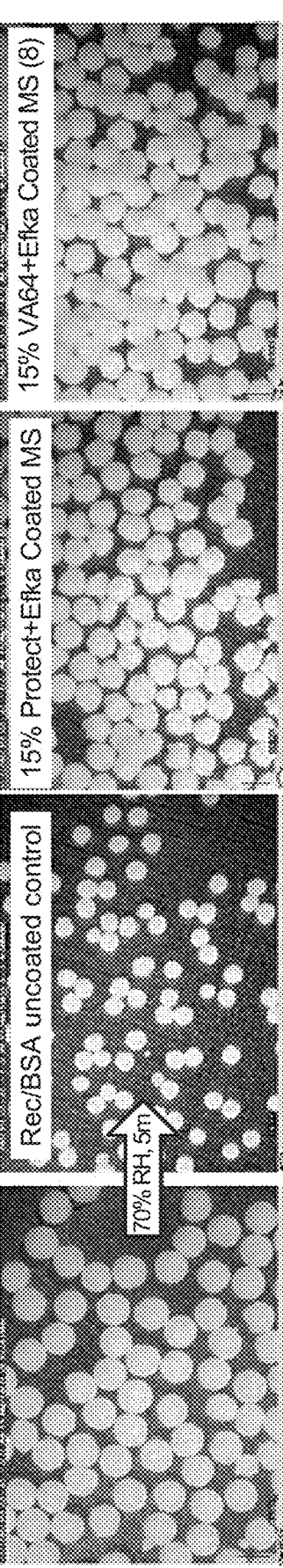

Results of measurement of tolerance of microspheres against relative humidity by dynamic vapor sorption are shown in FIGS. 32A-32F. Isoleucine in matrix increases humidity tolerance of ffN microspheres. FIG. 32A demonstrates results of a ffN Ctrl (18% T, 2% HCD) are shown in FIG. 32A, results of 2% Kollicoat® Protect matrix (10% dry) are shown in FIG. 32B, results of +1% Efka® IO 6783 Matrix (5% dry) are shown in FIG. 32C, results of 1% Kollidon® VA64 matrix (5% dry) are shown in FIG. 32D, results of +1.5% Trizma matrix (7.5% dry) are shown in FIG. 32E, and results of +1.5% isoleucine matrix (7.5% dry) are shown in FIG. 32F.

Figure 34A:
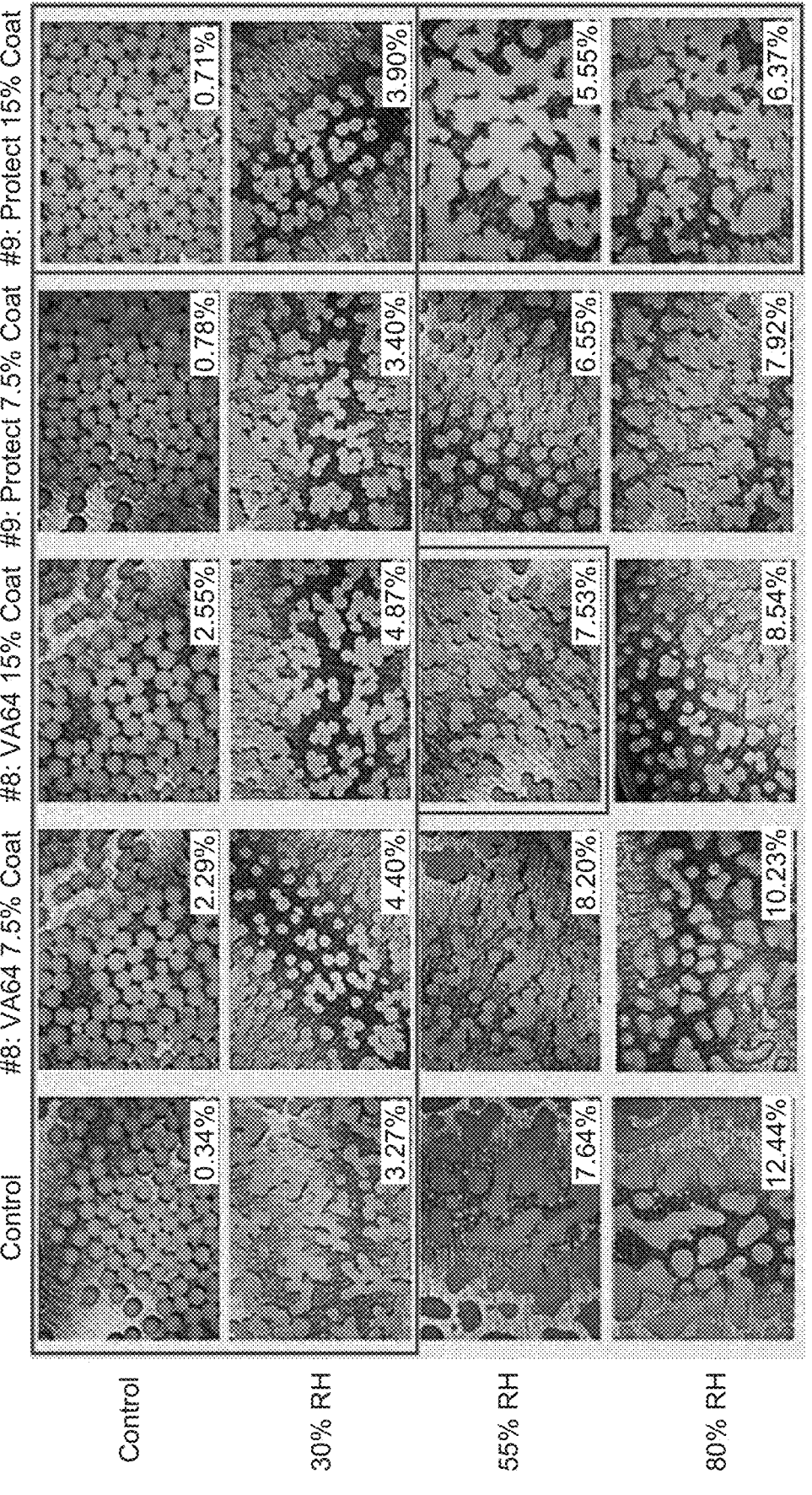

Results of Kollicoat® Protect and Kollidon® VA64 coating, which provided improved moisture protection of Rec/BSA MS, are shown in FIGS. 33A-33D. Coating minimizes moisture uptake of Rec/BSA microspheres (FIGS. 34A-34B). Rec/BSA microspheres were tested using two different coating materials: Kollidon® VA64 (#8) and Kollicoat® Protect (#9). The coating thickness was adjusted by coating level or how much coating weight applied on the surface of microspheres. In this case, 7.5% and 15% coating level were demonstrated, which was controlled by the amount of coating material sprayed onto the microspheres. In particular, Kollicoat® Protect coating performed better than Kollidon® VA64 in terms of moisture barrier. These are unexpected findings. Microspheres with 15% coating level demonstrates improvement over uncoated control. In particular, they show a 10% higher tolerance to humidity (by dynamic vapor sorption, DVS), slower moisture uptake at different humidity level, and less shrinkage and melting of microspheres with coating. Microspheres with 7.5% and 15% coating level containing Kollicoat® Protect performs better than Kollidon® VA64.

Numerous unexpected results were found upon the discovery of the present disclosure. For example, additives were identified that are compatible against ExAmp activity. Second, additives were identified that are compatible against ffN stability. Third, additives were identified that are compatible against sequencing. Fourth, additives were identified that are demonstrating anti-static properties (minimizing tribocharging) in dry format as lyophilized microspheres (matrix format). Fifth, additives were identified that are demonstrating anti-static properties (minimizing tribocharging) coated microspheres (blend of excipients as coating formulation).

Example 12—Discussion of Shell Additives and Core Additives

Various shell additives are found to improve stability of both the shell and core of the compositions described herein.

Water soluble polymers, such as hydroxypropyl methylcellulose (HPMC), polyvinyl pyrrolidone, and polyvinyl alcohol, have been used in film coating of pharmaceutical tablets. These materials are used due to their commercial availability in accordance with the present disclosure. Time-delayed release can be exemplified by HPMC or Methocel coating.

Cationic and anionic charged polymers are used as film coating of pharmaceutical coating due to their entero-solubility or enteric protection. Cationic charged polymer is exemplified as amino dimethyl or diethyl methacrylate copolymer, which are known commercially as Eudragit® E and Kollicoat® Smartseal 30D. Anionic charhed polymer is exemplified as methacrylic acid copolymers or Eudragit® S/L, whereby L100-55, L100 and S100 are used for triggered-release at pH 5.5, 7.0, and 8.0, respectively. Another anionic polymers are cellulose derivatives, such as carboxymethylcellulose (Akucel), cellulose acetate phthalate (Aquacoat CPD), cellulose acetate butyrate (Eastman CAB). These charged polymers are used due to their commercial availability in accordance with the present disclosure.

Water-insoluble polymers are typically designed to give sustained or prolonged release of drugs. As coating materials these polymers can be blended with water-soluble polymers, such as PEG or PVP, whereby the latter form pores (porogen) to enable drugs to diffuse slowly from the core. These water-insoluble polymers are exemplified as ethylcellulose (Ethocel), cellulose acetate (Opadry CA), ammonio methacrylate copolymers (Eudragit® RS100/RL100), and polyvinyl acetate (Kollicoat® SR). These polymers are used due to their commercial availability in accordance with the present disclosure.

In summary, materials used for controlled release may include, for example, materials for immediate release such as Opadry AMB (II), Opadry II (TF), AquaPolish, Starch 1500, Methocel E3, E5, Kollidon® VA64, Kollicoat® Protect/IR, and Soluplus. Other materials for controlled release may include sustained release materials such as Eudragit® RL PO, Eudragit® RS PO, Methocel E15, K4M, Kollidon® SR (30D), Surelease, Ethocel/Klucel, Methocel E15, K4M, Aquacoat, Opadry CA. Other materials for controlled release may include delayed release materials such as Kollicoat® MAE-100, Eudragit® L100, Eudragit® S100, Sureteric, HPMC acetate succinate, or CMC.

Typically, polymers that are used for moisture barrier film coating exhibit low water permeability, which are exhibited often by water-insoluble polymers. Nevertheless, water-soluble polymers, such as Kollidon® VA64, Kollicoat® Protect, Eudragit® L100/S100 were investigated for their moisture uptake as well. Often high coating thickness/level (≥20%) or the addition of hydrophobic/water-insoluble additive, such as steric acid, help to decrease moisture uptake.

Materials that may be used further include those described in Table 3 below. These materials are reviewed based on their chemical and physical properties. Their potential functions for moisture barrier and static mitigation are estimated based on the commercial product specification and chemical properties.

TABLE 3

Material Review and Selection.

| | Function | Water-Solubility | Viscosity | Moisture Barrier | Anti-static |
|---|---|---|---|---|---|
| PVP copolymer i.e., BASF Kollidon ® VA64 | Tablet binder, film coating | Yes, 6:4 PVP:PVAc, can be combined with sugar | Low: 20 mPa · s at 20% in water (MW 45-75 kDa) | Yes, less hygroscopic than Kollidon ® 30 | No, maybe with TiO$_2$ |
| Luviquat ® Polyquaternium 1 6 | Conditioner, anti-static (hair care) | Yes, PVP & quart. Pvinyl-imidazole | Low at K-value of K −30: <10 mPs · s at 10% (40-80 kDa) | No. very hydrophilic | Yes, Luviquat ® Excellence and FC 550 (6.0 and 3.3) |
| HPMC (i.e., Dow Methocel K3, E5) | Film coating. ShinEtsu Pharmacoat 603-615 | Yes, at 0-30° C.: K3, E3, E5, E6, E15, E50 | Low (LV): 2-50 mPa · s at 2% (MW 10-25 kDa) | No, maybe mixed w/MC A15 or SM-4 | No, maybe with TiO$_2$ (in Opadry 11) |
| PVA (i.e., Colorcon Opadry ® AMB II) | Film coating. Exist as II, AMB and AMB II | Yes, PEG-containing AMB maybe better | Medium: 110 mPa · s at 20%, lower than AMB | Yes, better than AMB and II | Maybe due to TiO$_2$ |
| PVA (i.e., BASF Kollicoat ® IR, Protect) | Film coating. As IR/Protect (+40% PVA) | Yes, 3:1 PVA:PEG graft. Protect: +40% PVA | Medium: IR 115 mPa · s at 20%, MW 45 kDa. Protect 240 mPa · s. | Yes, Kollicoat ® Protect | No, maybe with TiO$_2$, Inherently, contains 0.2% SiO$_2$ |

TABLE 3-continued

| | | | | | |
|---|---|---|---|---|---|
| | | | Material Review and Selection. | | |
| | Function | Water-Solubility | Viscosity | Moisture Barrier | Anti-static |
| Eudragit ® L100 (L12.5) L100-55 | Enteric film coating. 1:1 PMAA:PMMA 1:1 PMAA:PEA | Yes, pH >10 (1N NaOH) or pH >7 (1N buffer, i.e.. Tris). | Medium: L100 MW 125 kDa (50-200 mPa · s) L100-55 MW 320 kDa | Yes, L100-55 better than L100 | No, maybe with $TiO_2$ |

Figure 35:
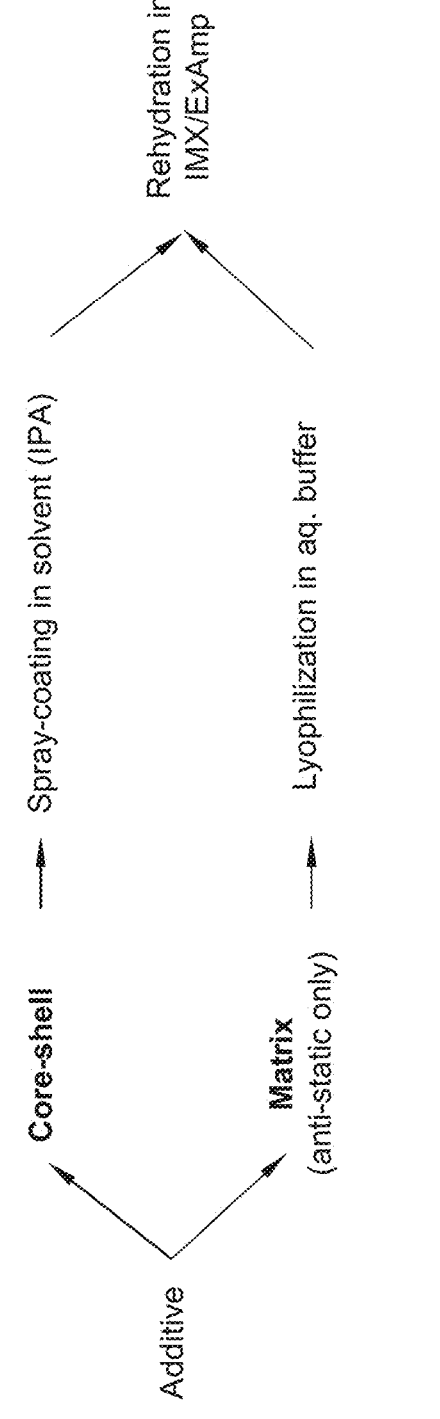
FIG. 35 depicts a concept for solubility screening.
Figure 37A:
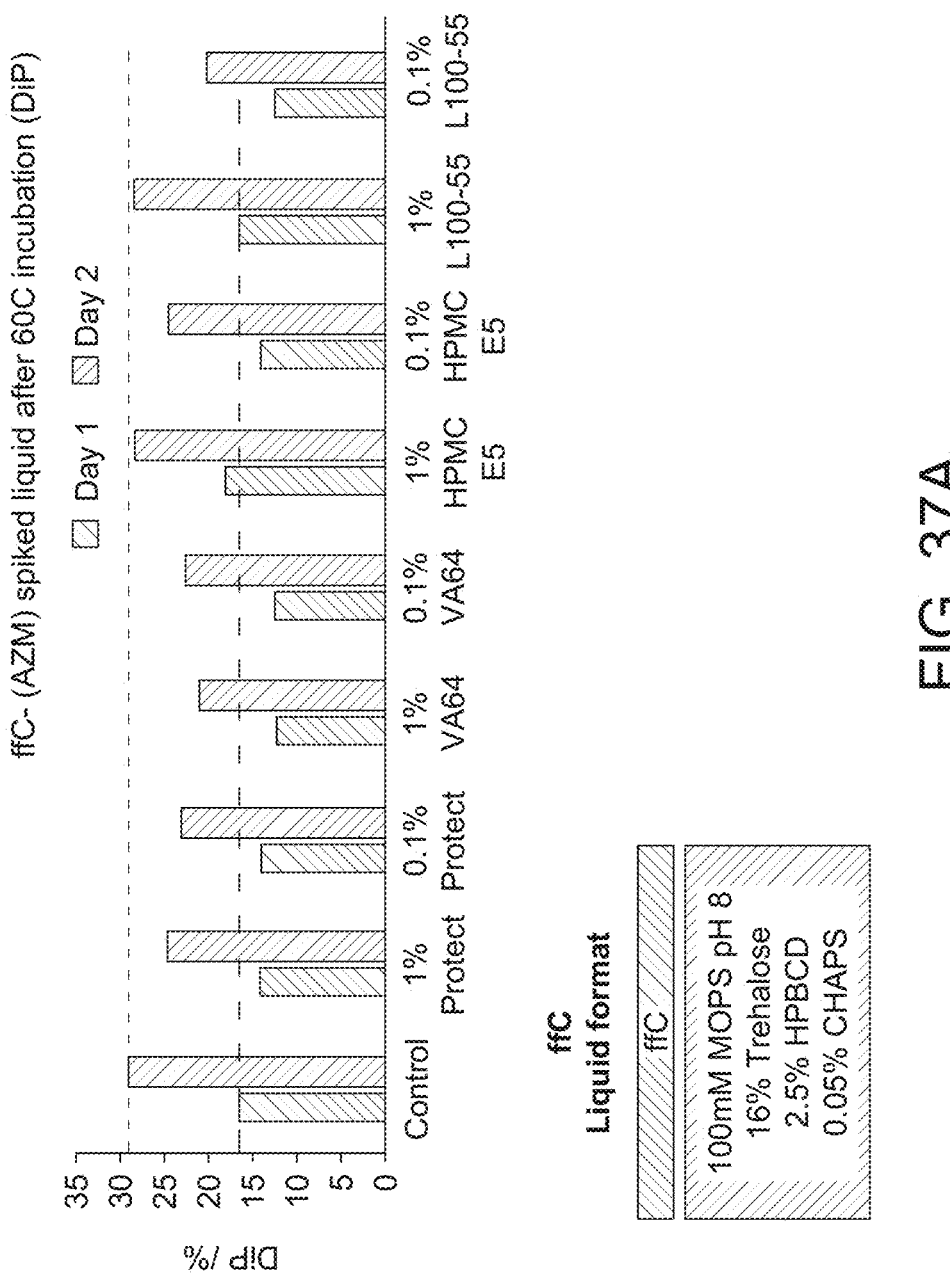
Figure 37B:
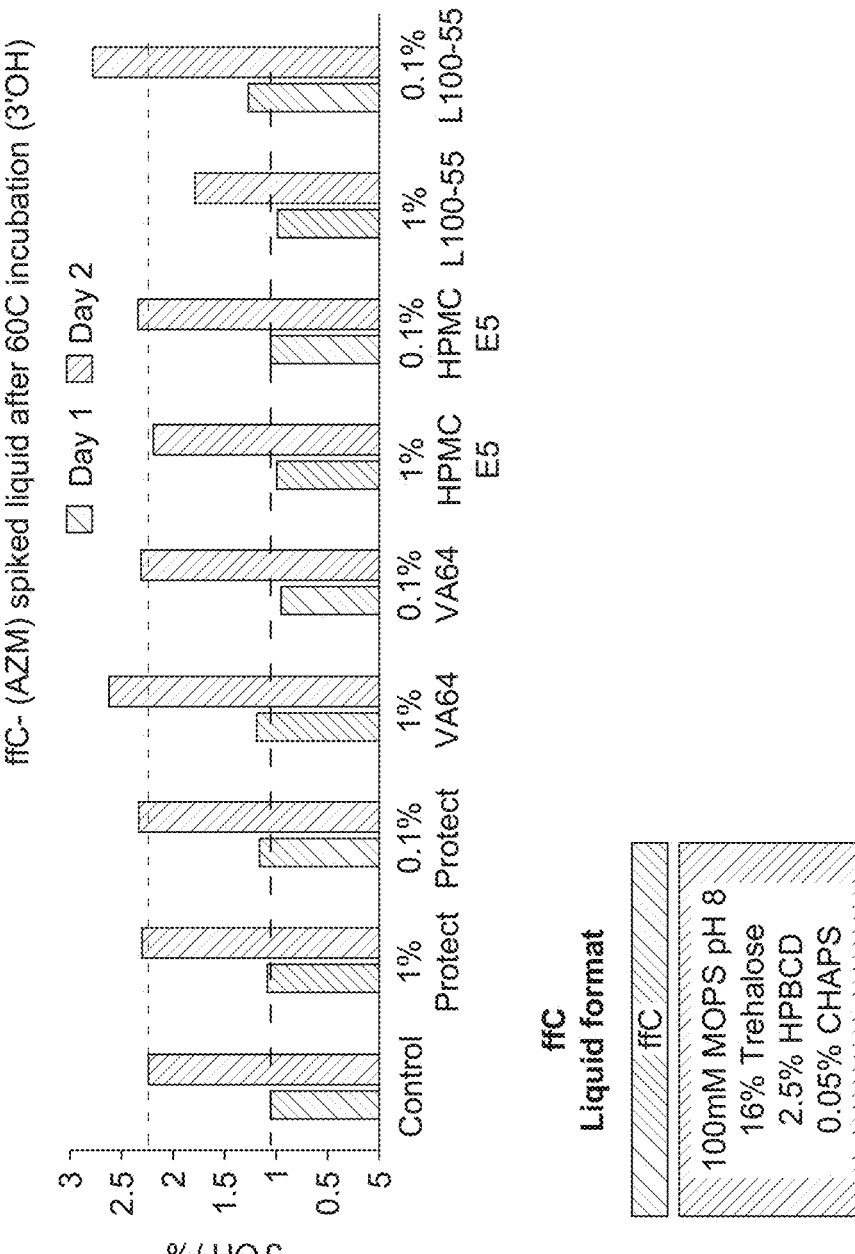
Figure 38:
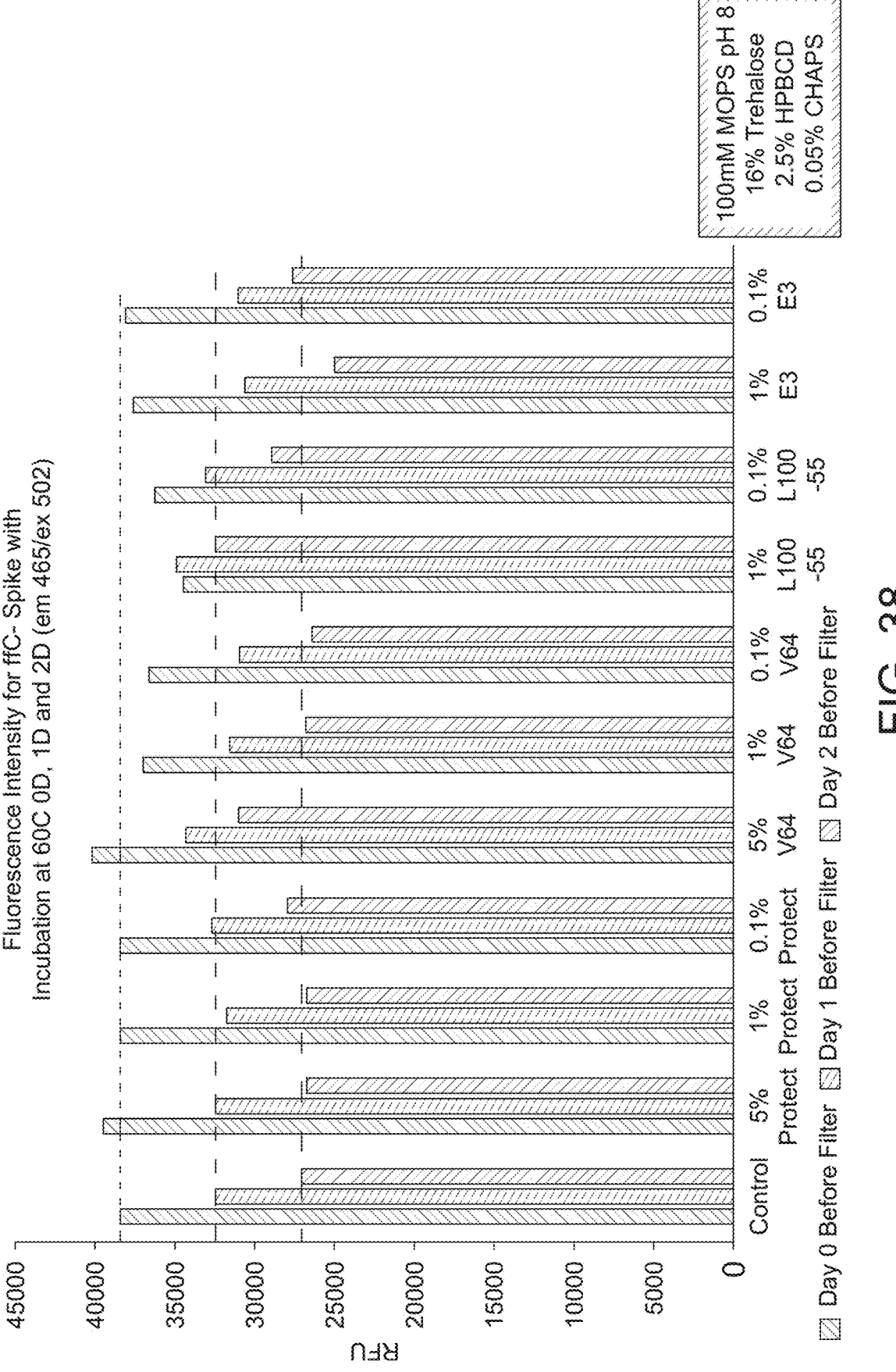
FIG. 38 shows fluorescence intensity for particular ffCs in the presence of polymers.
Figure 39:
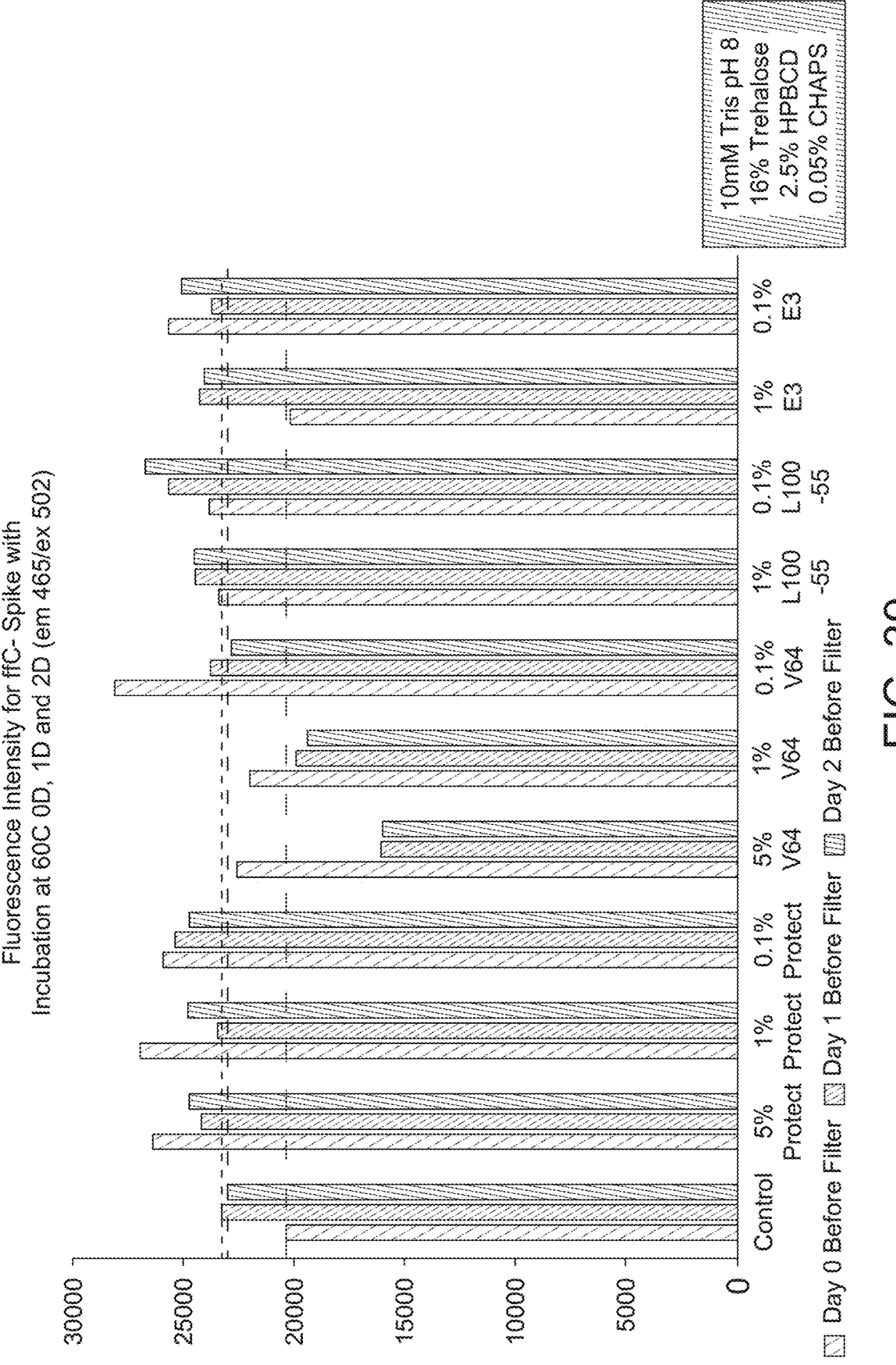
FIG. 39 shows fluorescence intensity for particular ffCs in the presence of polymers.
Figure 40A:
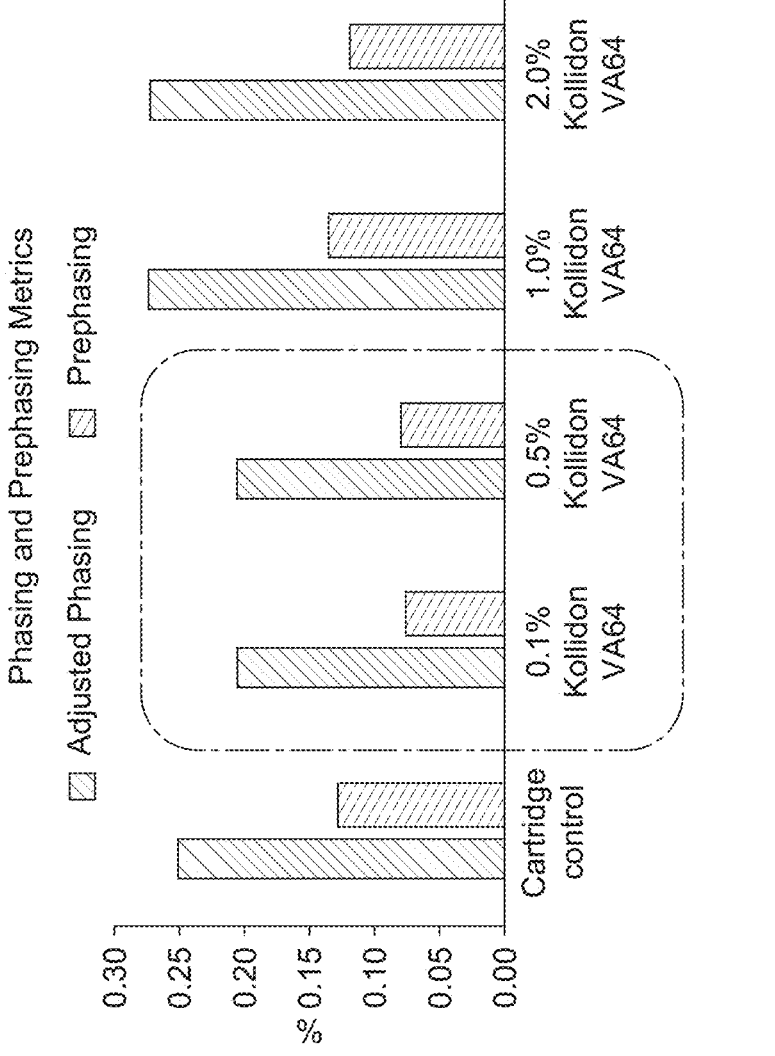
FIGS. 40A-40C show results of a coating materials screen based on Sequencing Compatibility.
Figure 40B:
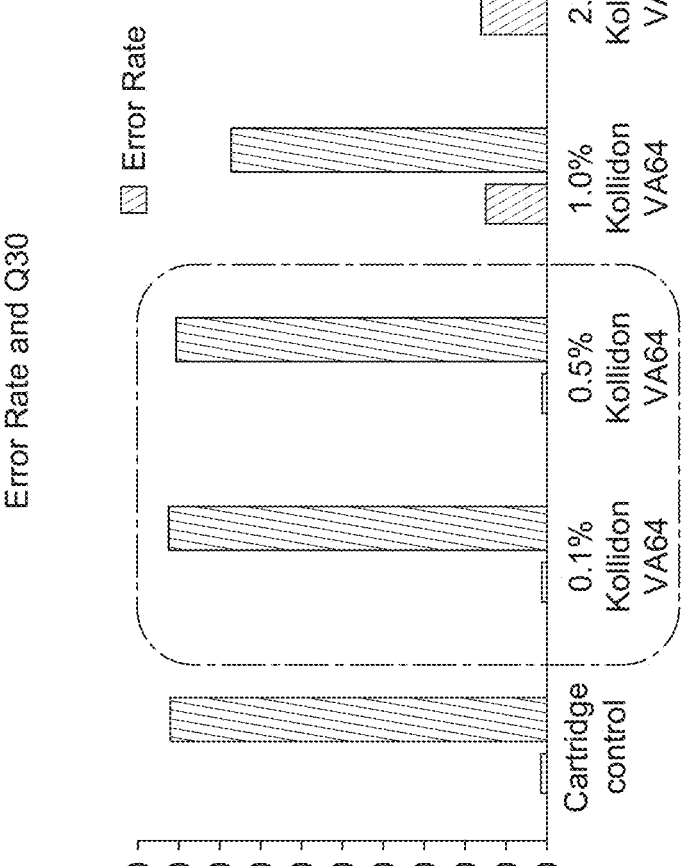
Figure 40C:
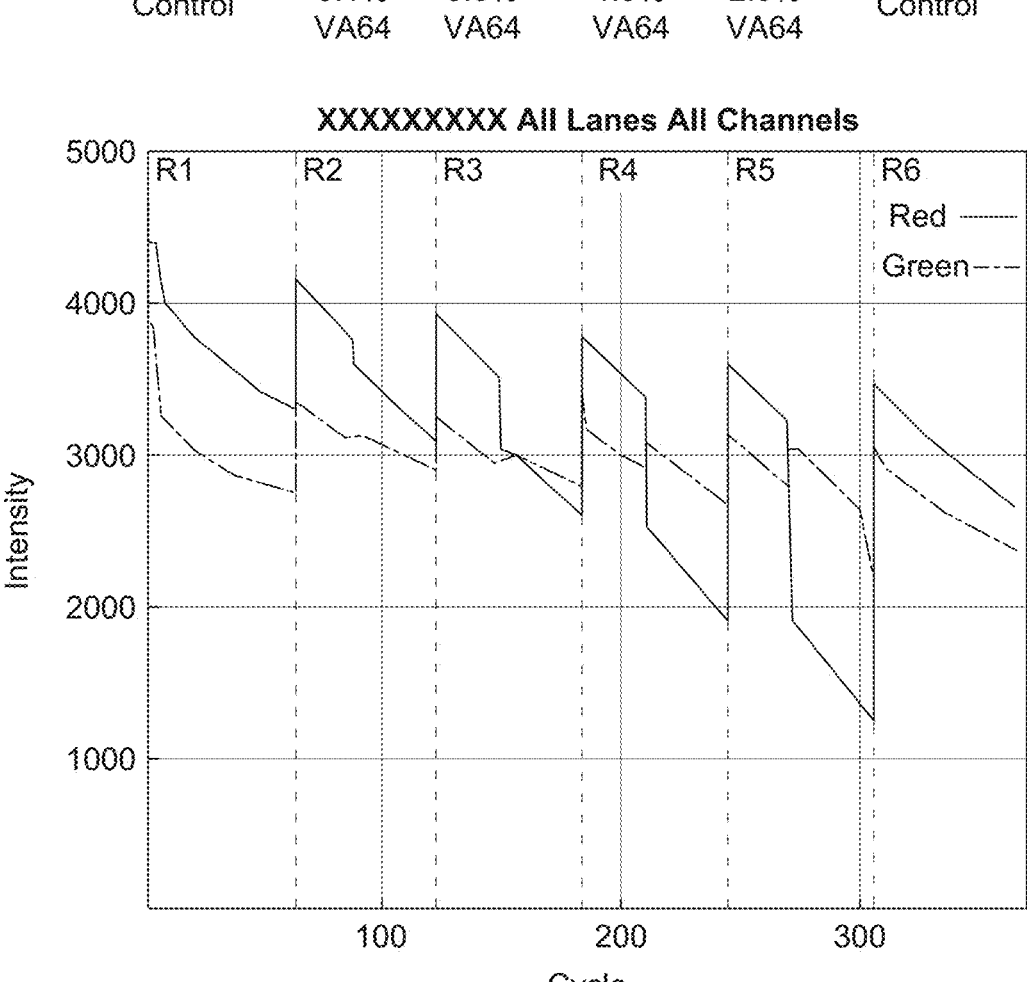
Figure 41A:
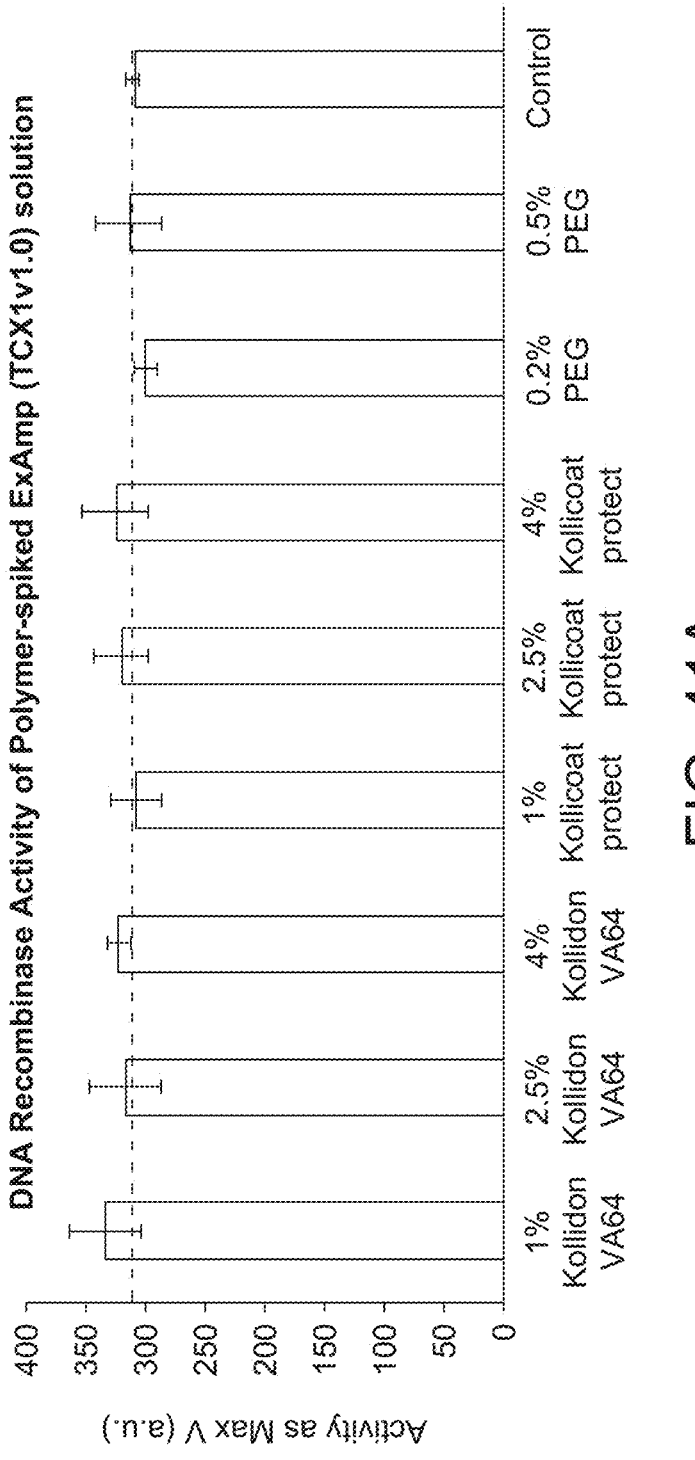
FIGS. 41A-41B show results of screening of polymers for DNA recombinase activity and clustering performance (cBOT), as well as DNA recombinase activity of ExAmp in the presence of a polymer as described herein.
Figure 41B:
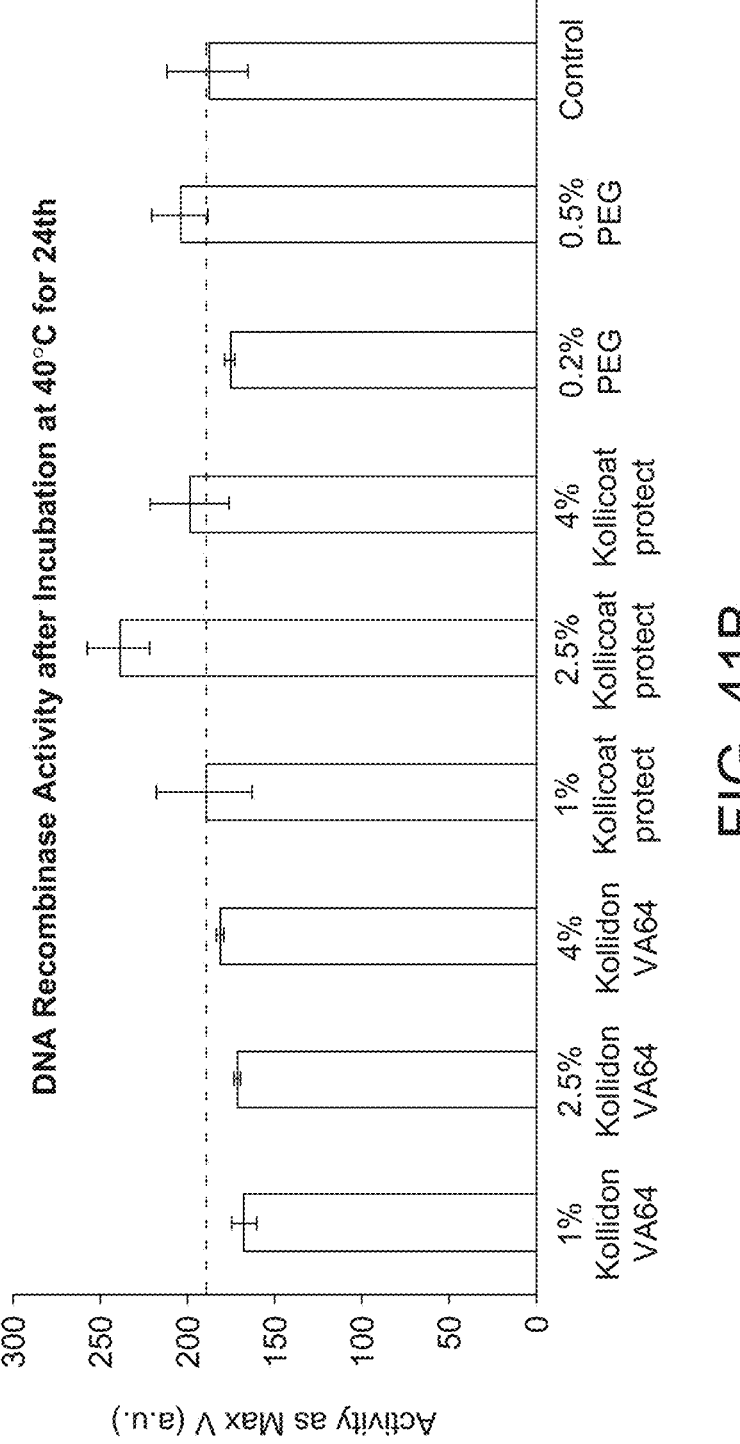
Figure 42A:
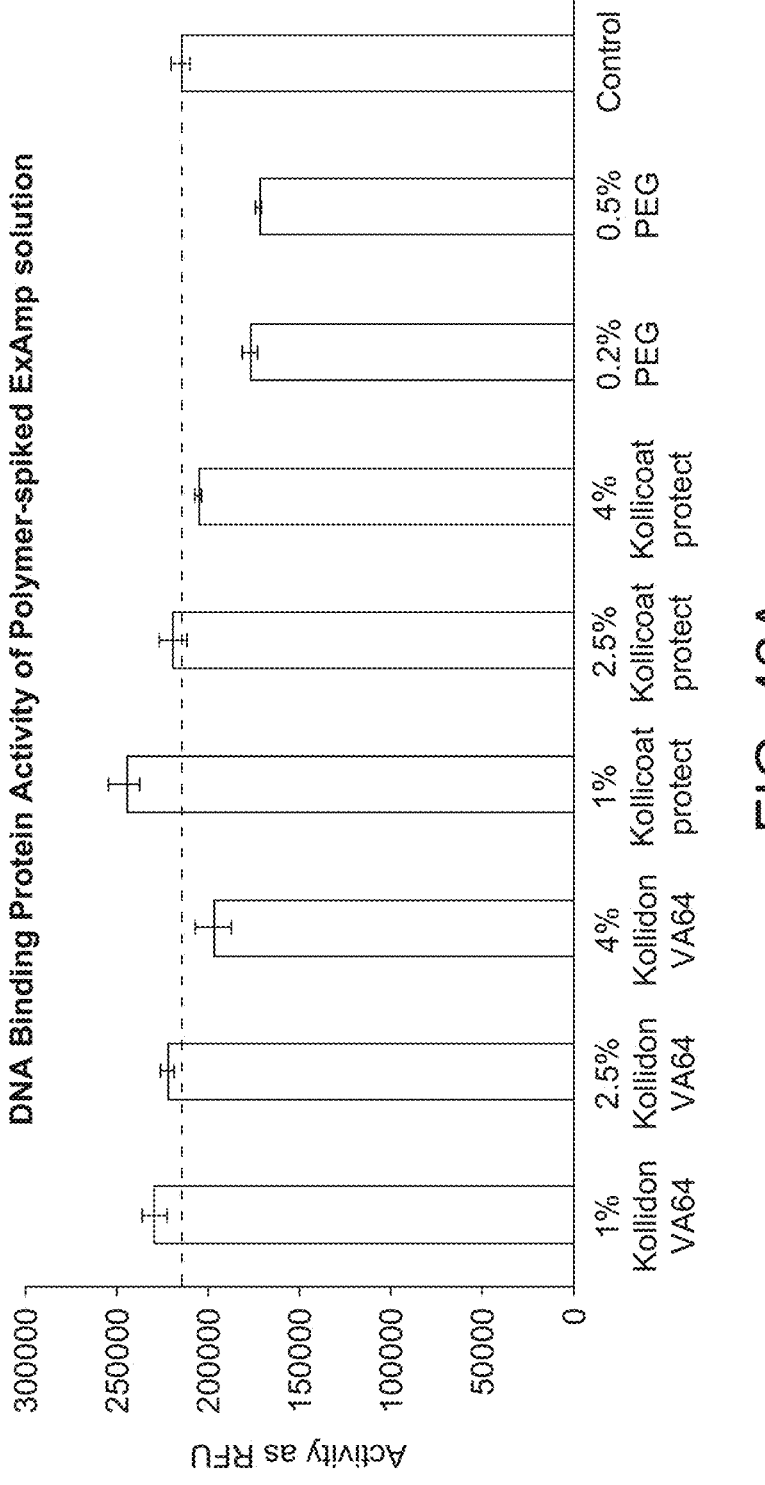
FIGS. 42A-42B show results of DNA binding protein activity of ExAmp in the presence of a polymer as described herein after staging and results of DNA binding protein activity of ExAmp in the presence of a polymer as described herein after staging.
Figure 42B:
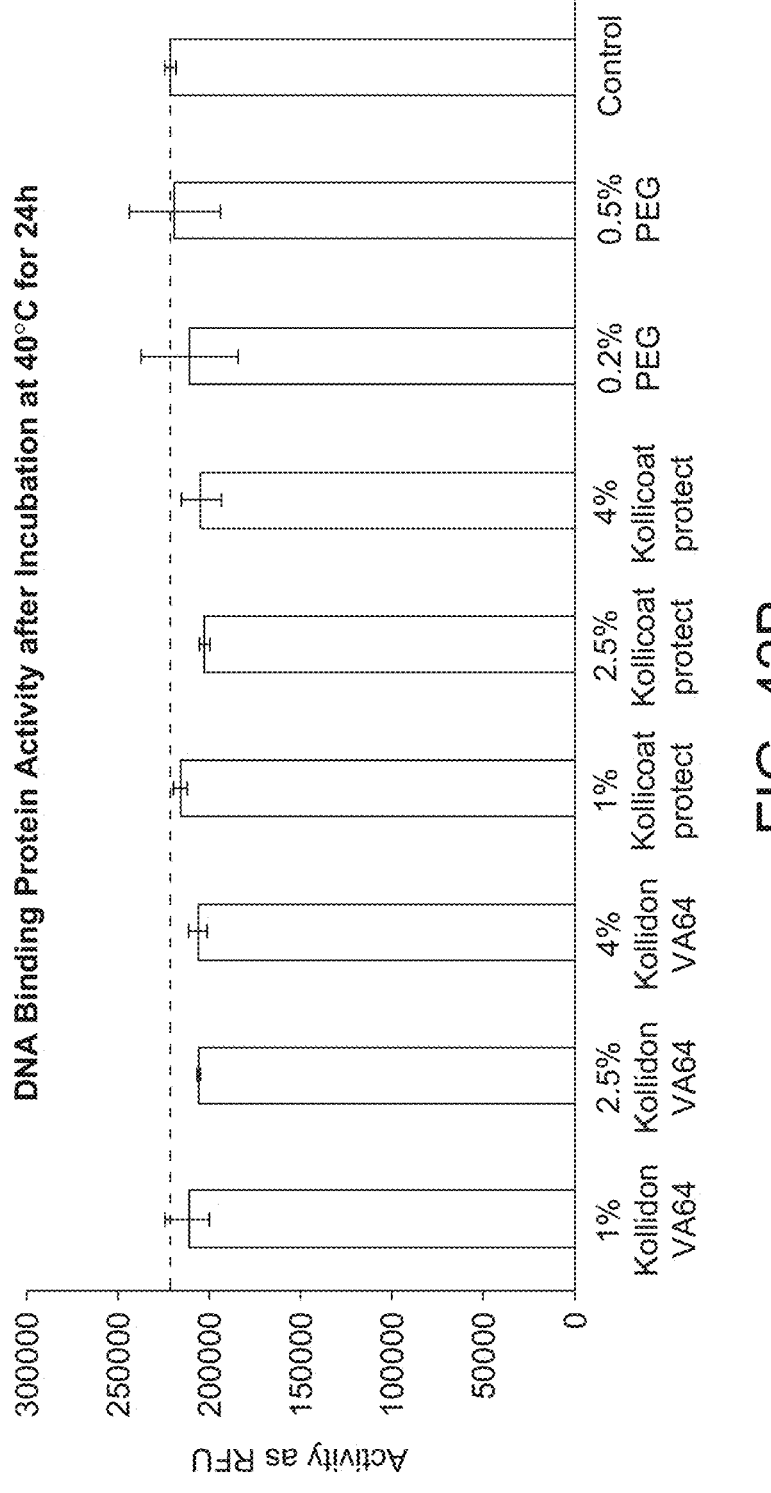
Figure 43A:
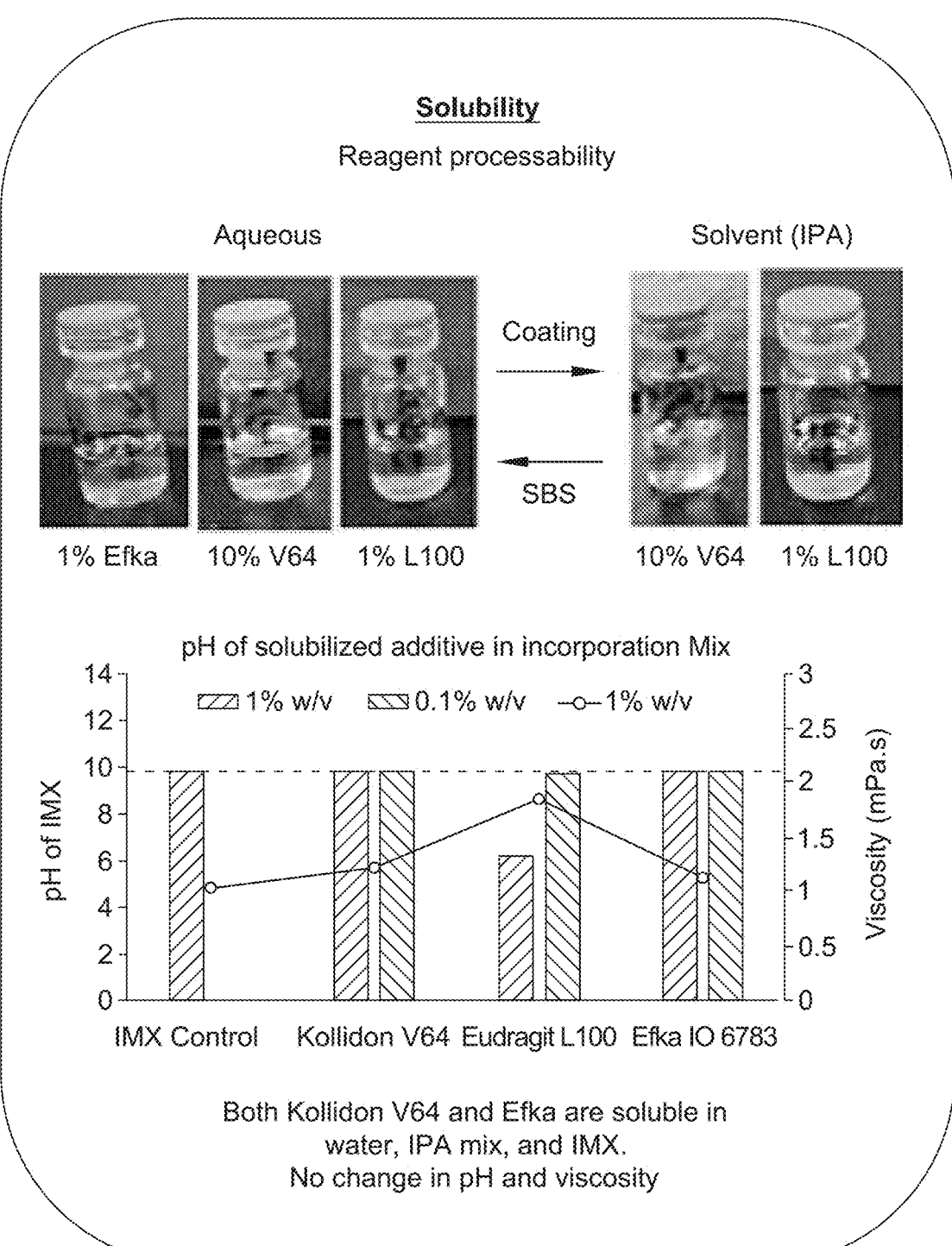
FIGS. 43A-43D shows that microencapsulation improves SBS reagent stability.
Figure 43B:
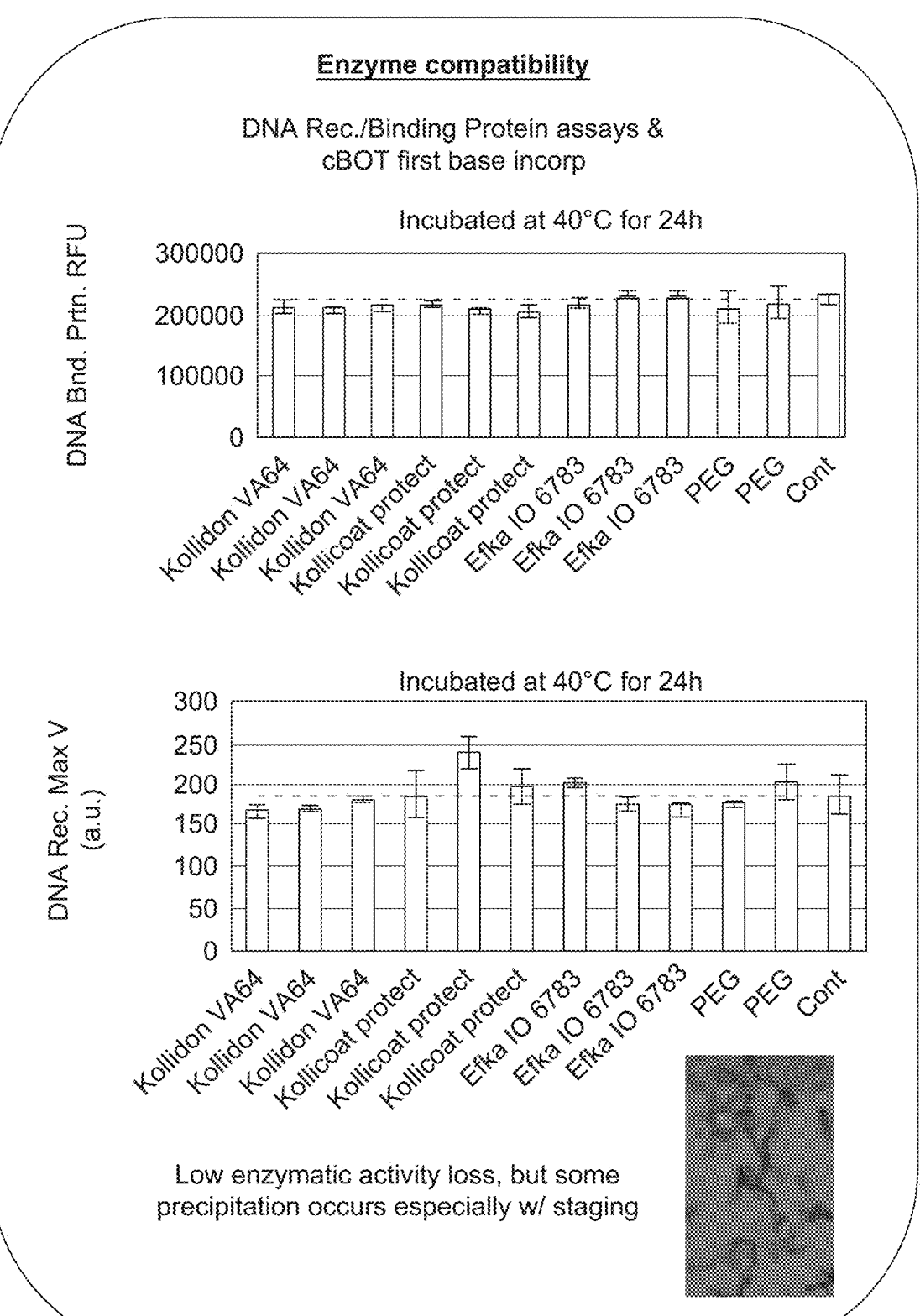
Figure 43C:
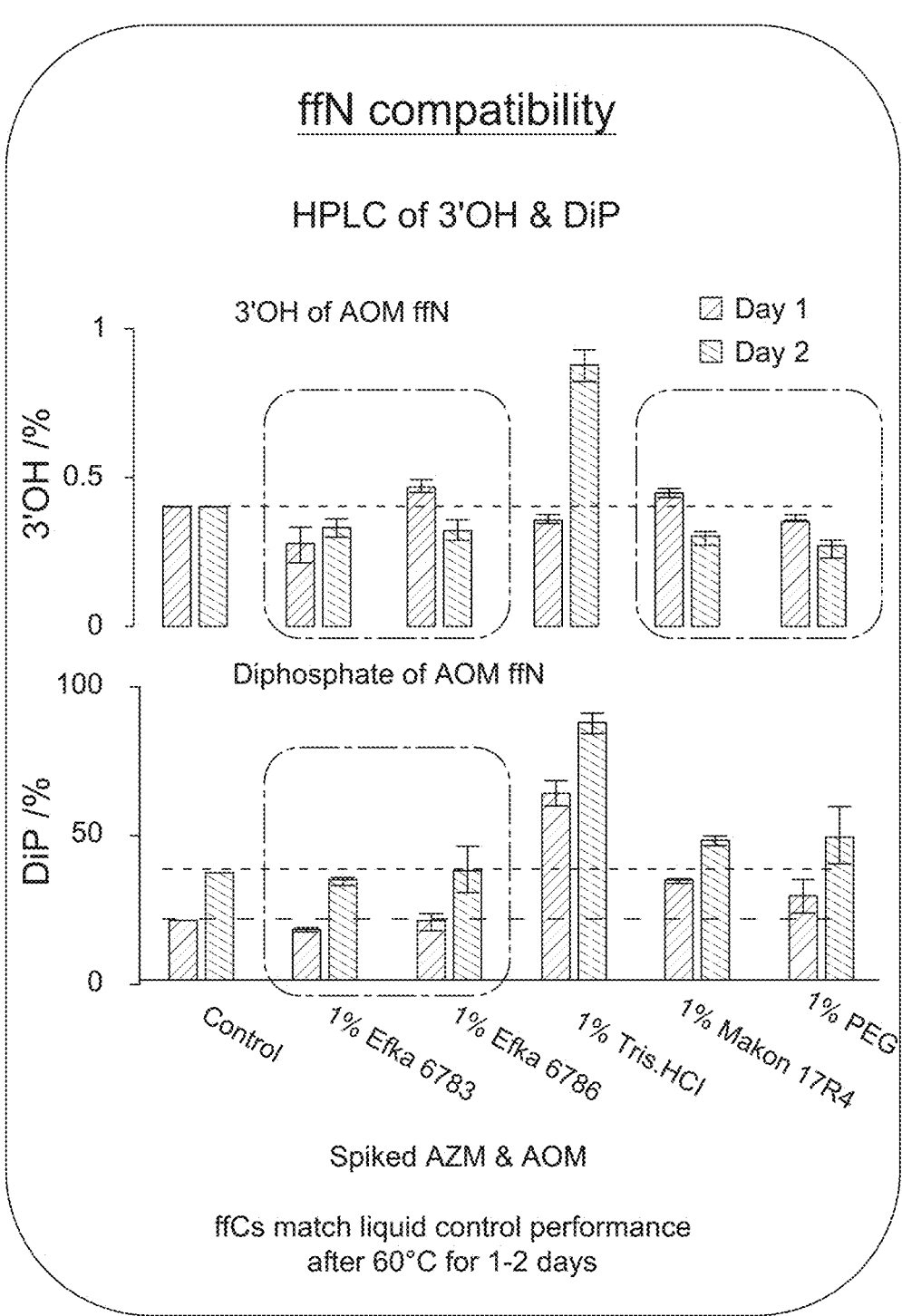
Figure 43D:
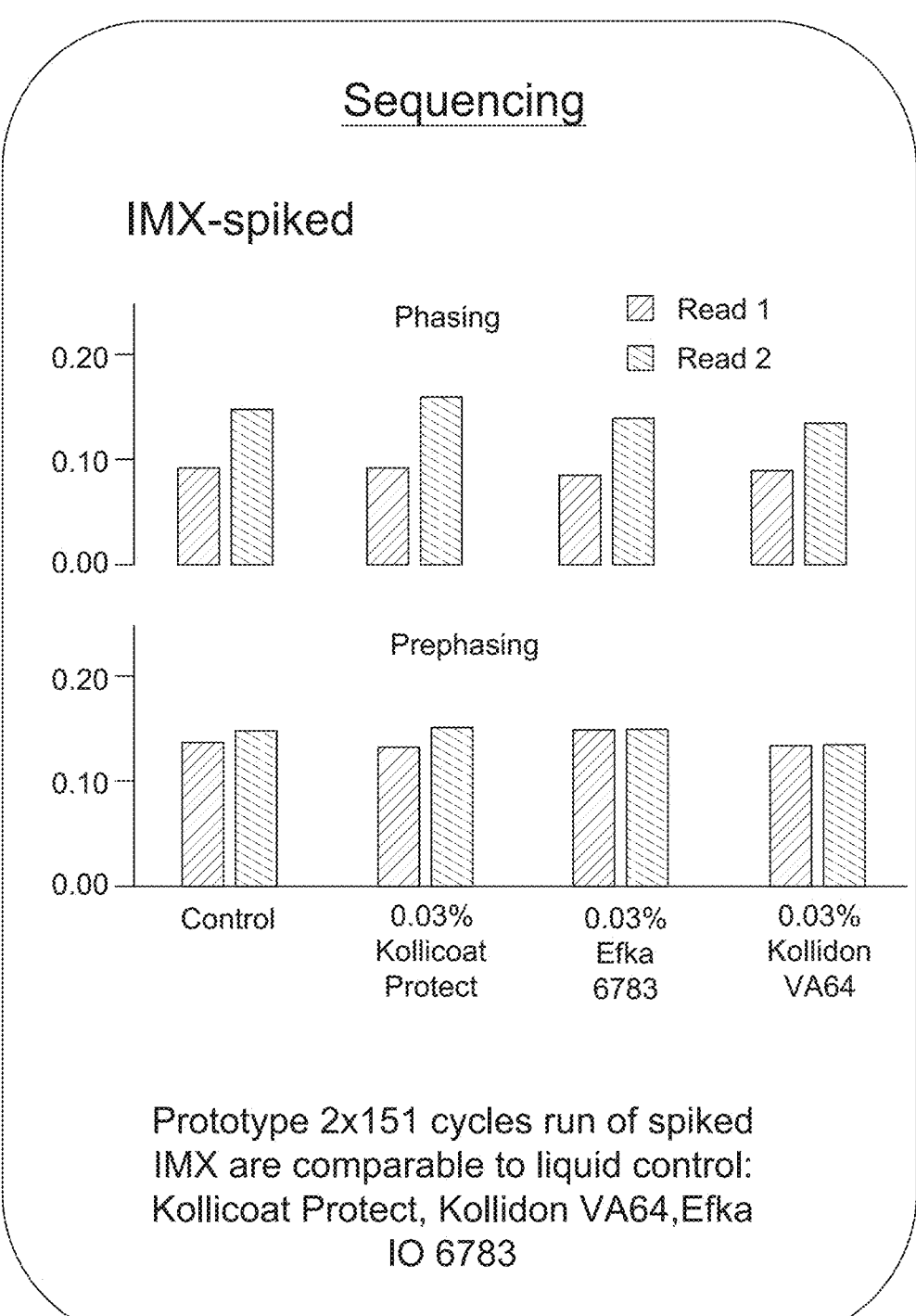

Example 13—Core-Shell Format: Excipient to be Soluble in Spray Solvent and Rehydration Buffer A concept for solubility screening is shown in FIG. 35.

Results of Kollidon® VA64, Efka®, Eudragit® which are soluble in spray-coating solution (15% water/solvent) and buffer are shown in FIG. 36.

Polymers solubility and pH screening results are described in Table 4. Polymers, such as Kollicoat® IR, Protect, Kollidon® V6 VA64, Methocel and Metolose are preferred due to their solubility in aqueous solution.

TABLE 4

Solubility screening of polymers that are selected to minimize moisture uptake of lyophilized microspheres. Weight % of polymer soluble and its effect on pH in solution (promising additives).

| Polymer (Moisture protection) | Water | | IPA | MOPS ph 7.5 | | IMX pH 9.9 | |
|---|---|---|---|---|---|---|---|
| Kollicoat ® Protect | 10.0% | 6.92 | x | 10.0% | 7.71 | 10.0% | 8.83 |
| Kollicoat ® IR | 10.0% | 6.58 | x | 10.0% | 7.56 | 10.0% | 8.93 |
| Kollicoat ® MAE-100P | x | | x | 1.0% | 6.83 | 1.0% | 6.87 |
| Kollidon ® V64 | 10.0% | 5.21 | 10.0% | 10.0% | 7.53 | 10.0% | 9.06 |
| Kollidon ® 30 | 10.0% | 3.84 | 10.0% | 10.0% | 7.40 | 10.0% | 9.52 |
| Kollicoat ® SR | x | | x | x | | x | |
| Methocel LV E3 | 10.0% | 7.51 | x | 10.0% | 7.67 | 10.0% | 9.78 |
| Methocel LV E5 | 10.0% | 7.85 | x | 10.0% | 7.62 | 10.0% | 9.75 |
| Methocel LV E15 | 10.0% | 8.07 | x | 10.0% | 7.57 | 10.0% | 9.76 |
| Opadry II | x | | x | x | | x | |
| Opadry AMB II | x | | x | x | | x | |
| Opadry TF | x | | x | x | | x | |
| Eudragit ® L100-55 | x | | 1.0% | 1.0% | 6.82 | 1.0% | 6.25 |
| Eudragit ® L100 | x | | 1.0% | 1.0% | 6.74 | 1.0% | 6.36 |
| Metolose SM-4 | 1.0% | 8.24 | x | 1.0% | 7.54 | 1.0% | 9.9 |
| Goshenol EG-05PW | 1.0% | 8.18 | x | x | | x | |
| Opadry SGR | x | | x | x | | x | |

For coating applications, polymers that are not soluble in organic solvent (e.g., IPA) can be formulated as solid dispersion in a water/alcohol mixture. For instance, Kollicoat® IR and Methocel are not soluble in solvent and use a fraction of water, the parameters of which are described in Table 5 below.

IPA addition into pre-solubilized Kollicoat® keeps 2.5% polymer in suspension (25% water/IPA). Decreasing the water fraction leads to precipitation. IPA addition into pre-solubilized HPMC keeps 1.4% HPMC in solution (14% water). Replacing IPA with ethanol (and removal of acetone) was found to improve the formulation to keep the polymers in a stable solid dispersion, which deemed to be sprayable for coating process.

TABLE 5

Kollicoat ® IR and Methocel with Water Fraction.

| Polymers | 10:7:3 IPA:Acetone:Water (15% water) | 10:6:4 IPA:Acetone:Water (20% water) | 17:3 Ethanol:Water (15% water) |
|---|---|---|---|
| Kollicoat ® Protect | x | x | 3% w/v (dispersion) |
| Kollicoat ® IR | x | x | 3% w/v (dispersion) |

TABLE 5-continued

| | 10:7:3 IPA:Acetone:Water (15% water) | 10:6:4 IPA:Acetone:Water (20% water) | 17:3 Ethanol:Water (15% water) |
|---|---|---|---|
| Polymers | | | |
| Kollidon ® V64 | 10% w/v | NA | N/A |
| Kollidon ® 30 | 10% w/v | NA | N/A |
| Methocel LV E3 | <1% w/v | 1% w/v | 5% w/v |
| Methocel LV E5 | <1% w/v | 1% w/v | 5% w/v |
| Methocel LV E15 | x | x | 5% w/v |
| Eudragit ® L100-55 | 10% w/v | NA | N/A |
| Eudragit ® L100 | 10% w/v | NA | N/A |
| Eudragit ® S100 | 10 w/v | NA | N/A |

Kollicoat ® IR and Methocel with Water Fraction.

Many polymers tested did not reduce pH of IMX significantly at 1%, except Eudragit®. Kollidon® V64 and K30 are soluble in both aqueous solution and IPA at 10% w/v, which are suitable for a relevant spray-coating process. Other polymers tested are not soluble in IPA; a water/solvent mixture may be beneficial, whereby greater than 15% v/v water may be used. Most polymers reduced pH of IMX, whereby Eudragit® L100 is more effective and HPMC is less effective (which is preferable) (see Table 6 below).

TABLE 6

Solubility of polymers in incorporation buffer (IMX pH 9.9) and their effect on pH of solution.

| Polymers | Weight % of polymers soluble in IMX (pH 9.9) and its effect on pH of IMX | | | | | | | |
|---|---|---|---|---|---|---|---|---|
| Kollicoat ® Protect | 10% | 8.83 | 5% | 9.42 | 1% | 9.78 | 0.1% | 9.88 |
| Kollicoat ® IR | 10% | 8.93 | 5% | 9.42 | 1% | 9.77 | 0.1% | 9.84 |
| Kollidon ® V64 | 10% | 9.06 | 5% | 9.43 | 1% | 9.75 | 0.1% | 9.88 |
| Kollidon ® 30 | 10% | 9.52 | 5% | 9.72 | 1% | 9.84 | 0.1% | 9.89 |
| Methocel LV E3 | 10% | 9.78 | 5% | 9.80 | 1% | 9.87 | 0.1% | 9.89 |
| Methocel LV E5 | 10% | 9.75 | 5% | 9.81 | 1% | 9.88 | 0.1% | 9.89 |
| Methocel LV E15 | 10% | 9.76 | 2% | 9.83 | 0.5% | 9.88 | 0.1% | 9.88 |
| Eudragit ® L100-55 | 1% | 6.25 | 0.1% | 9.79 | — | — | — | — |
| Eudragit ® L100 | 1% | 6.36 | 0.1% | 9.78 | — | — | — | — |

There was comparable 3'OH and diphosphate level of ffCs in the presence of polymers described herein (as shown in FIGS. 38, 39, 40A-40C, 41A-41B, 42A-42B, and 43A-43D).

Coating Materials Screen Results based on Sequencing Compatibility is shown in Table 7.

TABLE 7

Coating Materials Screen Results

| Classification of additives | IMX spiked with additives | % Phasing (≤0.2) | % Prephasing (≤0.2) | Q30 (%≥90) | Error Rate |
|---|---|---|---|---|---|
| Polymers | 0.5% Kollidon ® VA64 | ✓ | ✓ | 90.86 | 0.82 |
| | 1% Kollicoat ® Protect | ✓ | ✓ | 94.15 | 0.35 |
| | 1% Kollicoat ® IR | ✓ | ✓ | 93.22 | 0.37 |
| | 1% Methocel E3 | ✓ | ✓ | 88.90 | 0.66 |
| | 1% Methocel E5 | ✓ | ✓ | 86.99 | 0.88 |
| | 0.5% PEG4k | ✓ | ✓ | 94.22 | 0.29 |
| | 0.1% Eudragit ® L100 | x | x | 65.15 | 15.26 |
| | 0.1% Eudragit ® L100-55 | x | x | 58.88 | 42.17 |

57

58

Results of screening of polymers for DNA recombinase activity and clustering performance (cBOT) described herein are shown in FIGS. 45A-451B and 46A-46C. Quality of tested ffNs was not substantially affected by spray-coating process: a peak area (FIG. 45A) and 3'OH level (FIG. 451B) are comparable to control and no diphosphate was detected. FIGS. 46A-46C shows that Shell encapsulation was shown to improve moisture barrier and mitigate static (FIGS. 46A-46C).

Comparable DNA recombinase and DNA binding protein activity of ExAmp in the presence of a polymer as described herein after staging is shown in FIGS. 41A-41B and 42A-42B.

A summary of polymeric coating materials based on their ExAmp and clustering capability is shown in Table 8.

TABLE 8

Summary of polymers and static mitigating additives based on ExAmp and Clustering Compatibility.

| Liquid ExAmp spiked with additives | Solubility in TCX1 v.1.0 (ExAmp w/7.5% HPBCD) | DNA recombinase activity comparable to control | Cbot comparable to control (20 min incubation) | Cbot comparable to control (60 min incubation) |
|---|---|---|---|---|
| Methocel E5 | ✓ | ✓ | ✓ | ✓ |
| Kollidon ® VA64 | ✓ | ✓ | ✓ | ✓ |
| Kollicoat ® IR (Protect) | ✓ | ✓ | ✓ | ✓ |
| Eudragit ® L100-55 | ✓ | x | x | x |
| Gohsenol EG 05 | ✓ | ✓ | x | ✓ |
| Luviquat ® FC370 | ✓ | x | x | x |
| Poly(sodium 4-styrene sulfonate) | ✓ | x | x | x |
| Ethoxylated PEI | ✓ | x | x | x |
| Polyaniline | x (1:1 DMSO needed) | ✓ | ✓ | ✓ |
| Efka ® IO 6783 | ✓ | ✓ | ✓ <1.0% | ✓ <1.0% |
| Efka ® IO 6786 | ✓ | ✓ <1.0% | x | x |
| Tween ® 80 | ✓ | ✓ <1.0% | ✓ <1.0% | ✓ <1.0% |
| Lauric diethanolamide | ✓ | ✓ <1.0% | ✓ <1.0% | ✓ <1.0% |
| Makon ® 17R4 | ✓ | ✓ | ✓ | ✓ |
| α-tocopherol acetate | x (1:1 DMSO needed) | ✓ | ✓ | ✓ |
| Glycerol trioleate | x (1:1 DMSO needed) | ✓ | ✓ | ✓ |

Example 14—Improvement of SBS Reagent Stability with Microencapsulation

Microencapsulation to improve SBS reagent stability is shown in FIGS. 43A-43D. Formulations to reduce static and increase moisture barrier are down-selected via a screening pipeline.

Table 9 shows a materials summary for the compositions described herein.

TABLE 9

Materials Table Summary.

| Polymer | Potential use as moisture barrier | Anti-static (matrix) | Solubility water | Solubility IPA | pH of IMX* | Viscosity* (mPa · s) | ExAmp compatible | ffN compatible | Sequencing |
|---|---|---|---|---|---|---|---|---|---|
| Eudragit ® L100-55 | ✓ | ✓ | In pH >7, 1% w/v | 10% w/v | 6.25-9.79 | 1.14-1.85 | x | ✓ | x |
| Kollidon ® VA64 | ✓ | x | 10% w/v | 10% w/v | 9.06-9.88 | 1.01-1.22 | ✓ | ✓ (≤0.5%) | ✓ (≤0.1%) |
| Kollicoat ® IR/Protect | ✓ (Protect ®) | x | 10% w/v | x | 8.83-9.88 | 1.11-1.33 | ✓ | ✓ (≤1%) | ✓ (≤1%) |
| Methocel LV E5 | x | N/A | 10% w/v | w/15% water | 9.78-9.89 | 1.08-2.27 | ✓ | ✓ (≤1%) | ✓ (≤1%) |
| Opadry AMB II | ✓ | N/A | x | x | N/A | N/A | N/A | N/A | N/A |

TABLE 9-continued

| | Potential use as moisture barrier | Anti-static (matrix) | Solubility water | Solubility IPA | pH of IMX* | Viscosity* (mPa · s) | ExAmp compatible | ffN compatible | MiniSeq |
|---|---|---|---|---|---|---|---|---|---|
| Static mitigating Additive | | | | | | | | | |
| Lauric diethanolamide | ✗ (water-soluble, liquid) | ✓ | 2% w/v | 2% w/v | 9.99 | 1.04 | ✓ (0.1%) | ✓ | ✓ (≤0.5%) |
| Efka ® 6783 (ammonium) | ✗ (water-soluble, liquid) | ✓ | 2% w/v | 2% w/v | 9.78-9.92 | 1.00-1.13 | ✓ | ✓ | ✓ (≤1%) |
| Makon ® 17R4 (EO/PO block) | ✗ (water-soluble, liquid) | ✓ | 2% w/v | 2% w/v | 9.94 | 1.10 | ✓ | ✗ (<1%) | ✓ (≤1%) |
| Efka ® 6786 (imidazolium) | ✗ (water-soluble, liquid) | ✗ | 2% w/v | 2% w/v | 9.78-9.92 | 1.00-1.13 | ✗ (<1%) | ✓ | ✓ (≤0.5%) |
| Magnesium stearate | ✓ | ✓ | ✗ | 2% w/v | N/A | N/A | N/A | N/A | N/A |
| Luviquat ® FC370 | ✗ (water-soluble) | ✗ | 2% w/v | 2% w/v | 9.7 | 1.03-1.49 | ✗ | ✗ | ✗ |
| Tocopherol acetate | ✓ | ✓ | 0.5% w/0.5% DMSO | 1% w/v | 9.9 at 0.5% with 0.5% DMSO | 1.0 at 0.5% with 0.5% DMSO | ✓ | ✓ | ✓ (≤0.5%) |

Microspheres were used (~20% w/v), both ffN and DNA recombinase/BSA, where the targeted coating level resulted in a 10-15% weight gain. The coating formulations tested dry content: Formulation A: PEG (plasticizer), Kollidon® VA64, Efka® IO 6783; Formulation B: PEG, Kollidon® VA64; Formulation C: PEG, Kollicoat® Protect, Efka® IO 6783; and Formulation D: PEG, Kollicoat® Protect. Physical characterization of encapsulated microspheres nearly complete, staging and activity tests is shown in FIG. 44.

Figure 45A:
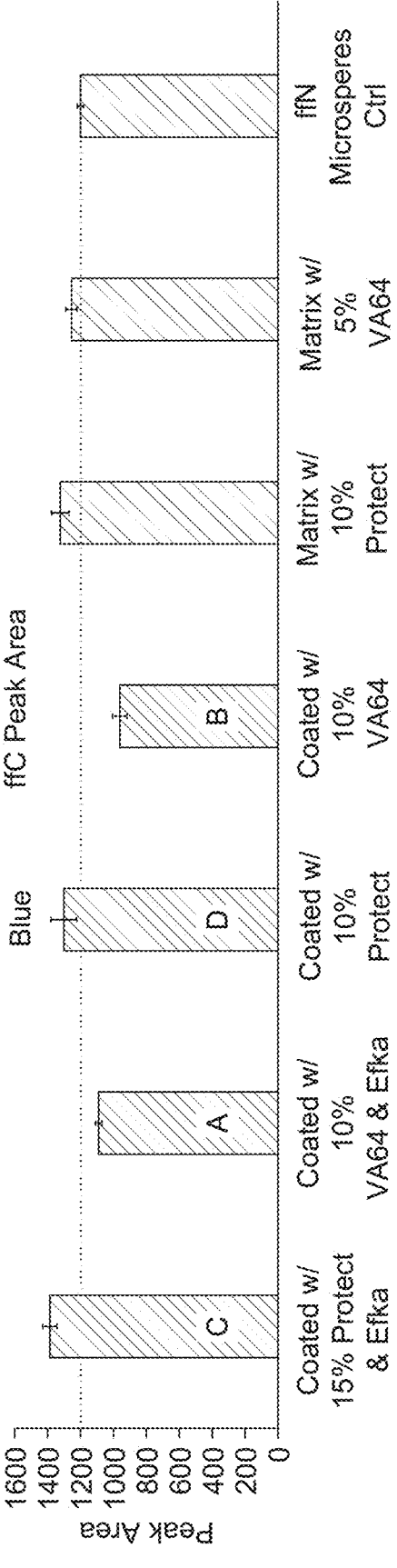
FIGS. 45A-45B show that the quality of tested ffNs may not be affected by spray-coating process: a peak area (FIG. 45A) and 3'OH level (FIG. 45B) are comparable to control and no diphosphate was detected.
Figure 45B:
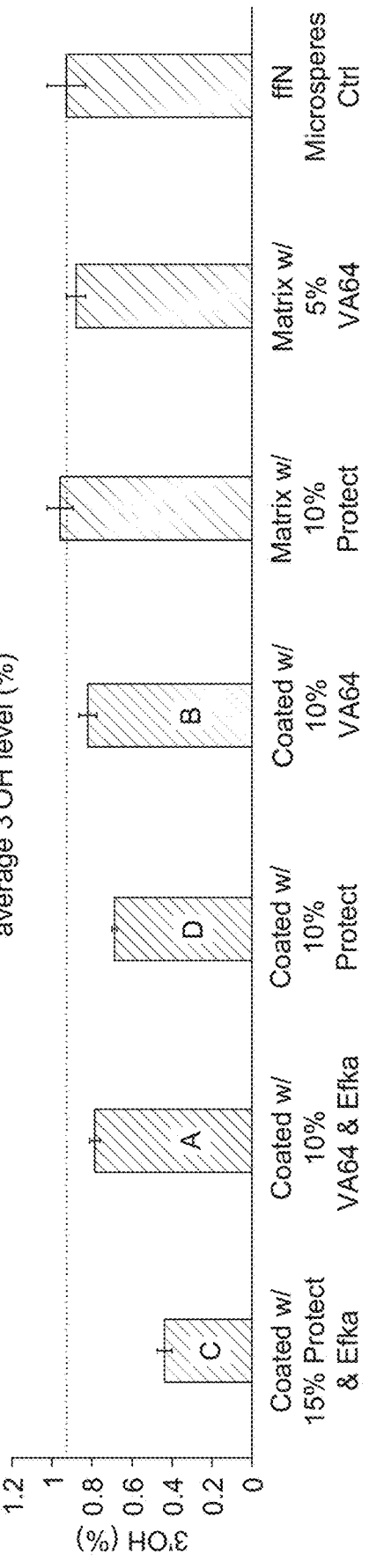

The quality of ffN was not substantially affected by spray-coating process: a peak area and 3'OH level are comparable to control and no diphosphate was detected (see FIGS. 45A-45B).

Shell encapsulation improves moisture barrier and mitigates static (see FIGS. 46A-46C). Matrix encapsulation may be limited to static mitigation, whereas core shell may address both, as shown and described in FIGS. 46A-46C.

Figure 49A:
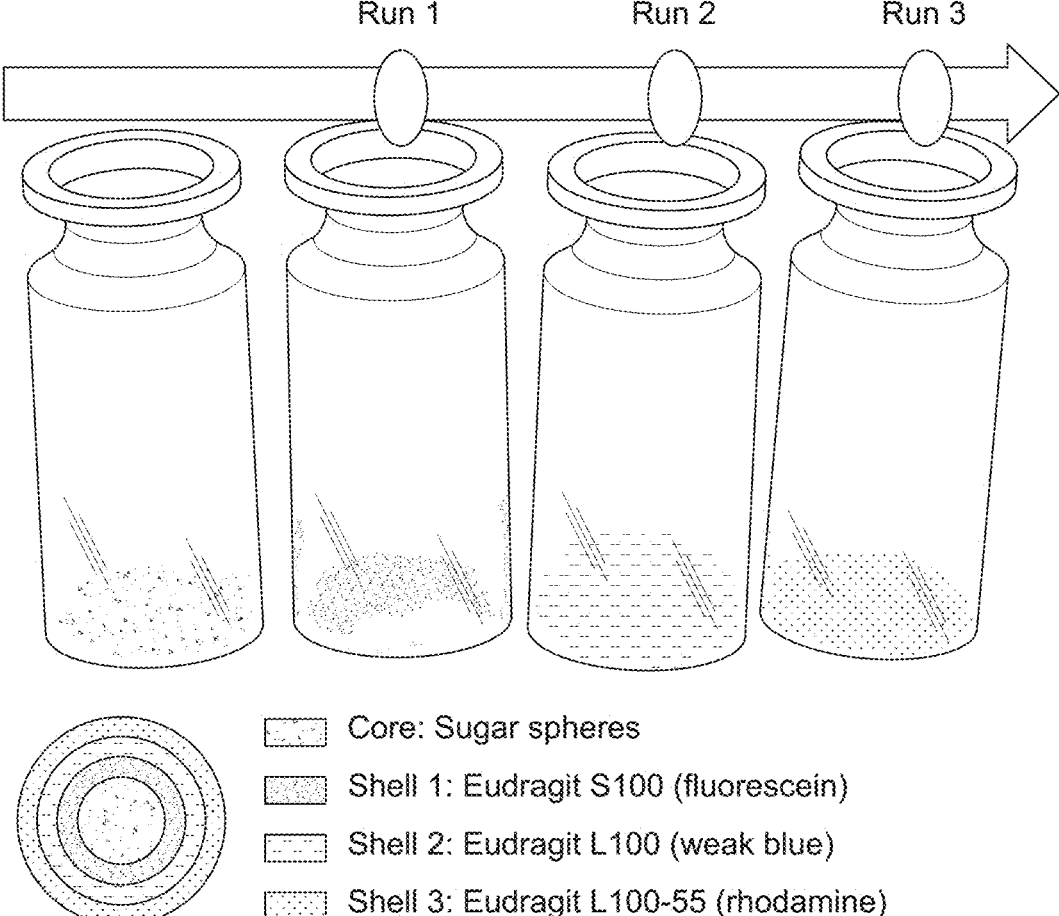
FIGS. 49A-49C show a triple-coated microsphere with sequential pH triggers for release.
Figure 49B:
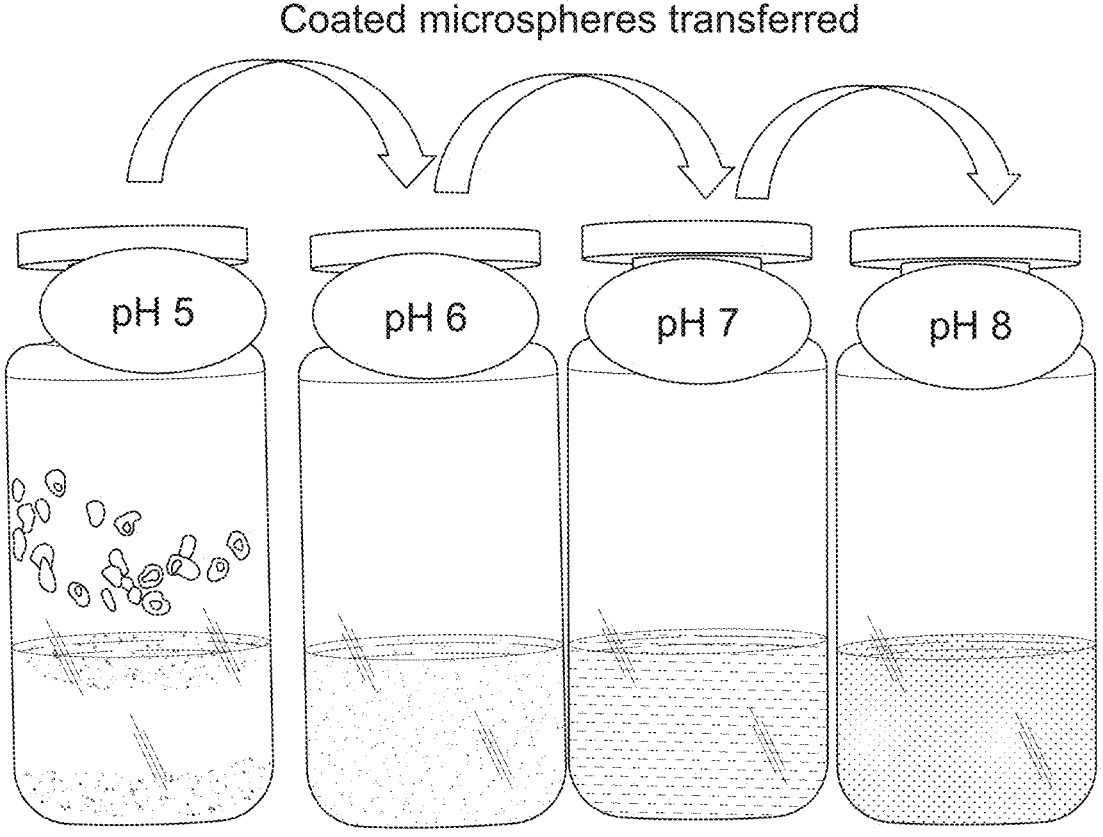
Figure 49C:
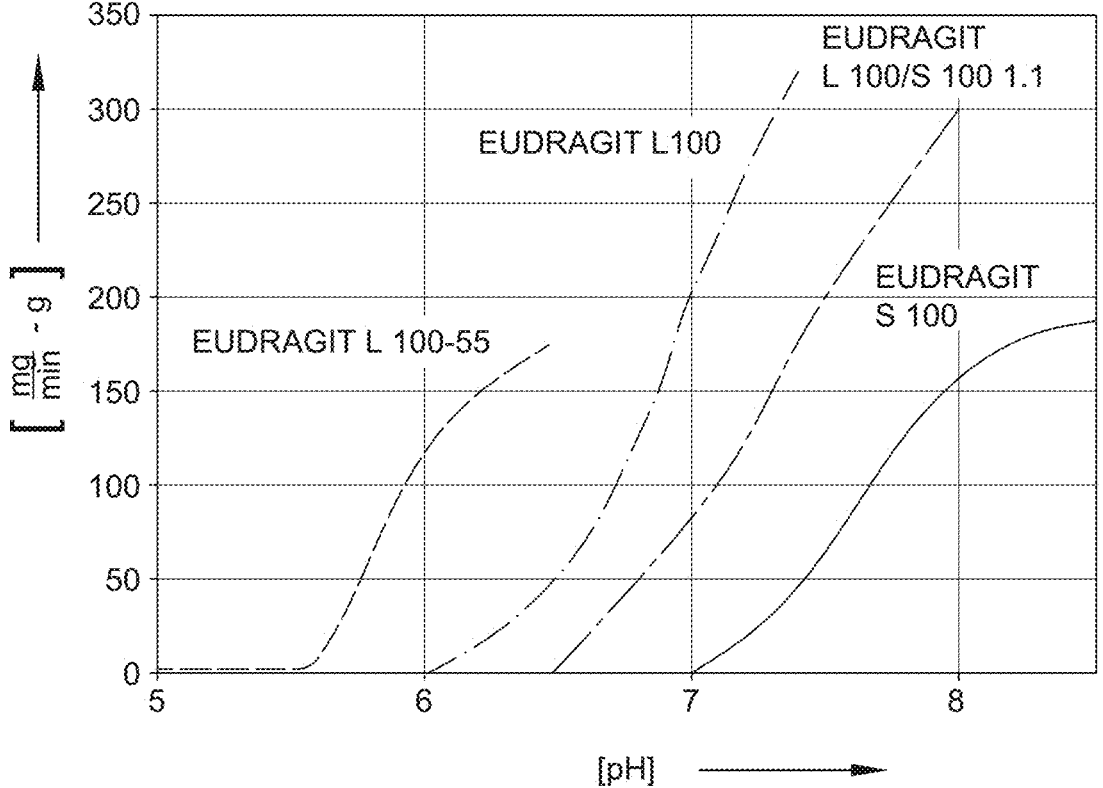

Spheres that were triple-coated (e.g., with Eudragit® S100 (fluorescein) in Shell 1, Eudragit® L100 (weak blue) in Shell 2, and Eudragit® L100-55 (rhodamine) in Shell 3) provided improved results as shown in FIGS. 49A-49C, with regard to sequential release based on pH triggers (e.g., pH 5, pH 6, pH 7, pH 8).

Although preferred implementation have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A composition comprising:
a shell surrounding a core, wherein said shell comprises a shell additive and said shell additive comprises a static mitigation material, a moisture barrier material, or a combination thereof, and wherein said core comprises one or more lyophilised microspheres; wherein said core comprises a polymerase.

2. The composition of claim 1, wherein the shell additive is a static mitigation material present in an amount no more than 40% w/w concentration of the shell.

3. The composition of claim 1, wherein the shell additive is a moisture barrier material present in an amount no more than 90% w/w concentration of the shell.

4. The composition of claim 1, wherein the shell additive comprises one or more of a polymer, a copolymer, a block copolymer, a second polyvinyl alcohol (PVA), an ammonium salt, a stearate derivative, an oleate derivative, a laurate derivative, a polyether compound, an amino acid, tocopherol acetate, piperidyl sebacate, sodium salt, a buffer, a chelating agent, imidazolium salt, polyaniline, or any combination thereof.

5. The composition of claim 4, wherein the polyether compound is selected from polyethylene glycol, polypropylene glycol, a block copolymer derived from ethylene oxide (EO) and propylene oxide (PO), or any combination thereof.

6. The composition of claim 4, wherein the amino acid is selected from one or more of leucine, isoleucine, phenylalanine, or any combination thereof.

7. The composition of claim 4, wherein the sodium salt is selected from one or more of sodium chloride, sodium bisulfite, sodium citrate, or any combination thereof.

8. The composition of claim 4, wherein the buffer is Tris HCl.

9. The composition of claim 4, wherein the ammonium salt is selected from tetraalkyl ammonium chloride, tris (hydroxyethyl) alkylammonium chloride, or a combination thereof.

10. The composition of claim 4, wherein the imidazolium salt is selected from 1-ethyl-3-methyl-imidazolium salt, or polyquaternium, or copolymer of vinyl pyrrolidone and quaternized vinylimidazole, or a combination thereof.

11. The composition of claim 1, wherein the shell additive comprises ammonium salt, copolymer, polyvinyl alcohol graft polyethylene glycol copolymer, polyvinyl alcohol (PVA), or any combination thereof.

12. The composition of claim 1, wherein said core comprises one or more reagent selected from one or more enzyme, salt, surfactant, buffering agent, enzyme inhibitor, primer, nucleotide, organic osmolite, magnetic bead, molecular probe, crowding agent, labelled-nucleotide, a fluorophore, or any combination thereof.

13. The composition of claim 1, wherein said core further comprises one or more additional agent, wherein said one or more additional agent is selected from one or more sugar, one or more amino acid, one or more polymer, one or more mesoporous silica, one or more quaternary amine, and any combination thereof.

14. The composition of claim 13, wherein, when said one or more additional agent comprises one or more sugar, said one or more sugar is selected from trehalose, mannitol, cyclodextrin, dextran, sucrose, or any combination thereof.

15. The composition of claim 13, wherein, when said one or more additional agent comprises one or more amino acid, said one or more amino acid has a hydrophobic side chain.

16. A composition comprising:

a shell surrounding a core, wherein said core comprises a core additive and said core additive comprises a static mitigation material;

wherein said core comprises a polymerase; and wherein
- (i) the core additive is a static mitigation material present in an amount no more than 25% w/w concentration of the core, or
- (ii) the core additive is in an amount between about 2% w/w and about 10% w/w concentration of the core.

17. The composition of claim 16, wherein the core additive comprises one or more of a polymer, a copolymer, a block copolymer, a second polyvinyl alcohol (PVA), an ammonium salt, an imidazolium salt, a polyether compound, or any combination thereof.

18. The composition of claim 16, wherein the core additive is a static mitigation material present in an amount no more than 25% w/w concentration of the core.

19. The composition of claim 17, wherein one or more of:
- (i) the polyether compound is selected from polyethylene glycol, polypropylene glycol, a block copolymer derived from ethylene oxide (EO) and propylene oxide (PO), or any combination thereof;
- (ii) the polymer is neutral, cationic, or anionic;
- (iii) the ammonium salt is selected from tetraalkyl ammonium chloride, tris(hydroxyethyl) alkylammonium chloride, or a combination thereof; and
- (iv) the imidazolium salt is selected from 1-ethyl-3-methyl-imidazolium salt, or polyquaternium, or copolymer of vinyl pyrrolidone and quaternized vinylimidazole, or a combination thereof.

20. The composition of claim 16, wherein said shell comprises more than one lyophilised microsphere, and wherein one of said reagents in a first of said more than one lyophilised microsphere is different from another of said reagents in a second of said more than one lyophilised microsphere.

* * * * *